US009587247B2

(12) United States Patent
Zhang et al.

(10) Patent No.: US 9,587,247 B2
(45) Date of Patent: Mar. 7, 2017

(54) PLANTS WITH ALTERED PHYTOCHROMES

(71) Applicant: WISCONSIN ALUMNI RESEARCH FOUNDATION, Madison, WI (US)

(72) Inventors: Junrui Zhang, Madison, WI (US); Richard David Vierstra, Madison, WI (US); Robert Joseph Stankey, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 740 days.

(21) Appl. No.: 13/803,403

(22) Filed: Mar. 14, 2013

(65) Prior Publication Data

US 2014/0075599 A1 Mar. 13, 2014

Related U.S. Application Data

(60) Provisional application No. 61/683,983, filed on Aug. 16, 2012.

(51) Int. Cl.
*C12N 15/29* (2006.01)
*C12N 15/82* (2006.01)
*C07K 14/415* (2006.01)

(52) U.S. Cl.
CPC ........ *C12N 15/8269* (2013.01); *C07K 14/415* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 4,945,050 | A | 7/1990 | Sanford et al. |
| 5,240,855 | A | 8/1993 | Tomes |
| 5,322,783 | A | 6/1994 | Tomes et al. |
| 5,324,646 | A | 6/1994 | Buising et al. |
| 5,563,055 | A | 10/1996 | Townsend et al. |
| 5,736,369 | A | 4/1998 | Bowen et al. |
| 5,879,918 | A | 3/1999 | Tomes et al. |
| 5,886,244 | A | 3/1999 | Tomes et al. |
| 5,932,782 | A | 8/1999 | Bidney |
| 5,981,840 | A | 11/1999 | Zhao et al. |
| 2003/0204872 | A1 | 10/2003 | Kim et al. |
| 2006/0260009 | A1 | 11/2006 | Kim et al. |
| 2015/0307565 | A1 | 10/2015 | Burgie et al. |

FOREIGN PATENT DOCUMENTS

| | | |
|---|---|---|
| WO | 2007/123876 | 11/2007 |
| WO | 2014/028562 | 2/2014 |

OTHER PUBLICATIONS

Song et al. (Plant Mol Biol (2015) 87:633-643).*
Guo et al. (2004, Proc. Natl. Acad. Sci. USA 101: p. 9205-9210).*
Wagner et al. The Journal of Biological Chemistry vol. 283, No. 18, pp. 12212-12226, May 2, 2008.*
Altschul et al., "Gapped BLAST and PSI-BLAST: a new generation of protein database search programs," 1997, Nucl. Acids Res. 25: 3389-3402.
Bytebier et al., "T-DNA organization in tumor cultures and transgenic plants of the monocotyledon Asparagus officinalis," (1987) Proc. Natl. Acad. Sci. USA 84:5345-5349.
Christou and Ford, "Parameters Influencing Stable Transformation of Rice Immature Embryos and Revovery of Transgenic Plants using Electric Discharge Particle Acceleration," (1995) Annals of Botany 75:407-413.
Christou et al., "Stable Transformation of Soybean Callus by DNA-Coated Gold Particles," (1988) Plant Physiol. 87:671-674.
Crossway et al., "Micromanipulation Techniques in Plant Biotechnology," (1986) Biotechniques 4:320-334.
Datta et al., "Genrically Engineered Fertile Indica-Rice Recovered From Protopwts," (1990) Biotechnology 8:736-740.
De Wet et al., "Exogenous gene transfer in maize (*Zea mays*) using DNA-treated pollen," (1985) in The Experimental Manipulation of Ovule Tissues, ed. Chapman et al. (Longman, N.Y.), pp. 197-209.
D'Halluin et al., "Transgenic Maize Plants by Tissue Electroporation," (1992) Plant Cell 4:1495-1505.
Finer and McMullen, "Transformation of Soybean Via Particle Bombardment of Embryogenic Suspension Culture Tissue," (1991) In Vitro Cell Dev. Biol. 27P:175-182.
Fromm et al., "Inheritance and Expression of Chimeric Genes in the Progeny of Transgenic Maize Plants," (1990) Biotechnology 8:833-839.
Hiei et al., "Efficient transformation of rice (*Oryza sativa* L.) mediated by Agrobacterium and sequence analysis of the boundaries of the T-DNA," Plant J. 1994 (2):271-282.
HooykaasVan Slogteren et al., "Expression of Ti plasmid genes in *Monocotyledonous* plants infected with Agrobacterium tumefaciens," (1984) Nature (London) 311:763-764.
Ishida et al., "Agrobacterium-mediated transformation of maize," Nat. Protoc. 2: 1614-1621 (2007).
Ishida et al., "High efficiency transformation of maize (*Zea mays* L.) mediated by Agrobacterium tumefaciens," (1996) Nature Biotechnology 14:745-750.
Kaeppler et al., "Silicon carbide fiber-mediated DNA delivery into plant cells," (1990) Plant Cell Reports 9:415-418.
Kaeppler et al., "Silicon carbide fiber-mediated stable transformation of plant cells," (1992) Theor. Appl. Genet. 84:560-566.
Karlin and Altschul, "Methods for assessing the statistical significance of molecular sequence features by using general scoring schemes," 1990, Proc. Natl. Acad. Sci. USA 87: 2264-2268.
Klein et al., "Factors Influencing Gene Delivery Into *Zea mays* Cells by High-Velocity Microprojectiles," (1988) Biotechnology 6:559-563.
Klein et al., "Genetic Transformation of Maize Cells by Particle Bombardment," (1988) Plan Physiol. 91:440-444.
Klein et al., "Transfer of foreign genes into intact maize cells with high-velocity microprojectiles," (1988) Proc. Natl. Acad. Sci. USA 85:4305-4309.

(Continued)

*Primary Examiner* — Elizabeth McElwain
*Assistant Examiner* — Charles Logsdon
(74) *Attorney, Agent, or Firm* — Michael Best & Friedrich LLP

(57) ABSTRACT

Polynucleotides encoding polypeptides that increase the light sensitivity of plants were identified. Introduction of the polynucleotides into plants produces plants having altered characteristics, such as decreased height, decreased diameter, decreased petiole length, decreased internode length, decreased hypocotyl length, increased hyponasty or enhanced germination.

21 Claims, 18 Drawing Sheets

(56) References Cited

OTHER PUBLICATIONS

Li et al., "An improved rice transformation system using the biolistic method," (1993) Plant Cell Reports 12:250-255.
McCabe et al. "Stable Transformation of Soybean (Glycine Max) by Particle Acceleration," (1988) Biotechnology 6:923-926.
McCormick et al., "Leaf disc transformation of cultivated tomato (L. esculentum) using agrobacterium tumefaciens," (1986) Plant Cell Reports 5:81-84.
Paszkowski et al., "Direct gene transfer to plants," (1984) EMBO J. 3:2717-2722.
Riggs et al., "Stable transformation of tobacco by electroporation: Evidence for plasmid concatenation," (1986) Proc. Natl. Acad. Sci. USA 83:5602-5606.
Sanford et al. "Delivery of Substances Into Cells and Tissues Using a Particle Bombardment Process," (1987) Particulate Science and Technology 5:27-37.
Singh et al., "Cytological characterization of transgenic soybean," (1998) Theor. Appl. Genet. 96:319-324.
Thompson et al., "CLUSTAL W: improving the sensitivity of progressive multiple sequence alignment through sequence weighting, position-specific gap penalties and weight matrix choice," (1994) Nucleic Acids Res. 22(22);4673-4680.
Tomes et al. (1995) in Plant Cell, Tissue, and Organ Culture: Fundamental Methods, ed. Gamborg and Phillips (Springer-Verlag, Berlin); (16 pages).
Weissinger et al., "Foreign Genes in Plants: Transfer, Structure, Expression, and Applications," (1988) Ann. Rev. Genet. 22:421-477.
Book et al., "Affinity Purification of the Arabidopsis 26 S Proteasome Reveals a Diverse Array of Plant Proteolytic Complexes," J. Biol. Chem. 285:25554-25569 (2010).
Burgie et al., "A Photo-Labile Thioether Linkage to Phycoviolobilin Provides the Foundation for the Blue/Green Photocycles in DXCF-Cyanobacteriochromes," Structure 21:88-97 (2013).
Chen et al., "Mo/Probity: all-atom structure validation for macromolecular crystallography," Acta Crystallogr D Biol. Crystallogr 66:12-21 (2010).
Emlsey et al., "Coot: model-building tools for molecular graphics," Acta Crystallogr D Biol. Crystallogr 60:2126-2132 (2004).
Essen et al., "The structure of a complete phytochrome sensory module in the Pr ground state," Proc. Natl. Acad. Sci. USA 105:14709-14714 (2008).
"Gambetta et al., ""Genetic engineering of phytochrome biosynthesisin bacteria,"" Proc. Natl. Acad. Sci. USA 98:10566-10571 (2001)".

Hirschfeld et al., "Coordination of Phytochrome Levels in phyBMutants of Arabidopsis as Revealed by Apoprotein-Specific Monoclonal Antibodies," Genetics 149:523-535 (1998).
Kabsch, "A solution for the best rotation to relate two sets of vectors," Acta Crystallogr A 32:922-923 (1976).
Kyte et al., "A Simple Method for Displaying the Hydropathic Character of a Protein," J. Mol. Biol. 157:105-132 (1982).
McCoy et al., "Phaser crystallographic software," J. Appl. Crystallogr 40:658-674 (2007).
Oh et al. "PIL5, a Phytochrome-Interacting bHLH Protein, Regulates Gibberellin Responsiveness by Binding Directly to the GAI and RGA Promoters in Arabidopsis Seeds," Plant Cell 19, 1192-1208, 2007.
Ishida et al., "High efficiency transfortnation of tnaize (Zea mays L.) tnediated by Agrobacterium tumefaciens," Nature Biotechnology 14:745-750 (1996).
Otwinowski et al., "Processing of X-Ray Diffraction Data Collected in Oscillation Mode," Method Enzymol. 276-307-326 (1997).
Pearson and Lipman 1988, "Improved tools for biological sequence comparison ," Proc. Natl. Acad. Sci. USA 85: 2444-2448.
Perbal, A Practical Guide to Molecular Cloning, 2nd edition, John Wiley & Sons, New York, N.Y. (1988).
Sharrock and Quail, "Novel phytochrome sequences in Arabidopsis thaliana: structure, evolution, and differential expression of a plant regulatory photoreceptor family,"Genes Dev. 3: 1745-1757 (1989).
Shanklin et al., "Partial Purification and Peptide Mapping of Ubiquitin-hytochrome Conjugates from Oat," Biochemistry 28:6028-6034 (1989).
Sheehan et al., "Subfunctionalization of PhyB1 and PhyB2 in the control of seedling and mature plant traits in maize," Plant J 49:338-353 (2007).
Zhang et al., "Structure-Guided Engineering of Plant Phytochrome B with Altered Photochemistry and Light Signaling," Plant Physiol. 161:1445-1457 (2013).
Sato et al., "Production of transgenic plants and their early seed set in Japanese soybean variety, Kariyutaka," Plant Biotechnol. 2007, (24): 533-536.
International Search Report and Written Opinion for Application No. PCT/US2015/024185 dated Jun. 26, 2015 (17 pages).
Database Geneseq, "Polypeptide for crop improvement SEQ ID No. 178," 2010, retrieved from EBI accession No. GSP: AYI49493.
Database Geneseq, "Polypeptide for crop improvement SEQ ID No. 33272," 2010, retrieved from EBI accession No. GSP: AYJ71650.
Database Geneseq, "Polypeptide for crop improvement SEQ ID No. 26318," retrieved from EBI accession No. GSP: AYJ64696.

* cited by examiner

FIGURE 1

```
At phyB     1  MVSGVGGSGGGRGGGRGGEEEPSSSHTPNNRRGGEQAQSSGTKSLRPRS...........
ZmphyB      1  ....MASGSRATPTRSPSSARPEAPRHAHHHHHSQS..SGGSTSRAGGG...........
Os phyB     1  ....MGSGSRATPTRSPSSARPAAPRHQHHHSQSSG....GSTSRAGGGGGGGGGGGG.
Sb phyB     1  ....MASGSRATPTRSPSSARPEAPRHAHHHHHHHSQSSGGSTSRAGGGGGGGGGGGTA
GmphyB1     1  ....MASASGAANSSVPP........PQIHTSRTKLSHHSSNNNNN..............
GmphyB2     1  ....MASASGAENSSVPPSPLPPPPPPQIHTSRTKLSHHHHNNNNNNNN...........
GmphyB3     1  ..........................................................
GmphyB4     1  ..........................................................
St phyB     1  ..................MASGSRTKHSHHNSSQAQSSGTSNVN...............
Ps phyB     1  ..............................SNNNNNRNIKR.................
Vv phyB     1  ....................MSSGNRGTQSHHQAQSS.GTSNLRVY.............

At phyB    50  ......NTESMSKAIQQYTVDARLHAVFEQSGESGKSFDYSQSLKTTTYGSSVPEQQITA
ZmphyB     44  ....AAATESVSKAVAQYTLDARLHAVFEQSGASGRSFDYSQSLRAPPTP..SSEQQIAA
Os phyB    52  ....AAAAESVSKAVAQYTLDARLHAVFEQSGASGRSFDYTQSLRASPTP..SSEQQIAA
Sb phyB    57  ATATATATESVSKAVAQYTLDARLHAVFEQSGASGRSFDYSQSLRAPPTP..SSEQQIAA
GmphyB1    35  ......IDSMSKATAQYTEDARLHAVFEQSGESGRSFNYSESIRIASES..VPEQQITA
GmphyB2    46  ......NIDSTSKATAQYTEDARLHAVFEQSGESGRSFDYSQSIRVTSES..VPEQQITA
GmphyB3     1  ............MSKATAQYTEDARLHAVFEQSGESGRSFNYSESIRIASES..VPEQQITA
GmphyB4     1  ..........................................................
St phyB    27  ......YKDSISKATAQYTADARLHAVFEQSGESGKFEDYSESVKTTTQ..SVPERQITA
Ps phyB    12  ......ESLSMRKATAQYTEDAXLHAVEEKSG.DSFDYAQSIRVTAATES..VPEQQITA
Vv phyB    26  ......HTDSMSKATAQYTMDARLHAVYEQSGESGKSFDYSQSVRTTTQ..SVPEQQITA At phyB   104  YLSRIQRGGYIQPFGCMIAVDESS.FRIIGYSENAREMLGIMPQSVPTLEKPE....ILA
ZmphyB     98  YLSRIQRGGHIQPFGCTLAVADDSSRLLAFSENSPDLIDLSPHHSVPSLDS.SAPPHVS
Os phyB   106  YLSRIQRGGHIQPFGCTLAVADDSSRLLAFSENAADLIDLSPHHSVPSLDS.AAPPPVS
Sb phyB   115  YLSRIQRGGHIQPFGCTLAVADDSSRLLAFSENAADLIDLSPHHSVPSLDS.AAPPPVS
GmphyB1    86  YLVKIQRGGFIQPFGSMIAVDEPS.FRILGYSDNARDMLGITPQSVPSLDDKN..DAAFA
GmphyB2    98  YLLKIQRGGFIQPFGSMIAVDEPS.FRILAYSDNARDMLGITPQSVPSLDDKN..DAAFA
GmphyB3    49  YLVKIQRGGFIQPFGSMIAVDEPS.FRILGYSDNARDMLGITPQSVPSLDDKN..DAAFA
GmphyB4     1  ............MIAVDEPS.FRILAYSDNARDMLGITPQSVPSLDDKN..DAAFA
St phyB    79  YLTKIQRGGHIQPFGCMIAVDEAS.FRVIAYSENAFEMLSLTPQSVPSLEKCE....ILT
Ps phyB    63  YLAKIQRGGFIQPFGSMIAVDETS.FRVLAYSENARDMLGIAPQSVPSMEDDSSSSSFFS
Vv phyB    78  YLSKIQRGGHIQPFGCMLAVDEAT.FRVIAFSENAREMLGLTPQSVPSLEKPE....ILL At phyB   159  MGTDVRSLFTSSSSILERAFVAREITLLNPVWIHSKNTGKPFYAILHRIDVGVVIDLEP
ZmphyB    157  LGADARLLFSPSSAVLLERAFAAREISLLNPIWIHSRVSSKPFYAILHRIDVGVVIDLEP
Os phyB   166  LGADARLLFAPSSAVLLERAFAAREISLLNPLWIHSRVSSKPFYAILHRIDVGVVIDLEP
Sb phyB   174  LGADARLLFSPSSAVLLERAFAAREISLLNPLWIHSRVSSKPFYAILHRIDVGVVIDLEP
GmphyB1   143  LGTDVRALFTHSSALLLEKAFSAREISLMNPIWIHSRTSGKPFYGILHRIDVGIVIDLEP
GmphyB2   155  LGTDIRTLFTPSSAVLLEKAFSAREISLVNPIWIHSRTSGKPFYGILHRIDVGVVIDLEP
GmphyB3   106  LGTDVRALFTHSSALLLEKAFSAREISLVNPIWIHSRTSGKPFYGILHRIDVGIVIDLEP
GmphyB4    42  LGTDIRTLFTHSSAVLLEKAFSAREISLVNPIWIHSRTSGKPFYGILHRIDVGIVIDLEP
St phyB   134  IGTDVRTLFTPSSVLLERAFGAREITLLNPIWIHSKNSGKPFYAILHRVDVGIAIDLEP
Ps phyB   122  LGVDVRSLFSASSSVLLEKAFSAREISLMNPIWIHSRSTGKPFYGILHRIDIGVVIDLEP
Vv phyB   133  VGTDVRTLFTIPSSAVLLEKAFRAREITLLNPVWIHSKNSGKPFYAILHRIDVGIVIDLEP At phyB   219  ARTEDPALSIAGAVQSQKLAVRAISQLQALPGGDIKLLCDTVVESVRDLTGYDRVMVYKF
ZmphyB    217  ARTEDPALSIAGAVQSQKLAVRAISRLQALPGGDVKLLCDTVVEHVRELTGYDRVMVYRF
Os phyB   226  ARTEDPALSIAGAVQSQKLAVRAISRLQALPGGDIKLLCDTVVEHVRELTGYDRVMVYRF
Sb phyB   234  ARTEDPALSIAGAVQSQKLAVRAISRLQALPGGDIKLLCDTVVEHVRELTGYDRVMVYRF
GmphyB1   203  ARTEDPALSIAGAVQSQKLAVRAISQLQSLPGGDVKLLCDTVVESVRELTGYDRVMVYKF
GmphyB2   215  ARTEDPALSIAGAVQSQKLAVRAISQLQSLPGGDVKLLCDTVVESVRELTGYDRVMVYRF
GmphyB3   166  ARTEDPALSIAGAVQSQKLAVRAISQLQSLPGGDVKLLCDTVVESVRELTGYDRVMVYKF
GmphyB4   102  ARTEDPALSIAGAVQSQKLAVRAISQLQSLPGGDVKLLCDTVVESVRELTGYDRVMVYRF
St phyB   194  ARTEDPALSIAGAVQSQKLAVRAISHLQSLPGGDIKLLCDTVVESVRELTGYDRVMVYKF
Ps phyB   182  ARSEDPALSIAGAVQSQKLAVRAISQLQALPGGDVKLLCDAVVESVRELTGYDRVMVYKF
Vv phyB   193  ARTEDPALSIAGAVQSQKLAVRAISHLQSLPGGDINLLCETVVENVRELTGYDRVMVYKF
```

FIG. 12A

```
                    ▼ 307              ▼ 322
At phyB    279  HEDEHGEVVAESKRDDLEPYIGLHYPATDIPQASRFLFKQNRVRMIVDCNATPVLVVQDD
Zm phyB    277  HEDEHGEVVAESRRDNLEPYLGLHYPATDIPQASRFLFRQNRVRMIADCHATPVRVIQDP
Os phyB    286  HEDEHGEVVAESRRSNLEPYIGLHYPATDIPQASRFLFRQNRVRMIADCHAAPVRVIQDP
Sb phyB    294  HEDEHGEVVAESRRDNLEPYLGLHYPATDIPQASRFLFRQNRVRMIADCHATPVRVIQDP
Gm phyB1   263  HEDEHGEVVSESKRPDLEPYIGLHYPATDIPQASRFLFKQNRVRMIVDCHASAVRVVQDE
Gm phyB2   275  HEDEHGEVVAETKRPDLEPYIGLHYPATDIPQASRFLFKQNRVRMIVDCHASAVRVVQDE
Gm phyB3   226  HEDEHGEVVSESKRPDLEPYIGLHYPATDIPQASRFLFKQNRVRMIVDCHASAVRVVQDE
Gm phyB4   162  HEDEHGEVVAETKRPDLEPYIGLHYPATDIPQASRFLFKQNRVRMIVDCHASAVRVVQDE
St phyB    254  HEDEHGEVVAESKRSDLEPYIGLHYPATDIPQASRFLFKQNRVRMIVDCHATPVRVTQDE
Ps phyB    242  HEDEHGEVVAESKRVDLEPYIGLHYPATDIPQASRFLFKQNRVRMIVDCNASPVRVFQDE
Vv phyB    253  HEDEHGEVVAESKRSDLEPYIGLHYPATDIPQASRFLFRQNRVRMIVDCHATPVLVIQDE ▼ 352              ▼ 361
At phyB    339  RLTQSMCLVGSTLRAPHGCHSQYMANMGSIASLAMAVIINGN.EDDGSNVASG.RSSMRL
Zm phyB    337  GLSQPLCLVGSTLRAPHGCHAQYMANMGSIASLVMAVIISSG.GDDEQTGRGGISSAMKL
Os phyB    346  ALTQPLCLVGSTLRSPHGCHAQYMANMGSIASLVMAVIISSGGDDDHNIARGSIPSAMKL
Sb phyB    354  GMSQPLCLVGSTLRAPHGCHAQYMANMGSIASLVMAVIISSG.GDDEQTGRGGISSAMKL
Gm phyB1   323  ALVQPLCLVGSTLRAPHGCHAQYMANMGSIASLVMAVIINGN.DEEGVGG....RSSMRL
Gm phyB2   335  ALVQPLCLVGSTLRAPHGCHAQYMANMGSTASLVMAVIINGN.DEEGVGG....RTSMRL
Gm phyB3   286  ALVQPLCLVGSTLRAPHGCHAQYMANMGSIASLVMAVIINGN.DEEGVGG....RSSMRL
Gm phyB4   222  ALVQPLCLVGSTLRAPHGCHAQYMANMGSTASLVMAVIINGN.DEEGVGG....RTSMRL
St phyB    314  SLMQPLCLVGSTLRAPHGCHAQYMANMGSIASLTLAVIINGN.DEEAVGGG...RNSMRL
Ps phyB    302  ALVQPVCLVGSTLRAPHGCHAQYMANMGSIASLAMAVIINGN.DEDGGGIGGAARGSMRL
Vv phyB    313  GLMQPLCLVGSTLRAPHGCHAQYMANMGSTASLAMAVIINGS.DEEAIGG....RNLMRL At phyB    397  WGLVVCHHTSSRCIPFPLRYACEFLMQAFGLQLNMELQLALQMSEKRVLRTQTLLCDMLL
Zm phyB    396  WGLVVCHHTSPRCIPFPLRYACEFLMQAFGLQLNMELQLAHQLSEKHILRTQTLLCDMLL
Os phyB    406  WGLVVCHHTSPRCIPFPLRYACEFLMQAFGLQLNMELQLAHQLSEKHILRTQTLLCDMLL
Sb phyB    413  WGLVVCHHTSPRCIPFPLRYACEFLMQAFGLQLNMELQLAHQLSEKHILRTQTLLCDMLL
Gm phyB1   378  WGLVVCHHTSARCIPFPLRYACEFLMQAFGLQLNMELQLAAQSLEKRVLRTQTLLCDMLL
Gm phyB2   390  WGLVICHHTSARCIPFPLRYACEFLMQAFGLQLNMELQLAAQSLEKRVLRTQTLLCDMLL
Gm phyB3   341  WGLVVCHHTSARCIPFPLRYACEFLMQAFGLQLNMELQLAAQSLEKRVLRTQTLLCDMLL
Gm phyB4   277  WGLVICHHTSARCIPFPLRYACEFLMQAFGLQLNMELQLAAQSLEKRVLRTQTLLCDMLL
St phyB    370  WGLVVGHHTSVRSIPFPLRYACEFLMQAFGLQLNMELQLASQLSEKHVLRTQTLLCDMLL
Ps phyB    361  WGLVVCHHTSARCIPFPLRYACEFLMQAFGLQLNMELQLAVQSLEKRVLKTQTLLCDMLL
Vv phyB    368  WGLVVCHHTSARCIPFPLRYACEFLMQAFGLQLNMELQLASQLSEKHVLRTQTLLCDMLL At phyB    457  RDSPAGVTQSPSIMDLVKCDGAAFLYHGKYYPLGVAPSEVQIKDVVEWLLANHADSTGL
Zm phyB    456  RDSPTGIVTQSPSIMDLVKCDGAALYYHGKYYPLGVTPTESQIKDIIEWLTVFHGDSTGL
Os phyB    466  RDSPTGIVTQSPSIMDLVKCDGAALYYHGKYYPLGVTPTEVQIKDIIEWLTVCHGDSTGL
Sb phyB    473  RDSPTGIVTQSPSIMDLVKCDGAALYYHGKYYPLGVTPTEAQIKDIIEWLTVCHGDSTGL
Gm phyB1   438  RDSPTGIVTQSPSIMDLVKCDGAALYFQGNYYPLGVTPTEAQIRDIIEWLLAFHGDSTGL
Gm phyB2   450  RDSPTGIVTQSPSIMDLVKCDGAALYYQGNYYPLGVTPTEAQIRDIIEWLLAFHRDSTGL
Gm phyB3   401  RDSPTGIVTQSPSIMDLVKCDGAALYFQGNYYPLGVTPTEAQIRDIIEWLLAFHGDSTGL
Gm phyB4   337  RDSPTGIVTQSPSIMDLVKCDGAALYYQGNYYPLGVTPTEAQIRDIIEWLLAFHRDSTGL
St phyB    430  RDSPPGIVTQSPSIMDLVKCDGAALYYQGKYYPLGVTPTEAQIKDIVEWLLAYHGDSTGL
Ps phyB    421  RDSHTGIVTQSPSIMDLVKCDGAALYYQGNYHPLGVTPTESQIRDIIDWLLAFHSDSTGL
Vv phyB    428  RDSPTGIVTQSPSIMDLVKCDGAALYYQGKYYPTGVTPTEAQIKDIAEWLANHADSTGL At phyB    517  STDSLGDAGYPGAAALGDAVCGMAVAYITKRDFLFWFRSHTAKEIKWGGAKHHPEDKDDG
Zm phyB    516  STDSLADAGYLGAAALGEAVCGMAVAYITPSDYLFWFRSHTAKEIKWGGAKHHPEDKDDG
Os phyB    526  STDSLADAGYSGAAALGDAVSGMAVAYITPSDYLFWFRSHTAKEIKWGGAKHHPEDKDDG
Sb phyB    533  STDSLADAGYLGAAALGDAVCGMAVAYITPSDYLFWFRSHTAKEIKWGGAKHHPEDKDDG
Gm phyB1   498  STDSLGDAGYPGAASLGDAVCGMAVAYITEKDFLFWFRSHTAKEIKWGGAKHHPEDKDDG
Gm phyB2   510  STDSLADAGYPGAASLGDAVCGMAVAYITEKDFLFWFRSHTAKEIKWGGAKHHPEDKDDG
Gm phyB3   461  STDSLGDAGYPGAASLGDAVCGMAVAYITEKDFLFWFRSHTAKEIKWGGAKHHPEDKDDG
Gm phyB4   397  STDSLADAGYPGAASLGDAVCGMAVAYITSSKDFLFWFRSHTAKEIKWGGAKHHPEDKDDG
St phyB    490  STDSLADAGYPGAASLGDAVCGMAVAYITEKDFLFWFRSHTAKEIKWGGAKHHPEDKDDG
Ps phyB    481  STDSLADAGYPGAASLGDAVCGMAVAYITEKDFLFWFRSHTAKEIKWGGAKHHPEDKDDG
Vv phyB    488  STDSLADAGYPGAASLGDAVCGMAVAYITRDFLFWFRSHTAKEIKWGGAKHHPEDKDDG
```

FIG. 12B

```
                  ▼ 582
At phyB    577  QRMHPRSSFQAFLEVVKSRSQPWETAEMDAIHSLQLILRDSFKESEAAM.NSKVVDGVVQ
ZmphyB     576  QRMHPRSSFKAFLEVVKSRSLPWENAEMDAIHSLQLILRDSFRDAAEGTNNSKAIVNGQV
Os phyB    586  QRMHPRSSFKAFLEVVKSRSLPWENAEMDAIHSLQLILRDSFRDSAEGTSNSKAIVNGQV
Sb phyB    593  QRMHPRSSFKAFLEVVKSRSLPWENAEMDAIHSLQLILRDSFRDAAEGTSNSKAIVNGQA
GmphyB1    558  QRMHPRSSFKAFLEVVKSRSLPWENAEMDAIHSLQLILRDSFKDAEHR..NSKAVLDPHV
GmphyB2    570  QRMHPRSSFKAFLEVVKSRSLPWENAEMDAIHSLQLILRDSFKDAEHS..NSKAVLDPRM
GmphyB3    521  QRMHPRSSFKAFLEVVKSRSLPWENAEMDAIHSLQLILRDSFKDAEHR..NSKAVADPRV
GmphyB4    457  QRMHPRSSFKAFLEVVKSRSLPWESAEMDAIHSLQLILRDSFKDAEHS..NSKAVLDPRM
St phyB    550  LRMHPRSSFKAFLEVVKSRSSPWENAEMDAIHSLQLILRDSFKDAEAS..NSKAIVHAHL
Ps phyB    541  QKMHPRSSFKAFLEVVKIRSMQWDNAEMDAIHSLQLILRDSFKEAENN..DSKAVVHTHM
Vv phyB    548  QRMHPRSSFKAFLEVVKSRSLPWENAEMDAIHSLQLILRDSFKDATDGS.NSKAVVHAQL At phyB    636  PCRDMAGEQGIDELGAVAREIVRLIETATVPIFAVDAGGCINGWNAKIAELTGLSVEEAM
ZmphyB     636  QLREIELRG.INELSSVAREIVRLIETATVPIFAVDTDGCINGWNAKIAELTGLSVEEAM
Os phyB    646  QLGEIELRG.IDELSSVAREIVRLIETATVPIFAVDTDGCINGWNAKIAELTGLSVEEAM
Sb phyB    653  QLGEIELRG.INELSSVPREIVRLIETATVPIFAVDTDGCINGWNAKIAELTGLSVEEAM
GmphyB1    616  SEQELQG...VDELSSVAREIVRLIETATAPIFAVDVDGHVNGWNAKVSELTGLPVEEAM
GmphyB2    628  SELELQG...VDELSSVAREIVRLIETATAPIFAVDVDGRINGWNAKVSELTGLPVEEAM
GmphyB3    579  SEQELQG...VDELSSVAREIVRLIETATAPIFAVDVDGRINGWNAKVSELTGLPVEEAM
GmphyB4    515  SELELQG...VDELSSVAREIVRLIETATAPIFAVDVDGRINGWNAKVSELTGLPVEEAM
St phyB    608  GEMELQG...IDELSSVAREIVRLIETATAPIFAVDVEGRINGWNAKVAELTGLSVEEAM
Ps phyB    599  AELELQG...VDELSSVAREIVRLIETATAPIFAVDVDGRINGWNAKVSELTGLLVEEAM
Vv phyB    607  GELELQG...MDELSSVAREIVRLIETATAPIFAVDVDGCINGWNAKVAELTGLSVEEAM At phyB    696  GKSLVSDLIYKENEATVNKLLSRALRGDEEKNVEVKLKTFSPELQGKAVFVVVNACSSKD
ZmphyB     695  GKSLVNDLIFKESEATVEKLLSRALRGEEDKNVEIKLKTFGSEQYKGPIFVVVNACSSRD
Os phyB    705  GKSLVNDLIFKESEETVNKLLSRALRGDEDKNVEIKLKTFGPEQSKGPIFVIVNACSSRD
Sb phyB    712  GKSLVNDLIFKESEEIVEKLLSRALRGEEDKNVEIKLKTFGSEQSNGAIFVIVNACSSRD
GmphyB1    673  GKSLVHDLVFKESEETMNKISRALKGEEDKNVEIKMRTFGPEHQNKAVFVVVNACSSKD
GmphyB2    685  GKSLVRDLVFKESEETVDKLLSRALKGEEDKNVEIKMRTFGPEHQNKAVFVVVNACSSKD
GmphyB3    636  GKSLVHDLVFKESEETMNKLLSRALKGEEDKNVEIKMRTFGPERQNKAVFLVVNACSSKD
GmphyB4    572  GKSLVRDLVFKESEETVDKLLSRALKGEEDKNVEIKMRTFGPEHQNKAVFVVVNACSSKD
St phyB    665  GKSLVHELVYKESQETAEKLLYNALRGEEDKNVEIKLRTFGAEQLEKAVFVVVNACASKD
Ps phyB    656  GKSLVHDLVYKESRETVDKLLSHALKGEEDKNVEIKMKTFGPGNQNKAVFIVVNACSSKD
Vv phyB    664  GKSLVHDLVYKESEETVDKLLHHALRGEEDKNVEIKLRTFDSQQHKKAVFVVVNACSSRD At phyB    756  YLNNIVGVCFVGQDVTSQKIVMDKFINIQGDYKAIVHSPNPLIPPIFAADENTCCLEWNM
ZmphyB     755  YTQNIVGVCFVGQDVTGQKVVMDKFVNIQGDYKAIVHNPNPLIPPIFASDENTSCSEWNT
Os phyB    765  YTKNIVGVCFVGQDVTGQKVVMDKFTNIQGDYKAIVHNPNPLIPPIFASDENTCCLEWNT
Sb phyB    772  YTQNIVGVCFVGQDVTGQKVVMDKFINIQGDYKAIVHNPNPLIPPIFASDENTSCSEWNT
GmphyB1    733  FTNNVVGVCFVGQDVTGQKIVMDKFINIQGDYKAIVHNPNPLIPPIFASDDNTCCLEWNT
GmphyB2    745  YTNNVVGVCFVGQDVTGQKIVMDKFINIQGDYKAIVHNPNPLIPPIFASDENTCCLEWNT
GmphyB3    696  FTNNVVGVCFVGQDVTGQKIVMDKFINIQGDYKAIVHSPNPLIPPIFASDDNTCCLEWNT
GmphyB4    632  YTNNVVGVCFVGQDVTGQKIVMDKFINIQGDYKAIVHNPNPLIPPIFASDDNTCCLEWNT
St phyB    725  YTNNIVGVCFVGQDVTGEKVVMDKFINIQGDYKAIVHSPNPLIPPIFASDENTCCLEWNN
Ps phyB    716  YTNNIVGVCFVGQDITGQKVVMDKFINIQGDYKAIVHSPNPLIPPIFASDDNTCCLEWNN
Vv phyB    724  YTNNIVGVCFVGQDVTGQKVVMDKFIHIQGDYKAIVHSPNPLIPPIFASDENTVCSEWNT At phyB    816  AMEKLTGWSRSEVIGKMIVGEVFGSCCMLKGPDALTKFMIVLHNAIGGQDTDKFPFPFFD
ZmphyB     815  AMEKLTGWSRGEVVGKFLIGEVFGNCCRLKGPDALTKFMVIIHNAIGGQDYEKFPFSFFD
Os phyB    825  AMEKLTGWSRGEVVGKLIVGEVFGNCCRLKGPDALTKFMIVIHNAIGGQDCEKFPFSFFD
Sb phyB    832  AMEKLTGWSRGEVVGKFLIGEVFGSFCRLKGPDALTKFMVVIHNAIGGQDYEKFPFSFFD
GmphyB1    793  AMEKLTGWGRVDVIGKMLVGEVFGSCCQLKGSDSITKFMIVLHNALGGQDTDKFPFSFLD
GmphyB2    805  AMEKLTGWSRADVIGKMLVGEVFGSCCQLKGSDSITKFMIVLHNALGGHDRDRFPFSFLD
GmphyB3    756  AMEKLTGWGRVDVIGKMLVGEVFGSCCQLKGSDSITKFMIVLHNALGGHDTDKFPFSFLD
GmphyB4    692  AMEKLTGWSRADVIGKMLVGEVFGSCCQLKGSDSITKFMIVLHNALGGHDTDRFPFSFLD
St phyB    785  AMEKLTGWSRGEIVGKMLVGEIFGSCCRLKGPDAMTKFMIVLHNAIGGQDTDKFPFSFFD
Ps phyB    776  AMEKLSGWSRADVIGKLLVGEVFGSFCQLKGSDAMTKFMIVLHNALGGHDTDKFPLSFLD
Vv phyB    784  AMEKLTGWSRGDIIGKILVGEIFGSSCRLKGPDALTKFMIVLHNAIGGQDTDKFPFSFFD
```

FIG. 12C

```
At phyB    876  RNGKFVQALLTANKRVSLEGKVIGAFCFLQIPSPELQQALAVQRRQDTECFTKAKELAYI
Zm phyB    875  KNGKYVQALLTANTRSKMDGKSIGAFCFLQIASTEIQQAFEIQRQQEKKCYARMKELAYI
Os phyB    885  KNGKYVQALLTANTRSRMDGEAIGAFCFLQIASPELQQAFEIQRHHEKKCYARMKELAYI
Sb phyB    892  KNGKYVQALLTANTRSKMDGKSIGAFCFLQIASAEIQQAFEIQRQQEKKCYARMKELAYI
GmphyB1    853  RHGKYVQTFLTANKRVNMEGQIIGAFCFLQMSPELQQALKAQRQQEKNSFGRMKELAYI
GmphyB2    865  RYGKHVQAFLTANKRVNMDGQIIGAFCFLQIVSPELQQALKAQRQQEKNSFARMKELAYI
GmphyB3    816  RHGKYVQTFLTANKRVNMEGQIIGAFCFLQMSPELQQALKAQRQQEKNSFGRMKELAYI
GmphyB4    752  RYGKHVQAFLTANKRVNMDGQIIGAFCFLQIVSPELQQALKAQRQQEKNSFARMKELAYI
St phyB    845  RNGKYVQALLTANKRVNMEGNTIGAFCFLQIASPELQQALRVQRQQEKKCYSQMKELAYI
Ps phyB    836  RHGKYVHTFLTANKRVNMDGQTIGAFCFLQIVNPELQQALTVQRQQDSSSLARMKELAYI
Vv phyB    844  QNGKYVQALLTANKRVNIEGQIIGAFCFLQIASPELQQALKVQRQQEKKCFARMKELAYI At phyB    936  CQVIKNPLSGVRFANSLLEATDLNEDQKQLLETSVSCEKQISRIVGDMDLESIEDGSFVL
Zm phyB    935  CQEIKNPLSGIRFTNSLLQMTDLNDDQRQFLETSSACEKQMSKIVKDASLQSIEDGSTVL
Os phyB    945  YQEIKNPLNGIRFTNSLLEMTDLKDDQRQFLETSTACEKQMSKIVKDASLQSIEDGSIVL
Sb phyB    952  CQEIKNPLSGIRFTNSLLQMTDLNDDQRQFLETCSACEKQMSKIVKDATLQSIEDGSIVL
GmphyB1    913  CQGVKNPLSGIRFTNSLLEATSLTNEQKQFLETSVACEKQMLKIIRDVDLESIEDGSLEL
GmphyB2    925  CQGVKNPLSGIRFTNSLLEATCLSNEQKQFLETSAACEKQMLKIIHDVDLESIEDGSLEL
GmphyB3    876  CQGVKNPLSGIRFTNSLLEATSLTNEQKQFLETSVACEKQMLKIIRDVDLESIEDGSLEL
GmphyB4    812  CQGVKNPLSGIRFTNSLLEATCLSNEQKQFLETSAACEKQMLKIIHDVDIESIEDG....
St phyB    905  CQEIKSPLNGIRFTNSLLEATNLTENQKQYLETSAACERQMSKIIRDVDLENIEDGSTTL
Ps phyB    896  CQEVKNPLSGIRFTNSLLESTCLTDEQKQLLETSVACEKQMLKIVRDIALESIEDGSLEL
Vv phyB    904  CQEIKNPLSGIRFTNSLLEATDLTEDQKQFLETSAACEKQMSKIIRDVDLDSIEDGSLEL At phyB    996  KREEFLGSVINAIVSQAMFLLRDRGLQLIRDIPEEIKSIEVFGDQIRIQQLLAEFLLSII
Zm phyB    995  EQSEFSLGDVMNAVVSQVMLLRERDLQLIRDIPDEIKEASAYGDOCRIQQVLADFLLSM
Os phyB   1005  KGEFSLGSVMNAVVSQVMIQLRERDLQLIRDIPDEIKEASAYGDQYRIQQVLCDFLLSM
Sb phyB   1012  EKSEFSFGDVMNAVVSQAMLLRERDLQLIRDIPDEIKDASAYGDQFRIQQVLADFLLSM
GmphyB1    973  EKGEELLGNVINAVVSQVMLLRERNLQLIRDIPEEIKTLAVYGDQLRIQQVLSDFLLNI
GmphyB2    985  EKGEELLGNVINAVVSQVMLLLRERNLQLIRDIPEEIKTLAVYGDQLRIQQVLSDFLLNI
GmphyB3    936  EKGEELLGNVINAVVSQVMLLLRERNLQLIRDIPEEIKTLAVYGDQLRIQQVLSDFLLNI
GmphyB4         ............................................................
St phyB    965  EKEDFFLGSVIDANVVSQVMLLLREKGVQLIRDIPEEIKTLTVHGDQVRIQQVLADFLLNM
Ps phyB    956  EKQEELLENVINAVVSQVMLLLRDRKLQLIRDIPEEIKALAVYGDQLRIQQVLADFLMNV
Vv phyB    964  ERAEFLLGSVINAVVSQVMILLRERDLQLIRDIPEEVKTLAVYGDQVRIQQVLADFLLNM At phyB   1056  IRYAPSQEEWVEIHLSQLSKQMADGFAAIRTEFRMACPGEGLPPELVRDMHSSRWTSPE
Zm phyB   1055  VRSAPSENGWVEIQVRPNVKQNSDGTNTELFIFRFACPGEGLPADVVQDMSNSQWSTQE
Os phyB   1065  VREAPAENGWVEIQVRPNIKQNSDGTDTMLFLFRFACPGEGLPPEIVQDMFSNSRWTTQE
Sb phyB   1072  VRSAPSENGWVEIQVRPNVKQNSDGTDTELFIFRFACPGEGLPADIVQDMFSNSQWSTQE
GmphyB1   1033  VRYAPSPDGWVEIHVRPRIKQISDGLTLLHAEFRMVCPGEGLPPELIQDMFNNSRWGTQE
GmphyB2   1045  VRYAPSPDGWVEIHVHPRIKQISDGLTLLHAEFRMVCPGEGLPPELIQNMFNNSGWGTQE
GmphyB3    996  VRYAPSPDGWVEIHVRPRIKQISDGLTLLHAEFRMVCPGEGLPPELIQDMFNNSRWGTQE
GmphyB4         ............................................................
St phyB   1025  VRYAPSPDGWVEIQLRPSMMPISDGVTGVHIELRIICPGEGLPPEVQDMHSSRWVTQE
Ps phyB   1016  VRYAPSPDGWVEIHVFPRIKQISEGLTLLHAEFRMVCPGEGLPPELIQDMFHNSRWVTQE
Vv phyB   1024  VRYAPSPDGWIEIQVRPCLKQISEEVKLMHIEFRMVCPGEGLPPNLIQDMFHSSRWMTQE At phyB   1115  GLGLSVCRKILKLMNGEVQYIRESERSYFLIIELPVPRKRPLSTASGSGDMMLMMPYFD
Zm phyB   1115  GVGLSTCRKILKLMGGEVQYIRESERSFFLVLELPQPRPAAGREIV...........FD
Os phyB   1125  GIGLSICRKILKLMGGEVQYIRESERSFFHIVLELPQPQQAASRGTS..........FD
Sb phyB   1132  GVGLSTCRKILKLMGGEVQYIRESERSFFLVLELPQPRPAADREIS...........FD
GmphyB1   1093  GLGLSMSRKILKLMNGEVQYIREAERCYFYVLLELPVTRRSSKKC............LD
GmphyB2   1105  GLGLSMSRKILKLMNGEVQYIREAQRCYFYVLLELPVTRRSSKKC............LD
GmphyB3   1056  GLGLSMSRKILKLMNGEVQYIREAERCYFYVLLELPVTRRSSKKC............LD
GmphyB4         ...........................................................LD
St phyB   1085  GLGLSTCRKVLKLMNGEIQYIREAERCYFLVLDLPMTRKGPKSVG............FD
Ps phyB   1076  GLGLSMSRKILKLMNGEVQYIREAERCYFLVLELPVTRRSSKAIN............LD
Vv phyB   1084  GLGLSMCRKILKLINGEVQYIRESERCYFLISIELPIPHRGSKSVD............FD
```

At phyB = SEQ ID NO.1
Zm phyB = SEQ ID NO.2
Os phyB = SEQ ID NO.3
Sb phyB = SEQ ID NO.4
GmphyB1 = SEQ ID NO.5
GmphyB2 = SEQ ID NO.6
GmphyB3 = SEQ ID NO.7
GmphyB4 = SEQ ID NO.8
St phyB = SEQ ID NO.9
Ps phyB = SEQ ID NO.10
Vv phyB = SEQ ID NO.11

SEQUENCE LISTING

<160> NUMBER OF SEQ ID NOS: 77

<210> SEQ ID NO 1
<211> LENGTH: 1172
<212> TYPE: PRT
<213> ORGANISM: Arabidopsis thaliana

<400> SEQUENCE: 1

```
Met Val Ser Gly Val Gly Gly Ser Gly Gly Gly Arg Gly Gly Gly Arg
1               5                   10                  15

Gly Gly Glu Glu Glu Pro Ser Ser Ser His Thr Pro Asn Asn Arg Arg
            20                  25                  30

Gly Gly Glu Gln Ala Gln Ser Ser Gly Thr Lys Ser Leu Arg Pro Arg
        35                  40                  45

Ser Asn Thr Glu Ser Met Ser Lys Ala Ile Gln Gln Tyr Thr Val Asp
    50                  55                  60

Ala Arg Leu His Ala Val Phe Glu Gln Ser Gly Glu Ser Gly Lys Ser
65                  70                  75                  80

Phe Asp Tyr Ser Gln Ser Leu Lys Thr Thr Thr Tyr Gly Ser Ser Val
                85                  90                  95

Pro Glu Gln Gln Ile Thr Ala Tyr Leu Ser Arg Ile Gln Arg Gly Gly
            100                 105                 110

Tyr Ile Gln Pro Phe Gly Cys Met Ile Ala Val Asp Glu Ser Ser Phe
        115                 120                 125

Arg Ile Ile Gly Tyr Ser Glu Asn Ala Arg Glu Met Leu Gly Ile Met
    130                 135                 140

Pro Gln Ser Val Pro Thr Leu Glu Lys Pro Glu Ile Leu Ala Met Gly
145                 150                 155                 160

Thr Asp Val Arg Ser Leu Phe Thr Ser Ser Ser Ile Leu Leu Glu
                165                 170                 175
```

```
Arg Ala Phe Val Ala Arg Glu Ile Thr Leu Leu Asn Pro Val Trp Ile
                180                 185                 190
His Ser Lys Asn Thr Gly Lys Pro Phe Tyr Ala Ile Leu His Arg Ile
            195                 200                 205
Asp Val Gly Val Val Ile Asp Leu Glu Pro Ala Arg Thr Glu Asp Pro
        210                 215                 220
Ala Leu Ser Ile Ala Gly Ala Val Gln Ser Gln Lys Leu Ala Val Arg
225                 230                 235                 240
Ala Ile Ser Gln Leu Gln Ala Leu Pro Gly Gly Asp Ile Lys Leu Leu
                245                 250                 255
Cys Asp Thr Val Val Glu Ser Val Arg Asp Leu Thr Gly Tyr Asp Arg
            260                 265                 270
Val Met Val Tyr Lys Phe His Glu Asp Glu His Gly Glu Val Val Ala
        275                 280                 285
Glu Ser Lys Arg Asp Asp Leu Glu Pro Tyr Ile Gly Leu His Tyr Pro
290                 295                 300
Ala Thr Asp Ile Pro Gln Ala Ser Arg Phe Leu Phe Lys Gln Asn Arg
305                 310                 315                 320
Val Arg Met Ile Val Asp Cys Asn Ala Thr Pro Val Leu Val Val Gln
                325                 330                 335
Asp Asp Arg Leu Thr Gln Ser Met Cys Leu Val Gly Ser Thr Leu Arg
            340                 345                 350
Ala Pro His Gly Cys His Ser Gln Tyr Met Ala Asn Met Gly Ser Ile
        355                 360                 365
Ala Ser Leu Ala Met Ala Val Ile Ile Asn Gly Asn Glu Asp Asp Gly
370                 375                 380
Ser Asn Val Ala Ser Gly Arg Ser Ser Met Arg Leu Trp Gly Leu Val
385                 390                 395                 400
Val Cys His His Thr Ser Ser Arg Cys Ile Pro Phe Pro Leu Arg Tyr
                405                 410                 415
Ala Cys Glu Phe Leu Met Gln Ala Phe Gly Leu Gln Leu Asn Met Glu
            420                 425                 430
Leu Gln Leu Ala Leu Gln Met Ser Glu Lys Arg Val Leu Arg Thr Gln
        435                 440                 445
Thr Leu Leu Cys Asp Met Leu Leu Arg Asp Ser Pro Ala Gly Ile Val
450                 455                 460
Thr Gln Ser Pro Ser Ile Met Asp Leu Val Lys Cys Asp Gly Ala Ala
465                 470                 475                 480
Phe Leu Tyr His Gly Lys Tyr Tyr Pro Leu Gly Val Ala Pro Ser Glu
                485                 490                 495
Val Gln Ile Lys Asp Val Val Glu Trp Leu Leu Ala Asn His Ala Asp
            500                 505                 510
Ser Thr Gly Leu Ser Thr Asp Ser Leu Gly Asp Ala Gly Tyr Pro Gly
        515                 520                 525
Ala Ala Ala Leu Gly Asp Ala Val Cys Gly Met Ala Val Ala Tyr Ile
530                 535                 540
Thr Lys Arg Asp Phe Leu Phe Trp Phe Arg Ser His Thr Ala Lys Glu
545                 550                 555                 560
Ile Lys Trp Gly Gly Ala Lys His His Pro Glu Asp Lys Asp Asp Gly
                565                 570                 575
Gln Arg Met His Pro Arg Ser Ser Phe Gln Ala Phe Leu Glu Val Val
            580                 585                 590
Lys Ser Arg Ser Gln Pro Trp Glu Thr Ala Glu Met Asp Ala Ile His
```

595                 600                 605
Ser Leu Gln Leu Ile Leu Arg Asp Ser Phe Lys Glu Ser Glu Ala Ala
    610                 615                 620

Met Asn Ser Lys Val Val Asp Gly Val Val Gln Pro Cys Arg Asp Met
625                 630                 635                 640

Ala Gly Glu Gln Gly Ile Asp Glu Leu Gly Ala Val Ala Arg Glu Met
                645                 650                 655

Val Arg Leu Ile Glu Thr Ala Thr Val Pro Ile Phe Ala Val Asp Ala
                660                 665                 670

Gly Gly Cys Ile Asn Gly Trp Asn Ala Lys Ile Ala Glu Leu Thr Gly
                675                 680                 685

Leu Ser Val Glu Glu Ala Met Gly Lys Ser Leu Val Ser Asp Leu Ile
    690                 695                 700

Tyr Lys Glu Asn Glu Ala Thr Val Asn Lys Leu Leu Ser Arg Ala Leu
705                 710                 715                 720

Arg Gly Asp Glu Glu Lys Asn Val Glu Val Lys Leu Lys Thr Phe Ser
                725                 730                 735

Pro Glu Leu Gln Gly Lys Ala Val Phe Val Val Asn Ala Cys Ser
                740                 745                 750

Ser Lys Asp Tyr Leu Asn Asn Ile Val Gly Val Cys Phe Val Gly Gln
    755                 760                 765

Asp Val Thr Ser Gln Lys Ile Val Met Asp Lys Phe Ile Asn Ile Gln
770                 775                 780

Gly Asp Tyr Lys Ala Ile Val His Ser Pro Asn Pro Leu Ile Pro Pro
785                 790                 795                 800

Ile Phe Ala Ala Asp Glu Asn Thr Cys Cys Leu Glu Trp Asn Met Ala
                805                 810                 815

Met Glu Lys Leu Thr Gly Trp Ser Arg Ser Glu Val Ile Gly Lys Met
                820                 825                 830

Ile Val Gly Glu Val Phe Gly Ser Cys Cys Met Leu Lys Gly Pro Asp
                835                 840                 845

Ala Leu Thr Lys Phe Met Ile Val Leu His Asn Ala Ile Gly Gly Gln
    850                 855                 860

Asp Thr Asp Lys Phe Pro Phe Pro Phe Phe Asp Arg Asn Gly Lys Phe
865                 870                 875                 880

Val Gln Ala Leu Leu Thr Ala Asn Lys Arg Val Ser Leu Glu Gly Lys
                885                 890                 895

Val Ile Gly Ala Phe Cys Phe Leu Gln Ile Pro Ser Pro Glu Leu Gln
                900                 905                 910

Gln Ala Leu Ala Val Gln Arg Arg Gln Asp Thr Glu Cys Phe Thr Lys
    915                 920                 925

Ala Lys Glu Leu Ala Tyr Ile Cys Gln Val Ile Lys Asn Pro Leu Ser
930                 935                 940

Gly Met Arg Phe Ala Asn Ser Leu Leu Glu Ala Thr Asp Leu Asn Glu
945                 950                 955                 960

Asp Gln Lys Gln Leu Leu Glu Thr Ser Val Ser Cys Glu Lys Gln Ile
                965                 970                 975

Ser Arg Ile Val Gly Asp Met Asp Leu Glu Ser Ile Glu Asp Gly Ser
                980                 985                 990

Phe Val Leu Lys Arg Glu Glu Phe Phe Leu Gly Ser Val Ile Asn Ala
    995                 1000                1005

Ile Val Ser Gln Ala Met Phe Leu Leu Arg Asp Arg Gly Leu Gln
    1010                1015                1020

```
Leu Ile Arg Asp Ile Pro Glu Glu Ile Lys Ser Ile Glu Val Phe
    1025                1030                1035

Gly Asp Gln Ile Arg Ile Gln Gln Leu Leu Ala Glu Phe Leu Leu
    1040                1045                1050

Ser Ile Ile Arg Tyr Ala Pro Ser Gln Glu Trp Val Glu Ile His
    1055                1060                1065

Leu Ser Gln Leu Ser Lys Gln Met Ala Asp Gly Phe Ala Ala Ile
    1070                1075                1080

Arg Thr Glu Phe Arg Met Ala Cys Pro Gly Glu Gly Leu Pro Pro
    1085                1090                1095

Glu Leu Val Arg Asp Met Phe His Ser Ser Arg Trp Thr Ser Pro
    1100                1105                1110

Glu Gly Leu Gly Leu Ser Val Cys Arg Lys Ile Leu Lys Leu Met
    1115                1120                1125

Asn Gly Glu Val Gln Tyr Ile Arg Glu Ser Glu Arg Ser Tyr Phe
    1130                1135                1140

Leu Ile Ile Leu Glu Leu Pro Val Pro Arg Lys Arg Pro Leu Ser
    1145                1150                1155

Thr Ala Ser Gly Ser Gly Asp Met Met Leu Met Met Pro Tyr
    1160                1165                1170

<210> SEQ ID NO 2
<211> LENGTH: 1161
<212> TYPE: PRT
<213> ORGANISM: Zea mays

<400> SEQUENCE: 2

Met Ala Ser Gly Ser Arg Ala Thr Pro Thr Arg Ser Pro Ser Ala
1               5                   10                  15

Arg Pro Glu Ala Pro Arg His Ala His His His His Ser Gln Ser
                20                  25                  30

Ser Gly Gly Ser Thr Ser Arg Ala Gly Gly Ala Ala Ala Thr Glu
            35                  40                  45

Ser Val Ser Lys Ala Val Ala Gln Tyr Thr Leu Asp Ala Arg Leu His
        50                  55                  60

Ala Val Phe Glu Gln Ser Gly Ala Ser Gly Arg Ser Phe Asp Tyr Ser
65                  70                  75                  80

Gln Ser Leu Arg Ala Pro Pro Thr Pro Ser Glu Gln Gln Ile Ala
                85                  90                  95

Ala Tyr Leu Ser Arg Ile Gln Arg Gly Gly His Ile Gln Pro Phe Gly
                100                 105                 110

Cys Thr Leu Ala Val Ala Asp Asp Ser Ser Phe Arg Leu Leu Ala Phe
                115                 120                 125

Ser Glu Asn Ser Pro Asp Leu Leu Asp Leu Ser Pro His His Ser Val
                130                 135                 140

Pro Ser Leu Asp Ser Ser Ala Pro Pro His Val Ser Leu Gly Ala Asp
145                 150                 155                 160

Ala Arg Leu Leu Phe Ser Pro Ser Ser Ala Val Leu Leu Glu Arg Ala
                165                 170                 175

Phe Ala Ala Arg Glu Ile Ser Leu Leu Asn Pro Ile Trp Ile His Ser
                180                 185                 190

Arg Val Ser Ser Lys Pro Phe Tyr Ala Ile Leu His Arg Ile Asp Val
                195                 200                 205

Gly Val Val Ile Asp Leu Glu Pro Ala Arg Thr Glu Asp Pro Ala Leu
```

```
            210                 215                 220
Ser Ile Ala Gly Ala Val Gln Ser Gln Lys Leu Ala Val Arg Ala Ile
225                 230                 235                 240

Ser Arg Leu Gln Ala Leu Pro Gly Gly Asp Val Lys Leu Leu Cys Asp
                245                 250                 255

Thr Val Val Glu His Val Arg Glu Leu Thr Gly Tyr Asp Arg Val Met
                260                 265                 270

Val Tyr Arg Phe His Glu Asp Glu His Gly Glu Val Val Ala Glu Ser
                275                 280                 285

Arg Arg Asp Asn Leu Glu Pro Tyr Leu Gly Leu His Tyr Pro Ala Thr
    290                 295                 300

Asp Ile Pro Gln Ala Ser Arg Phe Leu Phe Arg Gln Asn Arg Val Arg
305                 310                 315                 320

Met Ile Ala Asp Cys His Ala Thr Pro Val Arg Val Ile Gln Asp Pro
                325                 330                 335

Gly Leu Ser Gln Pro Leu Cys Leu Val Gly Ser Thr Leu Arg Ala Pro
                340                 345                 350

His Gly Cys His Ala Gln Tyr Met Ala Asn Met Gly Ser Ile Ala Ser
                355                 360                 365

Leu Val Met Ala Val Ile Ile Ser Ser Gly Gly Asp Asp Glu Gln Thr
                370                 375                 380

Gly Arg Gly Gly Ile Ser Ser Ala Met Lys Leu Trp Gly Leu Val Val
385                 390                 395                 400

Cys His His Thr Ser Pro Arg Cys Ile Pro Phe Pro Leu Arg Tyr Ala
                405                 410                 415

Cys Glu Phe Leu Met Gln Ala Phe Gly Leu Gln Leu Asn Met Glu Leu
                420                 425                 430

Gln Leu Ala His Gln Leu Ser Glu Lys His Ile Leu Arg Thr Gln Thr
                435                 440                 445

Leu Leu Cys Asp Met Leu Leu Arg Asp Ser Pro Thr Gly Ile Val Thr
                450                 455                 460

Gln Ser Pro Ser Ile Met Asp Leu Val Lys Cys Asp Gly Ala Ala Leu
465                 470                 475                 480

Tyr Tyr His Gly Lys Tyr Tyr Pro Leu Gly Val Thr Pro Thr Glu Ser
                485                 490                 495

Gln Ile Lys Asp Ile Ile Glu Trp Leu Thr Val Phe His Gly Asp Ser
                500                 505                 510

Thr Gly Leu Ser Thr Asp Ser Leu Ala Asp Ala Gly Tyr Leu Gly Ala
                515                 520                 525

Ala Ala Leu Gly Glu Ala Val Cys Gly Met Ala Val Ala Tyr Ile Thr
                530                 535                 540

Pro Ser Asp Tyr Leu Phe Trp Phe Arg Ser His Thr Ala Lys Glu Ile
545                 550                 555                 560

Lys Trp Gly Gly Ala Lys His His Pro Glu Asp Lys Asp Asp Gly Gln
                565                 570                 575

Arg Met His Pro Arg Ser Ser Phe Lys Ala Phe Leu Glu Val Val Lys
                580                 585                 590

Ser Arg Ser Leu Pro Trp Glu Asn Ala Glu Met Asp Ala Ile His Ser
                595                 600                 605

Leu Gln Leu Ile Leu Arg Asp Ser Phe Arg Asp Ala Ala Glu Gly Thr
                610                 615                 620

Asn Asn Ser Lys Ala Ile Val Asn Gly Gln Val Gln Leu Arg Glu Leu
625                 630                 635                 640
```

-continued

Glu Leu Arg Gly Ile Asn Glu Leu Ser Ser Val Ala Arg Glu Met Val
            645                 650                 655

Arg Leu Ile Glu Thr Ala Thr Val Pro Ile Phe Ala Val Asp Thr Asp
            660                 665                 670

Gly Cys Ile Asn Gly Trp Asn Ala Lys Ile Ala Glu Leu Thr Gly Leu
            675                 680                 685

Ser Val Glu Glu Ala Met Gly Lys Ser Leu Val Asn Asp Leu Ile Phe
        690                 695                 700

Lys Glu Ser Glu Ala Thr Val Glu Lys Leu Leu Ser Arg Ala Leu Arg
705                 710                 715                 720

Gly Glu Glu Asp Lys Asn Val Glu Ile Lys Leu Lys Thr Phe Gly Ser
                725                 730                 735

Glu Gln Tyr Lys Gly Pro Ile Phe Val Val Asn Ala Cys Ser Ser
            740                 745                 750

Arg Asp Tyr Thr Gln Asn Ile Val Gly Val Cys Phe Val Gly Gln Asp
            755                 760                 765

Val Thr Gly Gln Lys Val Val Met Asp Lys Phe Val Asn Ile Gln Gly
        770                 775                 780

Asp Tyr Lys Ala Ile Val His Asn Pro Asn Pro Leu Ile Pro Pro Ile
785                 790                 795                 800

Phe Ala Ser Asp Glu Asn Thr Ser Cys Ser Glu Trp Asn Thr Ala Met
                805                 810                 815

Glu Lys Leu Thr Gly Trp Ser Arg Gly Glu Val Val Gly Lys Phe Leu
            820                 825                 830

Ile Gly Glu Val Phe Gly Asn Cys Cys Arg Leu Lys Gly Pro Asp Ala
            835                 840                 845

Leu Thr Lys Phe Met Val Ile Ile His Asn Ala Ile Gly Gly Gln Asp
            850                 855                 860

Tyr Glu Lys Phe Pro Phe Ser Phe Phe Asp Lys Asn Gly Lys Tyr Val
865                 870                 875                 880

Gln Ala Leu Leu Thr Ala Asn Thr Arg Ser Lys Met Asp Gly Lys Ser
                885                 890                 895

Ile Gly Ala Phe Cys Phe Leu Gln Ile Ala Ser Thr Glu Ile Gln Gln
            900                 905                 910

Ala Phe Glu Ile Gln Arg Gln Gln Glu Lys Lys Cys Tyr Ala Arg Met
            915                 920                 925

Lys Glu Leu Ala Tyr Ile Cys Gln Glu Ile Lys Asn Pro Leu Ser Gly
        930                 935                 940

Ile Arg Phe Thr Asn Ser Leu Leu Gln Met Thr Asp Leu Asn Asp Asp
945                 950                 955                 960

Gln Arg Gln Phe Leu Glu Thr Ser Ser Ala Cys Glu Lys Gln Met Ser
                965                 970                 975

Lys Ile Val Lys Asp Ala Ser Leu Gln Ser Ile Glu Asp Gly Ser Leu
            980                 985                 990

Val Leu Glu Gln Ser Glu Phe Ser Leu Gly Asp Val Met Asn Ala Val
            995                 1000                1005

Val Ser Gln Ala Met Leu Leu Leu Arg Glu Arg Asp Leu Gln Leu
        1010                1015                1020

Ile Arg Asp Ile Pro Asp Glu Ile Lys Asp Ala Ser Ala Tyr Gly
        1025                1030                1035

Asp Gln Cys Arg Ile Gln Gln Val Leu Ala Asp Phe Leu Leu Ser
        1040                1045                1050

```
Met Val Arg Ser Ala Pro Ser Glu Asn Gly Trp Val Glu Ile Gln
    1055                1060                1065

Val Arg Pro Asn Val Lys Gln Asn Ser Asp Gly Thr Asn Thr Glu
    1070                1075                1080

Leu Phe Ile Phe Arg Phe Ala Cys Pro Gly Glu Gly Leu Pro Ala
    1085                1090                1095

Asp Val Val Gln Asp Met Phe Ser Asn Ser Gln Trp Ser Thr Gln
    1100                1105                1110

Glu Gly Val Gly Leu Ser Thr Cys Arg Lys Ile Leu Lys Leu Met
    1115                1120                1125

Gly Gly Glu Val Gln Tyr Ile Arg Glu Ser Glu Arg Ser Phe Phe
    1130                1135                1140

Leu Ile Val Leu Glu Gln Pro Gln Pro Arg Pro Ala Ala Gly Arg
    1145                1150                1155

Glu Ile Val
    1160

<210> SEQ ID NO 3
<211> LENGTH: 1171
<212> TYPE: PRT
<213> ORGANISM: Oryza sativa

<400> SEQUENCE: 3

Met Gly Ser Gly Ser Arg Ala Thr Pro Thr Arg Ser Pro Ser Ala
1               5                   10                  15

Arg Pro Ala Ala Pro Arg His Gln His His Ser Gln Ser Ser Gly
                20                  25                  30

Gly Ser Thr Ser Arg Ala Gly Gly Gly Gly Gly Gly Gly Gly Gly
            35                  40                  45

Gly Gly Gly Ala Ala Ala Ala Glu Ser Val Ser Lys Ala Val Ala Gln
        50                  55                  60

Tyr Thr Leu Asp Ala Arg Leu His Ala Val Phe Glu Gln Ser Gly Ala
65                  70                  75                  80

Ser Gly Arg Ser Phe Asp Tyr Thr Gln Ser Leu Arg Ala Ser Pro Thr
                85                  90                  95

Pro Ser Ser Glu Gln Gln Ile Ala Ala Tyr Leu Ser Arg Ile Gln Arg
                100                 105                 110

Gly Gly His Ile Gln Pro Phe Gly Cys Thr Leu Ala Val Ala Asp Asp
                115                 120                 125

Ser Ser Phe Arg Leu Leu Ala Tyr Ser Glu Asn Thr Ala Asp Leu Leu
    130                 135                 140

Asp Leu Ser Pro His His Ser Val Pro Ser Leu Asp Ser Ser Ala Val
145                 150                 155                 160

Pro Pro Pro Val Ser Leu Gly Ala Asp Ala Arg Leu Leu Phe Ala Pro
                165                 170                 175

Ser Ser Ala Val Leu Leu Glu Arg Ala Phe Ala Ala Arg Glu Ile Ser
                180                 185                 190

Leu Leu Asn Pro Leu Trp Ile His Ser Arg Val Ser Ser Lys Pro Phe
                195                 200                 205

Tyr Ala Ile Leu His Arg Ile Asp Val Gly Val Ile Asp Leu Glu
                210                 215                 220

Pro Ala Arg Thr Glu Asp Pro Ala Leu Ser Ile Ala Gly Ala Val Gln
225                 230                 235                 240

Ser Gln Lys Leu Ala Val Arg Ala Ile Ser Arg Leu Gln Ala Leu Pro
                245                 250                 255
```

```
Gly Gly Asp Val Lys Leu Leu Cys Asp Thr Val Val Glu His Val Arg
        260                 265                 270

Glu Leu Thr Gly Tyr Asp Arg Val Met Val Tyr Arg Phe His Glu Asp
        275                 280                 285

Glu His Gly Glu Val Val Ala Glu Ser Arg Arg Ser Asn Leu Glu Pro
    290                 295                 300

Tyr Ile Gly Leu His Tyr Pro Ala Thr Asp Ile Pro Gln Ala Ser Arg
305                 310                 315                 320

Phe Leu Phe Arg Gln Asn Arg Val Arg Met Ile Ala Asp Cys His Ala
            325                 330                 335

Ala Pro Val Arg Val Ile Gln Asp Pro Ala Leu Thr Gln Pro Leu Cys
        340                 345                 350

Leu Val Gly Ser Thr Leu Arg Ser Pro His Gly Cys His Ala Gln Tyr
            355                 360                 365

Met Ala Asn Met Gly Ser Ile Ala Ser Leu Val Met Ala Val Ile Ile
    370                 375                 380

Ser Ser Gly Gly Asp Asp His Asn Ile Ala Arg Gly Ser Ile Pro
385                 390                 395                 400

Ser Ala Met Lys Leu Trp Gly Leu Val Val Cys His His Thr Ser Pro
            405                 410                 415

Arg Cys Ile Pro Phe Pro Leu Arg Tyr Ala Cys Glu Phe Leu Met Gln
            420                 425                 430

Ala Phe Gly Leu Gln Leu Asn Met Glu Leu Gln Leu Ala His Gln Leu
        435                 440                 445

Ser Glu Lys His Ile Leu Arg Thr Gln Thr Leu Leu Cys Asp Met Leu
    450                 455                 460

Leu Arg Asp Ser Pro Thr Gly Ile Val Thr Gln Ser Pro Ser Ile Met
465                 470                 475                 480

Asp Leu Val Lys Cys Asp Gly Ala Ala Leu Tyr Tyr His Gly Lys Tyr
            485                 490                 495

Tyr Pro Leu Gly Val Thr Pro Thr Glu Val Gln Ile Lys Asp Ile Ile
        500                 505                 510

Glu Trp Leu Thr Met Cys His Gly Asp Ser Thr Gly Leu Ser Thr Asp
    515                 520                 525

Ser Leu Ala Asp Ala Gly Tyr Ser Gly Ala Ala Leu Gly Asp Ala
530                 535                 540

Val Ser Gly Met Ala Val Ala Tyr Ile Thr Pro Ser Asp Tyr Leu Phe
545                 550                 555                 560

Trp Phe Arg Ser His Thr Ala Lys Glu Ile Lys Trp Gly Gly Ala Lys
            565                 570                 575

His His Pro Glu Asp Lys Asp Asp Gly Gln Arg Met His Pro Arg Ser
        580                 585                 590

Ser Phe Lys Ala Phe Leu Glu Val Val Lys Ser Arg Ser Leu Pro Trp
    595                 600                 605

Glu Asn Ala Glu Met Asp Ala Ile His Ser Leu Gln Leu Ile Leu Arg
    610                 615                 620

Asp Ser Phe Arg Asp Ser Ala Glu Gly Thr Ser Asn Ser Lys Ala Ile
625                 630                 635                 640

Val Asn Gly Gln Val Gln Leu Gly Glu Leu Glu Leu Arg Gly Ile Asp
            645                 650                 655

Glu Leu Ser Ser Val Ala Arg Glu Met Val Arg Leu Ile Glu Thr Ala
            660                 665                 670
```

-continued

Thr Val Pro Ile Phe Ala Val Asp Thr Asp Gly Cys Ile Asn Gly Trp
675                     680                 685

Asn Ala Lys Val Ala Glu Leu Thr Gly Leu Ser Val Glu Glu Ala Met
690                 695                 700

Gly Lys Ser Leu Val Asn Asp Leu Ile Phe Lys Glu Ser Glu Thr
705                 710                 715                 720

Val Asn Lys Leu Leu Ser Arg Ala Leu Arg Gly Asp Glu Asp Lys Asn
                725                 730                 735

Val Glu Ile Lys Leu Lys Thr Phe Gly Pro Glu Gln Ser Lys Gly Pro
                740                 745                 750

Ile Phe Val Ile Val Asn Ala Cys Ser Ser Arg Asp Tyr Thr Lys Asn
                755                 760                 765

Ile Val Gly Val Cys Phe Val Gly Gln Asp Val Thr Gly Gln Lys Val
                770                 775                 780

Val Met Asp Lys Phe Ile Asn Ile Gln Gly Asp Tyr Lys Ala Ile Val
785                 790                 795                 800

His Asn Pro Asn Pro Leu Ile Pro Pro Ile Phe Ala Ser Asp Glu Asn
                805                 810                 815

Thr Cys Cys Leu Glu Trp Asn Thr Ala Met Glu Lys Leu Thr Gly Trp
                820                 825                 830

Ser Arg Gly Glu Val Val Gly Lys Leu Leu Val Gly Glu Val Phe Gly
                835                 840                 845

Asn Cys Cys Arg Leu Lys Gly Pro Asp Ala Leu Thr Lys Phe Met Ile
                850                 855                 860

Val Leu His Asn Ala Ile Gly Gly Gln Asp Cys Glu Lys Phe Pro Phe
865                 870                 875                 880

Ser Phe Phe Asp Lys Asn Gly Lys Tyr Val Gln Ala Leu Leu Thr Ala
                885                 890                 895

Asn Thr Arg Ser Arg Met Asp Gly Glu Ala Ile Gly Ala Phe Cys Phe
                900                 905                 910

Leu Gln Ile Ala Ser Pro Glu Leu Gln Gln Ala Phe Glu Ile Gln Arg
                915                 920                 925

His His Glu Lys Lys Cys Tyr Ala Arg Met Lys Glu Leu Ala Tyr Ile
                930                 935                 940

Tyr Gln Glu Ile Lys Asn Pro Leu Asn Gly Ile Arg Phe Thr Asn Ser
945                 950                 955                 960

Leu Leu Glu Met Thr Asp Leu Lys Asp Gln Arg Gln Phe Leu Glu
                965                 970                 975

Thr Ser Thr Ala Cys Glu Lys Gln Met Ser Lys Ile Val Lys Asp Ala
                980                 985                 990

Ser Leu Gln Ser Ile Glu Asp Gly Ser Leu Val Leu Glu Lys Gly Glu
                995                 1000                1005

Phe Ser Leu Gly Ser Val Met Asn Ala Val Val Ser Gln Val Met
1010                1015                1020

Ile Gln Leu Arg Glu Arg Asp Leu Gln Leu Ile Arg Asp Ile Pro
1025                1030                1035

Asp Glu Ile Lys Glu Ala Ser Ala Tyr Gly Asp Gln Tyr Arg Ile
1040                1045                1050

Gln Gln Val Leu Cys Asp Phe Leu Leu Ser Met Val Arg Phe Ala
1055                1060                1065

Pro Ala Glu Asn Gly Trp Val Glu Ile Gln Val Arg Pro Asn Ile
1070                1075                1080

Lys Gln Asn Ser Asp Gly Thr Asp Thr Met Leu Phe Leu Phe Arg

```
                  1085               1090               1095

Phe  Ala  Cys  Pro  Gly  Glu  Gly  Leu  Pro  Pro  Glu  Ile  Val  Gln  Asp
                  1100               1105               1110

Met  Phe  Ser  Asn  Ser  Arg  Trp  Thr  Thr  Gln  Glu  Gly  Ile  Gly  Leu
                  1115               1120               1125

Ser  Ile  Cys  Arg  Lys  Ile  Leu  Lys  Leu  Met  Gly  Gly  Glu  Val  Gln
                  1130               1135               1140

Tyr  Ile  Arg  Glu  Ser  Glu  Arg  Ser  Phe  Phe  His  Ile  Val  Leu  Glu
                  1145               1150               1155

Leu  Pro  Gln  Pro  Gln  Gln  Ala  Ala  Ser  Arg  Gly  Thr  Ser
                  1160               1165               1170

<210> SEQ ID NO 4
<211> LENGTH: 1178
<212> TYPE: PRT
<213> ORGANISM: Sorghum bicolor

<400> SEQUENCE: 4

Met  Ala  Ser  Gly  Ser  Arg  Ala  Thr  Pro  Thr  Arg  Ser  Pro  Ser  Ser  Ala
1                 5                  10                 15

Arg  Pro  Glu  Ala  Pro  Arg  His  Ala  His  His  His  His  His  His  His  Ser
                  20                 25                 30

Gln  Ser  Ser  Gly  Gly  Ser  Thr  Ser  Arg  Ala  Gly  Gly  Gly  Gly  Gly  Gly
             35                 40                 45

Gly  Gly  Gly  Gly  Gly  Gly  Thr  Ala  Ala  Thr  Ala  Thr  Ala  Thr
        50                 55                 60

Glu  Ser  Val  Ser  Lys  Ala  Val  Ala  Gln  Tyr  Thr  Leu  Asp  Ala  Arg  Leu
65                70                 75                 80

His  Ala  Val  Phe  Glu  Gln  Ser  Gly  Ala  Ser  Gly  Arg  Ser  Phe  Asp  Tyr
                  85                 90                 95

Ser  Gln  Ser  Leu  Arg  Ala  Pro  Pro  Thr  Pro  Ser  Ser  Glu  Gln  Gln  Ile
             100                105                110

Ala  Ala  Tyr  Leu  Ser  Arg  Ile  Gln  Arg  Gly  Gly  His  Ile  Gln  Pro  Phe
         115                120                125

Gly  Cys  Thr  Leu  Ala  Val  Ala  Asp  Asp  Ser  Ser  Phe  Arg  Leu  Leu  Ala
         130                135                140

Phe  Ser  Glu  Asn  Ala  Ala  Asp  Leu  Leu  Asp  Leu  Ser  Pro  His  His  Ser
145               150                155                160

Val  Pro  Ser  Leu  Asp  Ser  Ala  Ala  Pro  Pro  Val  Ser  Leu  Gly  Ala
                  165                170                175

Asp  Ala  Arg  Leu  Leu  Phe  Ser  Pro  Ser  Ser  Ala  Val  Leu  Leu  Glu  Arg
             180                185                190

Ala  Phe  Ala  Ala  Arg  Glu  Ile  Ser  Leu  Leu  Asn  Pro  Leu  Trp  Ile  His
         195                200                205

Ser  Arg  Val  Ser  Ser  Lys  Pro  Phe  Tyr  Ala  Ile  Leu  His  Arg  Ile  Asp
         210                215                220

Val  Gly  Val  Val  Ile  Asp  Leu  Glu  Pro  Ala  Arg  Thr  Glu  Asp  Pro  Ala
225               230                235                240

Leu  Ser  Ile  Ala  Gly  Ala  Val  Gln  Ser  Gln  Lys  Leu  Ala  Val  Arg  Ala
                  245                250                255

Ile  Ser  Arg  Leu  Gln  Ala  Leu  Pro  Gly  Gly  Asp  Ile  Lys  Leu  Leu  Cys
             260                265                270

Asp  Thr  Val  Val  Glu  His  Val  Arg  Glu  Leu  Thr  Gly  Tyr  Asp  Arg  Val
         275                280                285
```

-continued

```
Met Val Tyr Arg Phe His Glu Asp Glu His Gly Glu Val Val Ala Glu
    290                 295                 300

Ser Arg Arg Asp Asn Leu Glu Pro Tyr Leu Gly Leu His Tyr Pro Ala
305                 310                 315                 320

Thr Asp Ile Pro Gln Ala Ser Arg Phe Leu Phe Arg Gln Asn Arg Val
                325                 330                 335

Arg Met Ile Ala Asp Cys His Ala Thr Pro Val Arg Val Ile Gln Asp
            340                 345                 350

Pro Gly Met Ser Gln Pro Leu Cys Leu Val Gly Ser Thr Leu Arg Ala
        355                 360                 365

Pro His Gly Cys His Ala Gln Tyr Met Ala Asn Met Gly Ser Ile Ala
    370                 375                 380

Ser Leu Val Met Ala Val Ile Ile Ser Ser Gly Gly Asp Asp Glu Gln
385                 390                 395                 400

Thr Gly Arg Gly Gly Ile Ser Ser Ala Met Lys Leu Trp Gly Leu Val
                405                 410                 415

Val Cys His His Thr Ser Pro Arg Cys Ile Pro Phe Pro Leu Arg Tyr
            420                 425                 430

Ala Cys Glu Phe Leu Met Gln Ala Phe Gly Leu Gln Leu Asn Met Glu
        435                 440                 445

Leu Gln Leu Ala His Gln Leu Ser Glu Lys His Ile Leu Arg Thr Gln
    450                 455                 460

Thr Leu Leu Cys Asp Met Leu Leu Arg Asp Ser Pro Thr Gly Ile Val
465                 470                 475                 480

Thr Gln Ser Pro Ser Ile Met Asp Leu Val Lys Cys Asp Gly Ala Ala
                485                 490                 495

Leu Tyr Tyr His Gly Lys Tyr Tyr Pro Leu Gly Val Thr Pro Thr Glu
            500                 505                 510

Ser Gln Ile Lys Asp Ile Ile Glu Trp Leu Thr Val Cys His Gly Asp
        515                 520                 525

Ser Thr Gly Leu Ser Thr Asp Ser Leu Ala Asp Ala Gly Tyr Leu Gly
    530                 535                 540

Ala Ala Ala Leu Gly Asp Ala Val Cys Gly Met Ala Val Ala Tyr Ile
545                 550                 555                 560

Thr Pro Ser Asp Tyr Leu Phe Trp Phe Arg Ser His Thr Ala Lys Glu
                565                 570                 575

Ile Lys Trp Gly Gly Ala Lys His His Pro Glu Asp Lys Asp Asp Gly
            580                 585                 590

Gln Arg Met His Pro Arg Ser Ser Phe Lys Ala Phe Leu Glu Val Val
        595                 600                 605

Lys Ser Arg Ser Leu Pro Trp Glu Asn Ala Glu Met Asp Ala Ile His
    610                 615                 620

Ser Leu Gln Leu Ile Leu Arg Asp Ser Phe Arg Asp Ala Ala Glu Gly
625                 630                 635                 640

Thr Ser Asn Ser Lys Ala Ile Val Asn Gly Gln Ala Gln Leu Gly Glu
                645                 650                 655

Leu Glu Leu Arg Gly Ile Asn Glu Leu Ser Ser Val Pro Arg Glu Met
            660                 665                 670

Val Arg Leu Ile Glu Thr Ala Thr Val Pro Ile Phe Ala Val Asp Thr
        675                 680                 685

Asp Gly Cys Ile Asn Gly Trp Asn Ala Lys Ile Ala Glu Leu Thr Gly
    690                 695                 700

Leu Ser Val Glu Glu Ala Met Gly Lys Ser Leu Val Asn Asp Leu Ile
```

-continued

```
            705                 710                 715                 720
        Phe Lys Glu Ser Glu Glu Ile Val Glu Lys Leu Leu Ser Arg Ala Leu
                        725                 730                 735
        Arg Gly Glu Glu Asp Lys Asn Val Glu Ile Lys Leu Lys Thr Phe Gly
                        740                 745                 750
        Ser Glu Gln Ser Asn Gly Ala Ile Phe Val Ile Val Asn Ala Cys Ser
                        755                 760                 765
        Ser Arg Asp Tyr Thr Gln Asn Ile Val Gly Val Cys Phe Val Gly Gln
                        770                 775                 780
        Asp Val Thr Gly Gln Lys Val Val Met Asp Lys Phe Ile Asn Ile Gln
        785                 790                 795                 800
        Gly Asp Tyr Lys Ala Ile Val His Asn Pro Asn Pro Leu Ile Pro Pro
                        805                 810                 815
        Ile Phe Ala Ser Asp Glu Asn Thr Ser Cys Ser Glu Trp Asn Thr Ala
                        820                 825                 830
        Met Glu Lys Leu Thr Gly Trp Ser Arg Gly Glu Val Val Gly Lys Phe
                        835                 840                 845
        Leu Ile Gly Glu Val Phe Gly Ser Phe Cys Arg Leu Lys Gly Pro Asp
                        850                 855                 860
        Ala Leu Thr Lys Phe Met Val Val Ile His Asn Ala Ile Gly Gly Gln
        865                 870                 875                 880
        Asp Tyr Glu Lys Phe Pro Phe Ser Phe Asp Lys Asn Gly Lys Tyr
                        885                 890                 895
        Val Gln Ala Leu Leu Thr Ala Asn Thr Arg Ser Lys Met Asp Gly Lys
                        900                 905                 910
        Ser Ile Gly Ala Phe Cys Phe Leu Gln Ile Ala Ser Ala Glu Ile Gln
                        915                 920                 925
        Gln Ala Phe Glu Ile Gln Arg Gln Gln Glu Lys Lys Cys Tyr Ala Arg
                        930                 935                 940
        Met Lys Glu Leu Ala Tyr Ile Cys Gln Glu Ile Lys Asn Pro Leu Ser
        945                 950                 955                 960
        Gly Ile Arg Phe Thr Asn Ser Leu Leu Gln Met Thr Asp Leu Asn Asp
                        965                 970                 975
        Asp Gln Arg Gln Phe Leu Glu Thr Cys Ser Ala Cys Glu Lys Gln Met
                        980                 985                 990
        Ser Lys Ile Val Lys Asp Ala Thr Leu Gln Ser Ile Glu Asp Gly Ser
                        995                 1000                1005
        Leu Val Leu Glu Lys Ser Glu Phe Ser Phe Gly Asp Val Met Asn
                        1010                1015                1020
        Ala Val Val Ser Gln Ala Met Leu Leu Leu Arg Glu Arg Asp Leu
                        1025                1030                1035
        Gln Leu Ile Arg Asp Ile Pro Asp Glu Ile Lys Asp Ala Ser Ala
                        1040                1045                1050
        Tyr Gly Asp Gln Phe Arg Ile Gln Gln Val Leu Ala Asp Phe Leu
                        1055                1060                1065
        Leu Ser Met Val Arg Ser Ala Pro Ser Glu Asn Gly Trp Val Glu
                        1070                1075                1080
        Ile Gln Val Arg Pro Asn Val Lys Gln Asn Ser Asp Gly Thr Asp
                        1085                1090                1095
        Thr Glu Leu Phe Ile Phe Arg Phe Ala Cys Pro Gly Glu Gly Leu
                        1100                1105                1110
        Pro Ala Asp Ile Val Gln Asp Met Phe Ser Asn Ser Gln Trp Ser
                        1115                1120                1125
```

```
Thr Gln Glu Gly Val Gly Leu Ser Thr Cys Arg Lys Ile Leu Lys
    1130                1135                1140

Leu Met Gly Gly Glu Val Gln Tyr Ile Arg Glu Ser Glu Arg Ser
    1145                1150                1155

Phe Phe Leu Ile Val Leu Glu Leu Pro Gln Pro Arg Pro Ala Ala
    1160                1165                1170

Asp Arg Glu Ile Ser
    1175

<210> SEQ ID NO 5
<211> LENGTH: 1137
<212> TYPE: PRT
<213> ORGANISM: Glycine max

<400> SEQUENCE: 5

Met Ala Ser Ala Ser Gly Ala Ala Asn Ser Ser Val Pro Pro Gln
1               5                   10                  15

Ile His Thr Ser Arg Thr Lys Leu Ser His His Ser Ser Asn Asn
                20                  25                  30

Asn Asn Ile Asp Ser Met Ser Lys Ala Ile Ala Gln Tyr Thr Glu Asp
                35                  40                  45

Ala Arg Leu His Ala Val Phe Glu Gln Ser Gly Glu Ser Gly Arg Ser
        50                  55                  60

Phe Asn Tyr Ser Glu Ser Ile Arg Ile Ala Ser Glu Ser Val Pro Glu
65                  70                  75                  80

Gln Gln Ile Thr Ala Tyr Leu Val Lys Ile Gln Arg Gly Gly Phe Ile
                85                  90                  95

Gln Pro Phe Gly Ser Met Ile Ala Val Asp Glu Pro Ser Phe Arg Ile
                100                 105                 110

Leu Gly Tyr Ser Asp Asn Ala Arg Asp Met Leu Gly Ile Thr Pro Gln
                115                 120                 125

Ser Val Pro Ser Leu Asp Asp Lys Asn Asp Ala Ala Phe Ala Leu Gly
            130                 135                 140

Thr Asp Val Arg Ala Leu Phe Thr His Ser Ser Ala Leu Leu Leu Glu
145                 150                 155                 160

Lys Ala Phe Ser Ala Arg Glu Ile Ser Leu Met Asn Pro Ile Trp Ile
                165                 170                 175

His Ser Arg Thr Ser Gly Lys Pro Phe Tyr Gly Ile Leu His Arg Ile
                180                 185                 190

Asp Val Gly Ile Val Ile Asp Leu Glu Pro Ala Arg Thr Glu Asp Pro
            195                 200                 205

Ala Leu Ser Ile Ala Gly Ala Val Gln Ser Gln Lys Leu Ala Val Arg
        210                 215                 220

Ala Ile Ser Gln Leu Gln Ser Leu Pro Gly Gly Asp Val Lys Leu Leu
225                 230                 235                 240

Cys Asp Thr Val Val Glu Ser Val Arg Glu Leu Thr Gly Tyr Asp Arg
                245                 250                 255

Val Met Val Tyr Lys Phe His Glu Asp Glu His Gly Glu Val Val Ser
                260                 265                 270

Glu Ser Lys Arg Pro Asp Leu Glu Pro Tyr Ile Gly Leu His Tyr Pro
            275                 280                 285

Ala Thr Asp Ile Pro Gln Ala Ser Arg Phe Leu Phe Lys Gln Asn Arg
        290                 295                 300

Val Arg Met Ile Val Asp Cys His Ala Ser Ala Val Arg Val Val Gln
```

```
            305                 310                 315                 320
Asp Glu Ala Leu Val Gln Pro Leu Cys Leu Val Gly Ser Thr Leu Arg
                325                 330                 335

Ala Pro His Gly Cys His Ala Gln Tyr Met Ala Asn Met Gly Ser Ile
                340                 345                 350

Ala Ser Leu Val Met Ala Val Ile Ile Asn Gly Asn Asp Glu Glu Gly
                355                 360                 365

Val Gly Gly Arg Ser Ser Met Arg Leu Trp Gly Leu Val Val Cys His
                370                 375                 380

His Thr Ser Ala Arg Cys Ile Pro Phe Pro Leu Arg Tyr Ala Cys Glu
385                 390                 395                 400

Phe Leu Met Gln Ala Phe Gly Leu Gln Leu Asn Met Glu Leu Gln Leu
                405                 410                 415

Ala Ala Gln Ser Leu Glu Lys Arg Val Leu Arg Thr Gln Thr Leu Leu
                420                 425                 430

Cys Asp Met Leu Leu Arg Asp Ser Pro Thr Gly Ile Val Thr Gln Ser
                435                 440                 445

Pro Ser Ile Met Asp Leu Val Lys Cys Asp Gly Ala Ala Leu Tyr Phe
                450                 455                 460

Gln Gly Asn Tyr Tyr Pro Leu Gly Val Thr Pro Thr Glu Ala Gln Ile
465                 470                 475                 480

Arg Asp Ile Ile Glu Trp Leu Leu Ala Phe His Gly Asp Ser Thr Gly
                485                 490                 495

Leu Ser Thr Asp Ser Leu Gly Asp Ala Gly Tyr Pro Gly Ala Ala Ser
                500                 505                 510

Leu Gly Asp Ala Val Cys Gly Met Ala Val Ala Tyr Ile Thr Glu Lys
                515                 520                 525

Asp Phe Leu Phe Trp Phe Arg Ser His Thr Ala Lys Glu Ile Lys Trp
                530                 535                 540

Gly Gly Ala Lys His His Pro Glu Asp Lys Asp Asp Gly Gln Arg Met
545                 550                 555                 560

His Pro Arg Ser Ser Phe Lys Ala Phe Leu Glu Val Val Lys Ser Arg
                565                 570                 575

Ser Leu Pro Trp Glu Asn Ala Glu Met Asp Ala Ile His Ser Leu Gln
                580                 585                 590

Leu Ile Leu Arg Asp Ser Phe Lys Asp Ala Glu His Arg Asn Ser Lys
                595                 600                 605

Ala Val Val Asp Pro His Val Ser Glu Gln Glu Leu Gln Gly Val Asp
610                 615                 620

Glu Leu Ser Ser Val Ala Arg Glu Met Val Arg Leu Ile Glu Thr Ala
625                 630                 635                 640

Thr Ala Pro Ile Phe Ala Val Asp Val Asp Gly His Val Asn Gly Trp
                645                 650                 655

Asn Ala Lys Val Ser Glu Leu Thr Gly Leu Pro Val Glu Glu Ala Met
                660                 665                 670

Gly Lys Ser Leu Val His Asp Leu Val Phe Lys Glu Ser Glu Glu Thr
                675                 680                 685

Met Asn Lys Leu Leu Ser Arg Ala Leu Lys Gly Glu Glu Asp Lys Asn
                690                 695                 700

Val Glu Ile Lys Met Arg Thr Phe Gly Pro Glu His Gln Asn Lys Ala
705                 710                 715                 720

Val Phe Leu Val Val Asn Ala Cys Ser Ser Lys Asp Phe Thr Asn Asn
                725                 730                 735
```

-continued

```
Val Val Gly Val Cys Phe Val Gly Gln Asp Val Thr Gly Gln Lys Ile
            740                 745                 750

Val Met Asp Lys Phe Ile Asn Ile Gln Gly Asp Tyr Lys Ala Ile Val
            755                 760                 765

His Ser Pro Asn Pro Leu Ile Pro Pro Ile Phe Ala Ser Asp Asp Asn
        770                 775                 780

Thr Cys Cys Leu Glu Trp Asn Thr Ala Met Glu Lys Leu Thr Gly Trp
785                 790                 795                 800

Gly Arg Val Asp Val Ile Gly Lys Met Leu Val Gly Glu Val Phe Gly
                805                 810                 815

Ser Cys Cys Gln Leu Lys Gly Ser Asp Ser Ile Thr Lys Phe Met Ile
                820                 825                 830

Val Leu His Asn Ala Leu Gly Gly Gln Asp Thr Asp Lys Phe Pro Phe
            835                 840                 845

Ser Phe Leu Asp Arg His Gly Lys Tyr Val Gln Thr Phe Leu Thr Ala
        850                 855                 860

Asn Lys Arg Val Asn Met Glu Gly Gln Ile Ile Gly Ala Phe Cys Phe
865                 870                 875                 880

Leu Gln Ile Met Ser Pro Glu Leu Gln Gln Ala Leu Lys Ala Gln Arg
                885                 890                 895

Gln Gln Glu Lys Asn Ser Phe Gly Arg Met Lys Glu Leu Ala Tyr Ile
                900                 905                 910

Cys Gln Gly Val Lys Asn Pro Leu Ser Gly Ile Arg Phe Thr Asn Ser
            915                 920                 925

Leu Leu Glu Ala Thr Ser Leu Thr Asn Glu Gln Lys Gln Phe Leu Glu
        930                 935                 940

Thr Ser Val Ala Cys Glu Lys Gln Met Leu Lys Ile Ile Arg Asp Val
945                 950                 955                 960

Asp Leu Glu Ser Ile Glu Asp Gly Ser Leu Glu Leu Glu Lys Gly Glu
                965                 970                 975

Phe Leu Leu Gly Asn Val Ile Asn Ala Val Val Ser Gln Val Met Leu
            980                 985                 990

Leu Leu Arg Glu Arg Asn Leu Gln  Leu Ile Arg Asp Ile  Pro Glu Glu
                995                 1000                1005

Ile Lys  Thr Leu Ala Val Tyr  Gly Asp Gln Leu Arg  Ile Gln Gln
    1010                1015                1020

Val Leu  Ser Asp Phe Leu Leu  Asn Ile Val Arg Tyr  Ala Pro Ser
    1025                1030                1035

Pro Asp  Gly Trp Val Glu Ile  His Val Arg Pro Arg  Ile Lys Gln
    1040                1045                1050

Ile Ser  Asp Gly Leu Thr Leu  Leu His Ala Glu Phe  Arg Met Val
    1055                1060                1065

Cys Pro  Gly Glu Gly Leu Pro  Pro Glu Leu Ile Gln  Asp Met Phe
    1070                1075                1080

Asn Asn  Ser Arg Trp Gly Thr  Gln Glu Gly Leu Gly  Leu Ser Met
    1085                1090                1095

Ser Arg  Lys Ile Leu Lys Leu  Met Asn Gly Glu Val  Gln Tyr Ile
    1100                1105                1110

Arg Glu  Ala Glu Arg Cys Tyr  Phe Tyr Val Leu Leu  Glu Leu Pro
    1115                1120                1125

Val Thr  Arg Arg Ser Ser Lys  Lys Cys
    1130                1135
```

<210> SEQ ID NO 6
<211> LENGTH: 1149
<212> TYPE: PRT
<213> ORGANISM: Glycine max

<400> SEQUENCE: 6

```
Met Ala Ser Ala Ser Gly Ala Glu Asn Ser Val Pro Ser Pro
1               5                   10                  15

Leu Pro Pro Pro Pro Pro Gln Ile His Thr Ser Arg Thr Lys Leu
                20                  25                  30

Ser His His His His Asn Asn Asn Asn Asn Asn Asn Asn Ile Asp
            35                  40                  45

Ser Thr Ser Lys Ala Ile Ala Gln Tyr Thr Glu Asp Ala Arg Leu His
    50                  55                  60

Ala Val Phe Glu Gln Ser Gly Glu Ser Gly Arg Ser Phe Asp Tyr Ser
65                  70                  75                  80

Gln Ser Ile Arg Val Thr Ser Glu Ser Val Pro Glu Gln Gln Ile Thr
                85                  90                  95

Ala Tyr Leu Leu Lys Ile Gln Arg Gly Gly Phe Ile Gln Pro Phe Gly
                100                 105                 110

Ser Met Ile Ala Val Asp Glu Pro Ser Phe Arg Ile Leu Ala Tyr Ser
                115                 120                 125

Asp Asn Ala Arg Asp Met Leu Gly Ile Thr Pro Gln Ser Val Pro Ser
130                 135                 140

Leu Asp Asp Lys Asn Asp Ala Ala Phe Ala Leu Gly Thr Asp Ile Arg
145                 150                 155                 160

Thr Leu Phe Thr His Ser Ser Ala Val Leu Leu Glu Lys Ala Phe Ser
                165                 170                 175

Ala Arg Glu Ile Ser Leu Met Asn Pro Ile Trp Ile His Ser Arg Thr
                180                 185                 190

Ser Gly Lys Pro Phe Tyr Gly Ile Leu His Arg Ile Asp Val Gly Ile
                195                 200                 205

Val Ile Asp Leu Glu Pro Ala Arg Thr Glu Asp Pro Ala Leu Ser Ile
210                 215                 220

Ala Gly Ala Val Gln Ser Gln Lys Leu Ala Val Arg Ala Ile Ser Gln
225                 230                 235                 240

Leu Gln Ser Leu Pro Gly Gly Asp Val Lys Leu Leu Cys Asp Thr Val
                245                 250                 255

Val Glu Ser Val Arg Glu Leu Thr Gly Tyr Asp Arg Val Met Val Tyr
                260                 265                 270

Arg Phe His Glu Asp Glu His Gly Glu Val Val Ala Glu Thr Lys Arg
                275                 280                 285

Pro Asp Leu Glu Pro Tyr Ile Gly Leu His Tyr Pro Ala Thr Asp Ile
                290                 295                 300

Pro Gln Ala Ser Arg Phe Leu Phe Lys Gln Asn Arg Val Arg Met Ile
305                 310                 315                 320

Val Asp Cys His Ala Ser Ala Val Arg Val Val Gln Asp Glu Ala Leu
                325                 330                 335

Val Gln Pro Leu Cys Leu Val Gly Ser Thr Leu Arg Ala Pro His Gly
                340                 345                 350

Cys His Ala Gln Tyr Met Ala Asn Met Gly Ser Thr Ala Ser Leu Val
                355                 360                 365

Met Ala Val Ile Ile Asn Gly Asn Asp Glu Glu Gly Val Gly Gly Arg
                370                 375                 380
```

```
Thr Ser Met Arg Leu Trp Gly Leu Val Ile Cys His His Thr Ser Ala
385                 390                 395                 400

Arg Cys Ile Pro Phe Pro Leu Arg Tyr Ala Cys Glu Phe Leu Met Gln
                405                 410                 415

Ala Phe Gly Leu Gln Leu Asn Met Glu Leu Gln Leu Ala Ala Gln Ser
            420                 425                 430

Leu Glu Lys Arg Val Leu Arg Thr Gln Thr Leu Leu Cys Asp Met Leu
        435                 440                 445

Leu Arg Asp Ser Pro Thr Gly Ile Val Thr Gln Ser Pro Ser Ile Met
450                 455                 460

Asp Leu Val Lys Cys Asp Gly Ala Ala Leu Tyr Tyr Gln Gly Asn Tyr
465                 470                 475                 480

Tyr Pro Leu Gly Val Thr Pro Thr Glu Ala Gln Ile Arg Asp Ile Ile
                485                 490                 495

Glu Trp Leu Leu Ala Phe His Arg Asp Ser Thr Gly Leu Ser Thr Asp
            500                 505                 510

Ser Leu Ala Asp Ala Gly Tyr Pro Gly Ala Ala Ser Leu Gly Asp Ala
        515                 520                 525

Val Cys Gly Met Ala Val Ala Tyr Ile Thr Glu Lys Asp Phe Leu Phe
530                 535                 540

Trp Phe Arg Ser His Thr Ala Lys Glu Ile Lys Trp Gly Gly Ala Lys
545                 550                 555                 560

His His Pro Glu Asp Lys Asp Asp Gly Gln Arg Met His Pro Arg Ser
                565                 570                 575

Ser Phe Lys Ala Phe Leu Glu Val Val Lys Ser Arg Ser Leu Pro Trp
            580                 585                 590

Glu Asn Ala Glu Met Asp Ala Ile His Ser Leu Gln Leu Ile Leu Arg
        595                 600                 605

Asp Ser Phe Lys Asp Ala Glu His Ser Asn Ser Lys Ala Val Leu Asp
610                 615                 620

Pro Arg Met Ser Glu Leu Glu Leu Gln Gly Val Asp Glu Leu Ser Ser
625                 630                 635                 640

Val Ala Arg Glu Met Val Arg Leu Ile Glu Thr Ala Thr Ala Pro Ile
                645                 650                 655

Phe Ala Val Asp Val Asp Gly Arg Ile Asn Gly Trp Asn Ala Lys Val
            660                 665                 670

Ser Glu Leu Thr Gly Leu Pro Val Glu Glu Ala Met Gly Lys Ser Leu
        675                 680                 685

Val Arg Asp Leu Val Phe Lys Glu Ser Glu Glu Thr Val Asp Lys Leu
690                 695                 700

Leu Ser Arg Ala Leu Lys Gly Glu Glu Asp Lys Asn Val Glu Ile Lys
705                 710                 715                 720

Met Arg Thr Phe Gly Pro Glu His Gln Asn Lys Ala Val Phe Val Val
                725                 730                 735

Val Asn Ala Cys Ser Ser Lys Asp Tyr Thr Asn Asn Val Val Gly Val
            740                 745                 750

Cys Phe Val Gly Gln Asp Val Thr Gly Gln Lys Ile Val Met Asp Lys
        755                 760                 765

Phe Ile Asn Ile Gln Gly Asp Tyr Lys Ala Ile Val His Asn Pro Asn
770                 775                 780

Pro Leu Ile Pro Pro Ile Phe Ala Ser Asp Asp Asn Thr Cys Cys Leu
785                 790                 795                 800
```

Glu Trp Asn Thr Ala Met Glu Lys Leu Thr Gly Trp Ser Arg Ala Asp
                805                 810                 815

Val Ile Gly Lys Met Leu Val Gly Glu Val Phe Gly Ser Cys Cys Gln
            820                 825                 830

Leu Lys Gly Ser Asp Ser Ile Thr Lys Phe Met Ile Val Leu His Asn
        835                 840                 845

Ala Leu Gly Gly His Asp Thr Asp Arg Phe Pro Phe Ser Phe Leu Asp
    850                 855                 860

Arg Tyr Gly Lys His Val Gln Ala Phe Leu Thr Ala Asn Lys Arg Val
865                 870                 875                 880

Asn Met Asp Gly Gln Ile Ile Gly Ala Phe Cys Phe Leu Gln Ile Val
                885                 890                 895

Ser Pro Glu Leu Gln Gln Ala Leu Lys Ala Gln Arg Gln Gln Glu Lys
            900                 905                 910

Asn Ser Phe Ala Arg Met Lys Glu Leu Ala Tyr Ile Cys Gln Gly Val
        915                 920                 925

Lys Asn Pro Leu Ser Gly Ile Arg Phe Thr Asn Ser Leu Leu Glu Ala
    930                 935                 940

Thr Cys Leu Ser Asn Glu Gln Lys Gln Phe Leu Glu Thr Ser Ala Ala
945                 950                 955                 960

Cys Glu Lys Gln Met Leu Lys Ile Ile His Asp Val Asp Ile Glu Ser
                965                 970                 975

Ile Glu Asp Gly Ser Leu Glu Leu Glu Lys Gly Glu Phe Leu Leu Gly
            980                 985                 990

Asn Val Ile Asn Ala Val Val Ser Gln Val Met Leu Leu Leu Arg Glu
        995                 1000                1005

Arg Asn Leu Gln Leu Ile Arg Asp Ile Pro Glu Glu Ile Lys Thr
    1010                1015                1020

Leu Ala Val Tyr Gly Asp Gln Leu Arg Ile Gln Gln Val Leu Ser
    1025                1030                1035

Asp Phe Leu Leu Asn Ile Val Arg Tyr Ala Pro Ser Pro Asp Gly
    1040                1045                1050

Trp Val Glu Ile His Val His Pro Arg Ile Lys Gln Ile Ser Asp
    1055                1060                1065

Gly Leu Thr Leu Leu His Ala Glu Phe Arg Met Val Cys Pro Gly
    1070                1075                1080

Glu Gly Leu Pro Pro Glu Leu Ile Gln Asn Met Phe Asn Asn Ser
    1085                1090                1095

Gly Trp Gly Thr Gln Glu Gly Leu Gly Leu Ser Met Ser Arg Lys
    1100                1105                1110

Ile Leu Lys Leu Met Asn Gly Glu Val Gln Tyr Ile Arg Glu Ala
    1115                1120                1125

Gln Arg Cys Tyr Phe Tyr Val Leu Leu Glu Leu Pro Val Thr Arg
    1130                1135                1140

Arg Ser Ser Lys Lys Cys
    1145

<210> SEQ ID NO 7
<211> LENGTH: 1100
<212> TYPE: PRT
<213> ORGANISM: Glycine max

<400> SEQUENCE: 7

Met Ser Lys Ala Ile Ala Gln Tyr Thr Glu Asp Ala Arg Leu His Ala
1               5                   10                  15

-continued

```
Val Phe Glu Gln Ser Gly Ser Gly Arg Ser Phe Asn Tyr Ser Glu
             20                  25                  30

Ser Ile Arg Ile Ala Ser Glu Ser Val Pro Glu Gln Ile Thr Ala
             35                  40                  45

Tyr Leu Val Lys Ile Gln Arg Gly Gly Phe Ile Gln Pro Phe Gly Ser
 50                  55                  60

Met Ile Ala Val Asp Glu Pro Ser Phe Arg Ile Leu Gly Tyr Ser Asp
65                   70                  75                   80

Asn Ala Arg Asp Met Leu Gly Ile Thr Pro Gln Ser Val Pro Ser Leu
                 85                  90                  95

Asp Asp Lys Asn Asp Ala Ala Phe Ala Leu Gly Thr Asp Val Arg Ala
                100                 105                 110

Leu Phe Thr His Ser Ser Ala Leu Leu Leu Glu Lys Ala Phe Ser Ala
                115                 120                 125

Arg Glu Ile Ser Leu Met Asn Pro Ile Trp Ile His Ser Arg Thr Ser
130                 135                 140

Gly Lys Pro Phe Tyr Gly Ile Leu His Arg Ile Asp Val Gly Ile Val
145                 150                 155                 160

Ile Asp Leu Glu Pro Ala Arg Thr Glu Asp Pro Ala Leu Ser Ile Ala
                165                 170                 175

Gly Ala Val Gln Ser Gln Lys Leu Ala Val Arg Ala Ile Ser Gln Leu
                180                 185                 190

Gln Ser Leu Pro Gly Gly Asp Val Lys Leu Leu Cys Asp Thr Val Val
                195                 200                 205

Glu Ser Val Arg Glu Leu Thr Gly Tyr Asp Arg Val Met Val Tyr Lys
                210                 215                 220

Phe His Glu Asp Glu His Gly Glu Val Val Ser Glu Ser Lys Arg Pro
225                 230                 235                 240

Asp Leu Glu Pro Tyr Ile Gly Leu His Tyr Pro Ala Thr Asp Ile Pro
                245                 250                 255

Gln Ala Ser Arg Phe Leu Phe Lys Gln Asn Arg Val Arg Met Ile Val
                260                 265                 270

Asp Cys His Ala Ser Ala Val Arg Val Val Gln Asp Glu Ala Leu Val
                275                 280                 285

Gln Pro Leu Cys Leu Val Gly Ser Thr Leu Arg Ala Pro His Gly Cys
                290                 295                 300

His Ala Gln Tyr Met Ala Asn Met Gly Ser Ile Ala Ser Leu Val Met
305                 310                 315                 320

Ala Val Ile Ile Asn Gly Asn Asp Glu Glu Gly Val Gly Gly Arg Ser
                325                 330                 335

Ser Met Arg Leu Trp Gly Leu Val Val Cys His His Thr Ser Ala Arg
                340                 345                 350

Cys Ile Pro Phe Pro Leu Arg Tyr Ala Cys Glu Phe Leu Met Gln Ala
                355                 360                 365

Phe Gly Leu Gln Leu Asn Met Glu Leu Gln Leu Ala Ala Gln Ser Leu
                370                 375                 380

Glu Lys Arg Val Leu Arg Thr Gln Thr Leu Leu Cys Asp Met Leu Leu
385                 390                 395                 400

Arg Asp Ser Pro Thr Gly Ile Val Thr Gln Ser Pro Ser Ile Met Asp
                405                 410                 415

Leu Val Lys Cys Asp Gly Ala Ala Leu Tyr Phe Gln Gly Asn Tyr Tyr
                420                 425                 430
```

-continued

Pro Leu Gly Val Thr Pro Thr Glu Ala Gln Ile Arg Asp Ile Ile Glu
            435                 440                 445

Trp Leu Leu Ala Phe His Gly Asp Ser Thr Gly Leu Ser Thr Asp Ser
450                 455                 460

Leu Gly Asp Ala Gly Tyr Pro Gly Ala Ala Ser Leu Gly Asp Ala Val
465                 470                 475                 480

Cys Gly Met Ala Val Ala Tyr Ile Thr Glu Lys Asp Phe Leu Phe Trp
                485                 490                 495

Phe Arg Ser His Thr Ala Lys Glu Ile Lys Trp Gly Gly Ala Lys His
            500                 505                 510

His Pro Glu Asp Lys Asp Gly Gln Arg Met His Pro Arg Ser Ser
            515                 520                 525

Phe Lys Ala Phe Leu Glu Val Val Lys Ser Arg Ser Leu Pro Trp Glu
530                 535                 540

Asn Ala Glu Met Asp Ala Ile His Ser Leu Gln Leu Ile Leu Arg Asp
545                 550                 555                 560

Ser Phe Lys Asp Ala Glu His Arg Asn Ser Lys Ala Val Ala Asp Pro
                565                 570                 575

Arg Val Ser Glu Gln Glu Leu Gln Gly Val Asp Glu Leu Ser Ser Val
            580                 585                 590

Ala Arg Glu Met Val Arg Leu Ile Glu Thr Ala Thr Ala Pro Ile Phe
            595                 600                 605

Ala Val Asp Val Asp Gly His Val Asn Gly Trp Asn Ala Lys Val Ser
        610                 615                 620

Glu Leu Thr Gly Leu Pro Val Glu Glu Ala Met Gly Lys Ser Leu Val
625                 630                 635                 640

His Asp Leu Val Phe Lys Glu Ser Glu Thr Met Asn Lys Leu Leu
            645                 650                 655

Ser Arg Ala Leu Lys Gly Glu Glu Asp Lys Asn Val Glu Ile Lys Met
            660                 665                 670

Arg Thr Phe Gly Pro Glu Arg Gln Asn Lys Ala Val Phe Leu Val Val
            675                 680                 685

Asn Ala Cys Ser Ser Lys Asp Phe Thr Asn Asn Val Val Gly Val Cys
        690                 695                 700

Phe Val Gly Gln Asp Val Thr Gly Gln Lys Ile Val Met Asp Lys Phe
705                 710                 715                 720

Ile Asn Ile Gln Gly Asp Tyr Lys Ala Ile Val His Ser Pro Asn Pro
                725                 730                 735

Leu Ile Pro Pro Ile Phe Ala Ser Asp Asp Asn Thr Cys Cys Leu Glu
            740                 745                 750

Trp Asn Thr Ala Met Glu Lys Leu Thr Gly Trp Gly Arg Val Asp Val
            755                 760                 765

Ile Gly Lys Met Leu Val Gly Glu Val Phe Gly Ser Cys Cys Gln Leu
        770                 775                 780

Lys Gly Ser Asp Ser Ile Thr Lys Phe Met Ile Val Leu His Asn Ala
785                 790                 795                 800

Leu Gly Gly Gln Asp Thr Asp Lys Phe Pro Phe Ser Phe Leu Asp Arg
                805                 810                 815

His Gly Lys Tyr Val Gln Thr Phe Leu Thr Ala Asn Lys Arg Val Asn
            820                 825                 830

Met Glu Gly Gln Ile Ile Gly Ala Phe Cys Phe Leu Gln Ile Met Ser
            835                 840                 845

Pro Glu Leu Gln Gln Ala Leu Lys Ala Gln Arg Gln Gln Glu Lys Asn

```
                     850                 855                 860
Ser Phe Gly Arg Met Lys Glu Leu Ala Tyr Ile Cys Gln Gly Val Lys
865                 870                 875                 880

Asn Pro Leu Ser Gly Ile Arg Phe Thr Asn Ser Leu Leu Glu Ala Thr
                885                 890                 895

Ser Leu Thr Asn Glu Gln Lys Gln Phe Leu Glu Thr Ser Val Ala Cys
                900                 905                 910

Glu Lys Gln Met Leu Lys Ile Ile Arg Asp Val Asp Leu Glu Ser Ile
                915                 920                 925

Glu Asp Gly Ser Leu Glu Leu Glu Lys Gly Glu Phe Leu Leu Gly Asn
            930                 935                 940

Val Ile Asn Ala Val Val Ser Gln Val Met Leu Leu Leu Arg Glu Arg
945                 950                 955                 960

Asn Leu Gln Leu Ile Arg Asp Ile Pro Glu Ile Lys Thr Leu Ala
                965                 970                 975

Val Tyr Gly Asp Gln Leu Arg Ile Gln Gln Val Leu Ser Asp Phe Leu
            980                 985                 990

Leu Asn Ile Val Arg Tyr Ala Pro  Ser Pro Asp Gly Trp  Val Glu Ile
            995                 1000                1005

His Val  Arg Pro Arg Ile Lys  Gln Ile Ser Asp Gly  Leu Thr Leu
    1010                1015                1020

Leu His  Ala Glu Phe Arg Met  Val Cys Pro Gly Glu  Gly Leu Pro
    1025                1030                1035

Pro Glu  Leu Ile Gln Asp Met  Phe Asn Asn Ser Arg  Trp Gly Thr
    1040                1045                1050

Gln Glu  Gly Leu Gly Leu Ser  Met Ser Arg Lys Ile  Leu Lys Leu
    1055                1060                1065

Met Asn  Gly Glu Val Gln Tyr  Ile Arg Glu Ala Glu  Arg Cys Tyr
    1070                1075                1080

Phe Tyr  Val Leu Leu Glu Leu  Pro Val Thr Arg Arg  Ser Ser Lys
    1085                1090                1095

Lys Cys
    1100

<210> SEQ ID NO 8
<211> LENGTH: 867
<212> TYPE: PRT
<213> ORGANISM: Glycine max

<400> SEQUENCE: 8

Met Ile Ala Val Asp Glu Pro Ser Phe Arg Ile Leu Ala Tyr Ser Asp
1               5                   10                  15

Asn Ala Arg Asp Met Leu Gly Ile Thr Pro Gln Ser Val Pro Ser Leu
                20                  25                  30

Asp Asp Lys Asn Asp Ala Ala Phe Ala Leu Gly Thr Asp Ile Arg Thr
            35                  40                  45

Leu Phe Thr His Ser Ser Ala Val Leu Leu Glu Lys Ala Phe Ser Ala
        50                  55                  60

Arg Glu Ile Ser Leu Met Asn Pro Ile Trp Ile His Ser Arg Thr Ser
65                  70                  75                  80

Gly Lys Pro Phe Tyr Gly Ile Leu His Arg Ile Asp Val Gly Ile Val
                85                  90                  95

Ile Asp Leu Glu Pro Ala Arg Thr Glu Asp Pro Ala Leu Ser Ile Ala
                100                 105                 110
```

```
Gly Ala Val Gln Ser Gln Lys Leu Ala Val Arg Ala Ile Ser Gln Leu
            115                 120                 125
Gln Ser Leu Pro Gly Gly Asp Val Lys Leu Leu Cys Asp Thr Val Val
        130                 135                 140
Glu Ser Val Arg Glu Leu Thr Gly Tyr Asp Arg Val Met Val Tyr Arg
145                 150                 155                 160
Phe His Glu Asp Glu His Gly Glu Val Val Ala Glu Thr Lys Arg Pro
                165                 170                 175
Asp Leu Glu Pro Tyr Ile Gly Leu His Tyr Pro Ala Thr Asp Ile Pro
            180                 185                 190
Gln Ala Ser Arg Phe Leu Phe Lys Gln Asn Arg Val Arg Met Ile Val
        195                 200                 205
Asp Cys His Ala Ser Ala Val Arg Val Val Gln Asp Glu Ala Leu Val
210                 215                 220
Gln Pro Leu Cys Leu Val Gly Ser Thr Leu Arg Ala Pro His Gly Cys
225                 230                 235                 240
His Ala Gln Tyr Met Ala Asn Met Gly Ser Thr Ala Ser Leu Val Met
                245                 250                 255
Ala Val Ile Ile Asn Gly Asn Asp Glu Glu Gly Val Gly Gly Arg Thr
            260                 265                 270
Ser Met Arg Leu Trp Gly Leu Val Ile Cys His His Thr Ser Ala Arg
        275                 280                 285
Cys Ile Pro Phe Pro Leu Arg Tyr Ala Cys Glu Phe Leu Met Gln Ala
290                 295                 300
Phe Gly Leu Gln Leu Asn Met Glu Leu Gln Leu Ala Ala Gln Ser Leu
305                 310                 315                 320
Glu Lys Arg Val Leu Arg Thr Gln Thr Leu Leu Cys Asp Met Leu Leu
                325                 330                 335
Arg Asp Ser Pro Thr Gly Ile Val Thr Gln Ser Pro Ser Ile Met Asp
            340                 345                 350
Leu Val Lys Cys Asp Gly Ala Ala Leu Tyr Tyr Gln Gly Asn Tyr Tyr
        355                 360                 365
Pro Leu Gly Val Thr Pro Thr Glu Ala Gln Ile Arg Asp Ile Ile Glu
370                 375                 380
Trp Leu Leu Ala Phe His Arg Asp Ser Thr Gly Leu Ser Thr Asp Ser
385                 390                 395                 400
Leu Ala Asp Ala Gly Tyr Pro Gly Ala Ala Ser Leu Gly Asp Ala Val
                405                 410                 415
Cys Gly Met Ala Val Ala Tyr Ile Thr Glu Lys Asp Phe Leu Phe Trp
            420                 425                 430
Phe Arg Ser His Thr Ala Lys Glu Ile Lys Trp Gly Gly Ala Lys His
        435                 440                 445
His Pro Glu Asp Lys Asp Gly Gln Arg Met His Pro Arg Ser Ser
450                 455                 460
Phe Lys Ala Phe Leu Glu Val Val Lys Ser Arg Ser Leu Pro Trp Glu
465                 470                 475                 480
Ser Ala Glu Met Asp Ala Ile His Ser Leu Gln Leu Ile Leu Arg Asp
                485                 490                 495
Ser Phe Lys Asp Ala Glu His Ser Asn Ser Lys Ala Val Leu Asp Pro
            500                 505                 510
Arg Met Ser Glu Leu Glu Leu Gln Gly Val Asp Glu Leu Ser Ser Val
        515                 520                 525
Ala Arg Glu Met Val Arg Leu Ile Glu Thr Ala Thr Ala Pro Ile Phe
```

```
                    530                 535                 540
Ala Val Asp Val Asp Gly Arg Ile Asn Gly Trp Asn Ala Lys Val Ser
545                 550                 555                 560

Glu Leu Thr Gly Leu Pro Val Glu Glu Ala Met Gly Lys Ser Leu Val
                565                 570                 575

Arg Asp Leu Val Phe Lys Glu Ser Glu Thr Val Asp Lys Leu Leu
                580                 585                 590

Ser Arg Ala Leu Lys Gly Glu Glu Asp Lys Asn Val Glu Ile Lys Met
            595                 600                 605

Arg Thr Phe Gly Pro Glu His Gln Asn Lys Ala Val Phe Val Val Val
            610                 615                 620

Asn Ala Cys Ser Ser Lys Asp Tyr Thr Asn Val Val Gly Val Cys
625                 630                 635                 640

Phe Val Gly Gln Asp Val Thr Gly Gln Lys Ile Val Met Asp Lys Phe
                645                 650                 655

Ile Asn Ile Gln Gly Asp Tyr Lys Ala Ile Val His Asn Pro Asn Pro
            660                 665                 670

Leu Ile Pro Pro Ile Phe Ala Ser Asp Asp Asn Thr Cys Cys Leu Glu
            675                 680                 685

Trp Asn Thr Ala Met Glu Lys Leu Thr Gly Trp Ser Arg Ala Asp Val
            690                 695                 700

Ile Gly Lys Met Leu Val Gly Glu Val Phe Gly Ser Cys Cys Gln Leu
705                 710                 715                 720

Lys Gly Ser Asp Ser Ile Thr Lys Phe Met Ile Val Leu His Asn Ala
                725                 730                 735

Leu Gly Gly His Asp Thr Asp Arg Phe Pro Phe Ser Phe Leu Asp Arg
                740                 745                 750

Tyr Gly Lys His Val Gln Ala Phe Leu Thr Ala Asn Lys Arg Val Asn
            755                 760                 765

Met Asp Gly Gln Ile Ile Gly Ala Phe Cys Phe Leu Gln Ile Val Ser
            770                 775                 780

Pro Glu Leu Gln Gln Ala Leu Lys Ala Gln Arg Gln Gln Glu Lys Asn
785                 790                 795                 800

Ser Phe Ala Arg Met Lys Glu Leu Ala Tyr Ile Cys Gln Gly Val Lys
                805                 810                 815

Asn Pro Leu Ser Gly Ile Arg Phe Thr Asn Ser Leu Leu Glu Ala Thr
                820                 825                 830

Cys Leu Ser Asn Glu Gln Lys Gln Phe Leu Glu Thr Ser Ala Ala Cys
            835                 840                 845

Glu Lys Gln Met Leu Lys Ile Ile His Asp Val Asp Ile Glu Ser Ile
            850                 855                 860

Glu Asp Gly
865

<210> SEQ ID NO 9
<211> LENGTH: 1130
<212> TYPE: PRT
<213> ORGANISM: Solanum tuberosum

<400> SEQUENCE: 9

Met Ala Ser Gly Ser Arg Thr Lys His Ser His Asn Ser Ser Gln
1               5                   10                  15

Ala Gln Ser Gly Thr Ser Asn Val Asn Tyr Lys Asp Ser Ile Ser
            20                  25                  30
```

```
Lys Ala Ile Ala Gln Tyr Thr Ala Asp Ala Arg Leu His Ala Val Phe
            35                  40                  45

Glu Gln Ser Gly Glu Ser Gly Lys Phe Phe Asp Tyr Ser Glu Ser Val
 50                  55                  60

Lys Thr Thr Thr Gln Ser Val Pro Glu Arg Gln Ile Thr Ala Tyr Leu
 65                  70                  75                  80

Thr Lys Ile Gln Arg Gly Gly His Ile Gln Pro Phe Gly Cys Met Ile
                 85                  90                  95

Ala Val Asp Glu Ala Ser Phe Arg Val Ile Ala Tyr Ser Glu Asn Ala
            100                 105                 110

Phe Glu Met Leu Ser Leu Thr Pro Gln Ser Val Pro Ser Leu Glu Lys
            115                 120                 125

Cys Glu Ile Leu Thr Ile Gly Thr Asp Val Arg Thr Leu Phe Thr Pro
            130                 135                 140

Ser Ser Ser Val Leu Leu Glu Arg Ala Phe Gly Ala Arg Glu Ile Thr
145                 150                 155                 160

Leu Leu Asn Pro Ile Trp Ile His Ser Lys Asn Ser Gly Lys Pro Phe
                165                 170                 175

Tyr Ala Ile Leu His Arg Val Asp Val Gly Ile Ala Ile Asp Leu Glu
            180                 185                 190

Pro Ala Arg Thr Glu Asp Pro Ala Leu Ser Ile Ala Gly Ala Val Gln
            195                 200                 205

Ser Gln Lys Leu Ala Val Arg Ala Ile Ser His Leu Gln Ser Leu Pro
210                 215                 220

Gly Gly Asp Ile Lys Leu Leu Cys Asp Thr Val Val Glu Ser Val Arg
225                 230                 235                 240

Glu Leu Thr Gly Tyr Asp Arg Val Met Val Tyr Lys Phe His Glu Asp
                245                 250                 255

Glu His Gly Glu Val Val Ala Glu Ser Lys Arg Ser Asp Leu Glu Pro
            260                 265                 270

Tyr Ile Gly Leu His Tyr Pro Ala Thr Asp Ile Pro Gln Ala Ser Arg
            275                 280                 285

Phe Leu Phe Lys Gln Asn Arg Val Arg Met Ile Val Asp Cys His Ala
290                 295                 300

Thr Pro Val Arg Val Thr Gln Asp Glu Ser Leu Met Gln Pro Leu Cys
305                 310                 315                 320

Leu Val Gly Ser Thr Leu Arg Ala Pro His Gly Cys His Ala Gln Tyr
                325                 330                 335

Met Ala Asn Met Gly Ser Ile Ala Ser Leu Thr Leu Ala Val Ile Ile
            340                 345                 350

Asn Gly Asn Asp Glu Glu Ala Val Gly Gly Arg Asn Ser Met Arg
            355                 360                 365

Leu Trp Gly Leu Val Val Gly His His Thr Ser Val Arg Ser Ile Pro
            370                 375                 380

Phe Pro Leu Arg Tyr Ala Cys Glu Phe Leu Met Gln Ala Phe Gly Leu
385                 390                 395                 400

Gln Leu Asn Met Glu Leu Gln Leu Ala Ser Gln Leu Ser Glu Lys His
                405                 410                 415

Val Leu Arg Thr Gln Thr Leu Leu Cys Asp Met Leu Leu Arg Asp Ser
            420                 425                 430

Pro Pro Gly Ile Val Thr Gln Ser Pro Ser Ile Met Asp Leu Val Lys
            435                 440                 445

Cys Asp Gly Ala Ala Leu Tyr Tyr Gln Gly Lys Tyr Tyr Pro Leu Gly
```

```
                450                 455                 460
Val Thr Pro Thr Glu Ala Gln Ile Lys Asp Ile Val Glu Trp Leu Leu
465                 470                 475                 480

Ala Tyr His Gly Asp Ser Thr Gly Leu Ser Thr Asp Ser Leu Ala Asp
                485                 490                 495

Ala Gly Tyr Pro Gly Ala Ala Ser Leu Gly Asp Ala Val Cys Gly Met
                500                 505                 510

Ala Val Ala Tyr Ile Ser Ser Lys Asp Phe Leu Phe Trp Phe Arg Ser
                515                 520                 525

His Thr Ala Lys Glu Ile Lys Trp Gly Gly Ala Lys His His Pro Glu
                530                 535                 540

Asp Lys Asp Asp Gly Leu Arg Met His Pro Arg Ser Ser Phe Lys Ala
545                 550                 555                 560

Phe Leu Glu Val Val Lys Ser Arg Ser Ser Pro Trp Glu Asn Ala Glu
                565                 570                 575

Met Asp Ala Ile His Ser Leu Gln Leu Ile Leu Arg Asp Ser Phe Lys
                580                 585                 590

Asp Ala Glu Ala Ser Asn Ser Lys Ala Ile Val His Ala His Leu Gly
                595                 600                 605

Glu Met Glu Leu Gln Gly Ile Asp Glu Leu Ser Ser Val Ala Arg Glu
                610                 615                 620

Met Val Arg Leu Ile Glu Thr Ala Thr Ala Pro Ile Phe Ala Val Asp
625                 630                 635                 640

Val Glu Gly Arg Ile Asn Gly Trp Asn Ala Lys Val Ala Glu Leu Thr
                645                 650                 655

Gly Leu Ser Val Glu Glu Ala Met Gly Lys Ser Leu Val His Glu Leu
                660                 665                 670

Val Tyr Lys Glu Ser Gln Glu Thr Ala Glu Lys Leu Leu Tyr Asn Ala
                675                 680                 685

Leu Arg Gly Glu Glu Asp Lys Asn Val Glu Ile Lys Leu Arg Thr Phe
                690                 695                 700

Gly Ala Glu Gln Leu Glu Lys Ala Val Phe Val Val Asn Ala Cys
705                 710                 715                 720

Ala Ser Lys Asp Tyr Thr Asn Asn Ile Val Gly Val Cys Phe Val Gly
                725                 730                 735

Gln Asp Val Thr Gly Glu Lys Val Val Met Asp Lys Phe Ile Asn Ile
                740                 745                 750

Gln Gly Asp Tyr Lys Ala Ile Val His Ser Pro Asn Pro Leu Ile Pro
                755                 760                 765

Pro Ile Phe Ala Ser Asp Glu Asn Thr Cys Cys Ser Glu Trp Asn Thr
770                 775                 780

Ala Met Glu Lys Leu Thr Gly Trp Ser Arg Gly Glu Ile Val Gly Lys
785                 790                 795                 800

Met Leu Val Gly Glu Ile Phe Gly Ser Cys Cys Arg Leu Lys Gly Pro
                805                 810                 815

Asp Ala Met Thr Lys Phe Met Ile Val Leu His Asn Ala Ile Gly Gly
                820                 825                 830

Gln Asp Thr Asp Lys Phe Pro Phe Ser Phe Asp Arg Asn Gly Lys
                835                 840                 845

Tyr Val Gln Ala Leu Leu Thr Ala Asn Lys Arg Val Asn Met Glu Gly
                850                 855                 860

Asn Thr Ile Gly Ala Phe Cys Phe Ile Gln Ile Ala Ser Pro Glu Leu
865                 870                 875                 880
```

```
Gln Gln Ala Leu Arg Val Gln Arg Gln Glu Lys Lys Cys Tyr Ser
            885                 890                 895

Gln Met Lys Glu Leu Ala Tyr Ile Cys Gln Glu Ile Lys Ser Pro Leu
        900                 905                 910

Asn Gly Ile Arg Phe Thr Asn Ser Leu Leu Glu Ala Thr Asn Leu Thr
    915                 920                 925

Glu Asn Gln Lys Gln Tyr Leu Glu Thr Ser Ala Ala Cys Glu Arg Gln
930                 935                 940

Met Ser Lys Ile Ile Arg Asp Val Asp Leu Glu Asn Ile Glu Asp Gly
945                 950                 955                 960

Ser Leu Thr Leu Glu Lys Glu Asp Phe Phe Leu Gly Ser Val Ile Asp
            965                 970                 975

Ala Val Val Ser Gln Val Met Leu Leu Leu Arg Glu Lys Gly Val Gln
        980                 985                 990

Leu Ile Arg Asp Ile Pro Glu Glu Ile Lys Thr Leu Thr Val His Gly
            995                 1000                1005

Asp Gln Val Arg Ile Gln Gln Val Leu Ala Asp Phe Leu Leu Asn
        1010                1015                1020

Met Val Arg Tyr Ala Pro Ser Pro Asp Gly Trp Val Glu Ile Gln
        1025                1030                1035

Leu Arg Pro Ser Met Met Pro Ile Ser Asp Gly Val Thr Gly Val
        1040                1045                1050

His Ile Glu Leu Arg Ile Ile Cys Pro Gly Glu Gly Leu Pro Pro
        1055                1060                1065

Glu Leu Val Gln Asp Met Phe His Ser Ser Arg Trp Val Thr Gln
        1070                1075                1080

Glu Gly Leu Gly Leu Ser Thr Cys Arg Lys Met Leu Lys Leu Met
        1085                1090                1095

Asn Gly Glu Ile Gln Tyr Ile Arg Glu Ser Glu Arg Cys Tyr Phe
        1100                1105                1110

Leu Ile Val Leu Asp Leu Pro Met Thr Arg Lys Gly Pro Lys Ser
        1115                1120                1125

Val Gly
        1130

<210> SEQ ID NO 10
<211> LENGTH: 1121
<212> TYPE: PRT
<213> ORGANISM: Pisum sativum
<220> FEATURE:
<221> NAME/KEY: MISC_FEATURE
<222> LOCATION: (28)..(28)
<223> OTHER INFORMATION: Xaa can be any naturally occurring amino acid
      (Ser or Arg)

<400> SEQUENCE: 10

Ser Asn Asn Asn Asn Arg Asn Ile Lys Arg Glu Ser Leu Ser Met
1               5                   10                  15

Arg Lys Ala Ile Ala Gln Tyr Thr Glu Asp Ala Xaa Leu His Ala Val
            20                  25                  30

Phe Glu Lys Ser Gly Asp Ser Phe Asp Tyr Ala Gln Ser Ile Arg Val
        35                  40                  45

Thr Ala Ala Thr Glu Ser Val Pro Glu Gln Gln Ile Thr Ala Tyr Leu
    50                  55                  60

Ala Lys Ile Gln Arg Gly Gly Phe Ile Gln Pro Phe Gly Ser Met Ile
65                  70                  75                  80
```

```
Ala Val Asp Glu Thr Ser Phe Arg Val Leu Ala Tyr Ser Glu Asn Ala
            85                  90                  95

Arg Asp Met Leu Gly Ile Ala Pro Gln Ser Val Pro Ser Met Glu Asp
            100                 105                 110

Asp Ser Ser Ser Ser Ser Phe Phe Ser Leu Gly Val Asp Val Arg Ser
            115                 120                 125

Leu Phe Ser Ala Ser Ser Ser Val Leu Leu Glu Lys Ala Phe Ser Ala
            130                 135                 140

Arg Glu Ile Ser Leu Met Asn Pro Ile Trp Ile His Ser Arg Ser Thr
145                 150                 155                 160

Gly Lys Pro Phe Tyr Gly Ile Leu His Arg Ile Asp Ile Gly Val Val
            165                 170                 175

Ile Asp Leu Glu Pro Ala Arg Ser Glu Asp Pro Ala Leu Ser Ile Ala
            180                 185                 190

Gly Ala Val Gln Ser Gln Lys Leu Ala Val Arg Ala Ile Ser Gln Leu
            195                 200                 205

Gln Ala Leu Pro Gly Gly Asp Val Lys Leu Leu Cys Asp Ala Val Val
            210                 215                 220

Glu Ser Val Arg Glu Leu Thr Gly Tyr Asp Arg Val Met Val Tyr Lys
225                 230                 235                 240

Phe His Glu Asp Glu His Gly Glu Val Val Ala Glu Ser Lys Arg Val
            245                 250                 255

Asp Leu Glu Pro Tyr Ile Gly Leu His Tyr Pro Ala Thr Asp Ile Pro
            260                 265                 270

Gln Ala Ser Arg Phe Leu Phe Lys Gln Asn Arg Val Arg Met Ile Val
            275                 280                 285

Asp Cys Asn Ala Ser Pro Val Arg Val Phe Gln Asp Glu Ala Leu Val
            290                 295                 300

Gln Pro Val Cys Leu Val Gly Ser Thr Leu Arg Ala Pro His Gly Cys
305                 310                 315                 320

His Ala Gln Tyr Met Ala Asn Met Gly Ser Ile Ala Ser Leu Ala Met
            325                 330                 335

Ala Val Ile Ile Asn Gly Asn Asp Glu Asp Gly Gly Gly Ile Gly Gly
            340                 345                 350

Ala Ala Arg Gly Ser Met Arg Leu Trp Gly Leu Val Val Cys His His
            355                 360                 365

Thr Ser Ala Arg Cys Ile Pro Phe Pro Leu Arg Tyr Ala Cys Glu Phe
370                 375                 380

Leu Met Gln Ala Phe Gly Leu Gln Leu Asn Met Glu Leu Gln Leu Ala
385                 390                 395                 400

Val Gln Ser Leu Glu Lys Arg Val Leu Lys Thr Gln Thr Leu Leu Cys
            405                 410                 415

Asp Met Leu Leu Arg Asp Ser His Thr Gly Ile Val Thr Gln Ser Pro
            420                 425                 430

Ser Ile Met Asp Leu Val Lys Cys Asp Gly Ala Ala Leu Tyr Tyr Gln
            435                 440                 445

Gly Asn Tyr His Pro Leu Gly Val Thr Pro Thr Glu Ser Gln Ile Arg
            450                 455                 460

Asp Ile Ile Asp Trp Leu Leu Ala Phe His Ser Asp Ser Thr Gly Leu
465                 470                 475                 480

Ser Thr Asp Ser Leu Ala Asp Ala Gly Tyr Pro Gly Ala Ala Ser Leu
            485                 490                 495
```

```
Gly Asp Ala Val Cys Gly Met Ala Val Ala Tyr Ile Thr Glu Lys Asp
            500                 505                 510

Phe Leu Phe Trp Phe Arg Ser His Thr Ala Lys Glu Ile Lys Trp Gly
        515                 520                 525

Gly Ala Lys His His Pro Glu Asp Lys Asp Gly Gln Lys Met His
    530                 535                 540

Pro Arg Ser Ser Phe Lys Ala Phe Leu Glu Val Val Lys Ile Arg Ser
545                 550                 555                 560

Met Gln Trp Asp Asn Ala Glu Met Asp Ala Ile His Ser Leu Gln Leu
                565                 570                 575

Ile Leu Arg Asp Ser Phe Lys Glu Ala Glu Asn Asn Asp Ser Lys Ala
            580                 585                 590

Val Val His Thr His Met Ala Glu Leu Glu Leu Gln Gly Val Asp Glu
        595                 600                 605

Leu Ser Ser Val Ala Arg Glu Met Val Arg Leu Ile Glu Thr Ala Thr
    610                 615                 620

Ala Pro Ile Phe Ala Val Asp Val Asp Gly Arg Ile Asn Gly Trp Asn
625                 630                 635                 640

Ala Lys Val Ser Glu Leu Thr Gly Leu Leu Val Glu Glu Ala Met Gly
                645                 650                 655

Lys Ser Leu Val His Asp Leu Val Tyr Lys Glu Ser Arg Glu Thr Val
            660                 665                 670

Asp Lys Leu Leu Ser His Ala Leu Lys Gly Glu Glu Asp Lys Asn Val
        675                 680                 685

Glu Ile Lys Met Lys Thr Phe Gly Pro Gly Asn Gln Asn Lys Ala Val
    690                 695                 700

Phe Ile Val Val Asn Ala Cys Ser Ser Lys Asp Tyr Thr Asn Asn Ile
705                 710                 715                 720

Val Gly Val Cys Phe Val Gly Gln Asp Ile Thr Gly Gln Lys Val Val
                725                 730                 735

Met Asp Lys Phe Ile Asn Ile Gln Gly Asp Tyr Lys Ala Ile Val His
            740                 745                 750

Ser Pro Asn Pro Leu Ile Pro Pro Ile Phe Ala Ser Asp Asp Asn Thr
        755                 760                 765

Cys Cys Leu Glu Trp Asn Asn Ala Met Glu Lys Leu Ser Gly Trp Ser
    770                 775                 780

Arg Ala Asp Val Ile Gly Lys Leu Leu Val Gly Glu Val Phe Gly Ser
785                 790                 795                 800

Phe Cys Gln Leu Lys Gly Ser Asp Ala Met Thr Lys Phe Met Ile Val
                805                 810                 815

Leu His Asn Ala Leu Gly Gly His Asp Thr Asp Lys Phe Pro Leu Ser
            820                 825                 830

Phe Leu Asp Arg His Gly Lys Tyr Val His Thr Phe Leu Thr Ala Asn
        835                 840                 845

Lys Arg Val Asn Met Asp Gly Gln Ile Ile Gly Ala Phe Cys Phe Leu
    850                 855                 860

Gln Ile Val Asn Pro Glu Leu Gln Gln Ala Leu Thr Val Gln Arg Gln
865                 870                 875                 880

Gln Asp Ser Ser Ser Leu Ala Arg Met Lys Glu Leu Ala Tyr Ile Cys
                885                 890                 895

Gln Glu Val Lys Asn Pro Leu Ser Gly Ile Arg Phe Thr Asn Ser Leu
            900                 905                 910

Leu Glu Ser Thr Cys Leu Thr Asp Glu Gln Lys Gln Leu Leu Glu Thr
```

-continued

```
            915                 920                 925
Ser Val Ala Cys Glu Lys Gln Met Leu Lys Ile Val Arg Asp Ile Ala
    930                 935                 940
Leu Glu Ser Ile Glu Asp Gly Ser Leu Glu Leu Glu Lys Gln Glu Phe
945                 950                 955                 960
Leu Leu Glu Asn Val Ile Asn Ala Val Val Ser Gln Val Met Leu Leu
                965                 970                 975
Leu Arg Asp Arg Lys Leu Gln Leu Ile Arg Asp Ile Pro Glu Glu Ile
            980                 985                 990
Lys Ala Leu Ala Val Tyr Gly Asp Gln Leu Arg Ile Gln Gln Val Leu
        995                 1000                1005
Ala Asp Phe Leu Met Asn Val Val Arg Tyr Ala Pro Ser Pro Asp
    1010                1015                1020
Gly Trp Val Glu Ile His Val Phe Pro Arg Ile Lys Gln Ile Ser
    1025                1030                1035
Glu Gly Leu Thr Leu Leu His Ala Glu Phe Arg Met Val Cys Pro
    1040                1045                1050
Gly Glu Gly Leu Pro Pro Glu Leu Ile Gln Asp Met Phe His Asn
    1055                1060                1065
Ser Arg Trp Val Thr Gln Glu Gly Leu Gly Leu Ser Met Ser Arg
    1070                1075                1080
Lys Ile Ile Lys Leu Met Asn Gly Glu Val Gln Tyr Val Arg Glu
    1085                1090                1095
Ala Glu Arg Cys Tyr Phe Leu Val Leu Leu Glu Leu Pro Val Thr
    1100                1105                1110
Arg Arg Ser Ser Lys Ala Ile Asn
    1115                1120

<210> SEQ ID NO 11
<211> LENGTH: 1129
<212> TYPE: PRT
<213> ORGANISM: Vitis vinifera

<400> SEQUENCE: 11

Met Ser Ser Gly Asn Arg Gly Thr Gln Ser His His Gln Ala Gln Ser
1               5                   10                  15
Ser Gly Thr Ser Asn Leu Arg Val Tyr His Thr Asp Ser Met Ser Lys
            20                  25                  30
Ala Ile Ala Gln Tyr Thr Met Asp Ala Arg Leu His Ala Val Tyr Glu
        35                  40                  45
Gln Ser Gly Glu Ser Gly Lys Ser Phe Asp Tyr Ser Gln Ser Val Arg
    50                  55                  60
Thr Thr Thr Gln Ser Val Pro Glu Gln Gln Ile Thr Ala Tyr Leu Ser
65                  70                  75                  80
Lys Ile Gln Arg Gly Gly His Ile Gln Pro Phe Gly Cys Met Leu Ala
                85                  90                  95
Val Asp Glu Ala Thr Phe Arg Val Ile Ala Phe Ser Glu Asn Ala Arg
            100                 105                 110
Glu Met Leu Gly Leu Thr Pro Gln Ser Val Pro Ser Leu Glu Lys Pro
        115                 120                 125
Glu Ile Leu Leu Val Gly Thr Asp Val Arg Thr Leu Phe Thr Pro Ser
    130                 135                 140
Ser Ala Val Leu Leu Glu Lys Ala Phe Arg Ala Arg Glu Ile Thr Leu
145                 150                 155                 160
```

```
Leu Asn Pro Val Trp Ile His Ser Lys Asn Ser Gly Lys Pro Phe Tyr
            165                 170                 175
Ala Ile Leu His Arg Ile Asp Val Gly Ile Val Asp Leu Glu Pro
        180                 185                 190
Ala Arg Thr Glu Asp Pro Ala Leu Ser Ile Ala Gly Ala Val Gln Ser
        195                 200                 205
Gln Lys Leu Ala Val Arg Ala Ile Ser His Leu Gln Ser Leu Pro Gly
    210                 215                 220
Gly Asp Ile Asn Leu Leu Cys Glu Thr Val Val Glu Asn Val Arg Glu
225                 230                 235                 240
Leu Thr Gly Tyr Asp Arg Val Met Val Tyr Lys Phe His Glu Asp Glu
            245                 250                 255
His Gly Glu Val Val Ala Glu Ser Lys Arg Ser Asp Leu Glu Pro Tyr
        260                 265                 270
Ile Gly Leu His Tyr Pro Ala Thr Asp Ile Pro Gln Ala Ser Arg Phe
        275                 280                 285
Leu Phe Arg Gln Asn Arg Val Arg Met Ile Val Asp Cys His Ala Thr
    290                 295                 300
Pro Val Leu Val Ile Gln Asp Glu Gly Leu Met Gln Pro Leu Cys Leu
305                 310                 315                 320
Val Gly Ser Thr Leu Arg Ala Pro His Gly Cys His Ala Gln Tyr Met
            325                 330                 335
Ala Asn Met Gly Ser Thr Ala Ser Leu Ala Met Ala Val Ile Ile Asn
        340                 345                 350
Gly Ser Asp Glu Glu Ala Ile Gly Gly Arg Asn Leu Met Arg Leu Trp
        355                 360                 365
Gly Leu Val Val Cys His His Thr Ser Ala Arg Cys Ile Pro Phe Pro
    370                 375                 380
Leu Arg Tyr Ala Cys Glu Phe Leu Met Gln Ala Phe Gly Leu Gln Leu
385                 390                 395                 400
Asn Met Glu Leu Gln Leu Ala Ser Gln Leu Ser Glu Lys His Val Leu
            405                 410                 415
Arg Thr Gln Thr Leu Leu Cys Asp Met Leu Leu Arg Asp Ser Pro Thr
        420                 425                 430
Gly Ile Val Thr Gln Ser Pro Ser Ile Met Asp Leu Val Lys Cys Asp
        435                 440                 445
Gly Ala Ala Leu Tyr Tyr Gln Gly Lys Tyr Tyr Pro Thr Gly Val Thr
    450                 455                 460
Pro Thr Glu Ala Gln Ile Lys Asp Ile Ala Glu Trp Leu Leu Ala Asn
465                 470                 475                 480
His Ala Asp Ser Thr Gly Leu Ser Thr Asp Ser Leu Ala Asp Ala Gly
            485                 490                 495
Tyr Pro Gly Ala Ala Ser Leu Gly Asp Ala Val Cys Gly Met Ala Val
        500                 505                 510
Ala Tyr Ile Thr Ser Arg Asp Phe Leu Phe Trp Phe Arg Ser His Thr
        515                 520                 525
Ala Lys Glu Ile Lys Trp Gly Gly Ala Lys His His Pro Glu Asp Lys
    530                 535                 540
Asp Asp Gly Gln Arg Met His Pro Arg Ser Ser Phe Lys Ala Phe Leu
545                 550                 555                 560
Glu Val Val Lys Ser Arg Ser Leu Pro Trp Glu Asn Ala Glu Met Asp
            565                 570                 575
Ala Ile His Ser Leu Gln Leu Ile Leu Arg Asp Ser Phe Lys Asp Ala
```

-continued

```
                580                 585                 590
Thr Asp Gly Ser Asn Ser Lys Ala Val Met His Ala Gln Leu Gly Glu
                595                 600                 605
Leu Glu Leu Gln Gly Met Asp Glu Leu Ser Ser Val Ala Arg Glu Met
            610                 615                 620
Val Arg Leu Ile Glu Thr Ala Thr Ala Pro Ile Phe Ala Val Asp Val
625                 630                 635                 640
Asp Gly Cys Ile Asn Gly Trp Asn Ala Lys Val Ala Glu Leu Thr Gly
                645                 650                 655
Leu Ser Val Glu Glu Ala Met Gly Lys Ser Leu Val His Asp Leu Val
            660                 665                 670
Tyr Lys Glu Ser Glu Glu Thr Val Asp Lys Leu Leu His His Ala Leu
            675                 680                 685
Arg Gly Glu Glu Asp Lys Asn Val Glu Ile Lys Leu Arg Thr Phe Asp
            690                 695                 700
Ser Gln Gln His Lys Lys Ala Val Phe Val Val Asn Ala Cys Ser
705                 710                 715                 720
Ser Arg Asp Tyr Thr Asn Asn Ile Val Gly Val Cys Phe Val Gly Gln
                725                 730                 735
Asp Val Thr Gly Gln Lys Val Val Met Asp Lys Phe Ile His Ile Gln
            740                 745                 750
Gly Asp Tyr Lys Ala Ile Val His Ser Pro Asn Pro Leu Ile Pro Pro
            755                 760                 765
Ile Phe Ala Ser Asp Glu Asn Thr Val Cys Ser Glu Trp Asn Thr Ala
770                 775                 780
Met Glu Lys Leu Thr Gly Trp Ser Arg Gly Asp Ile Ile Gly Lys Ile
785                 790                 795                 800
Leu Val Gly Glu Ile Phe Gly Ser Ser Cys Arg Leu Lys Gly Pro Asp
                805                 810                 815
Ala Leu Thr Lys Phe Met Ile Val Leu His Asn Ala Ile Gly Gly Gln
            820                 825                 830
Asp Thr Asp Lys Phe Pro Phe Ser Phe Phe Asp Gln Asn Gly Lys Tyr
            835                 840                 845
Val Gln Ala Leu Leu Thr Ala Asn Lys Arg Val Asn Ile Glu Gly Gln
850                 855                 860
Ile Ile Gly Ala Phe Cys Phe Leu Gln Ile Ala Ser Pro Glu Leu Gln
865                 870                 875                 880
Gln Ala Leu Lys Val Gln Arg Gln Gln Glu Lys Lys Cys Phe Ala Arg
            885                 890                 895
Met Lys Glu Leu Ala Tyr Ile Cys Gln Glu Ile Lys Asn Pro Leu Ser
            900                 905                 910
Gly Ile Arg Phe Thr Asn Ser Leu Leu Glu Ala Thr Asp Leu Thr Glu
            915                 920                 925
Asp Gln Lys Gln Phe Leu Glu Thr Ser Ala Ala Cys Glu Lys Gln Met
            930                 935                 940
Ser Lys Ile Ile Arg Asp Val Asp Leu Asp Ser Ile Glu Asp Gly Ser
945                 950                 955                 960
Leu Glu Leu Glu Arg Ala Glu Phe Leu Leu Gly Ser Val Ile Asn Ala
                965                 970                 975
Val Val Ser Gln Val Met Ile Leu Leu Arg Glu Arg Asp Leu Gln Leu
            980                 985                 990
Ile Arg Asp Ile Pro Glu Glu Val  Lys Thr Leu Ala Val  Tyr Gly Asp
            995                 1000                1005
```

```
Gln Val Arg Ile Gln Val Leu Ala Asp Phe Leu Leu Asn Met
    1010            1015                1020

Val Arg Tyr Ala Pro Ser Pro Asp Gly Trp Ile Glu Ile Gln Val
    1025            1030                1035

Cys Pro Arg Leu Lys Gln Ile Ser Glu Glu Val Lys Leu Met His
    1040            1045                1050

Ile Glu Phe Arg Met Val Cys Pro Gly Glu Gly Leu Pro Pro Asn
    1055            1060                1065

Leu Ile Gln Asp Met Phe His Ser Ser Arg Trp Met Thr Gln Glu
    1070            1075                1080

Gly Leu Gly Leu Ser Met Cys Arg Lys Ile Leu Lys Leu Ile Asn
    1085            1090                1095

Gly Glu Val Gln Tyr Ile Arg Glu Ser Glu Arg Cys Tyr Phe Leu
    1100            1105                1110

Ile Ser Ile Glu Leu Pro Ile Pro His Arg Gly Ser Lys Ser Val
    1115            1120                1125

Asp

<210> SEQ ID NO 12
<211> LENGTH: 200
<212> TYPE: PRT
<213> ORGANISM: Arabidopsis thaliana

<400> SEQUENCE: 12

Ser Gln Lys Leu Ala Val Arg Ala Ile Ser Gln Leu Gln Ala Leu Pro
1               5                   10                  15

Gly Gly Asp Ile Lys Leu Leu Cys Asp Thr Val Val Glu Ser Val Arg
                20                  25                  30

Asp Leu Thr Gly Tyr Asp Arg Val Met Val Tyr Lys Phe His Glu Asp
                35                  40                  45

Glu His Gly Glu Val Val Ala Glu Ser Lys Arg Asp Asp Leu Glu Pro
        50                  55                  60

Tyr Ile Gly Leu His Tyr Pro Ala Thr Asp Ile Pro Gln Ala Ser Arg
65                  70                  75                  80

Phe Leu Phe Lys Gln Asn Arg Val Arg Met Ile Val Asp Cys Asn Ala
                85                  90                  95

Thr Pro Val Leu Val Val Gln Asp Asp Arg Leu Thr Gln Ser Met Cys
                100                 105                 110

Leu Val Gly Ser Thr Leu Arg Ala Pro His Gly Cys His Ser Gln Tyr
            115                 120                 125

Met Ala Asn Met Gly Ser Ile Ala Ser Leu Ala Met Ala Val Ile Ile
        130                 135                 140

Asn Gly Asn Glu Asp Asp Gly Ser Asn Val Ala Ser Gly Arg Ser Ser
145                 150                 155                 160

Met Arg Leu Trp Gly Leu Val Val Cys His His Thr Ser Ser Arg Cys
                165                 170                 175

Ile Pro Phe Pro Leu Arg Tyr Ala Cys Glu Phe Leu Met Gln Ala Phe
                180                 185                 190

Gly Leu Gln Leu Asn Met Glu Leu
            195                 200

<210> SEQ ID NO 13
<211> LENGTH: 201
<212> TYPE: PRT
<213> ORGANISM: Zea mays
```

-continued

<400> SEQUENCE: 13

```
Ser Gln Lys Leu Ala Val Arg Ala Ile Ser Arg Leu Gln Ala Leu Pro
 1               5                  10                  15

Gly Gly Asp Val Lys Leu Leu Cys Asp Thr Val Val Glu His Val Arg
            20                  25                  30

Glu Leu Thr Gly Tyr Asp Arg Val Met Val Tyr Arg Phe His Glu Asp
        35                  40                  45

Glu His Gly Glu Val Val Ala Glu Ser Arg Arg Asp Asn Leu Glu Pro
    50                  55                  60

Tyr Leu Gly Leu His Tyr Pro Ala Thr Asp Ile Pro Gln Ala Ser Arg
65                  70                  75                  80

Phe Leu Phe Arg Gln Asn Arg Val Arg Met Ile Ala Asp Cys His Ala
                85                  90                  95

Thr Pro Val Arg Val Ile Gln Asp Pro Gly Leu Ser Gln Pro Leu Cys
            100                 105                 110

Leu Val Gly Ser Thr Leu Arg Ala Pro His Gly Cys His Ala Gln Tyr
        115                 120                 125

Met Ala Asn Met Gly Ser Ile Ala Ser Leu Val Met Ala Val Ile Ile
    130                 135                 140

Ser Ser Gly Gly Asp Asp Glu Gln Thr Gly Arg Gly Ile Ser Ser
145                 150                 155                 160

Ala Met Lys Leu Trp Gly Leu Val Val Cys His His Thr Ser Pro Arg
                165                 170                 175

Cys Ile Pro Phe Pro Leu Arg Tyr Ala Cys Glu Phe Leu Met Gln Ala
            180                 185                 190

Phe Gly Leu Gln Leu Asn Met Glu Leu
        195                 200
```

<210> SEQ ID NO 14
<211> LENGTH: 202
<212> TYPE: PRT
<213> ORGANISM: Oryza sativa

<400> SEQUENCE: 14

```
Ser Gln Lys Leu Ala Val Arg Ala Ile Ser Arg Leu Gln Ala Leu Pro
 1               5                  10                  15

Gly Gly Asp Val Lys Leu Leu Cys Asp Thr Val Val Glu His Val Arg
            20                  25                  30

Glu Leu Thr Gly Tyr Asp Arg Val Met Val Tyr Arg Phe His Glu Asp
        35                  40                  45

Glu His Gly Glu Val Val Ala Glu Ser Arg Arg Ser Asn Leu Glu Pro
    50                  55                  60

Tyr Ile Gly Leu His Tyr Pro Ala Thr Asp Ile Pro Gln Ala Ser Arg
65                  70                  75                  80

Phe Leu Phe Arg Gln Asn Arg Val Arg Met Ile Ala Asp Cys His Ala
                85                  90                  95

Ala Pro Val Arg Val Ile Gln Asp Pro Ala Leu Thr Gln Pro Leu Cys
            100                 105                 110

Leu Val Gly Ser Thr Leu Arg Ser Pro His Gly Cys His Ala Gln Tyr
        115                 120                 125

Met Ala Asn Met Gly Ser Ile Ala Ser Leu Val Met Ala Val Ile Ile
    130                 135                 140

Ser Ser Gly Gly Asp Asp Asp His Asn Ile Ala Arg Gly Ser Ile Pro
145                 150                 155                 160
```

Ser Ala Met Lys Leu Trp Gly Leu Val Val Cys His His Thr Ser Pro
            165                 170                 175

Arg Cys Ile Pro Phe Pro Leu Arg Tyr Ala Cys Glu Phe Leu Met Gln
        180                 185                 190

Ala Phe Gly Leu Gln Leu Asn Met Glu Leu
        195                 200

<210> SEQ ID NO 15
<211> LENGTH: 201
<212> TYPE: PRT
<213> ORGANISM: Sorghum bicolor

<400> SEQUENCE: 15

Ser Gln Lys Leu Ala Val Arg Ala Ile Ser Arg Leu Gln Ala Leu Pro
1               5                   10                  15

Gly Gly Asp Ile Lys Leu Leu Cys Asp Thr Val Val Glu His Val Arg
            20                  25                  30

Glu Leu Thr Gly Tyr Asp Arg Val Met Val Tyr Arg Phe His Glu Asp
        35                  40                  45

Glu His Gly Glu Val Val Ala Glu Ser Arg Arg Asp Asn Leu Glu Pro
    50                  55                  60

Tyr Leu Gly Leu His Tyr Pro Ala Thr Asp Ile Pro Gln Ala Ser Arg
65                  70                  75                  80

Phe Leu Phe Arg Gln Asn Arg Val Arg Met Ile Ala Asp Cys His Ala
                85                  90                  95

Thr Pro Val Arg Val Ile Gln Asp Pro Gly Met Ser Gln Pro Leu Cys
            100                 105                 110

Leu Val Gly Ser Thr Leu Arg Ala Pro His Gly Cys His Ala Gln Tyr
        115                 120                 125

Met Ala Asn Met Gly Ser Ile Ala Ser Leu Val Met Ala Val Ile Ile
    130                 135                 140

Ser Ser Gly Gly Asp Asp Glu Gln Thr Gly Arg Gly Ile Ser Ser
145                 150                 155                 160

Ala Met Lys Leu Trp Gly Leu Val Val Cys His His Thr Ser Pro Arg
                165                 170                 175

Cys Ile Pro Phe Pro Leu Arg Tyr Ala Cys Glu Phe Leu Met Gln Ala
            180                 185                 190

Phe Gly Leu Gln Leu Asn Met Glu Leu
        195                 200

<210> SEQ ID NO 16
<211> LENGTH: 197
<212> TYPE: PRT
<213> ORGANISM: Glycine max

<400> SEQUENCE: 16

Ser Gln Lys Leu Ala Val Arg Ala Ile Ser Gln Leu Gln Ser Leu Pro
1               5                   10                  15

Gly Gly Asp Val Lys Leu Leu Cys Asp Thr Val Val Glu Ser Val Arg
            20                  25                  30

Glu Leu Thr Gly Tyr Asp Arg Val Met Val Tyr Lys Phe His Glu Asp
        35                  40                  45

Glu His Gly Glu Val Val Ser Glu Ser Lys Arg Pro Asp Leu Glu Pro
    50                  55                  60

Tyr Ile Gly Leu His Tyr Pro Ala Thr Asp Ile Pro Gln Ala Ser Arg
65                  70                  75                  80

```
Phe Leu Phe Lys Gln Asn Arg Val Arg Met Ile Val Asp Cys His Ala
                85                  90                  95

Ser Ala Val Arg Val Val Gln Asp Glu Ala Leu Val Gln Pro Leu Cys
            100                 105                 110

Leu Val Gly Ser Thr Leu Arg Ala Pro His Gly Cys His Ala Gln Tyr
        115                 120                 125

Met Ala Asn Met Gly Ser Ile Ala Ser Leu Val Met Ala Val Ile Ile
    130                 135                 140

Asn Gly Asn Asp Glu Glu Gly Val Gly Gly Arg Ser Ser Met Arg Leu
145                 150                 155                 160

Trp Gly Leu Val Val Cys His His Thr Ser Ala Arg Cys Ile Pro Phe
                165                 170                 175

Pro Leu Arg Tyr Ala Cys Glu Phe Leu Met Gln Ala Phe Gly Leu Gln
            180                 185                 190

Leu Asn Met Glu Leu
        195

<210> SEQ ID NO 17
<211> LENGTH: 197
<212> TYPE: PRT
<213> ORGANISM: Glycine max

<400> SEQUENCE: 17

Ser Gln Lys Leu Ala Val Arg Ala Ile Ser Gln Leu Gln Ser Leu Pro
1               5                   10                  15

Gly Gly Asp Val Lys Leu Leu Cys Asp Thr Val Val Glu Ser Val Arg
            20                  25                  30

Glu Leu Thr Gly Tyr Asp Arg Val Met Val Tyr Arg Phe His Glu Asp
        35                  40                  45

Glu His Gly Glu Val Val Ala Glu Thr Lys Arg Pro Asp Leu Glu Pro
    50                  55                  60

Tyr Ile Gly Leu His Tyr Pro Ala Thr Asp Ile Pro Gln Ala Ser Arg
65                  70                  75                  80

Phe Leu Phe Lys Gln Asn Arg Val Arg Met Ile Val Asp Cys His Ala
                85                  90                  95

Ser Ala Val Arg Val Val Gln Asp Glu Ala Leu Val Gln Pro Leu Cys
            100                 105                 110

Leu Val Gly Ser Thr Leu Arg Ala Pro His Gly Cys His Ala Gln Tyr
        115                 120                 125

Met Ala Asn Met Gly Ser Thr Ala Ser Leu Val Met Ala Val Ile Ile
    130                 135                 140

Asn Gly Asn Asp Glu Glu Gly Val Gly Gly Arg Thr Ser Met Arg Leu
145                 150                 155                 160

Trp Gly Leu Val Ile Cys His His Thr Ser Ala Arg Cys Ile Pro Phe
                165                 170                 175

Pro Leu Arg Tyr Ala Cys Glu Phe Leu Met Gln Ala Phe Gly Leu Gln
            180                 185                 190

Leu Asn Met Glu Leu
        195

<210> SEQ ID NO 18
<211> LENGTH: 197
<212> TYPE: PRT
<213> ORGANISM: Glycine max

<400> SEQUENCE: 18
```

-continued

```
Ser Gln Lys Leu Ala Val Arg Ala Ile Ser Gln Leu Gln Ser Leu Pro
1               5                   10                  15

Gly Gly Asp Val Lys Leu Leu Cys Asp Thr Val Val Glu Ser Val Arg
                20                  25                  30

Glu Leu Thr Gly Tyr Asp Arg Val Met Val Tyr Lys Phe His Glu Asp
            35                  40                  45

Glu His Gly Glu Val Val Ser Glu Ser Lys Arg Pro Asp Leu Glu Pro
        50                  55                  60

Tyr Ile Gly Leu His Tyr Pro Ala Thr Asp Ile Pro Gln Ala Ser Arg
65                  70                  75                  80

Phe Leu Phe Lys Gln Asn Arg Val Arg Met Ile Val Asp Cys His Ala
                85                  90                  95

Ser Ala Val Arg Val Val Gln Asp Glu Ala Leu Val Gln Pro Leu Cys
                100                 105                 110

Leu Val Gly Ser Thr Leu Arg Ala Pro His Gly Cys His Ala Gln Tyr
            115                 120                 125

Met Ala Asn Met Gly Ser Ile Ala Ser Leu Val Met Ala Val Ile Ile
        130                 135                 140

Asn Gly Asn Asp Glu Glu Gly Val Gly Gly Arg Ser Ser Met Arg Leu
145                 150                 155                 160

Trp Gly Leu Val Val Cys His His Thr Ser Ala Arg Cys Ile Pro Phe
                165                 170                 175

Pro Leu Arg Tyr Ala Cys Glu Phe Leu Met Gln Ala Phe Gly Leu Gln
                180                 185                 190

Leu Asn Met Glu Leu
            195

<210> SEQ ID NO 19
<211> LENGTH: 197
<212> TYPE: PRT
<213> ORGANISM: Glycine max

<400> SEQUENCE: 19

Ser Gln Lys Leu Ala Val Arg Ala Ile Ser Gln Leu Gln Ser Leu Pro
1               5                   10                  15

Gly Gly Asp Val Lys Leu Leu Cys Asp Thr Val Val Glu Ser Val Arg
                20                  25                  30

Glu Leu Thr Gly Tyr Asp Arg Val Met Val Tyr Arg Phe His Glu Asp
            35                  40                  45

Glu His Gly Glu Val Val Ala Glu Thr Lys Arg Pro Asp Leu Glu Pro
        50                  55                  60

Tyr Ile Gly Leu His Tyr Pro Ala Thr Asp Ile Pro Gln Ala Ser Arg
65                  70                  75                  80

Phe Leu Phe Lys Gln Asn Arg Val Arg Met Ile Val Asp Cys His Ala
                85                  90                  95

Ser Ala Val Arg Val Val Gln Asp Glu Ala Leu Val Gln Pro Leu Cys
                100                 105                 110

Leu Val Gly Ser Thr Leu Arg Ala Pro His Gly Cys His Ala Gln Tyr
            115                 120                 125

Met Ala Asn Met Gly Ser Thr Ala Ser Leu Val Met Ala Val Ile Ile
        130                 135                 140

Asn Gly Asn Asp Glu Glu Gly Val Gly Gly Arg Thr Ser Met Arg Leu
145                 150                 155                 160

Trp Gly Leu Val Ile Cys His His Thr Ser Ala Arg Cys Ile Pro Phe
```

165                 170                 175

Pro Leu Arg Tyr Ala Cys Glu Phe Leu Met Gln Ala Phe Gly Leu Gln
                180                 185                 190

Leu Asn Met Glu Leu
        195

<210> SEQ ID NO 20
<211> LENGTH: 198
<212> TYPE: PRT
<213> ORGANISM: Solanum tuberosum

<400> SEQUENCE: 20

Ser Gln Lys Leu Ala Val Arg Ala Ile Ser His Leu Gln Ser Leu Pro
1               5                   10                  15

Gly Gly Asp Ile Lys Leu Leu Cys Asp Thr Val Val Glu Ser Val Arg
                20                  25                  30

Glu Leu Thr Gly Tyr Asp Arg Val Met Val Tyr Lys Phe His Glu Asp
            35                  40                  45

Glu His Gly Glu Val Val Ala Glu Ser Lys Arg Ser Asp Leu Glu Pro
        50                  55                  60

Tyr Ile Gly Leu His Tyr Pro Ala Thr Asp Ile Pro Gln Ala Ser Arg
65                  70                  75                  80

Phe Leu Phe Lys Gln Asn Arg Val Arg Met Ile Val Asp Cys His Ala
                85                  90                  95

Thr Pro Val Arg Val Thr Gln Asp Glu Ser Leu Met Gln Pro Leu Cys
            100                 105                 110

Leu Val Gly Ser Thr Leu Arg Ala Pro His Gly Cys His Ala Gln Tyr
        115                 120                 125

Met Ala Asn Met Gly Ser Ile Ala Ser Leu Thr Leu Ala Val Ile Ile
    130                 135                 140

Asn Gly Asn Asp Glu Glu Ala Val Gly Gly Arg Asn Ser Met Arg
145                 150                 155                 160

Leu Trp Gly Leu Val Val Gly His His Thr Ser Val Arg Ser Ile Pro
                165                 170                 175

Phe Pro Leu Arg Tyr Ala Cys Glu Phe Leu Met Gln Ala Phe Gly Leu
                180                 185                 190

Gln Leu Asn Met Glu Leu
        195

<210> SEQ ID NO 21
<211> LENGTH: 201
<212> TYPE: PRT
<213> ORGANISM: Pisum sativum

<400> SEQUENCE: 21

Ser Gln Lys Leu Ala Val Arg Ala Ile Ser Gln Leu Gln Ala Leu Pro
1               5                   10                  15

Gly Gly Asp Val Lys Leu Leu Cys Asp Ala Val Val Glu Ser Val Arg
                20                  25                  30

Glu Leu Thr Gly Tyr Asp Arg Val Met Val Tyr Lys Phe His Glu Asp
            35                  40                  45

Glu His Gly Glu Val Val Ala Glu Ser Lys Arg Val Asp Leu Glu Pro
        50                  55                  60

Tyr Ile Gly Leu His Tyr Pro Ala Thr Asp Ile Pro Gln Ala Ser Arg
65                  70                  75                  80

Phe Leu Phe Lys Gln Asn Arg Val Arg Met Ile Val Asp Cys Asn Ala

```
                85                  90                  95
Ser Pro Val Arg Val Phe Gln Asp Glu Ala Leu Val Gln Pro Val Cys
                100                 105                 110

Leu Val Gly Ser Thr Leu Arg Ala Pro His Gly Cys His Ala Gln Tyr
            115                 120                 125

Met Ala Asn Met Gly Ser Ile Ala Ser Leu Ala Met Ala Val Ile Ile
    130                 135                 140

Asn Gly Asn Asp Glu Asp Gly Gly Ile Gly Gly Ala Ala Arg Gly
145                 150                 155                 160

Ser Met Arg Leu Trp Gly Leu Val Val Cys His His Thr Ser Ala Arg
                165                 170                 175

Cys Ile Pro Phe Pro Leu Arg Tyr Ala Cys Glu Phe Leu Met Gln Ala
                180                 185                 190

Phe Gly Leu Gln Leu Asn Met Glu Leu
            195                 200

<210> SEQ ID NO 22
<211> LENGTH: 197
<212> TYPE: PRT
<213> ORGANISM: Vitis vinifera

<400> SEQUENCE: 22

Ser Gln Lys Leu Ala Val Arg Ala Ile Ser His Leu Gln Ser Leu Pro
1               5                   10                  15

Gly Gly Asp Ile Asn Leu Leu Cys Glu Thr Val Val Glu Asn Val Arg
                20                  25                  30

Glu Leu Thr Gly Tyr Asp Arg Val Met Val Tyr Lys Phe His Glu Asp
            35                  40                  45

Glu His Gly Glu Val Val Ala Glu Ser Lys Arg Ser Asp Leu Glu Pro
        50                  55                  60

Tyr Ile Gly Leu His Tyr Pro Ala Thr Asp Ile Pro Gln Ala Ser Arg
65                  70                  75                  80

Phe Leu Phe Arg Gln Asn Arg Val Arg Met Ile Val Asp Cys His Ala
                85                  90                  95

Thr Pro Val Leu Val Ile Gln Asp Glu Gly Leu Met Gln Pro Leu Cys
                100                 105                 110

Leu Val Gly Ser Thr Leu Arg Ala Pro His Gly Cys His Ala Gln Tyr
            115                 120                 125

Met Ala Asn Met Gly Ser Thr Ala Ser Leu Ala Met Ala Val Ile Ile
    130                 135                 140

Asn Gly Ser Asp Glu Glu Ala Ile Gly Gly Arg Asn Leu Met Arg Leu
145                 150                 155                 160

Trp Gly Leu Val Val Cys His His Thr Ser Ala Arg Cys Ile Pro Phe
                165                 170                 175

Pro Leu Arg Tyr Ala Cys Glu Phe Leu Met Gln Ala Phe Gly Leu Gln
            180                 185                 190

Leu Asn Met Glu Leu
            195

<210> SEQ ID NO 23
<211> LENGTH: 3516
<212> TYPE: DNA
<213> ORGANISM: Arabidopsis thaliana

<400> SEQUENCE: 23
atggtttccg gagtcggggg tagtggcggt ggccgtggcg gtggccgtgg cggagaagaa      60
```

-continued

```
gaaccgtcgt caagtcacac tcctaataac cgaagaggag gagaacaagc tcaatcgtcg    120
ggaacgaaat ctctcagacc aagaagcaac actgaatcaa tgagcaaagc aattcaacag    180
tacaccgtcg acgcaagact ccacgccgtt tcgaacaat ccggcgaatc agggaaatca     240
ttcgactact cacaatcact caaaacgacg acgtacggtt cctctgtacc tgagcaacag    300
atcacagctt atctctctcg aatccagcga ggtggttaca ttcagccttt cggatgtatg    360
atcgccgtcg atgaatccag tttccggatc atcggttaca gtgaaaacgc cagagaaatg    420
ttagggatta tgcctcaatc tgttcctact cttgagaaac ctgagattct agctatggga    480
actgatgtga gatctttgtt cacttcttcg agctcgattc tactcgagcg tgctttcgtt    540
gctcgagaga ttaccttgtt aaatccggtt tggatccatt ccaagaatac tggtaaaccg    600
ttttacgcca ttcttcatag gattgatgtt ggtgttgtta ttgatttaga gccagctaga    660
actgaagatc ctgcgctttc tattgctggt gctgttcaat cgcagaaact cgcggttcgt    720
gcgatttctc agttacaggc tcttcctggt ggagatatta agcttttgtg tgacactgtc    780
gtggaaagtg tgagggactt gactggttat gatcgtgtta tggtttataa gtttcatgaa    840
gatgagcatg gagaagttgt agctgagagt aaacgagatg atttagagcc ttatattgga    900
ctgcattatc ctgctactga tattcctcaa gcgtcaaggt tcttgtttaa gcagaaccgt    960
gtccgaatga tagtagattg caatgccaca cctgttcttg tggtccagga cgataggcta   1020
actcagtcta tgtgcttggt tggttctact cttagggctc ctcatggttg tcactctcag   1080
tatatggcta acatgggatc tattgcgtct ttagcaatgg cggttataat caatggaaat   1140
gaagatgatg ggagcaatgt agctagtgga agaagctcga tgaggctttg gggtttggtt   1200
gtttgccatc acacttcttc tcgctgcata ccgtttccgc taaggtatgc ttgtgagttt   1260
ttgatgcagg ctttcggttt acagttaaac atggaattgc agttagcttt gcaaatgtca   1320
gagaaacgcg ttttgagaac gcagacactg ttatgtgata tgcttctgcg tgactcgcct   1380
gctggaattg ttacacagag tcccagtatc atggacttag tgaaatgtga cggtgcagca   1440
tttctttacc acgggaagta ttacccgttg gtgttgctc ctagtgaagt tcagataaaa     1500
gatgttgtgg agtggttgct tgcgaatcat gcggattcaa ccggattaag cactgatagt    1560
ttaggcgatg cggggtatcc cggtgcagct gcgttagggg atgctgtgtg cggtatggca    1620
gttgcatata tcacaaaaag agactttctt ttttggtttc gatctcacac tgcgaaagaa    1680
atcaaatggg gaggcgctaa gcatcatccg gaggataaag atgatgggca acgaatgcat    1740
cctcgttcgt cctttcaggc ttttcttgaa gttgttaaga gccggagtca gccatgggaa    1800
actgcggaaa tggatgcgat tcactcgctc cagcttattc tgagagactc ttttaaagaa    1860
tctgaggcgc tatgaactc taaagttgtg atggtgtgg ttcagccatg tagggatatg      1920 gcggggggaac agggggattga tgagttaggt gcagttgcaa gagagatggt taggctcatt   1980
gagactgcaa ctgttcctat attcgctgtg gatgccggag gctgcatcaa tggatggaac    2040
gctaagattg cagagttgac aggtctctca gttgaagaag ctatggggaa gtctctggtt    2100 tctgattta tatacaaaga gaatgaagca actgtcaata agcttctttc tcgtgctttg     2160
agaggggacg aggaaaagaa tgtggaggtt aagctgaaaa ctttcagccc cgaactacaa    2220
gggaaagcag ttttttgtggt tgtgaatgct tgttccagca aggactactt gaacaacatt    2280
gtcggcgttt gttttgttgg acaagacgtt actagtcaga aaatcgtaat ggataagttc    2340
atcaacatac aaggagatta caaggctatt gtacatagcc caaaccctct aatcccgcca    2400
```

```
atttttgctg ctgacgagaa cacgtgctgc ctggaatgga acatggcgat ggaaaagctt    2460
acgggttggt ctcgcagtga agtgattggg aaaatgattg tcggggaagt gtttgggagc    2520
tgttgcatgc taaagggtcc tgatgcttta accaagttca tgattgtatt gcataatgcg    2580
attggtggcc aagatacgga taagttccct ttcccattct ttgaccgcaa tgggaagttt    2640
gttcaggctc tattgactgc aaacaagcgg gttagcctcg agggaaaggt tattgggggct   2700 ttctgttttct tgcaaatccc gagccctgag ctgcagcaag ctttagcagt ccaacggagg   2760
caggacacag agtgtttcac gaaggcaaaa gagttggctt atatttgtca ggtgataaag    2820
aatcctttga gcggtatgcg tttcgcaaac tcattgttgg aggccacaga cttgaacgag    2880
gaccagaagc agttacttga aacaagtgtt tcttgcgaga aacagatctc aaggatcgtc    2940
ggggacatgg atcttgaaag cattgaagac ggttcatttg tgctaaagag ggaagagttt    3000
ttccttggaa gtgtcataaa cgcgattgta agtcaagcga tgttcttatt aagggacaga    3060
ggtcttcagc tgatccgtga cattcccgaa gagatcaaat caatagaggt ttttggagac    3120
cagataagga ttcaacagct cctggctgag tttctgctga gtataatccg gtatgcacca    3180
tctcaagagt gggtggagat ccatttaagc caactttcaa agcaaatggc tgatggattc    3240
gccgccatcc gcacagaatt cagaatggcg tgtccaggtg aaggtctgcc tccagagcta    3300
gtccgagaca tgttccatag cagcaggtgg acaagccctg aaggtttagg tctaagcgta    3360
tgtcgaaaga ttttaaagct aatgaacggt gaggttcaat acatccgaga atcagaacgg    3420
tcctatttcc tcatcattct ggaactccct gtacctcgaa agcgaccatt gtcaactgct    3480
agtggaagtg gtgacatgat gctgatgatg ccatat                              3516
```

<210> SEQ ID NO 24
<211> LENGTH: 3483
<212> TYPE: DNA
<213> ORGANISM: Zea mays

<400> SEQUENCE: 24

```
atggcgtcgg gcagccgcgc cacgcccacg cgctccccct cctccgcgcg gcccgaggcg    60
ccgcgtcacg cgcaccacca ccaccactcc cagtcgtcgg gcgggagcac gtcccgcgcg    120
ggcgggggag ccgcggccac ggagtcggtc tccaaggccg tcgcccagta caccctagac    180
gcgcgcctac acgcggtgtt cgagcaatcg ggcgcgtcgg gccgcagctt cgactactcc    240
caatcgctgc gcgcgccgcc cacgccgtcc tccgagcagc agatcgccgc ctacctctcc    300
cgcatccagc gcgcggcca catccagccc ttcggctgca cgctcgccgt cgccgacgac    360
tcctccttcc gcctcctcgc cttctccgag aactccccg acctgctcga cctgtcgcct   420
caccactccg ttccctcgct ggactcctct cgccgccccc acgtttccct gggtgccgac    480
gcgcgcctcc tcttctcccc ctcgtccgcg gtcctcctag agcgcgcctt cgccgcgcgc    540
gagatctcgc tgctcaaccc gatatggatc cactccaggg tctcctccaa gccgttctac    600
gccatcctcc accgcatcga cgtcggcgtc gtcatcgacc tcgagcccgc ccgcaccgag    660
gaccccgctc tctccatcgc cggtgcagtc cagtcccaga aactggcggt ccgcgccatc    720
tcccgcctcc aggcgctacc cggcggggac gtcaagcttc tctgcgacac agtcgtggag    780
catgttcgcg agctcacggg ttatgaccgt gtcatggtgt acaggttcca tgaagacgag    840
cacggggaag ttgtcgccga gagccgggcg acaacctgg agccttacct cggattgcat    900
tatcccgcca cagatatccc ccaggcgtcg cgcttcctgt tccggcagaa ccgcgtgcga    960
atgattgccg attgccatgc caccccggtg agagttattc aagatcctgg gctgtcgcag    1020
```

```
cctctgtgtt tggtaggctc cacgctacgc gctccacacg ggtgtcatgc acagtacatg   1080
gcgaacatgg ggtcaattgc gtcgcttgtt atggcagtca tcattagcag tggcggtgac   1140
gatgagcaaa caggtcgggg tggcatctcg tcggcaatga agttgtgggg gttagtggtg   1200
tgccaccata catcaccacg gtgtatccct tttccattga ggtatgcttg cgagtttctc   1260
atgcaggcat ttgggttgca gctcaacatg gagttgcagc ttgcgcacca gctgtcagag   1320
aagcacattc tgcgaactca gacgctattg tgtgacatgc tactacgaga ttcaccaact   1380
ggcatcgtca cgcagagccc cagcatcatg gaccttgtga agtgcgacgg ggctgcactg   1440
tattatcatg ggaaatacta tccattgggt gtcactccca ctgagtctca gattaaggat   1500
atcatcgagt ggttgacggt gtttcatggg gactcaacag ggctcagcac agatagcctg   1560
gctgatgcag gctaccttgg tgctgctgca ctaggggagg ctgtgtgtgg aatggcggtg   1620
gcttatatta caccgagtga ttacttgttt tggtttcggt cacacacagc taaagagatc   1680
aaatggggtg gcgcaaagca tcaccctgag gataaggatg atggtcagag gatgcaccca   1740
cggtcgtcat tcaaggcatt tcttgaagtg gttaaaagca gaagcctgcc atgggagaat   1800
gcagaaatgg acgcaataca ttccttgcag ctcatattgc gtgactcctt cagggatgct   1860
gcagagggca ccaacaactc aaaagccatt gtcaatggac aagttcagct tcgggagcta   1920
gaattgcggg ggataaatga gcttagttcc gtagcaagag agatggttcg gttgatagag   1980
acagcaacag tacccatatt tgcagtagat actgatgggt gtataaatgg ttggaatgca   2040
aagattgctg agttgacagg gctttcagtt gaggaggcaa tggcaaaatc tctggtaaat   2100
gatcttatct tcaaggaatc tgaggcgaca gttgaaaaac tactctcacg agctttaaga   2160
ggtgaggaag acaaaaatgt ggagataaag ttgaagacat ttgggtcaga gcaatataag   2220
ggaccaatat ttgttgttgt caatgcttgt tctagtagag attacacaca aaatattgta   2280
ggtgtctgtt ttgttggaca agatgtcaca ggacaaaagg tggtcatgga taaatttgtt   2340
aacatacaag gggactacaa agctattgta cacaatccta atcctctgat accaccaatt   2400
tttgcatcag atgagaacac ttcttgttca gaatggaata cagccatgga aaaacttaca   2460
ggatggtcga gaggtgaagt tgttggtaag tttcttattg gagaggtgtt tggaaattgt   2520
tgtcgactca agggcccaga tgcattgaca aaattcatgg ttattattca caacgctata   2580
ggaggacagg attatgagaa gttccctttt tcattttttg acaagaatgg aaagtatgtg   2640
caggccttat tgaccgccaa tacaaggagc aaaatggatg gtaaatccat tggagccttt   2700
tgtttcctgc agattgcaag cactgaaata cagcaagcct tgagattcga gagacaacaa   2760
gaaaagaagt gttacgcaag gatgaaagaa ttggcctata tttgccagga gataaagaat   2820
cctcttagtg gcatccgatt taccaactct ctgttgcaga tgactgattt aaatgatgac   2880
cagaggcagt tccttgaaac tagctctgct tgtgagaaac agatgtccaa gattgttaag   2940
gacgccagtc tccaaagtat cgaggacggc tcttttggtgc ttgagcaaag tgagttttct   3000
cttggagacg ttatgaatgc tgttgtcagc caagcaatgt tattgttgag agagagggat   3060
ttacaactta ttcgggacat ccctgatgaa atcaaggatg cgtcagcgta tggtgatcaa   3120
tgtagaattc aacaagtttt ggctgacttc ttgctaagca tggtgcggtc tgctccatcc   3180
gagaatggtt gggtagaaat acaagtcaga ccaaatgtaa aacagaattc tgatggaaca   3240
aatacagaac ttttcatatt caggtttgcc tgccctggtg agggcctccc tgctgacgtc   3300
gtccaggata tgttcagcaa ttcccaatgg tcaacacaag aaggcgtagg actaagcaca   3360
```

```
tgcaggaaga tcctcaaatt gatgggtggc gaggtccaat acatcagaga gtcagagcgg   3420
agtttcttcc tcatcgtcct cgagcagccc caacctcgtc cagcagctgg tagagaaatc   3480
gtc                                                                 3483

<210> SEQ ID NO 25
<211> LENGTH: 3513
<212> TYPE: DNA
<213> ORGANISM: Oryza sativa

<400> SEQUENCE: 25
atgggctcgg gtagccgcgc cacgcccacg cgctccccct cctccgcgcg gcccgcggcg     60
ccgcggcacc agcaccacca ctcgcagtcc tcgggcggga gcacgtcccg cgcgggaggg    120
ggtggcgggg cgggggagg  gggagggggc ggcgcggccg ccgcggagtc ggtgtccaag    180
gccgtggcgc agtacaccct ggacgcgcgc ctccacgccg tgttcgagca gtcgggcgcg    240
tcggccgcca gcttcgacta cacgcagtcg ctgcgtgcgt cccccacccc gtcctccgag    300
cagcagatcg ccgcctacct ctcccgcatc agcgcggcg  ggcacataca gcccttcggc    360
tgcacgctcg ccgtcgccga cgactcctcc ttccgcctcc tcgcctactc cgagaacacc    420
gccgacctgc tcgacctgtc gccccaccac tccgtcccct cgctcgactc ctccgcggtg    480 cctcccccg  tctcgctcgg cgcagacgcg cgcctccttt tcgctcccctc gtccgccgtc    540 ctcctcgagc gcgccttcgc cgcgcgcgag atctcgctgc tcaacccgct ctggatccac    600
tccagggtct cctctaaacc cttctacgcc atcctccacc gcatcgatgt cggcgtcgtc    660
atcgacctcg agcccgcccg caccgaggat cctgcactct ccatcgctgg cgcagtccag    720
tctcagaagc tcgcggtccg tgccatctcc cgcctccagg cgcttcccgg cggtgacgtc    780
aagctccttt gcgacaccgt tgttgagcat gttagagagc tcacaggtta tgaccgcgtt    840
atggtgtaca ggttccatga ggatgagcat ggagaagtcg ttgccgagag ccggcgcagt    900
aaccttgagc cctacatcgg gttgcattat cctgctacag atatcccaca ggcatcacgc    960
ttcctgttcc ggcagaaccg tgtgcggatg attgctgatt gccatgctgc gccggtgagg   1020
gtcatccagg atcctgcact aacacagccg ctgtgcttgg ttgggtccac gctgcgttcg   1080
ccgcatggtt gccatgcgca gtatatggcg aacatgggtt ccattgcatc tcttgttatg   1140
gcagtgatca ttagtagtgg tggggatgat gatcataaca ttgcacgggg cagcatcccg   1200
tcggcgatga agttgtgggg gttggtagta tgccaccaca catctccacg gtgcatccct   1260
ttcccactac ggtatgcatg cgagttcctc atgcaagcct ttgggttgca gctcaacatg   1320
gagttgcagc ttgcacacca actgtcagag aaacacattc tgcggacgca gacactgctg   1380
tgtgatatgc tactccggga ttcaccaact ggcattgtca cacaaagccc cagcatcatg   1440
gaccttgtga agtgtgatgg tgctgctctg tattaccatg ggaagtacta ccctcttggt   1500
gtcactccca cagaagttca gattaaggac atcatcgagt ggttgactat gtgccatgga   1560
gactccacag ggctcagcac agatagcctt gctgatgcag gctactctgg tgctgctgca   1620
ctaggagatg cagtgagcgg aatggcggta gcatatatca cgccaagtga ttatttgttt   1680
tggttccggt cacacacagc taaggagata aagtggggtg gtgcaaagca tcatccagag   1740
gataaggatg atggacaacg aatgcatcca cgatcatcgt tcaaggcatt tcttgaagtt   1800
gtgaagagta ggagcttacc atgggagaat gcagagatgg atgcaatca  ttccttgcag   1860 ctcatattgc gggactcttt cagagattct gcagagggca caagtaactc aaaagccata   1920
gtgaatggcc aggttcagct tggggagcta gaattacggg gaatagatga gcttagctcg   1980
```

```
gtagcgaggg agatggttcg gttgatcgag acagcaacag tacccatctt tgcagtagat    2040
actgatggat gtataaatgg ttggaatgca aaggttgctg agctgacagg cctctctgtt    2100
gaggaagcaa tgggcaaatc attggtaaat gatctcatct tcaaggaatc tgaggaaaca    2160
gtaaacaagc tactctcacg agctttaaga ggtgatgaag acaaaaatgt agagataaag    2220
ttgaagacat tcgggccaga acaatctaaa ggaccaatat tcgttattgt gaatgcttgt    2280
tctagcaggg attacactaa aaatattgtt ggtgtttgtt ttgttggcca agatgtcaca    2340
ggacaaaagg tggtcatgga taaatttatc aacatacaag gggattacaa ggctatcgta    2400
cacaacccta atcctctcat accccccaata tttgcttcag atgagaatac ttgttgtttg    2460
gagtggaaca cagcaatgga aaaactcaca ggatggtcaa gagggggaagt tgttggtaag    2520 cttctggtcg gtgaggtctt tggtaattgt tgtcgactca agggcccaga tgcattaacg    2580
aaattcatga ttgtcctaca aacgctata ggaggacagg attgtgaaaa gttccccttt    2640
tcattttttg acaagaatgg gaaatacgtg caggccttat tgactgcaaa cacgaggagc    2700
agaatggatg gtgaggccat aggagccttc tgtttcttgc agattgcaag tcctgaatta    2760
cagcaagcct ttgagattca gagacaccat gaaaagaagt gttatgcaag gatgaaggaa    2820
ttggcttaca tttaccagga aataaagaat cctctcaacg gtatccgatt tacaaactcg    2880
ttattggaga tgactgatct aaaggatgac cagaggcagt tcttgaaaac cagcactgct    2940
tgtgagaaac agatgtccaa aattgttaag gatgctagcc tccaaagtat tgaggatggc    3000
tctttggtgc ttgagaaagg tgaattttca ctaggtagtg ttatgaatgc tgttgtcagc    3060
caagtgatga tacagttgag agaaagagat ttacaactta ttcgagatat ccctgatgaa    3120 attaagaag cctcagcata tggtgaccaa tatagaattc aacaagttt atgtgacttt    3180 ttgctaagca tggtgaggtt tgctccagct gaaaatggct gggtggagat acaggtcaga    3240
ccaaatataa aacaaaattc tgatggaaca gacacaatgc ttttcctctt caggtttgcc    3300
tgtcctggcg aaggccttcc cccagagatt gttcaagaca tgtttagtaa ctcccgctgg    3360
acaacccaag agggtattgg cctaagcata tgcaggaaga tcctaaaatt gatgggtggc    3420
gaggtccaat atataaggga gtcggagcgg agtttcttcc atatcgtact tgagctgccc    3480
cagcctcagc aagcagcaag taggggggaca agc                                3513
```

<210> SEQ ID NO 26
<211> LENGTH: 3534
<212> TYPE: DNA
<213> ORGANISM: Sorghum bicolor

<400> SEQUENCE: 26

```
atggcgtcgg gcagccgcgc cacgcccacg cgctccccct cctccgcgcg acccgaggcg     60
ccgcgtcacg cgcaccacca ccaccaccac cactcgcagt cgtcgggcgg gagcacgtcc    120
cgcgcgggcg gggaggtgg aggaggagga ggtggcgggg gcaccgcggc cacggctacg    180
gccacggcca cggagtcggt ctccaaggcc gtggcgcagt acaccctaga cgcgcggctc    240
cacgcggtgt tcgagcaatc gggcgcgtcg ggccgcagct tcgactactc ccagtcgctg    300
cgcgcgccgc ccacgccgtc ctccgagcag cagatcgccg cctacctctc ccgcatccag    360
cgcggcggcc acatccagcc cttcggctgc acgctcgccg tcgccgacga ctcctccttc    420
cgcctcctcg ccttctccga gaacgccgcc gacctgctcg acctgtcgcc gcaccactcc    480
gttccctcgc tcgattccgc ggcgccgccc ccgtttccc tgggtgccga cgcgcgcctc    540
```

```
ctcttctccc cctcgtccgc ggtcctcctg gagcgcgcct tcgccgcgcg cgagatctcg    600
ctgctcaacc cgctatggat ccactccagg gtctcttcca agccgttcta cgccatcctc    660
caccgcatcg acgtcggcgt cgtcatcgac ctcgagcccg cccgcaccga ggaccccgct    720
ctctccatcg ccggcgcagt ccagtcccag aaactcgcgg tccgtgccat ctcccgcctc    780
caggcgctac ctggcgggga catcaagctc ctctgcgaca cagtcgtgga gcatgttcgc    840
gagctcacgg gttacgaccg tgtcatggtg tacaggttcc atgaagacga gcatggggaa    900
gttgtcgccg agagccggcg cgataacctt gagccttacc tcggattgca ttatcccgcc    960
acagatatcc cccaggcatc gcgcttcctg ttccggcaga accgcgtgcg gatgattgct   1020
gattgccatg ccaccccggt gagagtcata caagatcctg ggatgtcgca gccactgtgt   1080
ttggtaggct ccacgcttcg tgctccacac gggtgccatg cgcagtacat ggcgaacatg   1140
gggtcaattg catcacttgt tatggcagtc atcattagca gtggtggtga tgacgagcaa   1200
acaggtcggg gaggcatctc ctcggcaatg aagttgtggg ggttagtggt gtgtcaccat   1260
acgtcaccac ggtgtatccc ttttccattg aggtatgctt gcgagtttct catgcaggca   1320
tttgggctgc agctcaacat ggaattgcag cttgcgcatc agctgtcaga gaagcacatt   1380
ttgcgaactc agacgctatt gtgtgacatg ctattgcgag attcaccaac tggcatcgtc   1440
acgcagagcc ccagcatcat ggaccttgtg aagtgtgatg gggctgcact gtattatcat   1500
gggaagtact atccattggg tgtcactccc actgagtctc agattaagga tatcattgag   1560
tggttgacgg tgtgtcatgg ggactcaaca gggctcagca cagacagcct tgctgatgca   1620
ggctaccttg gtgctgctgc attaggggat gctgtgtgtg aatggcggt ggcttatatt   1680 acaccgagtg attacttgtt ttggtttcgg tcacacacag ctaaagagat caaatggggt   1740
ggcgcaaagc atcaccctga ggataaggat gatggtcaga ggatgcaccc acggtcatca   1800
ttcaaggcat ttcttgaagt ggttaaaagc agaagcctac catgggagaa tgcagaaatg   1860
gacgcgatac attccttgca actcatattg cgtgactcct tcagagatgc tgcagagggc   1920
actagcaact caaaagccat tgtcaatgga caagctcagc ttggggagct agaattgcgg   1980
gggataaatg agcttagctc tgtaccaaga gagatggttc ggttgataga gacagcaaca   2040
gtacccatat ttgcagtaga tactgatgga tgcataaatg gttggaatgc gaaaattgct   2100
gagttgacag cctttcagt tgaggaggca atgggcaaat ctctggtaaa cgatcttatc   2160
ttcaaggaat ctgaggagat agtcgaaaag ctactctcac gagctttaag aggtgaggaa   2220
gacaaaaatg tggagataaa gttgaagaca tttgggtcag agcaatctaa cggagcaata   2280
tttgttattg tcaatgcttg ttccagtaga gattacacac aaaatattgt tggtgtctgt   2340
tttgttggac aagatgtcac aggacaaaag gtggtcatgg ataaatttat caacatacaa   2400
ggggactata aagctattgt acacaatcct aatcctctga tacccccaat ttttgcatca   2460
gatgagaaca cttcttgttc agaatggaac acagccatgg aaaaacttac aggatggtcg   2520
agaggtgaag ttgttggtaa atttcttatt ggagaggtgt ttggaagttt ttgtcgactc   2580
aagggcccag atgcattgac aaagttcatg gttgtcattc acaatgctat aggagggcag   2640
gattatgaga agttcccttt ttcatttttc gacaagaatg gaaagtatgt gcaggcctta   2700
ttgaccgcca acacaaggag caaaatggat ggtaaatcca ttggcgcctt tgttttttg    2760 cagattgcaa gcgctgaaat acagcaagcc tttgagattc agagacaaca agaaaagaag   2820
tgttatgcaa ggatgaaaga attggccat atttgccagg agataaagaa tcctcttagt   2880
ggcatccgat ttaccaactc tctgttgcaa atgactgatt taaatgatga tcagaggcag   2940
```

-continued

| | |
|---|---|
| ttccttgaaa cttgctctgc ttgtgagaaa cagatgttca agattgttaa ggacgccact | 3000 |
| ctccaaagta ttgaggacgg ctctttggta cttgagaaaa gtgagttttc ttttggagac | 3060 |
| gttatgaatg ctgttgtcag ccaagcaatg ttattgttga gggagaggga tttacaactt | 3120 |
| attcgggata tccctgatga aatcaaggat gcatcagcat atggtgatca atttagaatt | 3180 |
| caacaagttt tggctgactt cttgctaagc atggtgcgat ctgctccgtc cgagaatggc | 3240 |
| tgggtagaaa tacaagtcag accaaatgta aaacagaatt ctgacggaac agatacagag | 3300 |
| cttttcatct tcaggtttgc ctgccctggt gagggccttc ccgctgacat tgtccaggat | 3360 |
| atgttcagca attcccagtg gtcaacccaa gaaggcgtag gactaagcac atgcaggaag | 3420 |
| atcctcaaat tgatgggcgg tgaggtccaa tacatcaggg agtcagagcg gagtttcttc | 3480 |
| ctcatcgtcc tcgagctgcc ccagcctcgt ccagcagctg atagagaaat cagt | 3534 |

<210> SEQ ID NO 27
<211> LENGTH: 3411
<212> TYPE: DNA
<213> ORGANISM: Glycine max

<400> SEQUENCE: 27

| | |
|---|---|
| atggcttcag caagcggagc ggcgaattcc tccgttccgc cgccgcaaat ccacacctca | 60 |
| cgaacaaagc tgagccacca cagcagcaac aacaacaaca acatcgactc catgagcaag | 120 |
| gccatcgcgc agtacacgga ggacgcgcgg ctccacgccg tcttcgagca gtccggcgag | 180 |
| tccgggaggt ccttcaacta ctccgaatca atccgcatcg catcggaatc cgtccccgag | 240 |
| cagcagataa cggcttacct tgtcaaaatc cagcgcggcg gcttcatcca gcccttcggc | 300 |
| tccatgatcg ccgtcgacga gccctccttc cgcatcctcg gttactccga caacgcccgc | 360 |
| gacatgctcg gcattactcc gcagtccgtc ccttcgctcg acgacaagaa cgacgccgcc | 420 |
| ttcgctctcg gcaccgatgt ccgagcccte ttcactcact ccagcgcctt actcctcgaa | 480 |
| aaggccttct ccgcacgcga aattagcctc atgaacccta tctggatcca ctccagaacc | 540 |
| tccgggaagc cttctatgg aatcctccac cgaattgacg tcggaattgt catcgatttg | 600 |
| gagcctgcgc gtacggagga tcctgcctc tctatcgctg agctgtcca gtcgcagaag | 660 |
| ctcgcggttc gcgcgatttc gcagcttcaa tctctccccg gcggtgatgt taagcttctc | 720 |
| tgtgacactg ttgtggaaag tgttagggaa ttgacgggtt atgatagggt tatggtttat | 780 |
| aagtttcatg aggatgagca tggagaggtt gtttctgaga gtaagaggcc tgatttggag | 840 |
| ccttacattg gattgcatta tcctgctact gatattcctc aggcttctag gttttttgttt | 900 |
| aagcaaaata gagttaggat gattgtggat tgtcatgctt ctgctgtgag ggtggtgcag | 960 |
| gatgaggctc ttgtgcagcc tttgtgtttg gttgggtcca cccttagggc acctcacggt | 1020 |
| tgtcatgctc agtatatggc taacatgggc tcgattgcgt cttttggtgat ggcagttatt | 1080 |
| atcaatggga atgacgagga aggcgttggt ggtcgcagtt cgatgaggct gtggggggctt | 1140 |
| gttgtctgcc accataccctc tgccaggtgt attccttttc ccttgaggta tgcttgtgag | 1200 |
| tttctgatgc aggcgtttgg gctgcagttg aacatggagc ttcagttggc cgcgcagtcg | 1260 |
| ttggagaagc gggttttgag gacacagact ctgttgtgtg atatgcttct tagggactcg | 1320 |
| cctactggca ttgttactca gagtcctagt ataatggact tggtgaagtg tgatggggct | 1380 |
| gccctttatt tccaagggaa ctattatccg ttgggtgtga ctccaactga agctcagatt | 1440 |
| agggatatta ttgagtggtt gttggccttc catggagatt cgaccggtttt gagtactgat | 1500 |

| | |
|---|---|
| agtctgggtg atgctggata tcccggggct gcctcgcttg ggatgcagt tgtgggatg | 1560 |
| gcggttgctt atattacaga gaaggatttt ctttctggt tcaggtcgca cacggccaaa | 1620 |
| gagatcaaat ggggtggtgc aaagcatcat cctgaggaca aggatgatgg gcagagaatg | 1680 |
| catccccgtt cttccttcaa ggcgttttta gaagtggtga aaagccgtag cttgccgtgg | 1740 |
| gagaatgcgg aaatggatgc aattcactct ttgcagctta ttctgcgtga ctcgtttaaa | 1800 |
| gatgctgagc atagaaattc taaggctgtt gtggatcccc atgtgtcaga caagagttg | 1860 |
| caaggggtgg atgaactaag ttctgtggcc agagagatgg ttagattgat agaaacagcc | 1920 |
| actgctccaa tatttgctgt tgatgtcgat ggccacgtaa atgggtggaa tgcaaaggtt | 1980 |
| tcagaattaa caggactccc agttgaggag gctatgggga agtccttggt tcacgatctt | 2040 |
| gtgtttaagg agtctgaaga aactatgaac aagcttcttt ctcgtgcttt aaaaggtgaa | 2100 |
| gaagataaga atgttgagat aaaaatgagg acgtttggcc cagaacatca aaataaggca | 2160 |
| gtgtttttag tggtaatgc ttgctccagc aaggatttta caaataatgt agttggagtg | 2220 |
| tgctttgttg gtcaggatgt tactggtcaa aaaattgtaa tggacaaatt catcaacata | 2280 |
| caaggtgact acaaggctat tgtacatagc ccaaatcctt tgatccctcc catttttgca | 2340 |
| tcggacgata acacatgttg cttagagtgg aacactgcaa tggaaaagct tactggttgg | 2400 |
| ggccgtgtgg atgtcattgg aaaaatgttg gtgggagagg ttttggtag ttgctgtcag | 2460 |
| ttgaagggtt cagattcaat aacaaagttc atgattgtct tacacaatgc acttggtgga | 2520 |
| caagatacag ataaattccc tttctcattt cttgatcggc acggaaagta tgtacaaact | 2580 |
| ttcctgactg caaataagag ggttaacatg gagggtcaga tcataggagc tttttgcttt | 2640 |
| ttgcaaatca tgagtccgga acttcagcag gctcttaagg cacagagaca acaagaaaag | 2700 |
| aattcctttg gtaggatgaa agagttagct tatatttgtc aaggagttaa gaatcctttg | 2760 |
| agtggcatac gctttacaaa ctctcttttg gaggctacaa gcttgaccaa tgagcaaaag | 2820 |
| cagtttcttg agactagtgt tgcttgtgag aagcaaatgt taaagataat acgcgacgtt | 2880 |
| gatcttgaaa gcatcgagga tgggtccctg gagcttgaaa aggggggaatt cttgcttgga | 2940 |
| aatgtcataa atgcagttgt tagccaagta atgttactgt taagagaaag aaatttacag | 3000 |
| ttgattcgtg atattcctga gaaaatcaag acattggcag tttatggtga tcaattgagg | 3060 |
| attcaacaag tgttgtctga tttcttgttg aatatagtgc gctatgcacc atctccagat | 3120 |
| ggctgggtag agattcatgt acgtccaaga ataaaacaaa tctcagatgg gctcactctt | 3180 |
| ctccatgctg aatttagaat ggtatgtcct ggtgaaggtc ttcctcctga attgattcaa | 3240 |
| gacatgttca ataacagtcg gtgggggact caagaaggtt tagggctgag catgagcagg | 3300 |
| aagattctaa agctaatgaa cggcgaagtg cagtatatca gggaggccga acggtgctac | 3360 |
| ttctatgttc ttcttgaact acctgtgaca cggagaagct ctaaaaagtg t | 3411 |

<210> SEQ ID NO 28
<211> LENGTH: 3447
<212> TYPE: DNA
<213> ORGANISM: Glycine max

<400> SEQUENCE: 28

| | |
|---|---|
| atggcttcag caagcggagc ggagaattcc tccgtcccgc cgtcgccgtt gccgcctccg | 60 |
| ccgccgccgc aaatccacac ctcgcggacg aagctgagcc accaccacca caacaacaac | 120 |
| aacaacaaca caacaacat cgactccacg agcaaggcca tcgcgcagta cacggaggac | 180 |
| gcgcggctcc acgccgtctt tgagcagtcc ggcgagtccg ggaggtcctt tgactactcc | 240 |

| | |
|---|---|
| caatcaatcc gcgtcacatc ggaatccgtc ccggagcagc agataacggc ttaccttctc | 300 |
| aaaattcagc gcggcggctt catccagccc ttcggctcca tgatcgccgt cgacgagccc | 360 |
| tccttccgca tccttgccta ctccgacaac gcccgtgaca tgctcggcat tactccacag | 420 |
| tccgtcccct cgctcgacga caagaacgac gccgccttcg cgctcggaac cgatatccga | 480 |
| accctcttca ctcactccag cgccgttctc ctcgaaaagg ccttctccgc gcgcgaaatt | 540 |
| agcctcatga accctatctg gattcactcc agaacctccg ggaagccttt ctatggaatc | 600 |
| ctccaccgaa ttgacgtcgg aattgtcatc gatttggagc ctgcgcggac ggaggatcct | 660 |
| gccctctcca tcgccggagc tgtccagtcg cagaagctcg cggttcgcgc gatttcgcag | 720 |
| cttcaatctc tccccggtgg cgatgttaag cttctttgtg atactgttgt tgagagtgtc | 780 |
| agggaattga cagggtatga tagggttatg gtttataggt ttcatgagga tgagcatggg | 840 |
| gaggttgttg ctgagactaa gaggcctgat ttggagcctt acattggatt gcattatccc | 900 |
| gctactgata ttcctcaggc ttctaggttt ttgtttaagc agaataggqt taggatgatt | 960 |
| gtggattgtc atgcttctgc tgtgagggtg gtgcaggatg aggctcttgt gcagcctctg | 1020 |
| tgtttggttg gtccacgct cagggcgcct cacggttgcc atgctcagta tatggctaac | 1080 |
| atgggctcga ctgcgtcgtt ggtgatggct gttattatca atgggaatga tgaggaaggt | 1140 |
| gttggtggcc gcacttcgat gaggttgtgg gggcttgtta tttgccacca tacctctgct | 1200 |
| aggtgtattc cttttccctt gaggtatgct tgtgagtttc tgatgcaggc gtttgggctg | 1260 |
| cagttgaaca tggagcttca gttggccgca cagtcgttgg agaagcgggt tttgaggaca | 1320 |
| cagactctgt tgtgtgatat gcttctcagg gactctccta ctggcattgt aactcagagt | 1380 |
| cctagtatta tggacttggt gaagtgtgac ggagctgctc tttattacca agggaactat | 1440 |
| tatccgttgg gtgtgactcc aactgaggct cagataaggg atattattga gtggttgttg | 1500 |
| gcctttcata gagattcgac tggtttgagt actgatagtc tggctgatgc tggctatcct | 1560 |
| ggggctgcct cgcttgggga tgcagtttgt gggatggcgg ttgcttatat tacagagaag | 1620 |
| gattttcttt tctggttcag gtcgcacacg gcgaaagaga tcaaatgggg tggtgcaaag | 1680 |
| catcatcctg aggacaagga tgatgggcag agaatgcatc cccgttcttc cttcaaggca | 1740 |
| ttttagaag tggtgaaaag ccgtagcttg ccgtgggaga atgcggaaat ggatgcaatt | 1800 |
| cactctttgc agcttattct gcgtgactcg tttaaagatg ctgagcatag caattctaag | 1860 |
| gctgttttgg atccccgtat gtcggaacta gagttgcaag gggtcgatga actaagttct | 1920 |
| gtagccagag agatggttag attgatcgaa acagccactg ctccaatatt tgctgttgat | 1980 |
| gttgatggcc gcataaatgg gtggaatgca aaggtttcag aattgacagg actcccagtt | 2040 |
| gaggaggcta tggggaagtc cttggttcgc gatcttgtgt ttaaggagtc tgaagaaact | 2100 |
| gtggacaagc ttctttctcg tgctttaaaa ggtgaagaag ataagaatgt tgagataaaa | 2160 |
| atgaggacgt ttgcccagaa acatcaaaat aaggcagttt ttgtagtggt gaatgcttgc | 2220 |
| tccagcaagg attatacaaa taatgtagtt ggagtgtgct ttgttggtca ggatgttact | 2280 |
| ggtcaaaaaa ttgtgatgga caaattcatc aacatacaag gcgactacaa ggctattgta | 2340 |
| cataatccaa atcctttgat ccctcccatt tttgcatcgg atgataacac gtgttgctta | 2400 |
| gagtggaaca ctgcaatgga aaagcttact ggttggagcc gcgcggatgt cattgcaaaa | 2460 |
| atgttggtgg gagaggtttt cggcagttgc tgtcagttga agggtcaga ttcaataaca | 2520 |
| aagttcatga ttgtcttaca caatgcgctt ggtggacatg atacagatag attccctttt | 2580 |

```
tcatttcttg atcggtatgg caagcatgtg caagctttcc tgactgcaaa taagagggtt    2640
aacatggatg gtcagatcat tggggcattt tgcttttttgc aaattgtgag tccggaactt    2700
caacaggctc tgaaggcaca gagacaacaa gagaagaatt catttgctag gatgaaagag    2760
ttagcttata tttgtcaagg agttaagaat cctttgagtg gcatacgctt tacaaactct    2820
cttttggagg ctacatgctt gtccaatgag caaaaacagt ttcttgagac tagtgctgct    2880
tgtgagaagc aaatgttaaa gataatacac gatgttgata ttgaaagcat tgaggatggg    2940
tccctggagc ttgaaaaggg ggaattcttg cttggaaatg tcataaatgc agttgttagc    3000
caagtaatgc tactgttaag agaaagaaat ttacagttga ttcgtgatat tcctgaagaa    3060
atcaagacat ggctgtttta tggtgatcaa ttgaggattc aacaagtgtt gtctgatttc    3120
ttattgaata tagtgcgcta tgcaccatct ccagatggct gggtagagat tcatgtacat    3180
ccaagaataa aacaaatctc agatgggctc actcttctcc atgctgaatt tagaatggta    3240
tgtcctggtg aaggtcttcc tcctgaattg attcaaaaca tgttcaataa cagtgggtgg    3300
gggactcaag aaggtttagg gctgagcatg agcaggaaga ttctaaagct aatgaacggc    3360
gaagtgcagt atatcaggga ggcccaacgg tgctacttct atgttcttct tgaactacct    3420
gtgacacgga gaagctctaa aaagtgt                                        3447
```

<210> SEQ ID NO 29
<211> LENGTH: 3300
<212> TYPE: DNA
<213> ORGANISM: Glycine max

<400> SEQUENCE: 29

```
atgagcaagg ccatcgcgca gtacacggag gacgcgcggc tccacgccgt cttcgagcag     60
tccggcgagt ccgggaggtc cttcaactac tccgaatcaa tccgcatcgc atcggaatcc    120
gtccccgagc agcagataac ggcttacctt gtcaaaatcc agcgcggcgg cttcatccag    180
cccttcggct ccatgatcgc cgtcgacgag ccctccttcc gcatcctcgg ttactccgac    240
aacgcccgcg acatgctcgg cattactccg cagtccgtcc cttcgctcga cgacaagaac    300
gacgccgcct cgctctcgg caccgatgtc cgagccctct tcactcactc cagcgcctta    360
ctcctcgaaa aggccttctc cgcacgcgaa attagcctca tgaacccctat ctggatccac    420 tccagaacct ccgggaagcc ttcctatgga atcctccacc gaattgacgt cggaattgtc    480
atcgatttgg agcctgcgcg tacggaggat cctgccctct ctatcgctgg agctgtccag    540
tcgcagaagc tcgcggttcg cgcgatttcg cagcttcaat ctctccccgg cggtgatgtt    600
aagcttctct gtgacactgt tgtggaaagt gttagggaat tgacgggtta tgatagggtt    660
atggtttata agtttcatga ggatgagcat ggagaggttg tttctgagag taagaggcct    720
gatttggagc cttacattgg attgcattat cctgctactg atattcctca ggcttctagg    780 ttttttgttta agcaaaatag agttaggatg attgtggatt gtcatgcttc tgctgtgagg    840
gtggtgcagg atgaggctct tgtgcagcct ttgtgtttgg ttgggtccac ccttagggca    900
cctcacggtt gtcatgctca gtatatggct aacatgggct cgattgcgtc tttggtgatg    960
gcagttatta tcaatgggaa tgacgaggaa ggcgttggtg gtcgcagttc gatgaggctg   1020
tgggggcttg ttgtctgcca ccatacctct gccaggtgta ttccttttcc cttgaggtat   1080
gcttgtgagt ttctgatgca ggcgtttggg ctgcagttga acatggagct tcagttggcc   1140
gcgcagtcgt tggagaagcg ggttttgagg acacagactc tgttgtgtga tatgcttctt   1200
agggactcgc ctactggcat tgttactcag agtcctagta aatggactt ggtgaagtgt   1260
```

```
gatgggctg ccctttattt ccaagggaac tattatccgt tgggtgtgac tccaactgaa    1320
gctcagatta gggatattat tgagtggttg ttggccttcc atggagattc gaccggtttg    1380
agtactgata gtctgggtga tgctggatat cccggggctg cctcgcttgg ggatgcagtt    1440
tgtgggatgg cggttgctta tattacagag aaggattttc ttttctggtt caggtcgcac    1500
acggccaaag agatcaaatg gggtggtgca aagcatcatc ctgaggacaa ggatgatggg    1560
cagagaatgc atccccgttc ttccttcaag gcgtttttag aagtggtgaa aagccgtagc    1620
ttgccgtggg agaatgcgga atggatgca attcactctt tgcagcttat tctgcgtgac    1680
tcgtttaaag atgctgagca tagaaattct aaggctgtcg cggatcccg tgtgtcagaa    1740 caagagttgc aaggggtgga tgaactaagt tctgtggcca gagagatggt tagattgata    1800
gaaacagcca ctgctccaat atttgctgtt gatgtcgatg ccacgtaaa tgggtggaat    1860 gcaaaggttt cagaattaac aggactccca gttgaggagg ctatggggaa gtccttggtt    1920
cacgatcttg tgtttaagga gtctgaagaa actatgaaca agcttctttc tcgtgcttta    1980 aaggtgaag aagataagaa tgttgagata aaaatgagga cgtttggccc agaacgtcaa    2040
aataaggcag tgttttagt ggtgaatgct tgctccagca aggattttac aaataatgta    2100
gttggagtgt gctttgttgg tcaggatgtt actggtcaaa aaattgtaat ggacaaattc    2160
atcaacatac aaggtgacta caaggctatt gtacatagcc caaatccttt gatccctccc    2220 attttgcat cggacgataa cacatgttgc ttagagtgga cactgcaat ggaaaagctt    2280 actggttggg gccgtgtgga tgtcattgga aaaatgttgg tgggagaggt ttttggtagt    2340
tgctgtcagt tgaagggttc agattcaata acaaagttca tgattgtctt acacaatgca    2400
cttggtggac aagatacaga taaattccct ttctcatttc ttgatcggca cggaaagtat    2460
gtacaaactt tcctgactgc aaataagagg gttaacatgg agggtcagat cataggagct    2520
ttttgctttt tgcaaatcat gagtccggaa cttcagcagg ctcttaaggc acagagacaa    2580
caagaaaaga attcctttgg taggatgaaa gagttagctt atatttgtca aggagttaag    2640
aatcctttga gtggcatacg ctttacaaac tctcttttgg aggctacaag cttgaccaat    2700
gagcaaaagc agtttcttga gactagtgtt gcttgtgaga agcaaatgtt aaagataata    2760
cgcgacgttg atcttgaaag catcgaggat gggtccctgg agcttgaaaa gggggaattc    2820
ttgcttggaa atgtcataaa tgcagttgtt agccaagtaa tgttactgtt aagagaaaga    2880
aatttacagt tgattcgtga tattcctgaa gaaatcaaga cattggcagt ttatggtgat    2940
caattgagga ttcaacaagt gttgtctgat ttccttgtta atatagtgcg ctatgcacca    3000
tctccagatg gctgggtaga gattcatgta cgtccaagaa taaacaaat ctcagatggg    3060 ctcactcttc tccatgctga atttagaatg gtatgtcctg gtgaaggtct tcctcctgaa    3120
ttgattcaag acatgttcaa taacagtcgg tggggggactc aagaaggttt agggctgagc    3180
atgagcagga agattctaaa gctaatgaac ggcgaagtgc agtatatcag ggaggccgaa    3240
cggtgctact tctatgttct tcttgaacta cctgtgacac ggagaagctc taaaaagtgt    3300
```

<210> SEQ ID NO 30
<211> LENGTH: 2601
<212> TYPE: DNA
<213> ORGANISM: Glycine max

<400> SEQUENCE: 30

```
atgatcgccg tcgacgagcc ctccttccgc atccttgcct actccgacaa cgcccgtgac    60
```

```
atgctcggca ttactccaca gtccgtccct tcgctcgacg acaagaacga cgccgccttc      120
gcgctcggaa ccgatatccg aaccctcttc actcactcca gcgccgttct cctcgaaaag      180
gccttctccg cgcgcgaaat tagcctcatg aaccctatct ggattcactc cagaacctcc      240
gggaagcctt tctatggaat cctccaccga attgacgtcg gaattgtcat cgatttggag      300
cctgcgcgga cggaggatcc tgccctctcc atcgccggag ctgtccagtc gcagaagctc      360
gcggttcgcg cgatttcgca gcttcaatct ctccccggtg gcgatgttaa gcttctttgt      420
gatactgttg ttgagagtgt cagggaattg acagggtatg ataggggttat ggtttatagg      480
tttcatgagg atgagcatgg ggaggttgtt gctgagacta agaggcctga tttggagcct      540
tacattggat tgcattatcc cgctactgat attcctcagg cttctaggtt tttgtttaag      600
cagaataggg ttaggatgat tgtggattgt catgcttctg ctgtgagggt ggtgcaggat      660
gaggctcttg tgcagcctct gtgtttggtt gggtccacgc tcagggcgcc tcacggttgc      720
catgctcagt atatggctaa catgggctcg actgcgtcgt tggtgatggc tgttattatc      780
aatgggaatg atgaggaagg tgttggtggc cgcacttcga tgaggttgtg ggggcttgtt      840
atttgccacc atacctctgc taggtgtatt ccttttccct tgaggtatgc ttgtgagttt      900
ctgatgcagg cgtttgggct gcagttgaac atggagcttc agttggccgc acagtcgttg      960
gagaagcggg ttttgaggac acagactctg ttgtgtgata tgcttctcag ggactctcct     1020
actggcattg taactcagag tcctagtatt atggacttgg tgaagtgtga cggagctgct     1080
ctttattacc aagggaacta ttatccgttg ggtgtgactc caactgaggc tcagataagg     1140
gatattattg agtggttgtt ggcctttcat agagattcga ctggtttgag tactgatagt     1200
ctggctgatg ctggctatcc tggggctgcc tcgcttgggg atgcagtttg tgggatggcg     1260
gttgcttata ttacagagaa ggattttctt ttctggttca ggtcgcacac ggcgaaagag     1320
atcaaatggg gtggtgcaaa gcatcatcct gaggacaagg atgatgggca gagaatgcat     1380
ccccgttctt ccttcaaggc atttttagaa gtggtgaaaa gccgtagctt gccgtgggag     1440
agtgcggaaa tggatgcaat tcactctttg cagcttattc tgcgtgactc gtttaaagat     1500
gctgagcata gcaattctaa ggctgttttg gatccccgta tgtcggaact agagttgcaa     1560
ggggtcgatg aactaagttc tgtagccaga gagatggtta gattgatcga aacagccact     1620
gctccaatat ttgctgttga tgttgatggc gcataaatg gtggaatgc aaaggtttca      1680
gaattgacag gactcccagt tgaggaggct atggggaagt ccttggttcg cgatcttgtg     1740
tttaaggagt ctgaagaaac tgtggacaag cttctttctc gtgctttaaa aggtgaagaa     1800
gataagaatg ttgagataaa aatgaggacg tttggcccag aacatcaaaa taaggcagtt     1860
tttgtagtgg tgaatgcttg ctccagcaag gattatacaa ataatgtagt tggagtgtgc     1920
tttgttggtc aggatgttac tggtcaaaaa attgtgatgg acaaattcat caacatacaa     1980
ggcgactaca aggctattgt acataatcca aatcctttga tccctcccat ttttgcatcg     2040
gatgataaca cgtgttgctt agagtggaac actgcaatgg aaaagcttac tggttggagc     2100
cgcgcggatg tcattggaaa aatgttggtg ggagaggttt cggcagttg  ctgtcagttg     2160
aagggttcag attcaataac aaagttcatg attgtcttac acaatgcgct tggtggacat     2220
gatacagata gattcccttt ttcatttctt gatcggtatg gcaagcatgt gcaagctttc     2280
ctgactgcaa ataagagggt taacatggat ggtcagatca ttggggcatt ttgcttttg      2340
caaattgtga gtccggaact tcaacaggct ctgaaggcac agacaacaa  agagaagaat     2400
tcatttgcta ggatgaaaga gttagcttat atttgtcaag gagttaagaa tcctttgagt     2460
```

```
ggcatacgct ttacaaactc tcttttggag gctacatgct tgtccaatga gcaaaaacag    2520
tttcttgaga ctagtgctgc ttgtgagaag caaatgttaa agataataca cgatgttgat    2580
attgaaagca ttgaggatgg a                                              2601
```

<210> SEQ ID NO 31
<211> LENGTH: 3390
<212> TYPE: DNA
<213> ORGANISM: Solanum tuberosum

<400> SEQUENCE: 31

```
atggcttctg gaagtagaac aaagcattcc catcataatt catctcaagc tcaatcttca      60
ggtacaagta atgtaaatta caaagattca ataagcaaag ctatagcaca gtacacagct     120
gatgctaggc ttcatgctgt gtttgaacaa tctggtgagt ctggaaagtt ttttgattat     180
tcagagtctg ttaaaactac tacacaatct gtgcctgaaa ggcaaatcac tgcttatttg     240
actaaaattc aaagaggagg tcatattcag ccttttggtt gtatgatagc tgtagatgag     300
gctagttttc gtgtaatagc ttatagtgaa aatgcctttg aaatgcttag tttaactcca     360
caatctgttc caagccttga gaagtgtgag atcctcacta ttggaactga tgttaggacc     420 cttttttaccc cttctagctc tgttttgcta gaaagagcat ttggggcacg tgagatcact     480
ttactcaacc caatttggat tcattccaag aattctggaa agcccttta tgcaattttg      540 cacagggttg atgttggtat tgccattgat ttggagcctg ctagaactga ggaccctgct     600
ttatctattg ctggagcagt gcagtcacag aaacttgcag tgagggctat ttctcatttg     660
caatcacttc ctggtgggga cattaagctt ttgtgtgata ctgttgttga gagtgtcagg     720
gagttaaccg gtatgaccg  ggttatggta tataaatttc atgaggatga gcatggagag     780
gtagtggctg agagtaaaag atcagattta gagccctata tcggtttgca ttatcctgct     840
actgatattc ctcaagcttc acggtttttg tttaagcaga acagggtgag aatgattgtg     900
gactgtcatg ctaccctgt  gcgggttact caggatgaat cactgatgca gcctttatgt     960
ctagttggtt ccacacttag agcacctcat ggttgccacg cacagtacat ggcaaatatg    1020
gggtctattg cctcattaac actggcagtt attatcaacg gaaatgatga ggaagctgtg    1080
ggtggcggtc gaaattcaat gaggctatgg ggcttggttg ttggacacca cacttctgtt    1140
cggtccattc ctttccctct taggtatgca tgtgaattcc ttatgcaggc ctttggactc    1200
caattgaaca tggagttgca attggcgtca cagttgtctg agaaacatgt tttaaggaca    1260
caaacactgt tatgtgacat gctccttcga gactctccac cggggattgt tacccaaagc    1320
cccagtatta tggaccttgt gaagtgcgat ggtgctgctc tatactacca ggggaagtac    1380
tatccattag gtgtcacacc aactgaagct cagataaagg acattgtgga gtggttattg    1440
gcttaccatg gagactcaac aggtttaagt actgacagtt tggctgatgc tgggtatcct    1500
ggagcagctt cacttggtga tgcagtttgt ggtatggctg tcgcttatat atcttctaaa    1560
gatttcttgt tttggtttcg ctcccacaca gcgaaagaaa taaagtgggg tggtgcaaag    1620
catcatcctg aagacaagga tgatggactg agaatgcatc cacgttcttc cttcaaggca    1680
tttctggaag ttgttaaaag tcggagctca ccatgggaaa atgccgaaat ggatgcaatc    1740
cactctttgc agctaattct gcgagattca tttaaggatg ctgaggcaag taattctaag    1800
gctattgtgc atgctcatct tggggaaatg gagttgcaag ggatagatga actgagttct    1860
gttgccagag aaatggttag attgatcgaa actgcaacag ctcccatatt tgctgttgat    1920
```

| | |
|---|---|
| gtcgaaggtc gcataaatgg gtggaatgca aaggtcgctg aattgacagg tttatcagtt | 1980 |
| gaagaagcaa tggggaagtc cttggttcat gagcttgtgt acaaagaatc acaggagact | 2040 |
| gctgagaagc ttctgtataa tgctctaaga ggcgaggaag ataaaaatgt agaaataaag | 2100 |
| ttgaggacat ttggagctga acaactggag aaagctgttt ttgtggtggt taatgcttgc | 2160 |
| gctagcaaag attacacaaa caacattgtt ggtgtttgct ttgttgggca ggatgttact | 2220 |
| ggggaaaaag ttgttatgga caagtttatt aacatccaag gtgattacaa ggccattgtg | 2280 |
| cacagcccca atcctctgat ccctccaata tttgcatcag atgagaacac ttgttgctcc | 2340 |
| gagtggaaca ctgccatgga aaaactcact ggttggtcta gagggagat tgttggaaaa | 2400 |
| atgttagttg gtgagatttt tggaagttgt tgtcggctca agggcccaga tgccatgaca | 2460 |
| aagttcatga tcgtgttgca taatgcaatt ggaggacagg atacagacaa gtttccattt | 2520 |
| tccttttttg accgaaatgg gaaatatgtg caagctcttt tgactgctaa caagagagtc | 2580 |
| aatatggagg gcaatactat tggggctttc tgtttcatac agatagccag tcccgaactg | 2640 |
| cagcaagctc taagagttca aaggcaacag gaaaagaagt gttattctca gatgaaagag | 2700 |
| ctggcataca tttgtcagga aataaaaagt cctcttaatg gtatacgctt tacaaattca | 2760 |
| ttgttggagg ccacaaattt gacagaaaat cagaagcagt atctagagac aagtgctgct | 2820 |
| tgtgagaggc agatgtctaa gatcattagg gatgttgatc tggaaaacat tgaggacggt | 2880 |
| tcactgaccc ttgagaaaga agatttttt cttgggagtg taatagatgc tgttgttagc | 2940 |
| caagtgatgt tattgctgag ggaaaaaggc gtgcagttaa tccgtgatat accagaggaa | 3000 |
| attaagacat taacagtaca tggtgatcaa gtgagaattc aacaggtctt ggcagatttc | 3060 |
| ttgttgaaca tggtacggta tgcaccatca cctgatgggt gggtagaaat ccaacttcga | 3120 |
| ccaagtatga tgccaatatc tgatggagta actggtgtgc atattgaact caggattata | 3180 |
| tgccctggcg aagggcttcc tcctgaattg gttcaagata tgttccacag cagtcggtgg | 3240 |
| gtaactcagg aaggcctagg actgagcacg tgcagaaaaa tgttaaagct tatgaatgga | 3300 |
| gaaatccagt atatcagaga atcagaaaga tgctatttcc tgattgtcct tgacctgcca | 3360 |
| atgacccgca aaggtccaaa gagtgttggc | 3390 |

<210> SEQ ID NO 32
<211> LENGTH: 3363
<212> TYPE: DNA
<213> ORGANISM: Pisum sativum
<220> FEATURE:
<221> NAME/KEY: misc_feature
<222> LOCATION: (84)..(84)
<223> OTHER INFORMATION: n is a, c, g, or t

<400> SEQUENCE: 32

| | |
|---|---|
| agcaacaaca ataacaacag aaatattaaa agagaatcgt tatcaatgag aaaagccata | 60 |
| gctcagtaca cagaagacgc aagnctccat gctgtttttg aaaaatccgg tgactctttc | 120 |
| gattatgccc aatccattcg cgtcacggcg gctactgaat cagttcctga acagcaaatc | 180 |
| actgcttact tagccaaaat ccaacgcggt ggtttcattc aacctttcgg ttcaatgatc | 240 |
| gccgtcgaca aaacttcttt tcgcgttctt gcttactctg aaaacgcacg tgacatgctt | 300 |
| ggtatcgcgc tcaatcggt tccttctatg gaagatgatt cttcttcttc ttcgtttttc | 360 |
| tctttaggcg ttgatgttcg ttctcttttt agtgcttcca gttctgtact tcttgagaaa | 420 |
| gcttttttcag ctcgggagat tagttttaatg aatcctattt ggatccactc tcgttctact | 480 |
| ggtaagcctt tttatggaat tcttcaccga attgatattg gtgttgttat tgatttggag | 540 |

```
cctgcgagat ctgaggatcc agcgctttcg attgccggtg ctgttcagtc tcagaagctt     600
gcggttcgtg cgatttcgca gctccaggcg cttcctggtg gtgatgtcaa gcttctttgt     660
gatgctgttg ttgagagtgt tagggaattg actggttatg atagggttat ggtttataag     720
tttcatgagg atgagcatgg tgaggttgtt gctgagagta agagggttga tttagagcct     780
tatattggtt tgcattatcc tgctactgat attcctcagg cttctaggtt tttgtttaag     840
cagaataggg ttaggatgat tgtggattgt aatgcttctc ctgttagggt ttttcaggat     900
gaggcgcttg ttcagcctgt ttgtttggtt gggagtactc ttcgggctcc tcatggttgt     960
catgctcagt acatggcaaa tatgggttcc attgcttctt ggctatggc tgttattatt     1020
aatgggaatg atgaagacgg tggtgggatt ggtggtgctg cacgtggctc gatgaggctt     1080
tggggtcttg ttgtttgtca tcatacttct gctaggtgta ttccttttcc tcttaggtat     1140
gcttgtgagt ttctaatgca ggcttttggg cttcagttga atatggagct tcagttagcc     1200
gtgcagtcgt tggagaaaag ggttttgaag acacagactc tgttgtgtga tatgttactt     1260
agggattctc atacagggat tgttactcag agtcctagta ttatggattt ggttaagtgt     1320
gatgggctg ctttgtatta tcaaggaaac taccaccctt tgggtgttac tccgaccgag     1380
tctcagataa gggatatcat agattggttg ttggcctttc atagtgattc gacgggtttg     1440
agtactgata gttggctga tgctggttat cctggggctg cttctcttgg ggatgcagtt     1500
tgtggaatgg ctgttgcgta tattactgaa aaagactttc ttttctggtt cagatctcat     1560
acggctaaag aaattaaatg gggtggtgca aagcatcacc cggaggataa ggatgacggg     1620
cagaaaatgc atcctcgttc ttctttcaag gccttttag aagtggtgaa gatccgtagt     1680
atgcagtggg ataatgcaga aatggatgca attcactcct tgcagcttat cctgcgagac     1740
tcgtttaagg aagctgagaa taacgattca aaggctgtcg tgcatacccca tatggcagaa     1800
ctagagttgc aaggggtgga tgaactgagt tctgtggcta gagaaatggt taggttgata     1860
gaaacagcca ctgctcccat atttgctgtt gatgtcgatg gtcgcatcaa tgggtggaat     1920
gcaaaggttt ctgaattgac aggacttctg gtagaggagg ctatgggcaa gtctttggtt     1980
catgatctcg tgtataagga gtctcgagaa actgtgacaa gcttctttc tcatgcttta     2040
aaaggtgaag aagataaaaa tgttgagata aaaatgaaga cttttggccc ggggaatcaa     2100
aataaggcag ttttatagt ggtgaatgct tgctccagca aggattatac aaataatata     2160
gttggagtgt gctttgttgg ccaggatatt actggtcaaa agttgtaat ggacaaattc     2220
attaacatac aaggtgacta caaggctatt gtacatagtc caaatccatt gatccctccc     2280
attttgcat cggatgacaa cacatgttgc ttagagtgga acaatgctat ggaaaagctc     2340
agcggctgga gccgtgcaga tgtcattggc aaattgttag tgggagaggt ttttggtagt     2400
ttctgtcagt tgaagggttc ggatgctatg acaaaattca tgattgtttt gcacaatgca     2460
cttggtggac acgacacaga caaattccca ttgtcatttc ttgacagaca tggaaagtat     2520
gtgcatactt tcttgaccgc aaataagagg gttaacatgg atggtcagat cattggcgca     2580
ttttgctttt tacaaattgt gaaccctgaa cttcaacagg ctttgacagt ccagagacaa     2640
caggatagta gttccttagc tagaatgaag gagttagctt atatttgtca agaagtaaag     2700
aatcccttga gtggcatacg ctttacaaac tctctttttgg agtctacatg cctgactgat     2760
gagcaaaagc agcttcttga gactagtgtt gcttgtgaga agcaaatgct gaagatagta     2820
cgggacattg ctctagaaag catcgaggat gggtccctgg agcttgaaaa gcaggaattc     2880
```

```
ttgctcgaga atgtcataaa tgcagttgtt agccaagtaa tgctattgct aagagataga   2940
aagttacagt taattcgtga tattcctgaa gaaatcaagg cattggctgt ttatggtgat   3000
cagttgagga ttcaacaagt cttggctgat ttcttaatga atgtggtgcg ctatgcacca   3060
tctccagatg gttgggtaga gattcatgta tttccaagaa taaaacaaat ttcagagggg   3120
ctcactcttc tgcatgctga atttaggatg gtgtgtcctg gtgaaggtct tccacctgaa   3180
ttgattcaag acatgttcca taacagtcgg tgggtgactc aagaaggctt agggctgagc   3240
atgagcagga agattataaa gttaatgaac ggcgaagtcc agtatgtaag ggaggcagaa   3300
cggtgctact tcttagttct tcttgaacta cccgtgacac ggagaagctc taaagctatt   3360
aat                                                                3363
```

<210> SEQ ID NO 33
<211> LENGTH: 3387
<212> TYPE: DNA
<213> ORGANISM: Vitis vinifera

<400> SEQUENCE: 33

```
atgagttcag gaaacagagg aacgcagtcg caccaccaag ctcagtcgtc ggggacaagc     60
aatttgagag tttaccacac tgattcaatg agcaaagcca ttgcgcaata tacaatggat    120
gctcgcctcc acgccgtata cgaacagtcc ggcgagtccg gtaagtcatt cgactactcg    180
cagtcggtta gaaccacaac gcaatcggtc cctgagcaac aaatcactgc gtatttatcg    240
aaaattcaac ggggtggcca tatacagccc tttgggtgta tgcttgcggt cgatgaggcc    300
acttttcggg tcattgcttt cagcgaaaat gcccgagaaa tgctcggtct cactccgcaa    360
tcggttccga gccttgagaa gcccgagatc ctcctagtag gtactgatgt tcgcacgctt    420
ttcactccct cgagcgcagt tctcctcgaa aaggcgtttc gggctcggga aattacgttg    480
ttaaatcccg tgtggattca ttccaagaat tctggaaaac ccttttacgc aattttgcat    540
agaattgatg tgggaattgt aattgatttg gagcctgcaa ggactgagga ccctgctctg    600
tccattgctg ggcggtgca gtcgcagaag ttggccgttc gagcaatttc ccatcttcaa    660
tctcttcccg tggtgatat taacctttg tgtgaaactg tggttgagaa tgtgagggag    720
cttactgggt atgatcgggt catggtttac aaatttcacg aggatgaaca tggtgaggtc    780
gtggctgaga gcaagaggtc tgatttggag ccttatattg ggttacacta tcctgccacg    840
gacattccac aggcttcaag gttttttgttt aggcagaatc gggttaggat gatcgttgat    900
tgccatgcca cgcctgttct ggtgattcaa gatgaagggc ttatgcagcc tctatgctta    960
gttggttcaa cccttcgggc tcctcatggc tgccatgcac agtatatggc caacatgggt   1020
tcaactgcct cattagcgat ggctgtcatc atcaatggaa gtgatgagga agctattggt   1080
gggcgaaaact tgatgaggct atggggcctg gttgtttgtc atcacacatc tgctaggtgc   1140
attccatttc ctcttcgata tgcctgtgag ttcctaatgc aggcatttgg actccaattg   1200
aacatggaac tgcagttagc atcgcaattg tctgagaaac atgttttaag gacacagact   1260
ctcttgtgtg acatgctcct tcgtgattcc cctactggaa ttgttaccca aagtcctagt   1320
attatggatc ttgtgaagtg tgatggagca gcactttatt accaggggaa gtattatcca   1380
actggggtga ccccgactga agcccagata aaggatattg cagagtggtt gttggcaaac   1440
catgcggatt caacaggttt aagcactgac agtttggctg atgctggcta ccctggggca   1500
gcctcacttg gtgatgcagt ttgtggaatg gctgttgctt atatcacttc aagagatttt   1560
ctattctggt ttcggtccca cacagcaaaa gagatcaaat ggggtggtgc aaagcatcat   1620
```

```
ccagaggaca aggacgatgg gcagaggatg catcctcgtt cttcattcaa ggcatttta    1680
gaagtggtca agagtcggag tttgccatgg gagaatgcgg aaatggatgc aattcattct    1740
ctgcagctta ttctgcgtga ctcttttaag gatgctactg atggaagcaa ttctaaggct    1800
gtaatgcatg ctcagctcgg ggagctagag ttgcaaggga tggatgagtt gagctctgtt    1860
gcaagagaaa tggttaggtt gattgaaact gcaacagctc ccatatttgc ggtcgatgtt    1920
gatggctgca taaatggttg gaatgcaaag gttgcggagt tgacgggggct ttctgttgag    1980
gaagctatgg ggaagtcctt ggttcatgat cttgtttaca aggaatctga gaaactgtt     2040
gacaagcttc ttcatcatgc tctacgaggt gaagaagata agaatgtaga gataaaattg    2100
aggacatttg actcacaaca gcataagaag gctgttttg tggtcgttaa tgcttgctcc     2160
agtagggatt acacaaataa tatagttgga gtttgctttg ttggtcagga tgttactggt    2220
cagaaagtgg taatggacaa atttatccat atacaaggtg attacaaagc tattgtacat    2280
agtcccaacc ctttgattcc tcctatattt gcttcagatg agaacacagt ttgctctgag    2340
tggaacactg ccatggaaaa gctcactggg tggagcaggg gggacatcat tgggaagatc    2400
ttggttgggg agattttgg cagtagctgt cggctgaagg gtccggatgc tctgacaaaa    2460
ttcatgattg tgttgcacaa tgcaattgga gggcaagaca cagacaagtt tccattttcc    2520
ttctttgacc agaatggaaa atatgtgcaa gctcttttga cagcaaataa gagagttaat    2580
attgagggcc agattattgg tgccttctgc tttttgcaga ttgcaagtcc tgaattgcag    2640
caagctctca agtccaaag gcaacaggag aaaaaatgtt ttgcaaggat gaaagagttg    2700
gcttacattt gtcaggaaat aaagaacct ttaagtggca tacgttccac taactctctt    2760
ttggaggcca ctgacttaac tgaagatcaa aagcagtttc ttgagactag tgctgcttgt    2820
gagaagcaga tgtcaaagat cataagggat gttgatctgg acagcattga ggatggttca    2880
ctggagcttg agagggctga atttttactt ggaagtgtca taaatgctgt tgttagccaa    2940
gtaatgatat tgttgaggga aagagattta caattgatcc gggacattcc tgaggaagtc    3000
aaaacactgg ctgtttatgg cgatcaagta agaattcaac aggttttggc tgatttctta    3060
ctgaatatgg tgcgttatgc accatcccca gacggttgga tagagattca agtttgtcca    3120
agattgaagc aaatttctga gaagtaaaaa cttatgcata ttgaattcag gatggtatgc    3180
cctggtgaag gtcttcctcc taatctgatt caagacatgt tccatagcag tcgttggatg    3240
actcaggaag gtctagggct gagcatgtgc aggaagatct taaagctcat taatggcgaa    3300
gtccaatata tcagagaatc agaaagatgt tattttctaa tcagcataga acttcctata    3360
cctcacagag gctcaaagag cgttgac                                       3387
```

<210> SEQ ID NO 34
<211> LENGTH: 187
<212> TYPE: PRT
<213> ORGANISM: Synechocystis PCC6803

<400> SEQUENCE: 34

Leu Gly Phe Tyr His Met Ala Asn Ala Ala Leu Asn Arg Leu Arg Gln
1               5                   10                  15

Gln Ala Asn Leu Arg Asp Phe Tyr Asp Val Ile Val Glu Glu Val Arg
            20                  25                  30

Arg Met Thr Gly Phe Asp Arg Val Met Leu Tyr Arg Phe Asp Glu Asn
        35                  40                  45

Asn His Gly Asp Val Ile Ala Glu Asp Lys Arg Asp Asp Met Glu Pro

```
                    50                  55                  60

Tyr Leu Gly Leu His Tyr Pro Glu Ser Asp Ile Pro Gln Pro Ala Arg
 65                  70                  75                  80

Arg Leu Phe Ile His Asn Pro Ile Arg Val Ile Pro Asp Val Tyr Gly
                     85                  90                  95

Val Ala Val Pro Leu Thr Pro Ala Val Asn Pro Ser Thr Asn Arg Ala
                    100                 105                 110

Val Asp Leu Thr Glu Ser Ile Leu Arg Ser Ala Tyr His Cys His Leu
                115                 120                 125

Thr Tyr Leu Lys Asn Met Gly Val Gly Ala Ser Leu Thr Ile Ser Leu
130                 135                 140

Ile Lys Asp Gly His Leu Trp Gly Leu Ile Ala Cys His His Gln Thr
145                 150                 155                 160

Pro Lys Val Ile Pro Phe Glu Leu Arg Lys Ala Cys Glu Phe Phe Gly
                165                 170                 175

Arg Val Val Phe Ser Asn Ile Ser Ala Gln Glu
                180                 185

<210> SEQ ID NO 35
<211> LENGTH: 187
<212> TYPE: PRT
<213> ORGANISM: Deinococcus radiodurans

<400> SEQUENCE: 35

Ser Thr Gly Pro His Ala Leu Arg Asn Ala Met Phe Ala Leu Glu Ser
  1               5                  10                  15

Ala Pro Asn Leu Arg Ala Leu Ala Glu Val Ala Thr Gln Thr Val Arg
                 20                  25                  30

Glu Leu Thr Gly Phe Asp Arg Val Met Leu Tyr Lys Phe Ala Pro Asp
             35                  40                  45

Ala Thr Gly Glu Val Ile Ala Glu Ala Arg Arg Glu Gly Leu His Ala
         50                  55                  60

Phe Leu Gly His Arg Phe Pro Ala Ser Asp Ile Pro Ala Gln Ala Arg
 65                  70                  75                  80

Ala Leu Tyr Thr Arg His Leu Leu Arg Leu Thr Ala Asp Thr Arg Ala
                 85                  90                  95

Ala Ala Val Pro Leu Asp Pro Val Leu Asn Pro Gln Thr Asn Ala Pro
                100                 105                 110

Thr Pro Leu Gly Gly Ala Val Leu Arg Ala Thr Ser Pro Met His Met
            115                 120                 125

Gln Tyr Leu Arg Asn Met Gly Val Gly Ser Ser Leu Ser Val Ser Val
130                 135                 140

Val Val Gly Gly Gln Leu Trp Gly Leu Ile Ala Cys His His Gln Thr
145                 150                 155                 160

Pro Tyr Val Leu Pro Pro Asp Leu Arg Thr Thr Leu Glu Tyr Leu Gly
                165                 170                 175

Arg Leu Leu Ser Leu Gln Val Gln Val Lys Glu
                180                 185

<210> SEQ ID NO 36
<211> LENGTH: 187
<212> TYPE: PRT
<213> ORGANISM: Pseudomonas aeruginosa

<400> SEQUENCE: 36

Thr Ser Phe Thr Leu Asn Ala Gln Arg Ile Ile Ala Gln Val Gln Leu
```

```
1               5                   10                  15
His Asn Asp Thr Ala Ser Leu Leu Ser Asn Val Thr Asp Glu Leu Arg
                    20                  25                  30

Arg Met Thr Gly Tyr Asp Arg Val Met Ala Tyr Arg Phe Arg His Asp
                    35                  40                  45

Asp Ser Gly Glu Val Val Ala Glu Ser Arg Arg Glu Asp Leu Glu Ser
                    50                  55                  60

Tyr Leu Gly Gln Arg Tyr Pro Ala Ser Asp Ile Pro Ala Gln Ala Arg
 65                 70                  75                  80

Arg Leu Tyr Ile Gln Asn Pro Ile Arg Leu Ile Ala Asp Val Ala Tyr
                    85                  90                  95

Thr Pro Met Arg Val Phe Pro Ala Leu Asn Pro Glu Thr Asn Glu Ser
                    100                 105                 110

Phe Asp Leu Ser Tyr Ser Val Leu Arg Ser Val Ser Pro Ile His Cys
                    115                 120                 125

Glu Tyr Leu Thr Asn Met Gly Val Arg Ala Ser Met Ser Ile Ser Ile
                    130                 135                 140

Val Val Gly Gly Lys Leu Trp Gly Leu Phe Ser Cys His His Met Ser
145                 150                 155                 160

Pro Lys Leu Ile Pro Tyr Pro Val Arg Met Ser Phe Gln Ile Phe Ser
                    165                 170                 175

Gln Val Cys Ser Ala Ile Val Glu Arg Leu Glu
                    180                 185
```

<210> SEQ ID NO 37
<211> LENGTH: 187
<212> TYPE: PRT
<213> ORGANISM: Rhodopseudomonas palustris

<400> SEQUENCE: 37

```
Asn Glu Phe Phe Arg Ser Val Arg Val Ala Ile Arg Arg Leu Gln Thr
 1               5                   10                  15

Ala Ala Asp Leu Pro Thr Ala Cys Trp Ile Ala Ala Ser Glu Val Arg
                    20                  25                  30

Arg Ile Thr Gly Phe Asp Arg Ile Lys Val Tyr Gln Phe Ala Ala Asp
                    35                  40                  45

Trp Ser Gly Gln Val Ile Ala Glu Asp Arg Asp Ser Gly Ile Pro Ser
 50                 55                  60

Leu Leu Asp Phe His Phe Pro Ser Ser Asp Ile Pro Ala Gln Ser Arg
 65                 70                  75                  80

Ala Leu Tyr Thr Ile Asn Pro Val Arg Ile Ile Pro Asp Ile Gly Tyr
                    85                  90                  95

Arg Pro Ser Pro Leu Val Pro Asp Ile Asn Pro Arg Leu Gly Gly Pro
                    100                 105                 110

Ile Asp Leu Ser Phe Ser Val Leu Arg Ser Val Ser Pro Thr His Leu
                    115                 120                 125

Glu Tyr Met Val Asn Met Gly Met His Ala Ala Met Ser Ile Ser Ile
                    130                 135                 140

Val Arg Asp Asn Arg Leu Trp Gly Met Ile Ser Cys His Asn Leu Thr
145                 150                 155                 160

Pro Arg Phe Val Ser Tyr Glu Val Arg Gln Ala Cys Glu Leu Ile Ala
                    165                 170                 175

Gln Val Leu Thr Trp Gln Ile Gly Val Leu Glu
                    180                 185
```

<210> SEQ ID NO 38
<211> LENGTH: 187
<212> TYPE: PRT
<213> ORGANISM: Synechococcus

<400> SEQUENCE: 38

```
Ser Arg Asp Ala Leu Ile Asn Arg Ile Thr His Gln Ile Arg Gln Ser
1               5                   10                  15

Leu Glu Leu Asp Gln Ile Leu Arg Ala Thr Val Glu Glu Val Arg Ala
            20                  25                  30

Phe Leu Gly Thr Asp Arg Val Lys Val Tyr Arg Phe Asp Pro Glu Gly
        35                  40                  45

His Gly Thr Val Val Ala Glu Ala Arg Gly Gly Glu Arg Leu Pro Ser
    50                  55                  60

Leu Leu Gly Leu Thr Phe Pro Ala Gly Asp Ile Pro Glu Glu Ala Arg
65                  70                  75                  80

Arg Leu Phe Arg Leu Ala Gln Val Arg Val Ile Val Asp Val Glu Ala
                85                  90                  95

Gln Ser Arg Ser Ile Ser Gln Pro Glu Ser Trp Gly Leu Ser Ala Arg
            100                 105                 110

Val Pro Leu Gly Glu Pro Leu Gln Arg Pro Val Asp Pro Cys His Val
        115                 120                 125

His Tyr Leu Lys Ser Met Gly Val Ala Ser Ser Leu Val Val Pro Leu
    130                 135                 140

Met His His Gln Glu Leu Trp Gly Leu Leu Val Ser His His Ala Glu
145                 150                 155                 160

Pro Arg Pro Tyr Ser Gln Glu Glu Leu Gln Val Val Gln Leu Leu Ala
                165                 170                 175

Asp Gln Val Ser Ile Ala Ile Ala Gln Ala Glu
            180                 185
```

<210> SEQ ID NO 39
<211> LENGTH: 8
<212> TYPE: PRT
<213> ORGANISM: Artificial
<220> FEATURE:
<223> OTHER INFORMATION: Synthetic Peptide

<400> SEQUENCE: 39

```
Lys Leu His His His His His His
1               5
```

<210> SEQ ID NO 40
<211> LENGTH: 11
<212> TYPE: PRT
<213> ORGANISM: Artificial
<220> FEATURE:
<223> OTHER INFORMATION: Synthetic Peptide

<400> SEQUENCE: 40

```
Gly Gly Gly Asp Tyr Lys Asp Asp Asp Asp Lys
1               5                   10
```

<210> SEQ ID NO 41
<211> LENGTH: 10
<212> TYPE: PRT
<213> ORGANISM: Artificial
<220> FEATURE:
<223> OTHER INFORMATION: Synthetic Peptide

<400> SEQUENCE: 41

```
Gly Gly Asp Tyr Lys Asp Asp Asp Lys
1               5                   10

<210> SEQ ID NO 42
<211> LENGTH: 6
<212> TYPE: PRT
<213> ORGANISM: Synechocystis PCC6803

<400> SEQUENCE: 42

Glu Ser Asp Ile Pro Gln
1               5

<210> SEQ ID NO 43
<211> LENGTH: 5
<212> TYPE: PRT
<213> ORGANISM: Synechocystis PCC6803

<400> SEQUENCE: 43

Pro Ile Arg Val Ile
1               5

<210> SEQ ID NO 44
<211> LENGTH: 5
<212> TYPE: PRT
<213> ORGANISM: Synechocystis PCC6803

<400> SEQUENCE: 44

Ile Leu Arg Ser Ala
1               5

<210> SEQ ID NO 45
<211> LENGTH: 5
<212> TYPE: PRT
<213> ORGANISM: Synechocystis PCC6803

<400> SEQUENCE: 45

Leu Thr Tyr Leu Lys
1               5

<210> SEQ ID NO 46
<211> LENGTH: 6
<212> TYPE: PRT
<213> ORGANISM: Synechocystis PCC6803

<400> SEQUENCE: 46

His Pro Arg Gln Ser Phe
1               5

<210> SEQ ID NO 47
<211> LENGTH: 6
<212> TYPE: PRT
<213> ORGANISM: Deinococcus radiodurans

<400> SEQUENCE: 47

Ala Ser Asp Ile Pro Ala
1               5

<210> SEQ ID NO 48
<211> LENGTH: 5
<212> TYPE: PRT
<213> ORGANISM: Deinococcus radiodurans

<400> SEQUENCE: 48

Leu Leu Arg Leu Thr
```

```
<210> SEQ ID NO 49
<211> LENGTH: 5
<212> TYPE: PRT
<213> ORGANISM: Deinococcus radiodurans

<400> SEQUENCE: 49

Val Leu Arg Ala Thr
1               5

<210> SEQ ID NO 50
<211> LENGTH: 5
<212> TYPE: PRT
<213> ORGANISM: Deinococcus radiodurans

<400> SEQUENCE: 50

Met Gln Tyr Leu Arg
1               5

<210> SEQ ID NO 51
<211> LENGTH: 6
<212> TYPE: PRT
<213> ORGANISM: Deinococcus radiodurans

<400> SEQUENCE: 51

Gly Pro Arg His Ser Phe
1               5

<210> SEQ ID NO 52
<211> LENGTH: 6
<212> TYPE: PRT
<213> ORGANISM: Pseudomonas aeruginosa

<400> SEQUENCE: 52

Ala Ser Asp Ile Pro Ala
1               5

<210> SEQ ID NO 53
<211> LENGTH: 5
<212> TYPE: PRT
<213> ORGANISM: Pseudomonas aeruginosa

<400> SEQUENCE: 53

Pro Ile Arg Leu Ile
1               5

<210> SEQ ID NO 54
<211> LENGTH: 5
<212> TYPE: PRT
<213> ORGANISM: Pseudomonas aeruginosa

<400> SEQUENCE: 54

Val Leu Arg Ser Val
1               5

<210> SEQ ID NO 55
<211> LENGTH: 5
<212> TYPE: PRT
<213> ORGANISM: Pseudomonas aeruginosa

<400> SEQUENCE: 55

Cys Glu Tyr Leu Thr
1               5
```

<210> SEQ ID NO 56
<211> LENGTH: 6
<212> TYPE: PRT
<213> ORGANISM: Pseudomonas aeruginosa

<400> SEQUENCE: 56

Thr Pro Arg Gly Ser Phe
1               5

<210> SEQ ID NO 57
<211> LENGTH: 6
<212> TYPE: PRT
<213> ORGANISM: Rhodopseudomonas palustris

<400> SEQUENCE: 57

Ser Ser Asp Ile Pro Ala
1               5

<210> SEQ ID NO 58
<211> LENGTH: 5
<212> TYPE: PRT
<213> ORGANISM: Rhodopseudomonas palustris

<400> SEQUENCE: 58

Pro Val Arg Ile Ile
1               5

<210> SEQ ID NO 59
<211> LENGTH: 5
<212> TYPE: PRT
<213> ORGANISM: Rhodopseudomonas palustris

<400> SEQUENCE: 59

Val Leu Arg Ser Val
1               5

<210> SEQ ID NO 60
<211> LENGTH: 5
<212> TYPE: PRT
<213> ORGANISM: Rhodopseudomonas palustris

<400> SEQUENCE: 60

Leu Glu Tyr Met Val
1               5

<210> SEQ ID NO 61
<211> LENGTH: 6
<212> TYPE: PRT
<213> ORGANISM: Rhodopseudomonas palustris

<400> SEQUENCE: 61

Gln Thr Arg Ala Ser Phe
1               5

<210> SEQ ID NO 62
<211> LENGTH: 6
<212> TYPE: PRT
<213> ORGANISM: Synechococcus OS-B

<400> SEQUENCE: 62

Ala Gly Asp Ile Pro Glu
1               5

<210> SEQ ID NO 63

```
<211> LENGTH: 5
<212> TYPE: PRT
<213> ORGANISM: Synechococcus OS-B

<400> SEQUENCE: 63

Gln Val Arg Val Ile
1               5

<210> SEQ ID NO 64
<211> LENGTH: 5
<212> TYPE: PRT
<213> ORGANISM: Synechococcus OS-B

<400> SEQUENCE: 64

Leu Gln Arg Pro Val
1               5

<210> SEQ ID NO 65
<211> LENGTH: 5
<212> TYPE: PRT
<213> ORGANISM: Synechococcus OS-B

<400> SEQUENCE: 65

Val His Tyr Leu Lys
1               5

<210> SEQ ID NO 66
<211> LENGTH: 6
<212> TYPE: PRT
<213> ORGANISM: Synechococcus OS-B

<400> SEQUENCE: 66

Leu Pro Leu Ile Ser Phe
1               5

<210> SEQ ID NO 67
<211> LENGTH: 6
<212> TYPE: PRT
<213> ORGANISM: Arabidopsis thaliana

<400> SEQUENCE: 67

Ala Thr Asp Ile Pro Gln
1               5

<210> SEQ ID NO 68
<211> LENGTH: 5
<212> TYPE: PRT
<213> ORGANISM: Arabidopsis thaliana

<400> SEQUENCE: 68

Lys Val Arg Met Ile
1               5

<210> SEQ ID NO 69
<211> LENGTH: 5
<212> TYPE: PRT
<213> ORGANISM: Arabidopsis thaliana

<400> SEQUENCE: 69

Arg Val Arg Met Ile
1               5

<210> SEQ ID NO 70
<211> LENGTH: 5
<212> TYPE: PRT
```

```
<213> ORGANISM: Arabidopsis thaliana

<400> SEQUENCE: 70

Thr Leu Arg Ala Pro
1               5

<210> SEQ ID NO 71
<211> LENGTH: 5
<212> TYPE: PRT
<213> ORGANISM: Arabidopsis thaliana

<400> SEQUENCE: 71

Leu Gln Tyr Met Ala
1               5

<210> SEQ ID NO 72
<211> LENGTH: 5
<212> TYPE: PRT
<213> ORGANISM: Arabidopsis thaliana

<400> SEQUENCE: 72

Ser Gln Tyr Met Ala
1               5

<210> SEQ ID NO 73
<211> LENGTH: 5
<212> TYPE: PRT
<213> ORGANISM: Arabidopsis thaliana

<400> SEQUENCE: 73

Ala Gln Tyr Met Ser
1               5

<210> SEQ ID NO 74
<211> LENGTH: 5
<212> TYPE: PRT
<213> ORGANISM: Arabidopsis thaliana

<400> SEQUENCE: 74

Ala Gln Tyr Met Thr
1               5

<210> SEQ ID NO 75
<211> LENGTH: 5
<212> TYPE: PRT
<213> ORGANISM: Arabidopsis thaliana

<400> SEQUENCE: 75

Thr Gln Tyr Met Ala
1               5

<210> SEQ ID NO 76
<211> LENGTH: 6
<212> TYPE: PRT
<213> ORGANISM: Arabidopsis thaliana

<400> SEQUENCE: 76

His Pro Arg Ser Ser Phe
1               5

<210> SEQ ID NO 77
<211> LENGTH: 6
<212> TYPE: PRT
<213> ORGANISM: Arabidopsis thaliana
```

```
<400> SEQUENCE: 77

Asn Pro Arg Ser Ser Phe
1               5
```

PLANTS WITH ALTERED PHYTOCHROMES

GOVERNMENT SUPPORT

This invention was made with government support under 07191530 awarded by the National Science Foundation and 13-CRHF-0-6055 awarded by the USDA/NIFA. The government has certain rights in the invention.

INCORPORATION OF SEQUENCE LISTING

The instant application contains a Sequence Listing which has been submitted in ASCII format via EFS-Web and is hereby incorporated by reference in its entirety. Said ASCII copy, created on Oct. 1, 2013, is named ASFILED_Substitute SequenceListing-Text.txt and is 188,936 bytes in size.

BACKGROUND

The rise of the global population and demands for carbon-neutral biofuels have accelerated the need to improve agricultural productivity. An emerging strategy is to control plant reproduction and architecture to better fit specific environments and to increase crop densities. Increasing crop densities may be achieved by producing plants that perform well in more competitive environments. Plant architecture, timing of reproduction, and plant responses to competition may be manipulated to produce plants adapted to growing in crowded conditions.

Phytochromes encompass a diverse collection of biliproteins that enable cellular light perception by photoconverting between a red-light (R)-absorbing ground state—Pr and a far-red light (FR)-absorbing active state—Pfr. In *Arabidopsis thaliana* there are five phytochromes, designated phytochrome A (phyA) to phytochrome E (phyE). Phytochrome B (phyB) is the predominant phytochrome regulating de-etiolation responses in R light and shade avoidance. Phytochromes are synthesized in the cytosol as an inactive Pr form, and are converted to the biologically active Pfr form by light irradiation which then is translocated into the nucleus. Phytochromes play fundamental roles in photoperception by a plant and adaptation of its growth to the ambient light environment.

SUMMARY

An isolated polynucleotide comprising a contiguous coding sequence encoding a polypeptide comprising an amino acid sequence having at least 80% identity to at least one sequence selected from SEQ ID NOs: 1-22 and containing an amino acid other than tyrosine at the position corresponding to Y361 of SEQ ID NO. 1, and plants and plant cells containing such polynucleotides are provided. In certain embodiments, a plant comprising the isolated polynucleotide exhibits increased expression of the polypeptide, relative to a control plant, and, relative to the control plant, may exhibit increased light sensitivity, decreased height, decreased diameter, decreased petiole length, decreased internode length, decreased stem diameter, decreased hypocotyl length under an R (red light) fluence rate of less than 1 $\mu$mole $m^{-2}$ $sec^{-1}$, modified hyponasty, or enhanced germination. In certain embodiments, increased light sensitivity results in a smaller plant adapted to provide an increased yield in shaded or competitive conditions.

In another embodiment the invention provides a method of producing a transgenic plant by introducing into a plant cell a polynucleotide encoding a polypeptide comprising an amino acid sequence having at least 80% identity to at least one amino acid sequence selected from SEQ ID NOs: 1-22 and having an amino acid other than tyrosine at the position corresponding to Y361 of SEQ ID NO:1, and regenerating the transformed cell to produce a transgenic plant.

In another embodiment, an isolated polypeptide comprising an amino acid sequence having at least 80% identity to at least one amino acid sequence selected from SEQ ID NOs: 1-22, and having an amino acid other than tyrosine at the position corresponding to Y361 of SEQ ID NO:1 is provided.

In another embodiment, an isolated polynucleotide is provided which comprises a contiguous coding sequence encoding a polypeptide having at least 80% identity to at least one amino acid sequence selected from SEQ ID NOs: 1-22 and which has at least one different amino acid at a select position. The different amino acid may be (i) an amino acid other than aspartate (D) at the position corresponding to 307 of SEQ ID NO:1, (ii) an amino acid other than arginine (R) at the position corresponding to 322 of SEQ ID NO: 1, (iii) an amino acid other than arginine (R) at the position corresponding to 352 of SEQ ID NO: 1, (iv) an amino acid other than arginine (R) at the position corresponding to 582 of SEQ ID NO: 1, or a combination thereof.

Other aspects of the invention will become apparent by consideration of the detailed description and accompanying drawings.

BRIEF DESCRIPTION OF THE DRAWINGS

FIG. 12A, FIG. 12B, FIG. 12C, and FIG. 12D. Chart depicting the alignment of the full-length polypeptide sequences of phyB from *Arabidopsis* and crop species. Residues corresponding to Tyr361 in *Arabidopsis* phyB are indicated by the arrowhead at 361. At, *Arabidopsis thaliana*; Zm, *Zea mays*; Os, *Oryza sativa*; Sb, *Sorghum bicolor*, Gm, *Glycine max*; St, *Solanum tuberosum* L.; Ps, *Pisum sativum*; Vv, *Vitis vinifera*. The protein sequences were obtained from National Center for Biotechnology Information except ZmphyB sequence which was from the Phytozome resource. Alignment was performed using ClustalW (*Nucleic Acids Res.* 22 (22); 4673-80).

FIG. 13. Chart depicting the alignment of the polypeptide sequences of GAF domains from microbial phys with available structures and phyB among Arabidopsis and crop species. Residues corresponding to Asp307, Arg322, Arg352, and Tyr361 in Arabidopsis phyB are indicated by the arrowhead. At, *Arabidopsis thaliana*; Zm, *Zea mays*; Os, *Oryza sativa*; Sb, *Sorghum bicolor*; Gm, *Glycine max*; St, *Solanum tuberosum* L.; Ps, *Pisum sativum*; Vv, *Vitis vinifera*; Dr, *Deinococcus radiodurans*; Pa, *Pseudomonas aeruginosa*; Rp, *Rhodopseudomonas palustris*; SyB, *Synechococcus* OS-B'; Syn, *Synechocystis* PCC6803. The protein sequences were obtained from National Center for Biotechnology Information except ZmphyB sequence which was from the Phytozome resource. Alignment was performed using ClustalW (*Nucleic Acids Res.* 22 (22); 4673-80).

DETAILED DESCRIPTION

Figure 1:
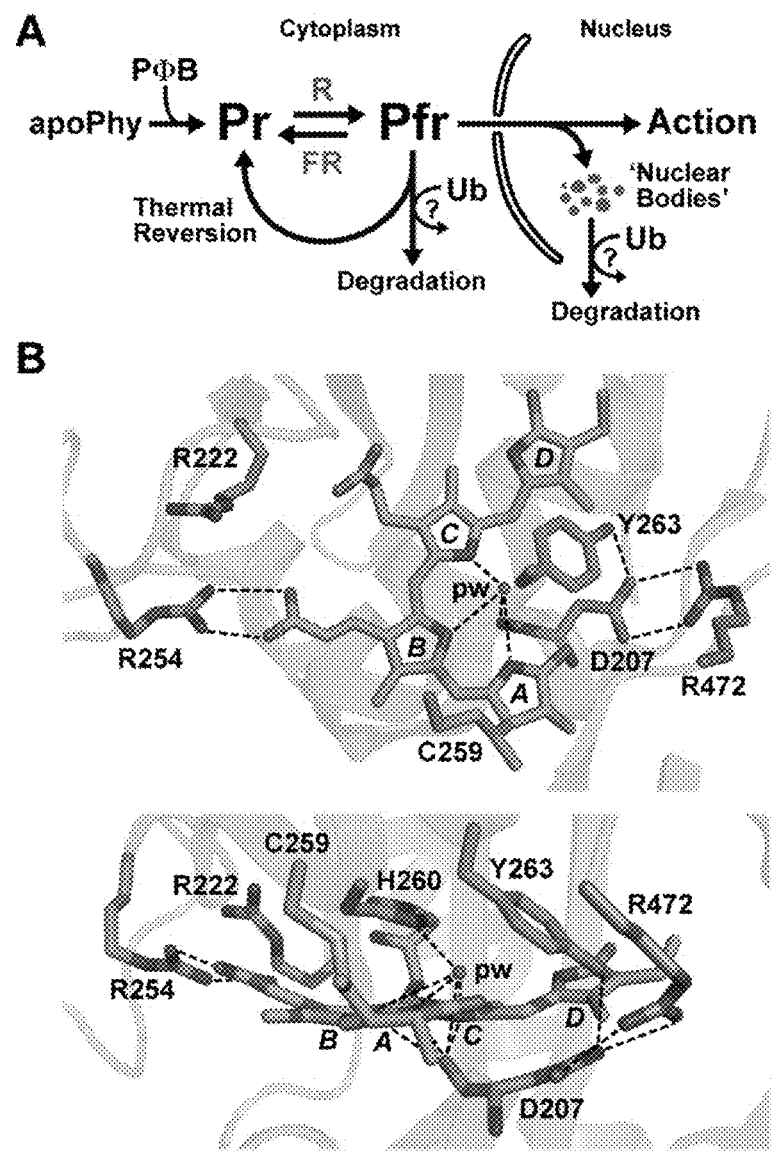
FIG. 1. Drawings depicting the scheme of phy action and the three-dimensional relationships of key amino acids within the bilin-binding photosensory module (PSM). (A) Scheme depicting the main steps involved in phy assembly, Pr/Pfr photointerconversion, stability, and action in higher plants. (B) Top (upper) and side (lower) three-dimensional views of the PSM from Syn-Cph1 (PDB code 2VEA [3]) assembled with phycocyanobilin (PCB) highlighting the positions of key conserved amino acids surrounding the bilin and the cysteine involved in bilin attachment (C259). The residue numbers are those for the homolog Syn-Cph1 from the cyanobacterium *Synechocystis* PCC6803. The GAF domain and PHY hairpin are colored in green and orange, respectively. PCB is colored in cyan with the individual pyrrole rings labeled. Sulfur, oxygen and nitrogen atoms are colored yellow, red, and deep blue, respectively. Important contacts are indicated by dashed lines. pw, pyrrole water. (C) Alignment of the GAF domain protein sequences among bacterial phys with available structures with those from the phyB-E family in *Arabidopsis*. Residues pertinent to this study are indicated by red arrowhead; their sequence positions are shown either above for Syn-Cph1 or below the alignment for *A. thaliana* phyA and phyB. At, *Arabidopsis thaliana*; Dr, *Deinococcus radiodurans*; Pa, *Pseudomonas aeruginosa*; Rp, *Rhodopseudomonas palustris*; SyB, *Synechococcus* OS-B'; Syn, *Synechocystis* PCC6803

The present disclosure relates to polynucleotides and polypeptides and use of the polynucleotides and polypeptides for modifying the phenotypes of plants or plant cells. Modified plants or plant cells comprising the polynucleotides and/or polypeptides are also provided. In certain embodiments, the modified plants or plant cells exhibit one or more of an altered light sensitivity, an improved or enhanced germination efficiency of seeds, such as in low light, a hypersensitivity to white and red light with respect to hypocotyl and stem growth, improved shade tolerance, and a smaller plant size.

The polypeptides discussed herein are phytochromes and show homology to certain phytochrome sequences from *Arabidopsis thaliana*. The term "phytochrome" is used generically to refer to a phytochrome from any plant species. Plant phytochromes include phyA, phyB, phyC, phyD and phyE.

Phytochrome domains from a variety of organisms may be used as starting points for modifications that will generate the modified phytochromes of the present invention, and isolated polynucleotides encoding the modified phy domains. In certain embodiments the phytochrome is a modified phyB plant phytochrome, or a modified cGMP phosphodiesterase/adenylyl cyclase/FhlA (GAF) domain or modified chromophore binding domain (CBD) of phyB. Modification of phytochromes and/or phytochrome domains can be performed by methods known in the art, e.g., site-directed mutations, additions, deletions, and/or substitutions of one or more amino acid residues of existing phytochromes and/or phytochrome domains. Alternatively, modified phytochromes and/or phytochrome domains can be synthesized de novo, for example by synthesis of novel genes that would encode phytochrome domains with desired modifications.

In certain embodiments, expression in plants of a modified phytochrome having an amino acid sequence with at least 80%, or at least 95% identity to at least one of SEQ ID NOs: 1-22 and having an amino acid other than tyrosine at the position corresponding to Y361 of SEQ ID NO: 1 (for example, by introducing a polynucleotide sequence having at least 95% identity to (i) a sequence selected from SEQ ID NOs 23-33 into the plant, or (ii) a GAF-encoding domain of a sequence selected from SEQ ID NOs: 23-33, and encoding an amino acid other than tyrosine at the position corresponding to Y361 of SEQ ID NO: 1) results in plants that have altered light sensitivity, including, but not limited to, an improved germination efficiency of seeds in low light, a hypersensitivity to white and red light with respect to hypocotyl and stem growth, improved shade tolerance, reduced leaf surface area and combinations thereof, relative to control plants that do not express the modified phytochrome. The shared sequence identity of the nucleotides encoding phyB from a variety of species is shown in Table 1.

TABLE 1

Percent Identities of phyB from a variety of species with *Arabidopsis* phyB

| Species phyB | Accession Number | Nucleotide SEQ ID NO: | Percent Identity to SEQ ID NO: 23 |
|---|---|---|---|
| *Arabidopsis* | NM_127435 | SEQ ID NO: 23 | 100% |
| *Zea mays* (maize) | GRMZM2G124532 | SEQ ID NO: 24 | 70.2% |
| *Oryza sativa* (rice) | JN594210 | SEQ ID NO: 25 | 70.3% |
| *Sorghum bicolor* (sorghum) | Y466089 | SEQ ID NO: 26 | 69.6% |
| *Glycine max* (soybean) phyB1 | EU428749 | SEQ ID NO: 27 | 73.1% |
| *G. max* phyB2 | EU428750 | SEQ ID NO: 28 | 72.6% |
| *G. max* phyB3 | EU428751 | SEQ ID NO: 29 | 72.5% |
| *G. max* phyB4 | EU428752 | SEQ ID NO: 30 | 58.6% |
| *Solanum tuberosum* L. (potato) | DQ342235 | SEQ ID NO: 31 | 75.1% |
| *Pisum sativum* (pea) | AF069305 | SEQ ID NO: 32 | 70.8% |
| *Vitis vinifera* (grape): | EU436650 | SEQ ID NO: 33 | 76.1% |

The terms "isolated," "purified", or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

Two nucleic acid sequences or polypeptides are said to be "identical" if the sequence of nucleotides or amino acid residues, respectively, in the two sequences are the same when aligned for maximum correspondence as described below. The term "complementary to" is used herein to mean that the sequence is complementary to all or a portion of a reference polynucleotide sequence. In the case of both expression of transgenes and inhibition of endogenous genes (e.g., by antisense or sense suppression) the inserted polynucleotide sequence need not be identical and may be "substantially identical" to a sequence of the gene from which it was derived.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

In the case where the inserted polynucleotide sequence is transcribed and translated to produce a functional polypeptide, because of codon degeneracy, a number of polynucleotide sequences will encode the same polypeptide. These variants are specifically covered by the term "polynucleotide sequence from" a particular gene. In addition, the term specifically includes sequences (e.g., full length sequences) that are substantially identical (determined as described below) with a gene sequence encoding a polypeptide of the present invention and that encode polypeptides or functional polypeptide fragments that retain the function of a polypeptide of the present invention, e.g., a modified bacterial phytochrome with increased fluorescence.

Optimal alignment of sequences for comparison may be conducted by methods commonly known in the art, for example by the search for similarity method described by Pearson and Lipman 1988, Proc. Natl. Acad. Sci. USA 85: 2444-2448, by computerized implementations of algorithms such as GAP, BESTFIT, BLAST®, FASTA, and TFASTA in the Wisconsin Genetics Software Package, Genetics Computer Group (GCG), Madison, Wis., or by inspection. In a preferred embodiment, protein and nucleic acid sequence identities are evaluated using the Basic Local Alignment Search Tool ("BLAST®"), which is well known in the art (Karlin and Altschul, 1990, Proc. Natl. Acad. Sci. USA 87: 2267-2268; Altschul et al., 1997, Nucl. Acids Res. 25: 3389-3402), the disclosures of which are incorporated by reference in their entireties. The BLAST® programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990). The BLAST® programs can be used with the default parameters or with modified parameters provided by the user.

"Percentage of sequence identity" is determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 25% sequence identity compared to a reference sequence as determined using the programs described herein; preferably BLAST® using standard parameters, as described. Alternatively, percent identity can be any integer from 25% to 100%. More preferred embodiments include polynucleotide sequences that have at least about: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% sequence identity compared to a reference sequence. These values can be appropriately adjusted to determine corresponding identity of proteins encoded by two nucleotide sequences by taking into account codon degeneracy, amino acid similarity, reading frame positioning, and the like. Accordingly, polynucleotides of the present invention encoding a protein of the present invention include nucleic acid sequences that have substantial identity to the nucleic acid sequences that encode the polypeptides of the present invention. Polynucleotides encoding a polypeptide comprising an amino acid sequence that has at least about: 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference polypeptide sequence are also preferred.

The term "substantial identity" of amino acid sequences (and of polypeptides having these amino acid sequences) normally means sequence identity of at least 40% compared to a reference sequence as determined using the programs described herein; preferably BLAST® using standard parameters, as described. Preferred percent identity of amino acids can be any integer from 40% to 100%. More preferred embodiments include amino acid sequences that have at least about: 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference sequence. Polypeptides that are "substantially identical" share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine. Accordingly, polypeptides or proteins of the present invention include amino acid sequences that have substantial identity to the amino acid sequences of the polypeptides of the present invention, which are modified phytochromes that result in plants having altered sensitivity compared with plants.

In one embodiment, a modified phyB phytochrome is created by substituting the tyrosine at the position corresponding to Tyr361 of SEQ ID NO:1 with a phenylalanine (Phe). It is contemplated that various modifications of this Tyr361 residue (and its functional equivalents in other phytochromes) will result in phytochromes useful for practicing the present invention. Some examples of modified phytochromes useful for the practice of this invention include modifications of the tyrosine domain corresponding to Y361 of SEQ ID NO: 1, for example: Tyr to Phe (i.e., Y to F); Tyr to Trp (i.e., Y to W); Tyr to Ile (i.e., Y to I); Tyr to Leu (i.e., Y to L); Tyr to Val (i.e., Y to V); Tyr to Ala (i.e., Y to A); Tyr to Pro (i.e., Y to P); Tyr to Asn (i.e., Y to N); Tyr to Glu (i.e., Y to E); and Tyr to Thr (i.e., Y to T), Tyr to Gly (i.e., Y to G); Tyr to Ser (i.e., Y to 5); Tyr to Cys (i.e., Y to C); Tyr to Lys (i.e., Y to K); Tyr to Arg (i.e., Y to R); Tyr to His (i.e., Y to H); Tyr to Met (i.e., Y to M); Tyr to Asp (i.e., Y to D); or Tyr to Gln (i.e., Y to Q).

The modified phyB phytochrome may contain amino acid substitutions described herein or known in the art at other locations in the phyB or phyB domain. In certain embodiments, the modified phytochrome may contain an amino acid substitution at the residue corresponding to D307, R322, R352, or R582 of the *Arabidopsis* phytochrome shown in SEQ ID NO: 1. For example, the modified phytochrome may contain at least one of (i) an amino acid other than aspartate (D) at the position corresponding to 307 of SEQ ID NO:1, (ii) an amino acid other than arginine (R) at the position corresponding to 322 of SEQ ID NO: 1, (iii) an amino acid other than arginine (R) at the position corresponding to 352 of SEQ ID NO: 1, and (iv) an amino acid other than arginine (R) at the position corresponding to 582 of SEQ ID NO: 1, or any combination thereof. These substitutions may be present alone, in any combination, including one or more substitutions in addition to a substitution at the position corresponding to Y361 of SEQ ID NO:1. The substitutions may include one or more of the following R352A, R582A, R322A and D307A.

The substitutions at R352 and R582, such as R352A, R582A produce a phytochrome phenotype that is slightly hyperactive with respect to signalling. For example, the substitution at R582 shows slightly stronger repression on hypocotyl growth at intermediate R fluence rates as compared to wild-type. The substitution at R322, such as R322A, produces a photchrome phenotype that is slightly hypoactive with respect to signalling.

As shown in the sequence alignment of FIG. 12, Tyr361 is conserved in plant phytochromes. Sequence identity of phyB from crop species compared with *Arabidopsis* phyB (SEQ ID NO: 1) is as follows: *Zea mays* (maize; SEQ ID NO: 2): 70.2%; *Oryza sativa* (rice; SEQ ID NO: 3): 70.3%; *Sorghum bicolor* (sorghum; SEQ ID NO: 4): 69.6%; *Glycine max* (soybean), phyB1 (SEQ ID NO: 5): 73.1%; phyB2 (SEQ ID NO: 6): 72.6%; phyB3 (SEQ ID NO: 7): 72.5%; phyB4 (SEQ ID NO: 8): 58.6%; *Solanum tuberosum* L. (potato; SEQ ID NO:9): 75.1%; *Pisum sativum* (pea; SEQ ID NO: 10): 70.8%; *Vitis vinifera* (grape; SEQ ID NO: 11): 76.1%.

As shown in FIG. 12, Tyr361 of SEQ ID NO: 1 (*Arabidopsis* phyB) corresponds to Tyr359 of SEQ ID NO: 2 (maize phyB), Tyr368 of SEQ ID NO: 3 (rice phyB), Tyr376 of SEQ ID NO: 4 (*sorghum* phyB), Tyr345 of SEQ ID NO: 5 (soybean phyB1), Ty357 of SEQ ID NO: 6 (soybean phyB2), Tyr308 of SEQ ID NO: 7 (soybean phyB3), Tyr244 of SEQ ID NO: 8 (soybean phyB4), Tyr336 of SEQ ID NO: 9 (potato phyB), Tyr324 of SEQ ID NO: 10 (pea phyB), and Tyr335 of SEQ ID NO: 11 (grape phyB).

Tyr361 of SEQ ID NO: 1 (*Arabidopsis* phyB) also corresponds to Tyr 263 of the cyanobacteriophytochrome from *Synechocystis* PCC6803, to Tyr 263 of the bacteriophytochrome from *Deinococcus radiodurans*, to Tyr 250 of the bacteriophytochrome from *Pseudomonas aeruginosa*, to Tyr272 of the bacteriophytochrome from *Rhodopseudomonas palustris*, and to Tyr142 of the cyanobacteriophytochrome from *Synechococcus* OS-B'.

Figure 13:
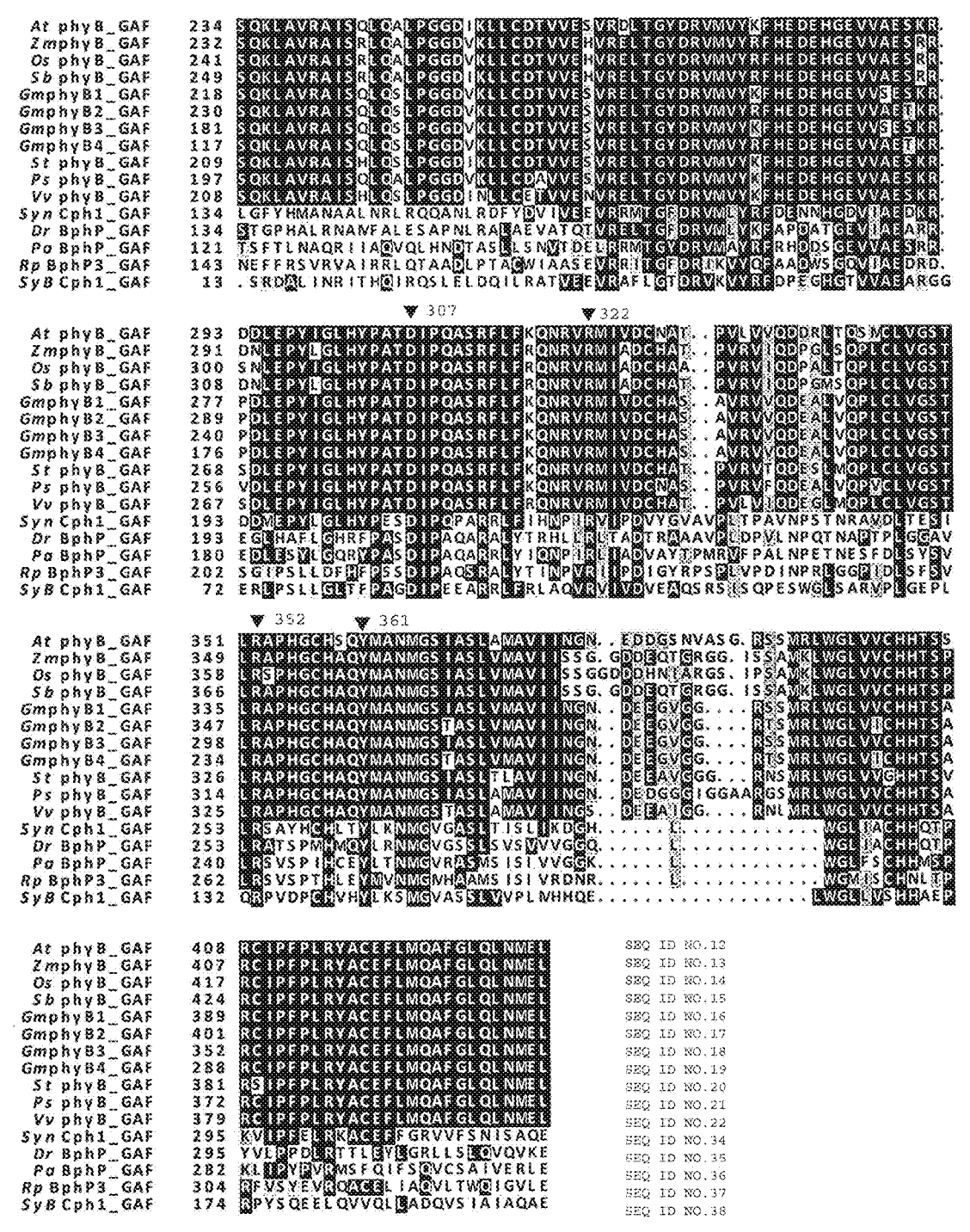

As shown in FIG. 13, the percent identity of the GAF domains to *Arabidopsis* phyB GAF domain (position 234 to 433 of SEQ ID NO: 1; SEQ ID NO. 12) are as follows: *Zea mays* (maize; position 232-432 of SEQ ID NO: 2; SEQ ID NO: 13): 82.1% *Oryza sativa* (rice; position 241 to 442 of SEQ ID NO: 3; SEQ ID NO: 14): 82.7%; *Sorghum bicolor* (*sorghum*; position 249 to 449 of SEQ ID NO: 4; SEQ ID NO: 15): 82.1%; *Glycine max* (soybean), phyB1 (position 218 to 414 of SEQ ID NO: 5; SEQ ID NO: 16): 87.5%; phyB2 (position 230 to 426 of SEQ ID NO: 6; SEQ ID NO: 17): 85.5%; phyB3 (position 181 to 377 of SEQ ID NO: 18): 87.5%; phyB4 (position 117 to 313 of SEQ ID NO: 8; SEQ ID NO: 19): 85.5%; *Solanum tuberosum* L. (potato; position 209 to 406 of SEQ ID NO:9; SEQ ID NO: 20): 87.0%; *Pisum sativum* (pea; position 197 to 397 of SEQ ID NO: 10; SEQ ID NO: 21): 88.1%; *Vitis vinifera* (grape; position 208 to 404 of SEQ ID NO: 11; SEQ ID NO: 22): 85.0%.

As shown in FIG. 13, Tyr361 of SEQ ID NO: 1 (*Arabidopsis* phyB) corresponds to Tyr128 of SEQ ID NO: 12 (*Arabidopsis* phyB GAF domain); Tyr128 of SEQ ID NO: 13 (maize phyB GAF domain), Tyr128 of SEQ ID NO: 14 (rice phyB GAF domain), Tyr128 of SEQ ID NO: (*sorghum* phyB GAF domain), Tyr128 of SEQ ID NO: 16 (soybean phyB1 GAF domain), Ty128 of SEQ ID NO: 17 (soybean phyB2 GAF domain), Tyr128 of SEQ ID NO: 18 (soybean phyB3 GAF domain), Tyr128 of SEQ ID NO: 19 (soybean phyB4 GAF domain), Tyr128 of SEQ ID NO: 20 (potato phyB GAF domain), Tyr128 of SEQ ID NO: 21 (pea phyB GAF domain), and Tyr128 of SEQ ID NO: 22 (grape phyB GAF domain).

As shown in FIG. 13, Tyr361 of SEQ ID NO: 1 (At phyB_GAF; *Arabidopsis* phyB) also corresponds to Tyr130 of the cyanobacteriophytochrome GAF domain from *Synechocystis* PCC6803 (Syn Cph_GAF; SEQ ID NO: 34), to Tyr 130 of the bacteriophytochrome GAF domain from *Deinococcus radiodurans* (Dr Bph_GAF; SEQ ID NO: 35), to Tyr 130 of the bacteriophytochrome GAF domain from *Pseudomonas aeruginosa* (Pa BphP_GAF; SEQ ID NO: 36), to Tyr130 of the bacteriophytochrome GAF domain from *Rhodopseudomonas palustris* (Rp BphP3_GAF; SEQ ID NO: 37), and to Tyr130 of the cyanobacteriophytochrome GAF domain from *Synechococcus* OS-B (SyB Cph_GAF; SEQ ID NO: 38).

The invention also relates to nucleic acids that selectively hybridize to the exemplified sequences, including hybridizing to the exact complements of these sequences. The specificity of single-stranded DNA to hybridize complementary fragments is determined by the "stringency" of the reaction conditions (Sambrook et al., 1989). Hybridization stringency increases as the propensity to form DNA duplexes decreases. In nucleic acid hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments.

DNA duplexes are stabilized by: (1) the number of complementary base pairs; (2) the type of base pairs; (3) salt concentration (ionic strength) of the reaction mixture; (4) the temperature of the reaction; and (5) the presence of certain organic solvents, such as formamide, which decrease DNA duplex stability. In general, the longer the probe, the higher the temperature required for proper annealing. A common approach is to vary the temperature; higher relative temperatures result in more stringent reaction conditions.

To hybridize under "stringent conditions" describes hybridization protocols in which nucleotide sequences at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Since the target sequences are generally present at excess, at Tm, 50% of the probes are occupied at equilibrium.

"Stringent hybridization conditions" are conditions that enable a probe, primer, or oligonucleotide to hybridize only to its target sequence (e.g., SEQ ID NO:1). Stringent conditions are sequence-dependent and will differ. Stringent conditions comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, e.g. 50% (v/v) formamide, 0.1% bovine serum albumin, 0.1% Ficoll, 0.1% polyvinylpyrrolidone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1×SSC containing EDTA at 55° C. Preferably, the conditions are such that sequences at least about 65%, 70%, 75%, 85%, 90%, 95%, 98%, or 99% homologous to each other typically remain hybridized to each other. These conditions are presented as examples and are not meant to be limiting.

"Moderately stringent conditions" use washing solutions and hybridization conditions that are less stringent, such that a polynucleotide will hybridize to the entire, fragments, derivatives, or analogs of the target sequence (e.g., SEQ ID NO:1). One example comprises hybridization in 6×SSC, 5×Denhardt's solution, 0.5% SDS and 100 µg/ml denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (Ausubel et al., 1993; Kriegler, 1990).

"Low stringent conditions" use washing solutions and hybridization conditions that are less stringent than those for moderate stringency, such that a polynucleotide will hybridize to the entire, fragments, derivatives, or analogs of the target sequence (e.g., SEQ ID NO:1). A nonlimiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 µg/ml denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross-species hybridizations, are well-described (Ausubel et al., 1993; Kriegler, 1990).

A "functional homolog," "functional equivalent," or "functional fragment" of a polypeptide of the present invention is a polypeptide that is homologous to the specified polypeptide but has one or more amino acid differences from the specified polypeptide. A functional fragment or equivalent of a polypeptide retains at least some, if not all, of the activity of the specified polypeptide.

Transgenic plants and methods of producing transgenic plants are provided. Such transgenic plants are produced, in certain embodiments, by introducing into a plant or plant cell a polynucleotide encoding a polypeptide comprising a sequence having at least about 80%, at least about 85%, at least about 90%, at least about 95%, at least about 98%, or at least about 99% identity to at least one amino acid sequence selected from SEQ ID NOs: 1-22, wherein the tyrosine corresponding to Y361 of SEQ ID NO:1 is replaced with a different amino acid. In certain embodiments, the polynucleotide is provided as a construct in which a promoter is operably linked to the polynucleotide. Such transgenic plants may also be produced, in certain embodiments, by introducing into a plant or plant cell a polynucleotide encoding a polypeptide comprising a sequence having at least about 80%, at least about 85%, at least about 90%, at least about 95%, at least about 98%, or at least about 99% identity to at least one sequence selected from the amino acid sequence selected from SEQ ID NOs: 1-22, wherein the tyrosine corresponding to Y361 of SEQ ID NO:1 is replaced with a different amino acid.

The polynucleotide sequences can be introduced into plants which do not express the corresponding native form of unmodified phyB, such as plants lacking the native gene, or containing a mutated, truncated or downregulated version of the native gene, such that little or no phyB polypeptide is expressed, or a phyB polypeptide is expressed that is partially or substantially inactive. The modified phyB replaces or substitutes for the native gene function. The polynucleotides can also be expressed in wild-type plants containing the corresponding native phyB gene sequence. In this case, the modified phyB over-rides the functions of the wild type endogenous gene in a dominant fashion, since it is hyperactive.

Plants expressing the modified phyB have surprisingly altered light sensitivity and altered photoresponses. Altered photoresponses relative to a control plant include, without limitation, at least one of an improved germination efficiency of seeds, such as in low light or following a pulse of white light, a hypersensitivity to white and red light with respect to hypocotyl and stem growth, improved shade tolerance, a smaller mature plant size, reduced plant height, smaller mature plant diameter, decreased petiole length, reduced internode length, shorter stems, smaller stem diameter, increased leaf chlorophyll concentration, decreased leaf length, increased root length, increased root branching, improved leaf unfolding, flatter leaves (increased hyponasty), reduced leaf surface area and combinations thereof.

Plants expressing modified phyB comprising a substitution at Tyr361 are smaller in size and more tolerant of low light conditions such as would be experienced in crowded field conditions. In one embodiment, plants expressing the modified phyB grow more effectively when planted in higher densities, permitting higher yields over a given planting area.

The Y361F substitution generates a hyperactive photoreceptor that still requires light for activation. As such, plants expressing the modified Y361F phytochrome display accentuated phyB signaling, useful in agricultural settings with fewer side effects. The replacement of wild-type phyB with phyB$^{Y361F}$ in plants increases the sensitivity of hypocotyls to R, generates seeds with a stronger germination response in white light, and further accentuates the end-of-day far-red light (EOD-FR) response of seedlings, substantially without altering flowering time, such as in short days. The phyB-mediated responses to R and EOD-FR are connected to the shade avoidance response. Without wishing to be bound to any theory, it is possible that increased signaling by the phyB$^{Y361F}$ variant attenuates shade avoidance response by enabling the small amounts of Pfr generated by low fluence R, or the residual Pfr remaining after EOD-FR (or presumably in high FR/R light environments) to more effectively promote normal photomorphogenesis.

It is envisaged that a plant produced following the introduction of a polynucleotide disclosed herein exhibits altered or modified characteristics relative to the control plant. The modified characteristics include, but are not limited to, increased hyponasty, decreased height, decreased diameter, decreased petiole length, decreased internode length, decreased stem diameter, decreased hypocotyl length under an R fluence rate of less than 1 µmole m$^{-2}$ sec$^{-1}$ (or less than 0.5 µmole m$^{-2}$ sec$^{-1}$, less than 0.6 µmole m$^{-2}$ sec$^{-1}$, less than 0.7 µmole m$^{-2}$ sec$^{-1}$, or less than 0.8 µmole m$^{-2}$ sec$^{-1}$), enhanced germination or any combination thereof. The altered characteristic may be decreased or enhanced by at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 175%, at least about 200%, at least about 250%, at least about 300%, or at least about 400% relative to a control plant.

As a nonlimiting example, such modified plants may have a compact size and have a height or diameter that is at least about 20%, at least about 30%, at least about 50%, at least about 75%, or at least about 100% smaller than the height or diameter of a control plant. As another nonlimiting example, such modified plants may provide an increased yield of seed, grain, forage, fruit, root, leaf, or combination thereof that is at least about 5%, at least about 10%, at least about 20%, at least about 25%, at least about 30%, at least about 40%, at least about 50%, at least about 60%, at least about 70%, at least about 75%, at least about 80%, at least about 90%, or at least about 100% increased over the yield from corresponding control plants. As used herein, "yield" refers to the maximum yield achievable per given planting area, and does not refer to the yield from an individual plant. Maximum or higher yields may be achieved by planting a higher number or density of plants in a given area.

As used herein, a "control plant" is a plant that is substantially equivalent to a test plant or modified plant in all parameters with the exception of the test parameters. For example, when referring to a plant into which a polynucleotide according to the present invention has been introduced, in certain embodiments, a control plant is an equivalent plant into which no such polynucleotide has been introduced. In certain embodiments, a control plant is an equivalent plant into which a control polynucleotide has been introduced. In such instances, the control polynucleotide is one that is expected to result in little or no phenotypic effect on the plant.

The polynucleotides of the present invention may be introduced into a plant cell to produce a transgenic plant. As used herein, "introduced into a plant" with respect to polynucleotides encompasses the delivery of a polynucleotide into a plant, plant tissue, or plant cell using any suitable polynucleotide delivery method. Methods suitable for introducing polynucleotides into a plant useful in the practice of the present invention include, but are not limited to, freeze-thaw method, microparticle bombardment, direct DNA uptake, whisker-mediated transformation, electroporation, sonication, microinjection, plant virus-mediated, and *Agrobacterium*-mediated transfer to the plant. Any suitable *Agrobacterium* strain, vector, or vector system for transforming the plant may be employed according to the present invention. In certain embodiments, the polynucleotide is introduced using at least one of stable transformation methods, transient transformation methods, or virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320-334), electroporation (Riggs et al. (1986) Proc. Natl. Acad. Sci. USA 83:5602-5606, *Agrobacterium*-mediated transformation (U.S. Pat. Nos. 5,981,840 and 5,563,055), direct gene transfer (Paszkowski et al. (1984) EMBO J. 3:2717-2722), and ballistic particle acceleration (see, for example, U.S. Pat. Nos. 4,945,050; 5,879,918; 5,886,244; 5,932,782; Tomes et al. (1995) in Plant Cell, Tissue, and Organ Culture: Fundamental Methods, ed. Gamborg and Phillips (Springer-Verlag, Berlin); and McCabe et al. (1988) Biotechnology 6:923-926). Also see Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); McCabe et al. (1988) Bio/Technology 6:923-926 (soybean); Finer and McMullen (1991) In Vitro Cell Dev. Biol. 27P:175-182 (soybean); Singh et al. (1998) Theor. Appl. Genet. 96:319-324 (soybean); Datta et al. (1990) Biotechnology 8:736-740 (rice); Klein et al. (1988) Proc. Natl. Acad. Sci. USA 85:4305-4309 (maize); Klein et al. (1988) Biotechnology 6:559-563 (maize); U.S. Pat. Nos. 5,240,855; 5,322,783 and 5,324,646; Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; U.S. Pat. No. 5,736,369 (cereals); Bytebier et al. (1987) Proc. Natl. Acad. Sci. USA 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via *Agrobacterium tumefaciens*); all of which are herein incorporated by reference in their entireties.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media and/or root induction media. See, for example, McCormick et al. (1986) Plant Cell Reports 5:81-84. These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. Thus as used herein, "transformed seeds" refers to seeds that contain the nucleotide construct stably integrated into the plant genome.

In certain embodiments, the polynucleotides to be introduced into the plant are operably linked to a promoter sequence and may be provided as a construct. As used herein, a polynucleotide is "operably linked" when it is placed into a functional relationship with a second polynucleotide sequence. For instance, a promoter is operably linked to a coding sequence if the promoter is connected to the coding sequence such that it may effect transcription of the coding sequence. In various embodiments, the polynucleotides may be operably linked to at least one, at least two, at least three, at least four, at least five, or at least ten promoters.

Promoters useful in the practice of the present invention include, but are not limited to, constitutive, inducible, temporally-regulated, developmentally regulated, chemically regulated, tissue-preferred and tissue-specific promoters. Suitably, the promoter causes sufficient expression in the plant to produce the phenotypes described herein. Suitable promoters include, without limitation, the 35S promoter of the cauliflower mosaic virus, ubiquitin, tCUP cryptic constitutive promoter, the Rsyn7 promoter, pathogen-inducible promoters, the maize In2-2 promoter, the tobacco PR-1a promoter, glucocorticoid-inducible promoters, and tetracycline-inducible and tetracycline-repressible promoters.

It is envisaged that analogous substitutions of tyrosine at positions corresponding to Tyr361 of SEQ ID NO: 1 should elicit similar altered light sensitivity and photo responses when expressed in other plants. Plants that may express a modified phytochrome include, among others, crop plants and ornamental plants.

Suitable plant species include, without limitation, corn (*Zea mays*), soybean (*Glycine max*), *Brassica* sp. (e.g., *Brassica napus, B. rapa*, and *B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena sativa*), barley (*Hordeum vulgare*), vegetables, ornamentals, and conifers.

Vegetables include, without limitation, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*).

Ornamental plants are plants that are grown for decorative purposes in gardens and landscapes, as houseplants, and for cut flowers. Suitable ornamentals include, without limitation, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum (*Chrysanthemum* spp.).

As used herein, the term "plant" includes reference to whole plants, plant organs (e.g., leaves, stems, roots, etc.), seeds, plant cells, and progeny of same. Parts of transgenic plants comprise, for example, plant cells, protoplasts, tissues, callus, embryos as well as flowers, ovules, stems, fruits, leaves, roots originating in transgenic plants or their progeny previously transformed with a DNA. As used herein, the term "plant cell" includes, without limitation, protoplasts and cells of seeds, suspension cultures, embryos, meristematic regions, callus tissue, leaves, roots, shoots, gametophytes, sporophytes, pollen, and microspores.

Consequently, this invention encompasses transgenic crops and other plants with improved shade tolerance needed for increased planting density and increased yields.

It will be apparent to those of skill in the art that variations may be applied to the compositions and methods described herein and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

It is to be understood that the invention is not limited in its application to the details of construction and the arrangement of components set forth in the following description. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The following non-limiting examples are purely illustrative.

Example 1

Materials and Methods

Recombinant phyB Protein Expression, Purification, and Analysis

All the site-directed mutations in PHYB were introduced into the cDNA by the Quikchange method (Stratagene). cDNA fragments encoding the photosensory modules (residues 1-624) were appended in-frame corresponding to the N-terminus of the 6His tag (KLHHHHHH) (SEQ ID NO: 39) by introduction into the pBAD plasmid (Invitrogen), and then co-transformed into *Escherichia coli* BL21 (AI) cells (Invitrogen) with the pPL-PΦB plasmid expressing the *Synechocystis* PCC6803 HO1 heme oxygenase and *A. thaliana* HY2 PΦB synthase enzymes [40, 41] to direct apoprotein expression and chromophore assembly. Following sequential induction of the HO1/HY2 genes and PHYB genes with IPTG and arabinose, the cells were disrupted by sonication in extraction buffer (50 mM HEPES-NaOH (pH 7.8), 300 mM NaCl, 30 mM imidazole, 0.1% Tween-20, 10% glycerol, 1 mM 2-mercaptoethanol, and 1 mM PMSF) with the addition of 1 tablet of protease inhibitor cocktail (Roche) before use. The clarified supernatant was applied to a HisTrap HP column (GE) pre-equilibrated in extraction buffer, and the column was washed with extraction buffer followed by elution with a 30-300 mM imidazole gradient in extraction buffer. The phyB-containing fractions were pooled, dialyzed against 10 mM HEPES-NaOH (pH 7.8), 100 mM NaCl, 5 mM 2-mercaptoethanol, 5 mM $Na_2EDTA$, 50 mM imidazole, and 0.05% Tween-20 overnight, and subjected to size-exclusion chromatography using a 24-ml Superose 6 (GE) column pre-equilibrated with the same buffer. phyB-containing fractions were pooled and stored in 10 mM HEPES-NaOH (pH 7.8), 50 mM NaCl, 1 mM 2-mercaptoethanol, 0.05% Tween-20, and 10% glycerol.

Pr-Pfr photointerconversion and Pfr→Pr thermal-reversion of each phyB preparation were assayed by UV-vis absorption spectroscopy at 24° C., using white light filtered through 650- and 730-nm interference filters (Orion) to drive Pr→Pfr and Pfr→Pr phototransformation, respectively.

Plant Materials and Growth Conditions

All the plant lines were derived from *A. thaliana* Col-0 ecotype. The phyB-9 and phyA-211 alleles were as described [30, 32]. Seeds were surface-sterilized in chlorine gas, and stratified in water for 3 d at 4° C. before sowing. Unless otherwise noted, seedlings were grown at 22° C. under white light in LD (16-hr light/8-hr dark) on 0.7% (w/v) agar medium containing 1× Gamborg's (GM) salts, 2% (w/v) sucrose, 0.5 g/L MES (pH 5.7). After 10 d, seedlings were transferred to soil and grown at 22° C. under continuous white light in LD or SD (8-hr light/16-hr dark).

Plasmid Constructions for Plant Transformation

The full coding regions of PHYA and PHYB [39] were inserted into the pDONR221 plasmid via BP reactions (Invitrogen), and appended the coding sequence in-frame for the FLAG-epitope (GGGDYKDDDDK) (SEQ ID NO: 40) to their 3' ends. The PHYA/B promoter and 5' UTRs (2634- and 1983-bp upstream beginning at the ATG translation initiation codon), and 3' UTRs (242- and 279-bp downstream of the translation termination codon) were amplified by PCR from the Col-0 genomic DNA, and then sequentially inserted into the pDONR211 plasmids to appropriately flank the coding regions. The completed PHYB and PHYA transgenes were introduced into the pMDC123 plasmid (Invitrogen) via LR reactions. The PHYB-yellow fluorescent protein (YFP) constructions (WT-YFP, R322A-YFP, Y361F-YFP, D307A-YFP, and R582A-YFP) were created by appending the UBQ10 promoter fragment (1986-bp fragment proximal to the ATG codon) and the cDNA encoding YFP, to the 5' and 3' ends of the PHYB cDNA in a pDONR211 plasmid, respectively. The complete transgenes were introduced into the pMDC123 plasmid via LR reactions.

Plant Transformation and Selection of Transgenic Lines

The PHYA and PHYB transgenes were introduced into the homozygous *Arabidopsis* phyA-211 or phyB-9 mutants, respectively, via the *Agrobacterium*-mediated floral dip method using the pMDC123-derived plasmids [42]. Transformed lines were selected by resistance to 10 μg/mL BASTA. T2 transgenic plants with a resistance segregation ratio of ~3:1 were used to obtain isogenic lines in the T4 or T5 generation for all the biochemical, phenotypic, and localization assays.

Protein Extraction and Immunoblot Analysis

Five-d-old, dark-grown *Arabidopsis* seedlings were frozen and pulverized at liquid nitrogen temperatures, and homogenized in 100 mM Tris-HCl (pH 8.5), 10 mM $Na_2EDTA$, 25% ethylene glycol, 2 mM PMSF, 10 mM N-ethylmaleimide, 5 μg/mL sodium metabisulfite, 2% (w/v) SDS, 10 μg/mL aprotinin, 10 μg/mL leupeptin and 0.5 μg/mL pepstatin [43]. The extracts were heated to 100° C. for 10 min and clarified by centrifugation at 13,000×g for 10 min. The supernatants were subjected to SDS-PAGE and immunoblot analysis with a monoclonal antibody against phyA (073D, [44]), phyB (B1-B7, [45]), or green fluorescent protein (GFP) (Sigma). Anti-PBA1 antiserum or anti-histone H3 antibodies were used to confirm equal protein loading [46].

To measure phyB degradation in response to Rc, seeds were sown in liquid medium containing half-strength Murashige and Skoog (MS) salts, 0.5 g/L MES (pH 5.7), and 10 g/L sucrose, and irradiated with white light (24 hr for seeds carrying the $PHYB^{D307A}$ transgene and 12 hr for all others) to initiate germination before maintaining the seedlings in the dark for 4 d. Seedlings were collected after various exposure times to continuous 20 μmol·m$^{-2}$·s$^{-1}$ R and subjected to immunoblot analysis as above. Seedlings were incubated for 12 hr in the dark with 100 μM MG132 or an equivalent volume of DMSO before R.

Phenotypic Assays

Germination efficiency was measured according to Oh et al. (Plant Cell 19, 1192-1208). The parental plants (5 per genotype) were grown side by side at 22° C. in LDs, and the resulting seeds were harvested as separate seed pools. At least 60 seeds from each pool were sown on 0.7% (w/v) water agar after 20-min FR irradiation (4 μmol m$^{-2}$ s$^{-1}$). The seeds were then exposed to white light for 2 hr, and either kept in dark or irradiated with 4 μmol m$^{-2}$ s$^{-1}$ FR for 5 min. The plates were kept in darkness for an additional 5 d before measurement of germination, which was scored as emergence of the radical from the seed coat. For hypocotyl elongation, seeds were sown on solid half-strength MS salts, 0.5 g/L MES (pH 5.7), and 0.7% (w/v) agar, and irradiated with 12-hr white light. The plates were exposed to either R or FR for 3.5 d using a bank of diodes (E-30LED-controlled environment chamber, Percival), before measurement of hypocotyl length. For measurement of the EOD-FR response, seedlings were irradiated over a 4-d cycle with 90 μmol·m$^{-2}$·s$^{-1}$ R for 8 hr followed by either darkness or by a 10-min pulse of 100 μmol·m$^{-2}$·s$^{-1}$ FR and then darkness for 16 hr. Effect on flowering time was measured for plants grown under white light in SD.

Confocal Microscopic Analysis

Transgenic seeds expressing wild-type and mutant versions of phyB-YFP were sown on solid medium containing half-strength MS salts, 0.5 g/L MES (pH 5.7), 2% (w/v) sucrose, and 0.7% (w/v) agar and irradiated for 12 hr at 22° C. with white light before incubation in the dark for 5 d. Fluorescence of hypocotyl cells, either kept in the dark or irradiated with 90 µmol·m$^{-2}$·s$^{-1}$ R for 12 hr, was imaged using a Zeiss 510-Meta laser scanning confocal microscope. YFP fluorescence was visualized in the single-track mode by excitation with 488-nm light using the BP 500-530 IR filter. Images were processed with the LSM510 image browser.

Example 2

Rational Design of phyB Variants to Alter Light Signaling

Site-directed substitutions of certain amino acids based on the microbial scaffolds were introduced into the *Arabidopsis* phyB isoform. The photochemistry of the mutant photosensory modules was examined after recombinant assembly with the native chromophore phytochromobilin (FOB), and the full-length versions were assessed for their phenotypic rescue of the phyB-9 null mutant using the native PHYB promoter to drive expression. The results collectively demonstrate that various aspects of phy dynamics and signaling can be adjusted (FIG. 1A), which in some cases generates plants with unique photobehavioral properties.

We examined five mutations predicted to compromise Pr to Pfr photoconversion, interaction of the bilin with its binding pocket, and/or possible signal transmission from the cGMP phosphodiesterase/adenylyl cyclase/FhlA (GAF) domain to the downstream phytochrome (PHY) domain in the photosensory module. As shown in FIGS. 1B and 1C, the D307A substitution removes a key aspartate (D207 in *Synechocystis* PCC6803 (Syn)-Cph1) that participates through its main chain carbonyl in a unique hydrogen-bonding lattice involving the A-C pyrrole rings of PΦB and the centrally positioned pyrrole water. This invariant aspartate is essential for the Pr to Pfr photoconversion of bacterial phys as most, if not all, substitutions are stalled in the deprotonation/protonation cycle following R irradiation and become highly fluorescent [18-20]. Two substitutions alter the hydrogen-bond contacts with D307. The relatively mild Y361F substitution (Y263 in SynCph1) maintains the aromatic character but is expected to eliminate the hydrogen bond that helps hold the side chain carboxyl group of D307 in place [18, 22], whereas the R582A substitution (R472 in SynCph1) removes a potential salt bridge between D307 and a novel hairpin, likely universal among canonical phys, that extends from the PHY domain to contact the GAF domain near the bilin. This hairpin may help transmit chromophore movements within the photosensory module to the C-terminal output region during photoconversion [3, 7, 10] (FIG. 1B,C). The last two mutations (R352A and R322A) eliminate salt bridges between the propionate side chains in PΦB and the bilin-binding pocket, which presumably help restrain the bilin within the photoreceptor (FIG. 1B,C). Prior studies with bacterial phys (R222 and R254 in *Synechococus* OS-B' (SyB)-Cph1) showed that these arginines stabilize and destabilize the Pfr conformer, respectively, with their guanidinium side chains undergoing dramatic conformational changes during Pr→Pfr photoconversion.

Based on the phy scheme presented in FIG. 1A, we tested how well the *Arabidopsis* phyB mutants would: (i) assemble with PΦB, (ii) photointerconvert between Pr and Pfr, (iii) revert thermally from Pfr back to Pr, (iv) accumulate and concentrate after R irradiation into nuclear bodies or "speckles" thought to be important for signaling and/or turnover [23], (v) degrade upon R irradiation, and (vi) stimulate several photomorphogenic processes under full or partial control by phyB, including R-stimulated seed germination, hypocotyl growth inhibition under R, effect of end-of-day (EOD) FR on the hypocotyl R response, and flowering time under a short-day photoperiod (SD) [2, 13, 14]. Pfr turnover is likely driven by the ubiquitin/26S proteasome system (UPS) based on mutant analyses and its sensitivity to the proteasome inhibitor MG132 ([24, 25] see FIG. 6A). Methods used to synthesize photoactive photosensory module fragments recombinantly from phyB assembled with PΦB and to generate the transgenic plants expressing full-length versions are provided in Example 1.

Figure 7:
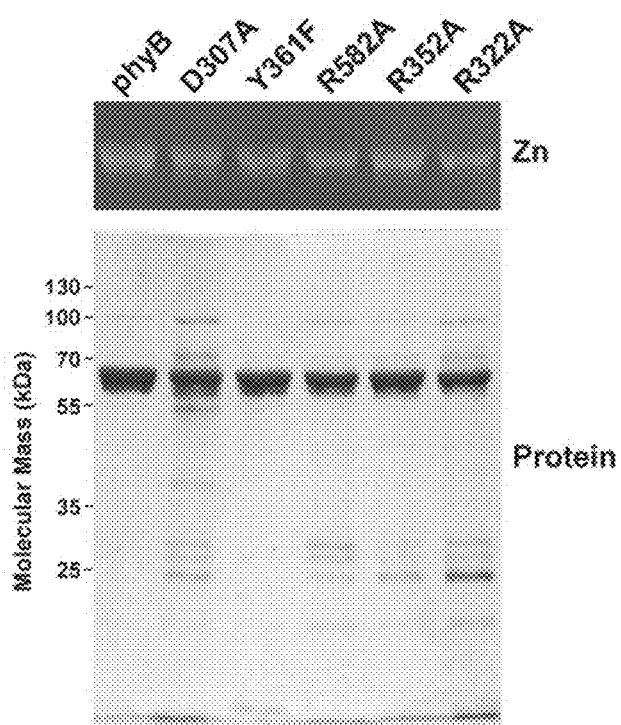
FIG. 7. Photographs of protein gels showing the purification and assembly of the PSM from wild-type phyB and the various site-directed mutants. The 6His-tagged polypeptides were co-expressed recombinantly with the dual enzyme system that synthesizes the higher plant phy chromophore phytochromobilin (PΦB). The purified chromoproteins were subjected to SDS-PAGE and either stained for protein with Coomassie blue or for the bound bilin by zinc-induced fluorescence (Zn).

The photosensory module of all the mutants could be expressed and readily assembled with PΦB in *Escherichia coli*, and generated reasonably normal Pr absorption spectra with maxima at ~663 nm, indicating that none of the substitutions compromised protein folding or bilin conjugation (FIG. 2A; FIG. 7). Given that *Arabidopsis* and other plants are highly sensitive to phy levels [26-29], we chose two isogenic phyB-9 lines in the T3 generation that expressed either unaltered phyB or the mutants to levels which matched most closely that in the wild-type Col-0 plants as judged by immunoblot analysis (FIG. 3D). Importantly, all of the complemented phyB-9 mutant lines had normal etiolated seedling development, indicating that none of the phyB variants signaled in the absence of photoactivation (FIG. 3B).

Figure 8:
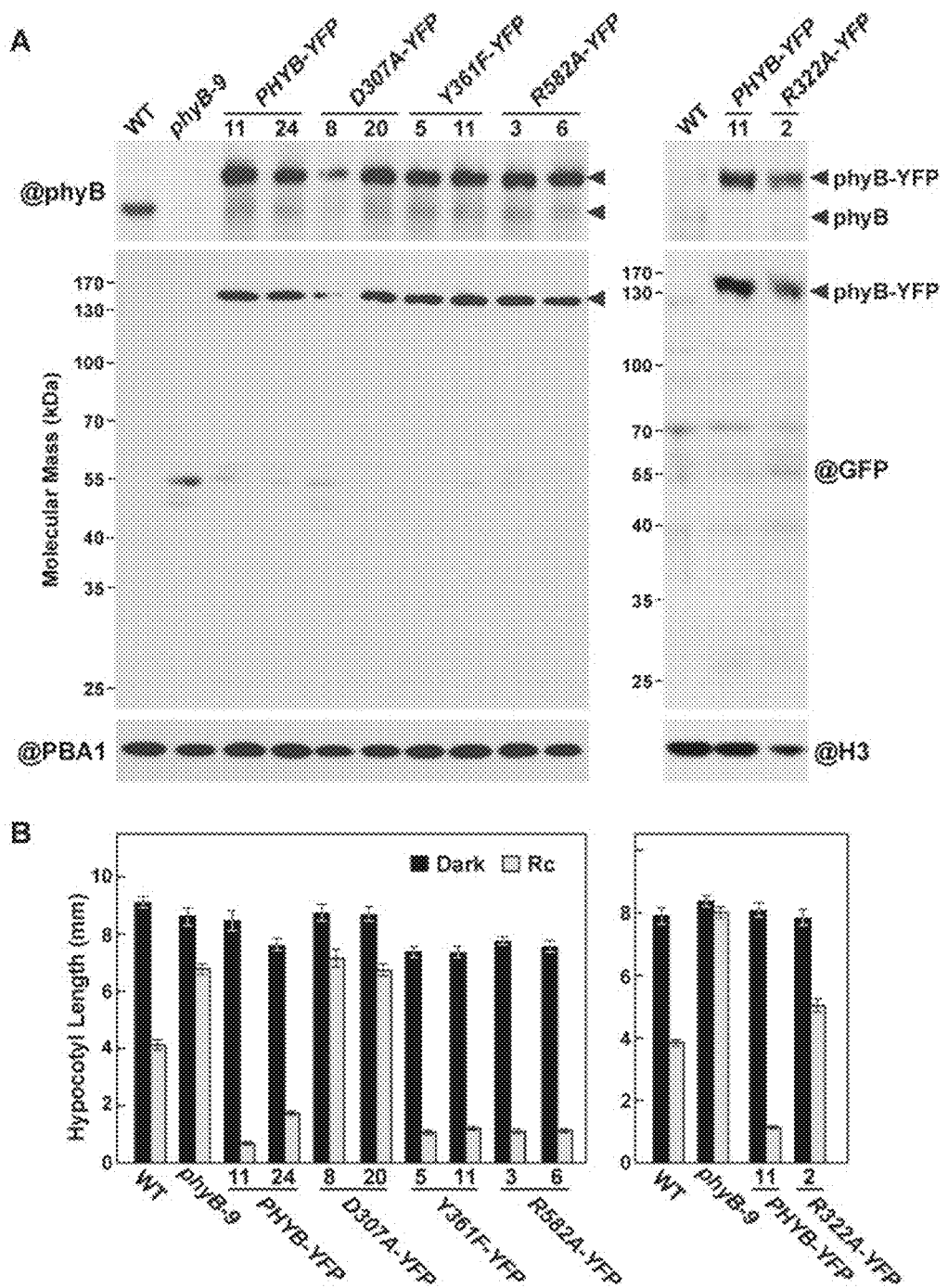
FIG. 8. Photographs (A) and graphs (B) showing the accumulation of YFP fusions of phyB in *Arabidopsis* seedlings. Full-length wild-type phyB or the various mutants (R322A, D307A, Y361F, and R582A) were expressed in the phyB-9 background as fusions to the N-terminus of YFP. Total crude extracts from 5-d-old dark grown seedlings were subjected to immunoblot analysis using a monoclonal antibody against either phyB or GFP (Sigma). Near equal loading was confirmed with anti-PBA1 or anti-histone H3 antibodies. The arrowheads locate phyB and the phyB-YFP fusions.

To examine the ability of the mutants to concentrate in nuclear bodies/speckles as Pfr, we also created a parallel set of transgenic lines expressing the phyB mutants as N-terminal fusions to yellow fluorescent protein (YFP). These bodies were easily seen by confocal fluorescence microscopy as numerous intense puncta that accumulate in the nucleus upon prolonged R irradiation (see FIG. 6B). The phyB-YFP mutant proteins also assembled well with PΦB in planta, and phenotypically resembled their non-tagged counterparts based on their ability (or inability) to suppress hypocotyl elongation in R when introduced into the phyB-9 background (FIG. 8).

Example 3 phyB$^{Y361F}$ is Hypersensitive to R

Given its predicted proximity to D307 within the bilin-binding pocket, Y361 likely helps enclose the GAF domain around the bilin and fix the position of D307 (FIG. 1B). Surprisingly, the Y361F substitution in *Arabidopsis* phyB permitted proper photochemistry but made the photoreceptor hyperactive with respect to signaling. Recombinant phyB$^{Y361F}$ had relatively normal Pr and Pfr absorption spectra, but displayed slightly reduced Pr→Pfr and Pfr→Pr photoconversion rates and a slower rate of thermal Pfr→Pr reversion (FIG. 2A,B).

Figure 9:
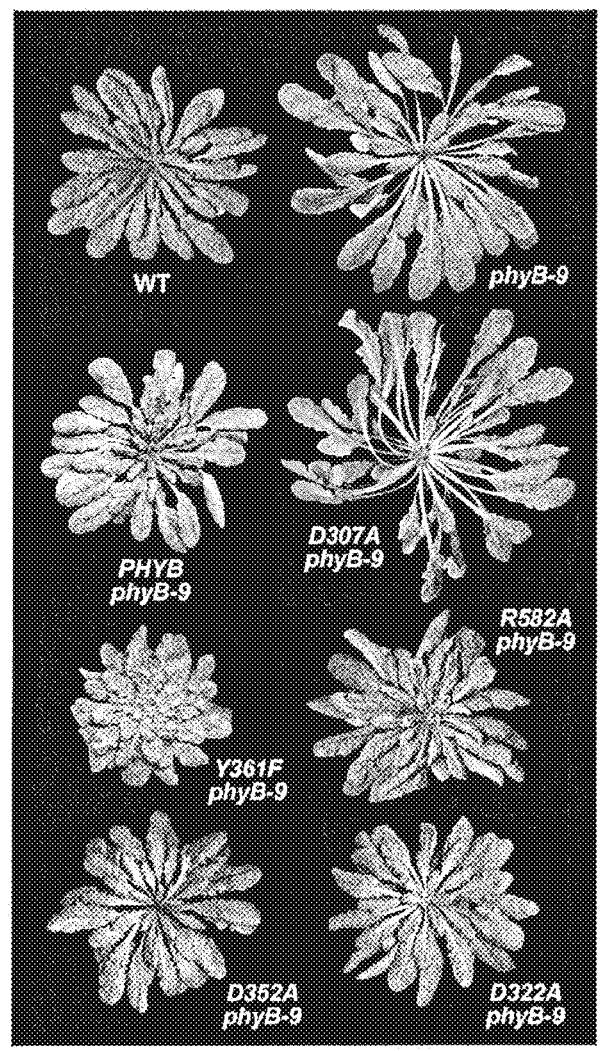
FIG. 9. Photographs showing the morphology of phyB null mutant *Arabidopsis* rescued with transgenes expressing wild-type or mutant versions of full length phyB. Shown are wild type (WT), the phyB-9 null mutant, and representative transgenic lines expressing either the wild-type or mutant PHYB cDNAs in the phyB-9 background grown under SD (short day) until bolting.
Figure 14:
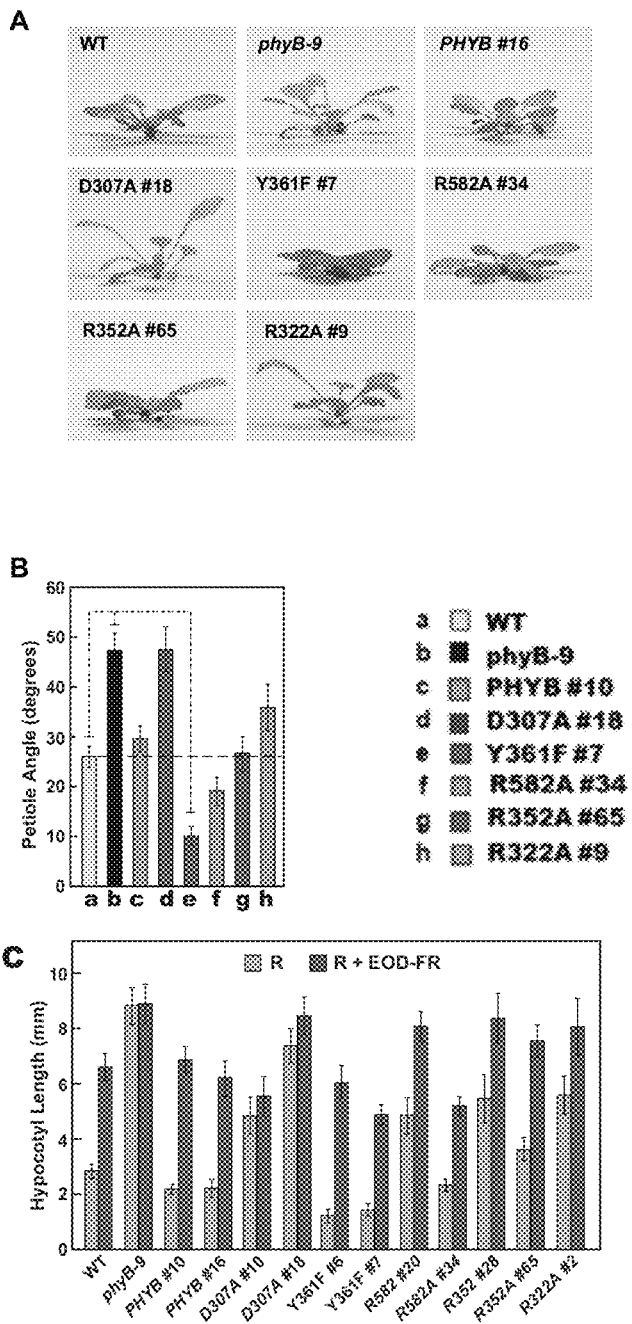
FIG. 14. Photograph and graphs depicting the sensitivity of phyB-9 plants rescued with various phyB mutants to photomorphogenic processes controlled by phyB. Shown are wild type (WT), the phyB-9 null mutant, and one or two independent transgenic lines expressing either the wild-type or mutant PHYB cDNAs in the phyB-9 background. See FIG. 3D for the description of the mutant lines. (A), Photograph showing the side view of 45-d-old seedlings grown in white light under SD illustrating the influence of phyB on leaf epinasty. (B), Quantification of leaf epinasty for seedlings in panel A. Each bar represents the average angle between the soil surface and the petiole for the 4th and 5th leaves of 10 plants (20 total angles). The 95% confidence interval for each average is shown. The values for WT, phyB-9, and Y361F lines are significantly different from each other by Student's t test (p<0.05). (C), Effect of R and EOD-FR on hypocotyl growth. Etiolated seedlings were subjected over 4 d to a 24-hr light regime of continuous R (90 µmole $m^{-2}$ $s^{-1}$) for 8 hr, followed by either darkness (R) or a 10-min pulse of 100 µmole $m^{-2}$ $s^{-1}$ FR(R+EOD-FR) and then 16-hr of darkness. Each bar represents the average (±SE) of 4 experiments involving at least 15 seedlings each. The Y361F #7 line was significantly different from WT and PHYB for both R and R+EOD-FR by Student's t-test (p<0.05).

Despite the expectations that some of these photochemical alterations might compromise signaling, phyB$^{Y361F}$ more effectively directed phyB-mediated responses compared to phyB$^{WT}$. Soon after germination, the PHYB$^{Y361F}$ phyB-9 seedlings were more sensitive to continuous R with respect to hypocotyl elongation, and as the seedling developed under a long-day (LD) photoperiod, homozygous PHYB$^{Y361F}$ phyB-9 plants had more compact rosettes with shorter petioles than wild type and PHYB$^{WT}$ phyB-9 plants, indicative of light hypersensitivity (FIGS. 3A,C and 4A). Analyses of hypocotyl elongation at very low R fluence rates (<1 µmol·m$^{-2}$·s$^{-1}$) estimated that the phyB$^{Y361F}$ biliprotein was at least 50 times more active at signaling at least with respect to this response (FIG. 4B). A modest but statistically significant hypersensitivity to R was also observed for seed germination and the effect of EOD-FR on R-suppressed hypocotyl growth (FIG. 5A,B). Light hypersensitivity continued for the rosettes of mature plants and dampened the SAR (shade avoidance response) as judged by increased hyponasty (i.e., more prostrate petiole angles) and the smaller leaves and shorter petioles seen for PHYB$^{Y361F}$ plants as compare to PHYB$^{WT}$ plants when grown in SD (FIGS. 14 A,B and 9). Flowering time in SD was not significantly altered (FIG. 5C), consistent with the minor role of phyB in detecting photoperiod as compared to phyA [30]. Because the hyperactivity of phyB$^{Y361F}$ in R could be canceled by EOD-FR, we concluded that phyB$^{Y361F}$ photoreceptor still functions in a R-FR reversible manner in planta. Light hypersensitivity was also evident in the rosettes of mature plants as judged by the smaller leaves and shorter petioles seen for PHYB$^{Y361F}$ phyB-9 plants as compared to PHYB$^{WT}$ phyB-9 plants when grown in SD (FIG. 9). Despite changes in photochemistry and signaling, the turnover of phyB$^{Y361F}$ as Pfr and its sequestering into nuclear bodies appeared normal (FIG. 6A,B).

Example 4

Figure 3:
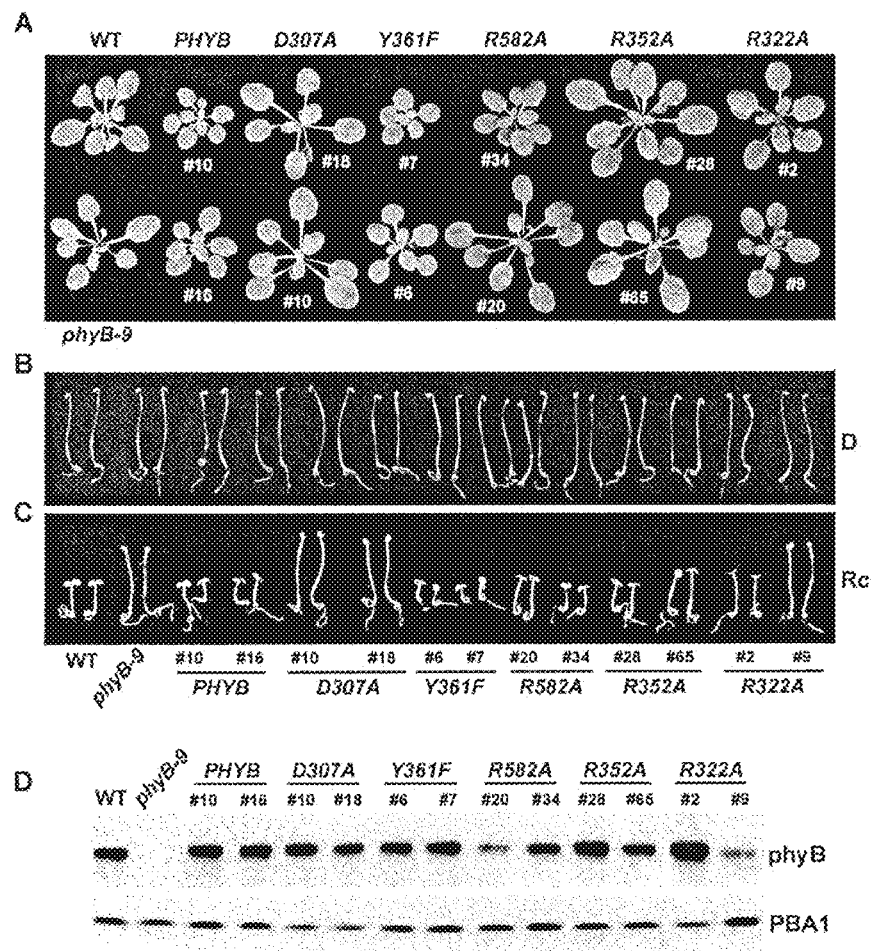
FIG. 3. Photographs showing the phenotypes of an *Arabidopsis* phyB null mutant rescued with transgenes expressing wild-type or mutant versions of full-length phyB. Shown are wild type (WT), the phyB-9 null mutant, and two independent transgenic lines expressing either the wild-type or mutant PHYB cDNAs in the phyB-9 background. (A) Representative 3-week-old plants grown in long days (LDs). (B) Representative 4-d-old seedlings either grown in the dark (D) or under continuous 13 μmol·m$^{-2}$·s$^{-1}$R. (C) Levels of the phyB protein in each of the lines examined in panels A and B as determined by immunoblot analysis of crude extracts from 5-d-old dark grown seedlings with an anti-phyB monoclonal antibody. Near equal protein loading was confirmed with anti-PBA1 antibodies.
Figure 4:
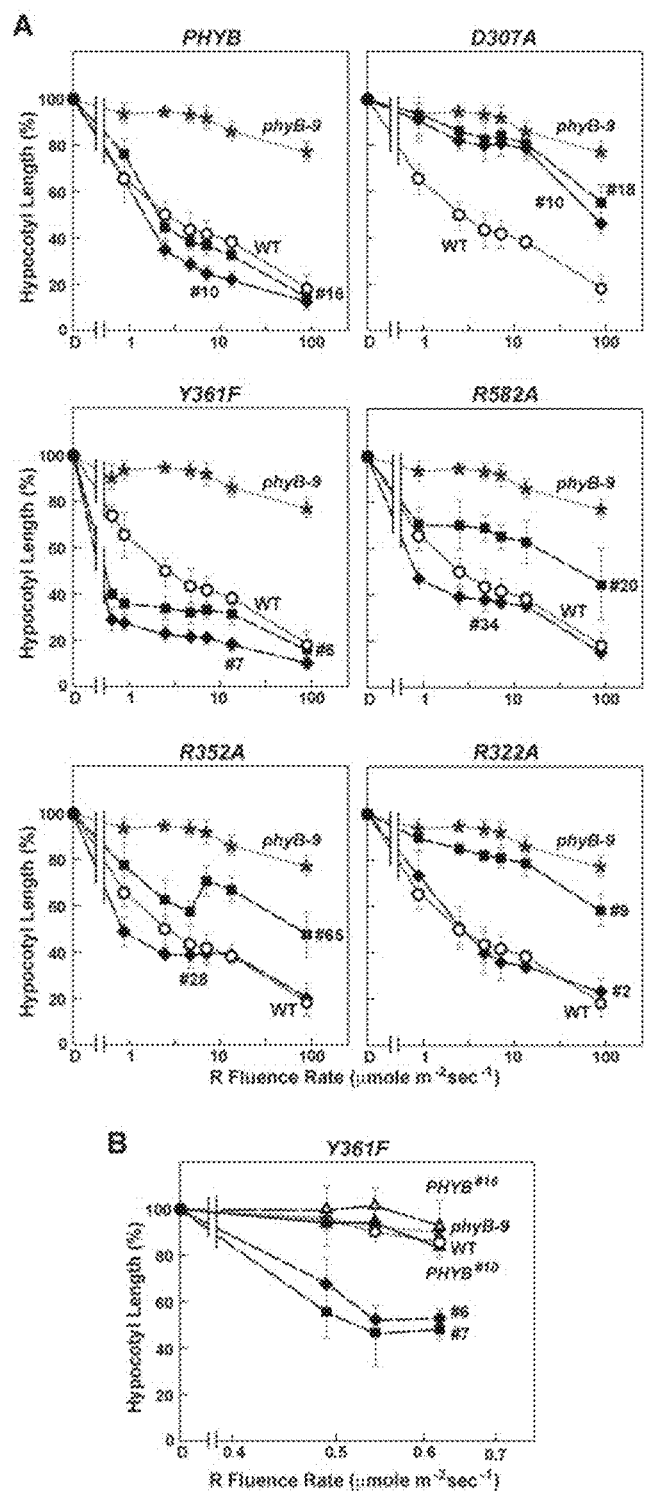
FIG. 4. Graphs depicting R sensitivity of hypocotyl elongation for a phyB null mutant rescued with transgenes expressing wild-type or mutant versions of full-length phyB. Shown are wild type (WT), the phyB-9 null mutant, and two independent transgenic lines expressing either the wild-type or mutant PHYB cDNAs in the phyB-9 background. Hypocotyl length of each line was expressed relative to that measured for dark-grown seedlings. Each data point represents the mean (±SE) from four independent experiments. (A) Sensitivity to a broad range of R fluence rates. (B) Sensitivity of the Y361F variant to very low fluence rates of R.
Figure 5:
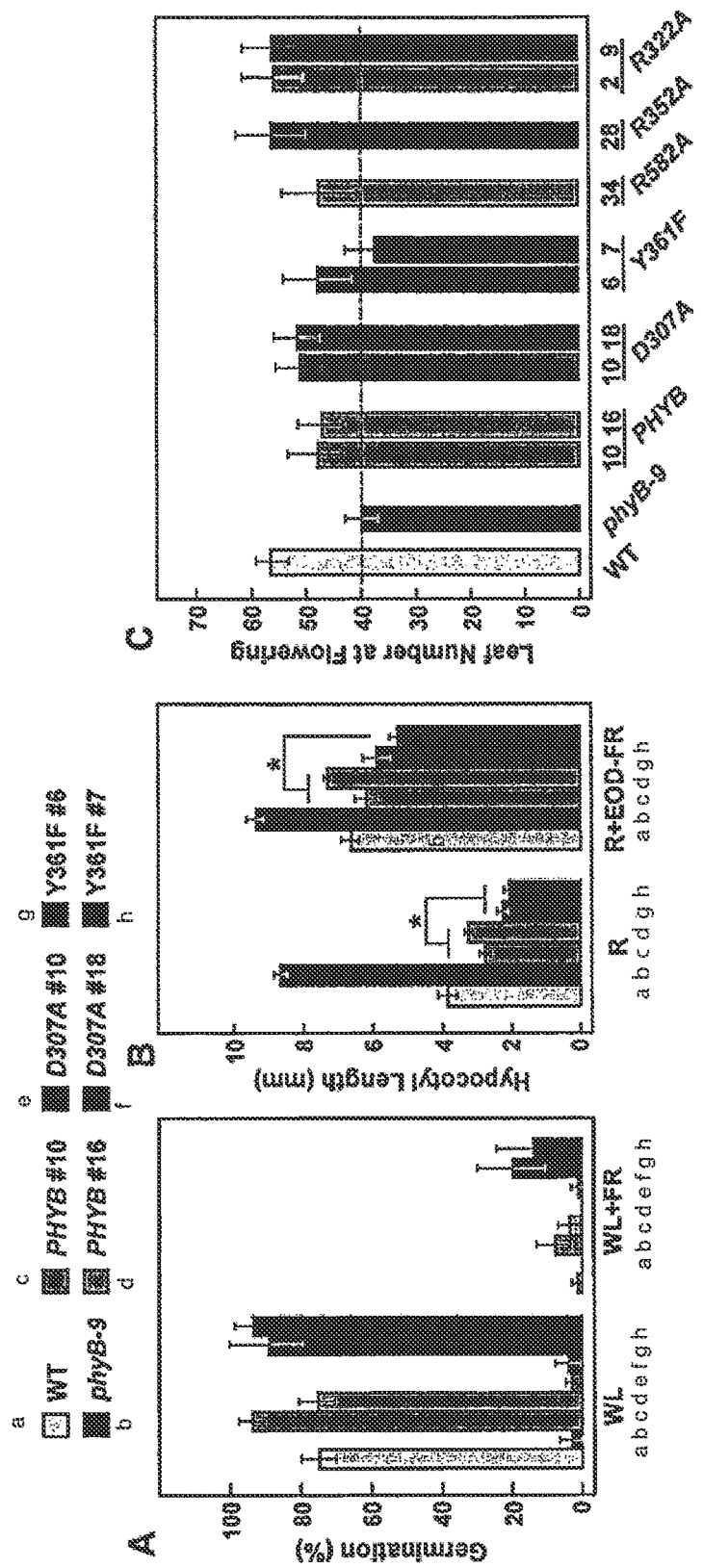
FIG. 5. Graphs depicting sensitivity of phyB-9 plants rescued with various phyB mutants to a collection of photomorphogenic processes controlled by phyB. Shown are wild type (WT), the phyB-9 null mutant, and two independent transgenic lines expressing either the wild-type or mutant PHYB cDNAs in the phyB-9 background. (A) Germination efficiency of seeds either treated with 2-hr pulse of WL (white light) alone or followed by a pulse of FR (far-red light). Germination was assessed after a subsequent 5-d incubation in darkness. Each bar represents the average (±SE) of 5 experiments involving at least 40 seeds each. (B) EOD-FR effect on hypocotyl growth. Etiolated seedlings were subject over 4 d to a light regime of continuous R (90 μmole·m$^{-2}$·s$^{-1}$) for 8 hr, followed by either darkness or a 10-min pulse of FR (R+EODFR, 100 μmole·m$^{-2}$·s$^{-1}$), and then 16-hr of darkness. Each bar represents the average (±SE) of 4 experiments involving at least 15 seedlings each. The two phyB$^{Y361F}$ lines were significantly more sensitive to R and line #7 was more derepressed by R+EOD-FR than the two phyB$^{WT}$ lines (*, Student's t test: P<0.05). (C) Flowering time in short days (SDs) (8-hr light/16-hr dark). Each bar represents the average number of leaves generated before emergence of the inflorescence stem for >20 plants (±SE).

D307 in phyB is Required for Photoconversion, Robust Signaling and Nuclear Body Formation but not Turnover In line with the predicted importance of D307 in phyB photochemistry [18-20], we found that the assembled phyB$^{D307A}$ biliprotein failed to photoconvert from Pr to Pfr in R and instead generated a bleached R-absorbing intermediate that would regenerate Pr upon irradiation with FR or more slowly upon prolonged dark incubation (FIG. 2A). Unlike phyB$^{WT}$ which restored R-suppressed hypocotyl elongation and enhanced seed germination in R when introduced into the phyB-9 background, the phyB$^{D307A}$ mutant appeared phenotypically inactive or was greatly reduced in phenotypic activity (FIGS. 3 and 4 and 14C). Such compromised activity was also apparent in mature plants as judged by the elongated leaf blades and petioles and strong leaf epinasty (as measured by the large upward angles of petioles) of PHYB$^{D307A}$ phyB-9 plants grown in SD, which better resembled phyB-9 plants as compared to their PHYB$^{WT}$ phyB-9 counterparts (FIGS. 14 A,B and 9). However, detailed fluence response analysis of hypocotyl growth under very high R fluences and the flowering time in SD revealed that phyB$^{D307A}$ retained some signaling activity despite its inability to photoconvert normally to Pfr (FIGS. 4 and 5). Consistent with diminished photochemistry, the accumulation of phyB$^{D307A}$-YFP in nuclear bodies upon R irradiation was undetectable even after prolonged irradiation with a high fluence rate of R, a condition where the bodies were clearly evident for the wild-type version. But surprisingly its MG132-sensitive turnover in R was only a little slower (FIG. 6A,B), thus providing the first indication that nuclear aggregation of phyB and its degradation after R irradiation are not coupled.

Example 5

The R322A, R352A, and R582A Mutations Poorly Compromise phyB Signaling

R472 in the PHY domain hairpin of Syn-Cph1 forms an inter-domain salt bridge with D207. We examined the effects of the comparably positioned arginine in Arabidopsis phyB (R582) using an alanine substitution. The phyB$^{R582A}$ PSM had normal Pr and Pfr absorption spectra and Pr→Pfr and Pfr→Pr photoconversion rates but was strikingly slower in Pfr→Pr thermal reversion (initial velocity 9.6 times slower than that of phyB$^{WT}$), indicating that R582 is not required for photochemistry but helps destabilize the Pfr conformer once formed (FIG. 2A,B). The more stable Pfr for phyB$^{R582A}$ in turn likely generates a slightly higher Pfr/Pr ratio in saturating R as evidenced by the reduced peak height at 655 nm versus that at 724 nm (FIG. 2A). However, phyB$^{R582A}$ appeared to signal normally based on the fluence response of hypocotyl growth to continuous R and its ability to delay flowering in SD (FIGS. 3C, 4A, and 5C). In fact, the phyB$^{R582A}$ chromoprotein appeared to be marginally hyperactive as judged by the slightly stronger repression on hypocotyl growth in R for the PHYB$^{R582A}$ phyB-9 #34 line at intermediate R fluence rates as compared to wild type and PHYB$^{WT}$ phyB-9 seedlings despite accumulating similar levels of photoreceptor (FIG. 4A). Moreover, petiole angles were more prostrate and the rosettes appeared more compact than wild-type and PHYB$^{WT}$ plants in SD (FIGS. 14A,B and 9). We speculate that at least some of this increased activity of the phyB$^{R582A}$ chromoprotein may be related to its higher Pfr/Pr photoequilibrium in continuous R. Regardless of the effects on photochemistry, the nuclear aggregation of phyB$^{R582A}$-YFP, and the turnover of phyB$^{R582A}$ in R appeared normal (FIG. 6A,B).

R352 is predicted to form an essential salt bridge with the propionate group of pyrrole ring B in PΦB, and, based on the mutational analyses of several prokaryotic phys, it appears to be important for bilin binding and proper photochemistry [9, 18, 20]. In fact, replacement of this residue with a glutamine in Dr-BphP (R254Q) is one of the few mutations that block covalent attachment of the bilin, whereas the more subtle arginine to alanine mutations in Dr-BphP and SyB-Cph1 effectively inhibit thermal reversion of Pfr back to Pr.

We found that the R352A substitution in Arabidopsis phyB has little impact on Pr and Pfr absorption and photochemistry, but like its bacterial relatives [4, 18], the mutation stabilizes Pfr against thermal reversion (FIG. 2A,B). When introduced into phyB-9 seedlings, phyB$^{R352A}$ behaved similarly to wild-type phyB with respect to its ability to suppress hypocotyl growth in R, restore normal rosette morphology to mature plants, delay flowering in SD, and rapidly degrade after photoconversion to Pfr (FIGS. 3A,C, 4A, 5C, and 6, FIG. 9). At most, phyB$^{R352A}$ was marginally hypoactive phenotypically as judged by the reduced response of the PHYB$^{R352A}$ phyB-9 hypocotyls to almost all fluences of R despite accumulating levels of photoreceptor comparable to that in wild type (FIG. 4A). Such subtle phenotypic effects for both phyB$^{R352A}$ and phyB$^{R582A}$ strongly suggest that the thermal reversion of phyB, which would be expected to diminish the active Pfr conformer over time, does not play a major role in phyB signaling under strong light conditions.

Figure 6:
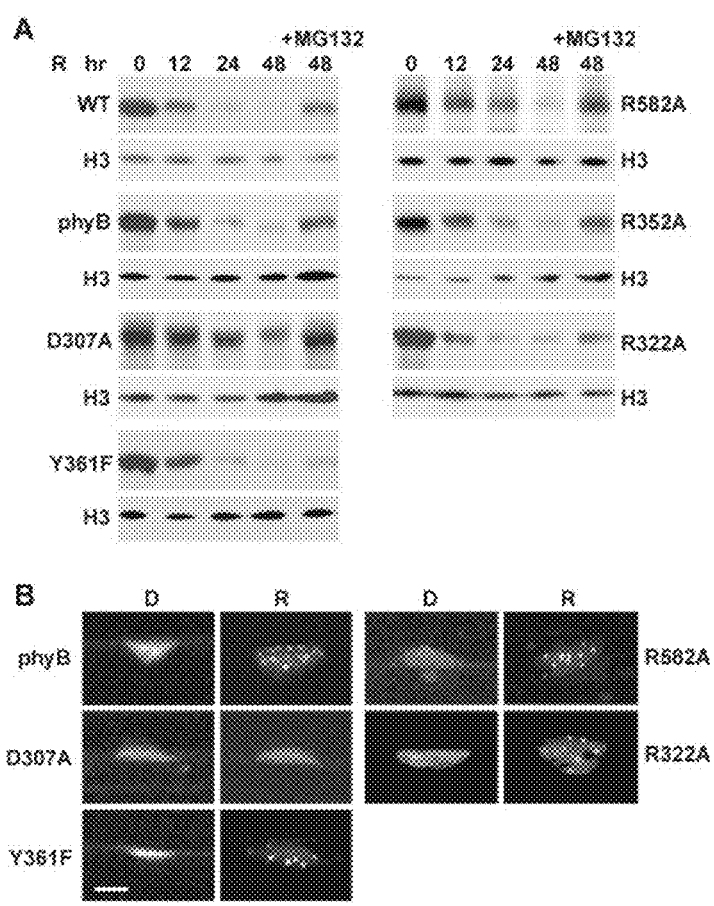
FIG. 6. Photographs showing the effect of the phyB mutations on the nuclear distribution and R-induced degradation of the photoreceptor. (A) Loss of phyB protein during continuous R irradiation of etiolated seedlings. phyB levels in 4-d-old dark-adapted *Arabidopsis* were measured after various length exposures to 90 μmol·m$^{-2}$·s$^{-1}$ R by immunoblot analysis using an anti-phyB monoclonal antibody. The seedlings were exposed to 100 μM MG132 or an equivalent volume of DMSO 12 hr before irradiation. Near equal protein loading was confirmed with anti-histone H3 antibodies. (B) Subcellular partitioning of wild-type and mutant phyB in continuous R. Wild-type phyB or the various mutants were expressed as fusions to the N-terminus of YFP in the phyB-9 background. Regions surrounding the nucleus were imaged by fluorescence confocal microscopy from hypocotyl cells either kept in the dark or irradiated for 12 hr with continuous 90 μmol·m$^{-2}$·s$^{-1}$ R. Scale bar represents 20 μm. Expression levels of the fusions and their ability to rescue the phyB-9 phenotype with respect to hypocotyl elongation in R can be found in FIG. 8.

Analogous to R352, R322 in the GAF domain is predicted to contact PΦB, with the solution NMR structure of SyB-Cph1 showing that flexibility of its guanidinium side chain allows for transient interactions with the ring C propionate. phyB$^{R322A}$ PSM assembled with PΦB retained normal absorption spectra and Pr→Pfr and Pfr→Pr photoconversion rates, but unlike the R352A substitution, phyB$^{R322A}$ had a substantially faster rate of Pfr→Pr thermal reversion than phyB$^{WT}$ (1.7 times faster; FIG. 2A, B). Thus, whereas R322 is not required for photochemistry, it helps stabilize the Pfr conformer of phyB once formed. Phenotypically, phyB$^{R322A}$ behaved similar to phyB$^{WT}$ as judged by its ability to suppress hypocotyl elongation under R in phyB-9 seedlings, rescue the rosette morphology of mature plants, and delay flowering in SD (FIGS. 3A,C, 4A, and 5C, FIG. 8). Similar to the PhyB$^{R582}$A, phyB$^{R322}$A relocalized into nuclear bodies and rapidly degraded like endogenous phyB in response to R (FIG. 6).

Example 6

Analysis of Comparable Mutations in *Arabidopsis* phyA

Figure 10:
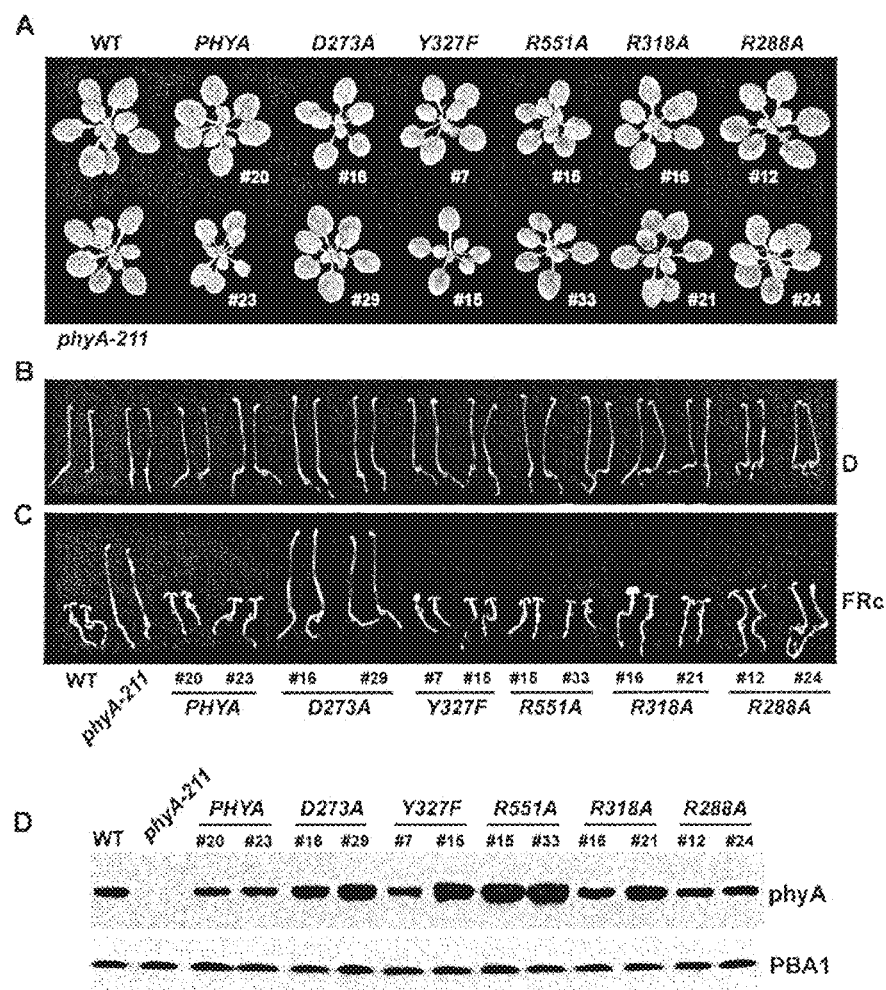
FIG. 10. Photographs showing the phenotype of an *Arabidopsis* phyA null mutant rescued with transgenes expressing wild-type or mutant versions of full-length phyA. Shown are wild-type (WT), the phyA-211 null mutant, and two independent transgenic lines expressing either the wild-type or mutant PHYA cDNAs in the phyA-211 background. (A) Representative 3-week-old plants grown under LD. (B) Representative 4-d-old seedlings either grown in the dark (D) or under continuous 5 μmole·m$^{-2}$·s$^{-1}$ FR. (C) Levels of the phyA protein in each of the lines examined in panels A and B as determined by immunoblot analysis of crude extracts from 5-d-old dark grown seedlings with an anti-phyA monoclonal antibody. Near equal protein loading was confirmed with anti-PBA1 antibodies.
Figure 11:
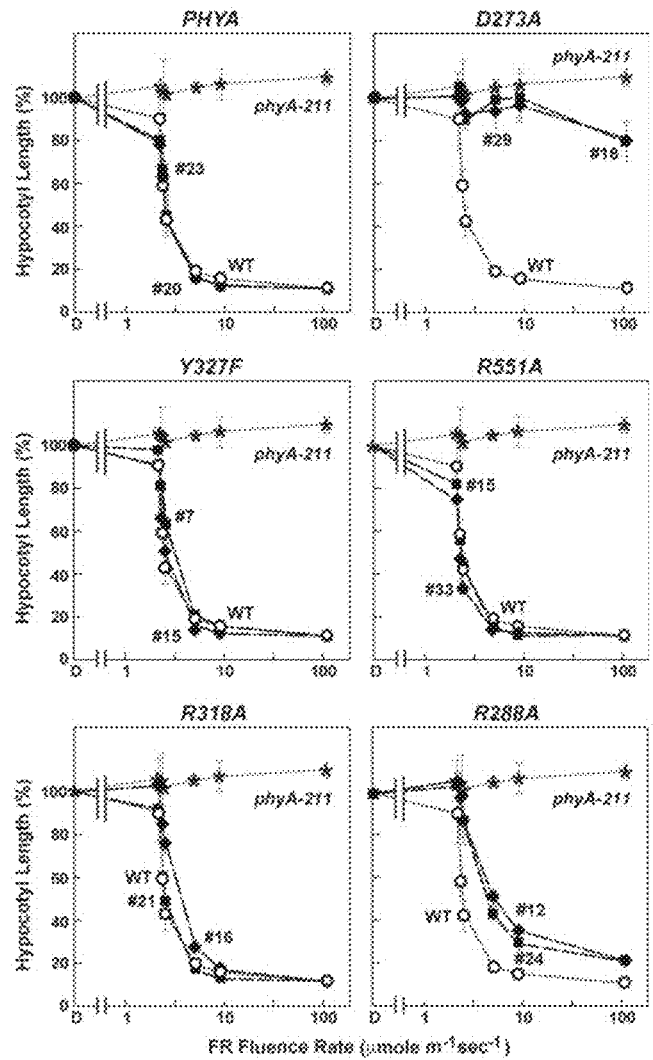
FIG. 11. Graphs depicting FR sensitivity of hypocotyl elongation for a phyA null mutant rescued with transgenes expressing wild-type or mutant versions of full-length phyA. Shown are wild type (WT), the phyA-211 null mutant, and two independent transgenic lines expressing either the wild-type or mutant PHYA cDNAs in the phyA-211 background. Hypocotyl length of each line was expressed relative to that measured for dark-grown seedlings. Each data point represents the mean (±SE) from four independent experiments.

Comparable mutations (D273A, Y327F, R551A, R318A and R288A (FIG. 1C)) were examined to determine if similar effects were observed on phyA signaling. Phenotypically, phyA is the dominant isoform in etiolated seedlings and in plants exposed to FR-rich environments. As shown in FIGS. 10 and 11, phyA signaling can be easily measured by its ability to restore FR suppression of hypocotyl elongation in phyA null mutants such as phyA-211. Using this assay, we found that the D273A mutation also strongly compromises signaling by phyA with a marginal activity seen only at high FR fluence rates (100 μmole·m$^{-2}$·s$^{-1}$). For the Y327F mutation in phyA, the response of the PHYA$^{Y327F}$ phyA-211 seedlings matched that of PHYA$^{WT}$ phyA-211 seedlings at all fluence rates tested. Whereas the R551A and R318A substitutions had no apparent effect on phyA signaling, a slight hypoactivity for phyA harboring the R288A substitution was observed, suggesting that like its phyB counterpart, phyA missing this C ring propionate contact has slightly compromised Pfr activity. When more mature plants grown under white light in LD were examined, all of the phyA mutants developed similar to WT, phyA-211, and PHYA$^{WT}$ phyA-211 plants, suggesting that none of the mutants interfered with phyB signaling or stimulated atypical photomorphogenesis.

Prophetic Example 7

Transgenic Maize

The promoter and coding regions of *Zea maize* (Zm) PHYB1 are cloned from maize genomic DNA and total mRNA, respectively, according to the publically available *Zea mays* genome sequence data (see Nucleic Acids Res. 40 (Database issue):D1178-86), and are built into a construction containing a Bar gene for Basta resistance and the nopaline synthase transcription terminator directly after the PHYB1 coding region. The corresponding Y361F mutation (Y359F in ZmPHYB1, ZmPHYB1$^{Y359F}$) is further introduced into the coding region of ZmPHYB1 in the construction via Quikchange method (Stratagene). Transgenic maize is made by *Agrobacterium tumefaciens*-mediated transformation (*Nat. Protoc.* 2: 1614-1621), and selected for Basta resistance. A total of eight transgenic lines at T1 generation are chosen for further screening based on transgene number, phyB protein level and genetic stability from a large pool of transgenic plants (>100 plants), and are grown, self-pollinated to T4 generation to produce isogenic lines for phenotypic assays.

The selected homogeneous transgenic maize containing ZmPHYB1$^{Y359F}$ are grown in green house for phenotypic characterization. After 30 days, the plant height, size of both the transgenic and wild-type maize will be measured, and the flowering time and seed yield will also be recorded in mature plants. These phenotypic data will also be statistically analyzed, and compared to wild-type plant. The transgenic lines are expected to have much reduced height and size with unaltered flowering time and seed yield. These dwarf maize are expected to require much less growth space and therefore increase the maize yield per acre.

Prophetic Example 8

Transgenic Rice

The promoter and coding regions of *Oryza sativa* L. (Os) PHYB are cloned from rice genomic DNA and total mRNA, respectively, according to the OsPHYB coding sequence data from National Center for Biotechnology Information, and are built into a construction containing a Neomycin Phosphotransferase II (NPTII) gene for kanamycin resistance and the nopaline synthase transcription terminator directly after the PHYB coding region. The corresponding Y361F mutation (Y368F in OsPHYB) is further introduced into the coding region of OsPHYB in the construction (OsPHYB$^{Y368F}$) via Quikchange method (Stratagene). Transgenic rice is made by *Agrobacterium tumefaciens*-mediated transformation (*Plant J.* 1994 (2):271-82), and selected for kanamycin resistance. A total of eight transgenic lines at T1 generation are chosen for further screening based on transgene number, phyB protein level and genetic stability from a pool of over 20 transgenic plants, and are grown and self-pollinated to T4 generation to produce isogenic lines for phenotypic assays.

The selected homogeneous transgenic rice containing OsPHYB1$^{Y368F}$ are grown in green house for phenotypic characterization. After 30 days, the plant height and size of both the transgenic and wild-type rice will be measured, and the flowering time and seed yield will also be recorded in mature plants. These phenotypic data will also be statistically analyzed. Compared to the wild-type plant, the transgenic lines are expected to have much reduced height and size with unaltered flowering time and seed yield. These dwarf rice are expected to require much less growth space and therefore increase the rice yield per acre.

Prophetic Example 9

Transgenic Soybean

The promoter and coding regions of *Glycine max* (Gm) PHYB1 are cloned from soybean genomic DNA and total mRNA, respectively, according to the GmPHYB1 coding sequence data from National Center for Biotechnology Information, and are built into a construction containing a Bar gene for Basta resistance and the nopaline synthase transcription terminator directly after the GmPHYB1 coding region. The corresponding Y361F mutation (Y345F in GmPHYB1) is further introduced into the coding region of GmPHYB1 in the construction (GmPHYB1$^{Y345F}$) via Quikchange method (Stratagene). Transgenic soybean is made by *Agrobacterium tumefaciens*-mediated transformation (*Plant Biotechnol.* 2007, (24): 533-536), and selected for Basta resistance. A total of eight transgenic lines at T1 generation are chosen for further screening based on transgene number, phyB protein level and genetic stability from a large pool of over 100 transgenic plants, and are grown and self-pollinated to T4 generation to produce isogenic lines for phenotypic assays.

The selected homogeneous transgenic soybean containing GmPHYB1$^{Y345F}$ are grown in the green house for phenotypic characterization. After 30 days, the plant height, size of both the transgenic and wild-type soybean will be measured, and the flowering time and seed yield will also be recorded in mature plants. These phenotypic data will also be statistically analyzed. Compared to the wild-type plant, the transgenic lines are expected to have much reduced height and size with unaltered flowering time and seed yield. These resulting dwarf soybean should require much less growth space and therefore increase the soybean yield per acre.

Prophetic Example 10

Spectroscopy Analyses of Maize phyB Mutants

A library of structure-guided variants has the potential to alter phy signaling in a number of ways, which in turn offers a host of opportunities to manipulate light perception in maize. To test this notion, we will examine how the mutations corresponding to D307A, Y361F, R582A, R352A and R322A of the *Arabidopsis* sequence affect maize phyB photochemistry and/or phyB-directed photomorphogenesis. The residues corresponding to D307A and Y361F alleles are of special interest given their ability to confer hypo- and hypersensitivity to phyB signaling. (For simplicity, the maize alleles are designated in this example using the *Arabidopsis* counterpart residue numbers; D307A is D305A in maize and Y361F is Y359F in maize.)

Figure 2:
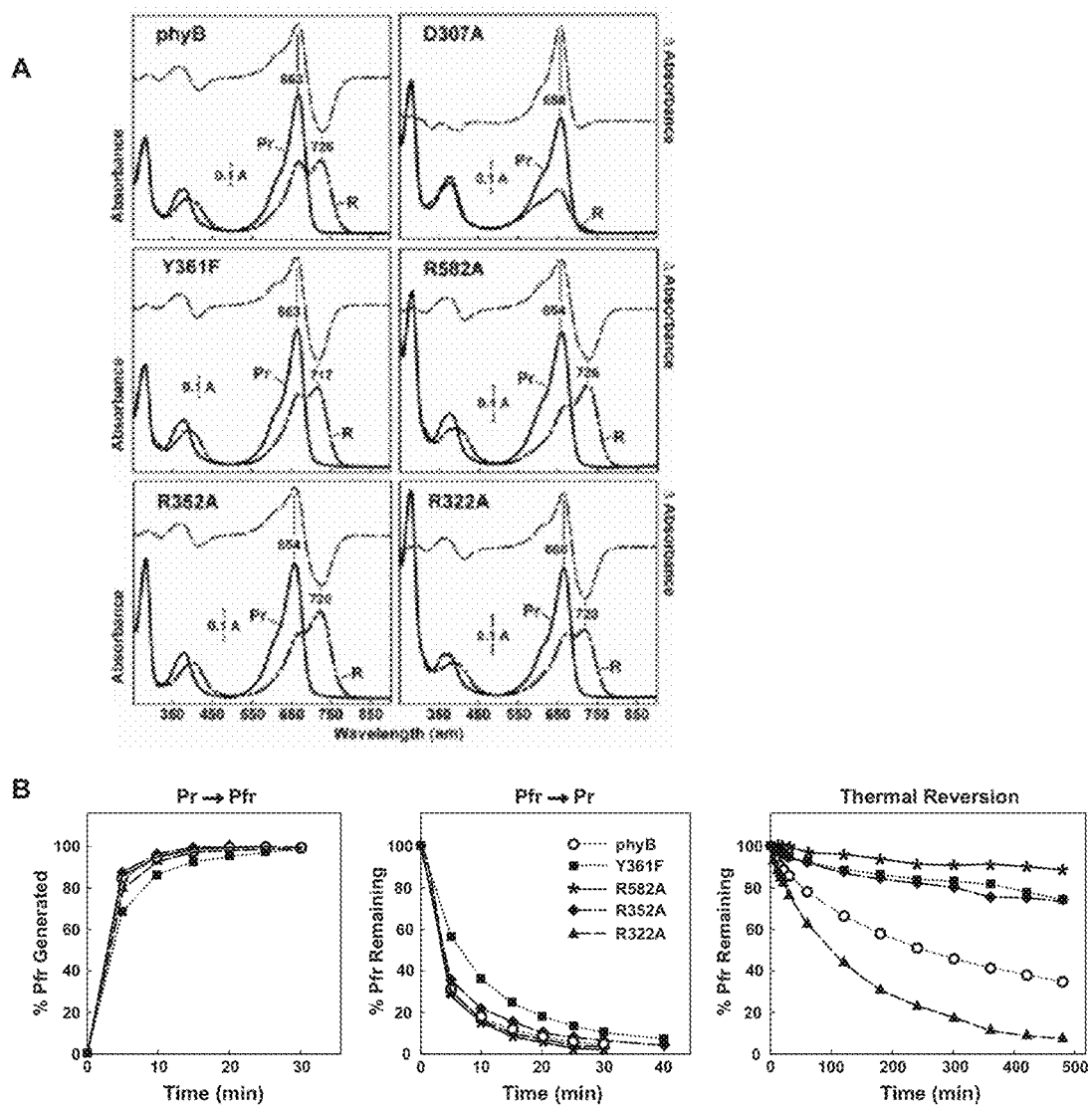
FIG. 2. Graphs depicting spectral properties, photochemistry, and thermal reversion rates of wild-type and mutant versions of *Arabidopsis* phyB. The PSM (PAS-GAF-PHY) of each phyB protein was synthesized recombinantly with a C-terminal 6His tag, assembled with P$\Phi$B in vivo, and purified. See FIG. 7 for SDS-PAGE analysis. (A) UV-vis absorption spectra of Pr (solid lines) or following its excitation with saturating R (dashed lines). Difference maxima and minima (Pr minus R) are indicated. (B) Rates of Pr→Pfr photoconversion (left), Pfr→Pr photoconversion (middle), and thermal reversion of Pfr back to Pr (right). All rates were expressed as the percent of Pfr in the sample using the absorption maximum of Pfr near 725 nm for quantification.

Using the protocols described herein and illustrated in FIG. 2, we will first examine the photochemical effects of these amino acid substitutions on the recombinant 6His-tagged PSM of maize phyB1 (amino acids 1-623), the dominance of the two maize phyB paralogs with respect to phenotypes. These mutations will be introduced by the Quikchange method (Stratagene) into the full-length ZmPHYB1 cDNA modified to also contain a C-terminal 6His sequence. They will be expressed in *E. coli* by our well defined, two-plasmid pBAD (Invitrogen) system; one LacZ-controlled plasmid encodes the HO (heme oxygenase) from *Synechocystis* PCC6803 and the PΦB synthase from *Arabidopsis* (HY2 locus) needed to synthesize the PΦB chromophore from heme, and the second arabinose-controlled plasmid encodes the ZmphyB1 polypeptide. By sequential induction with IPTG and arabinose, high level accumulation of fully assembled and photochemically active ZmphyB1 PSMs will be possible. The recombinant biliproteins will then be purified by nickel-nitrilotriacetic acid (NiNTA) affinity (Qiagen) chromatography based on the 6His tag, followed by Phenyl Sepharose chromatography. Bilin occupancy of the purified photoreceptors will be assessed by zinc-induced fluorescence of the bound chromophore following SDS-PAGE of the preparation. These samples will be examined for atypical absorption spectra, photoconversion rates, and Pfr stability by spectrometric techniques using techniques disclosed herein for FIG. 2.

The maize mutants are expected to show phenotypes similar to those described herein for *Arabidopsis*.

Prophetic Example 11

Assessment of Signaling Strength for the ZmphyB1 Mutants in Maize

The ZmphyB1 mutations generated in prophetic example 10 will be introduced into maize plants and tested for their ability to direct various processes under ZmphyB control. The amino acid substitutions will be introduced into the full-length ZmPHYB1 cDNA, also appended to a DNA sequence encoding a short C-terminal FLAG epitope tag (GGDYKDDDDK) (SEQ ID NO: 41), and expressed under the control of the native ZmPHYB1 promoter (2-kbp region upstream of the initiation codon). Use of the native promoter will help avoid artifactual responses generated by ectopic expression of the mutant chromoproteins. These transgenes along with a transgene encoding wild-type ZmphyB-FLAG will be stably introduced into maize using a Maize Transformation protocol which exploits the Hi Type-II background for most transformations, generated from a cross between the B73 and A188 hybrids followed by selection for efficient regeneration of plantlets from cultured embryos. The transgenic plants expressing a range of ZmphyB1 polypeptide levels will be identified by immunoblot analysis with available FLAG and phyB-specific monoclonal antibodies. Independent transformants that express the mutant phyB proteins near to that in wild-type plants will be identified since artificially increased or decreased levels of ZmphyB might significantly influence photomorphogenesis by themselves. Those lines deemed useful will then be backcrossed at least three times to the B73 inbred to generate lines suitable to phenotypic testing. A library of suitable independent lines for each mutation will be generated to avoid potential artifacts generated by insertion position of the transgene and/or differing accumulation of the ZmphyB1 biliprotein.

Some mutants (e.g., phyB$^{Y361F}$) are expected to work dominantly even in the presence of wild-type ZmphyB1/2. However, others will likely confer more subtle phenotypes that will require eliminating the wild-type photoreceptor for observation. This situation will be accomplished through crosses with the ZmphyB1 and ZmphyB2 mutants developed by Sheenan et al. (2007) using Mu insertional mutagenesis, followed by selfing to identify triple homozygous progeny. Single and double mutant combinations will be generated for the strongest ZmphyB1-Mu563 and ZmphyB2-Mu12053 alleles, which have been backcrossed 4 times into both the B73 and W22 backgrounds.

Plants containing unmodified ZmphyB1-FLAG or the mutant (phyB$^{D307A}$, phyB$^{Y361F}$, phyB$^{R582A}$, phyB$^{R352A}$, and phyB$^{R322A}$) in either the wild-type B73 or the ZmphyB1-Mu563 and ZmphyB2-Mu12053 B73-introgressed backgrounds will be examined by various phenotypic assays that specifically measure phyB activity. The germplasm will be tested along side several controls including, near isogenic wild-type B73, B73 expressing unmodified ZmphyB1, and the ZmphyB1-Mu563 and ZmphyB2-Mu12053 B73-introgressed lines either singly or as double mutants. To reduce environmental variability, the plants will be grown in controlled environment cabinets equipped with monochromatic R and FR LED light sources and growth chambers illuminated with white light within the lab and greenhouses supplemented with artificial lighting if needed. Randomized block design will be used to avoid biases based on positions of the plants within the group. Testing of plants in outdoor agricultural plots under natural lighting conditions will be carried out to assess their impact on maize seed yield and plant stature in more representative field settings.

The phenotypes to be tested have been well established in maize and include:

(1) Architecture of seedling grown in the dark (etiolated), which is expected to be unaffected by the mutations.
(2) Effect of R, FR. R-FR. and white light pulses on coleoptile, mesocotyl, and leaf sheath and blade elongation for young seedlings.
(3) Effect of EOD-FR on mesocotyl, and leaf blade elongation for young seedlings grown in light/dark cycles.

(4) Chlorophyll and anthocyanin accumulation in seedlings grown in light/dark cycles.
(5) Effect on internode length, stem diameter, and overall plant height on plants grown in long-day photoperiods.
(6) Effect on flowering time for plants grown in long- and short-day photoperiods.
(7) Number of tillers, cobs, and kernels produced in long-days.

Examining a range of R and FR fluence rates on the photomorphogenic responses of young seedlings will facilitate the quantification of the degree of hypo- or hyperactivity for each mutant, particularly the D307A and Y361F mutations that are expected to greatly impact phyB signaling. It is expected that at least some of the ZmphyB mutants will confer useful new traits such as altered flowering time or reduced SAR (shade avoidance response) to maize grown in field situations.

Sequences listed in this application include:
SEQ ID NO: 1 is the *Arabidopsis thaliana* phytochrome B (phyB) polypeptide (translation of SEQ ID NO: 23)
SEQ ID NO: 2 is the *Zea mays* phytochrome B polypeptide (translation of SEQ ID NO: 24)
SEQ ID NO: 3 is the *Oryza sativa* Japonica Group isolate SJ-CDI2 phytochrome B (phyB) polypeptide (translation of SEQ ID NO: 25)
SEQ ID NO: 4 is the *Sorghum bicolor* isolate PHYB-Rtx430 phytochrome B (phyB) polypeptide (translation of SEQ ID NO: 26)
SEQ ID NO: 5 is the *Glycine max* phytochrome B-1 (phyB) polypeptide (translation of SEQ ID NO: 27)
SEQ ID NO: 6 is the *Glycine max* phytochrome B-2 (phyB) polypeptide (translation of SEQ ID NO: 28)
SEQ ID NO: 7 is the *Glycine max* phytochrome B-3 (phyB) polypeptide (translation of SEQ ID NO: 29)
SEQ ID NO: 8 is the *Glycine max* phytochrome B-4 (phyB) polypeptide (translation of SEQ ID NO: 30)
SEQ ID NO: 9 is the *Solanum tuberosum* phytochrome B polypeptide (translation of SEQ ID NO: 31)
SEQ ID NO: 10 is the *Pisum sativum* phytochrome B (phyB) polypeptide (translation of SEQ ID NO: 32)
SEQ ID NO: 11 is the *Vitis vinifera* genotype PN40024 phytochrome B (phyB) polypeptide (translation of SEQ ID NO: 33)
SEQ ID NO: 12 is the *Arabidopsis* phyB GAF domain
SEQ ID NO: 13 is the maize phyB GAF domain
SEQ ID NO: 14 is the rice phyB GAF domain
SEQ ID NO: 15 is the *sorghum* phyB GAF domain
SEQ ID NO: 16 is the soybean phyB1 GAF domain
SEQ ID NO: 17 is the soybean phyB2 GAF domain
SEQ ID NO: 18 is the soybean phyB3 GAF domain
SEQ ID NO: 19 is the soybean phyB4 GAF domain
SEQ ID NO: 20 is the potato phyB GAF domain
SEQ ID NO: 21 is the pea phyB GAF domain
SEQ ID NO: 22 is the grape phyB GAF domain
SEQ ID NO: 23 is the *Arabidopsis thaliana* phytochrome B (PHYB) nucleotide (Gen Bank Accession No NM_127435)
SEQ ID NO: 24 is the *Zea mays* phytochrome B nucleotide (Phytozome Accession No. GRMZM2G124532)
SEQ ID NO: 25 is the *Oryza sativa* Japonica Group isolate SJ-CDI2 phytochrome B (PHYB) nucleotide (GenBank Accession No: JN594210)
SEQ ID NO: 26 is the *Sorghum bicolor* isolate PHYB-Rtx430 phytochrome B (PHYB) nucleotide (GenBank Accession No: AY466089)
SEQ ID NO: 27 is the *Glycine max* phytochrome B-1 (PHYB) nucleotide (GenBank: Accession No: EU428749)
SEQ ID NO: 28 is the *Glycine max* phytochrome B-2 (PHYB) nucleotide (GenBank Accession No: EU428750.2)
SEQ ID NO: 29 is the *Glycine max* phytochrome B-3 (PHYB) nucleotide (GenBank Accession No: EU428751.1)
SEQ ID NO: 30 is the *Glycine max* phytochrome B-4 (PHYB) nucleotide (GenBank Accession No: EU428752.1)
SEQ ID NO: 31 is the *Solanum tuberosum* phytochrome B nucleotide (GenBank Accession No: DQ342235.1
SEQ ID NO: 32 is the *Pisum sativum* phytochrome B (PHYB) nucleotide (GenBank Accession No: AF069305.1)
SEQ ID NO: 33 is the *Vitis vinifera* genotype PN40024 phytochrome B (PHYB) nucleotide (GenBank Accession No: EU436650.1)
SEQ ID NO: 34 is the cyanobacteriophytochrome GAF domain from *Synechocystis* PCC6803 (Syn Cph_GAF)
SEQ ID NO: 35 is the bacteriophytochrome GAF domain from *Deinococcus radiodurans* (Dr Bph_GAF)
SEQ ID NO: 36 is the bacteriophytochrome GAF domain from *Pseudomonas aeruginosa* (Pa BphP_GAF)
SEQ ID NO: 37 is the bacteriophytochrome GAF domain from *Rhodopseudomonas palustris* (Rp BphP3_GAF)
SEQ ID NO: 38 is the cyanobacteriophytochrome GAF domain from *Synechococcus* OS-B (SyB Cph_GAF)

```
                                                                (SEQ ID NO: 1)
MVSGVGGSGGGRGGGRGGEEEPSSSHTPNNRRGGEQAQSSGTKS

LRPRSNTESMSKAIQQYTVDARLHAVFEQSGESGKSFDYSQSLKTTTYGSSVPEQQIT

AYLSRIQRGGYIQPFGCMIAVDESSFRIIGYSENAREMLGIMPQSVPTLEKPEILAMG

TDVRSLFTSSSSILLERAFVAREITLLNPVWIHSKNTGKPFYAILHRIDVGVVIDLEP

ARTEDPALSIAGAVQSQKLAVRAISQLQALPGGDIKLLCDTVVESVRDLTGYDRVMVY

KFHEDEHGEVVAESKRDDLEPYIGLHYPATDIPQASRFLFKQNRVRMIVDCNATPVLV

VQDDRLTQSMCLVGSTLRAPHGCHSQYMANMGSIASLAMAVIINGNEDDGSNVASGRS

SMRLWGLVVCHHTSSRCIPFPLRYACEFLMQAFGLQLNMELQLALQMSEKRVLRTQTL

LCDMLLRDSPAGIVTQSPSIMDLVKCDGAAFLYHGKYYPLGVAPSEVQIKDVVEWLLA

NHADSTGLSTDSLGDAGYPGAAALGDAVCGMAVAYITKRDFLFWFRSHTAKEIKWGGA

KHHPEDKDDGQRMHPRSSFQAFLEVVKSRSQPWETAEMDAIHSLQLILRDSFKESEAA

MNSKVVDGVVQPCRDMAGEQGIDELGAVAREMVRLIETATVPIFAVDAGGCINGWNAK
```

```
IAELTGLSVEEAMGKSLVSDLIYKENEATVNKLLSRALRGDEEKNVEVKLKTFSPELQ
GKAVFVVVNACSSKDYLNNIVGVCFVGQDVTSQKIVMDKFINIQGDYKAIVHSPNPLI
PPIFAADENTCCLEWNMAMEKLTGWSRSEVIGKMIVGEVFGSCCMLKGPDALTKFMIV
LHNAIGGQDTDKFPFPFFDRNGKFVQALLTANKRVSLEGKVIGAFCFLQIPSPELQQA
LAVQRRQDTECFTKAKELAYICQVIKNPLSGMRFANSLLEATDLNEDQKQLLETSVSC
EKQISRIVGDMDLESIEDGSFVLKREEFFLGSVINAIVSQAMFLLRDRGLQLIRDIPE
EIKSIEVFGDQIRIQQLLAEFLLSIIRYAPSQEWVEIHLSQLSKQMADGFAAIRTEFR
MACPGEGLPPELVRDMFHSSRWTSPEGLGLSVCRKILKLMNGEVQYIRESERSYFLII
LELPVPRKRPLSTASGSGDMMLMMPY
```

(SEQ ID NO: 2)
```
MASGSRATPTRSPSSARPEAPRHAHHHHHSQSSGGSTSRAGGGAAATESVSKAVAQYT
LDARLHAVFEQSGASGRSFDYSQSLRAPPTPSSEQQIAAYLS
RIQRGGHIQPFGCTLAVADDSSFRLLAFSENSPDLLDLSPHHSVPSLDSSAPPHVSLG
ADARLLFSPSSAVLLERAFAAREISLLNPIWIHSRVSSKPFY
AILHRIDVGVVIDLEPARTEDPALSIAGAVQSQKLAVRAISRLQALPGGDVKLLCDTV
VEHVRELTGYDRVMVYRFHEDEHGEVVAESRRDNLEPYLGLH
YPATDIPQASRFLFRQNRVRMIADCHATPVRVIQDPGLSQPLCLVGSTLRAPHGCHAQ
YMANMGSIASLVMAVIISSGGDDEQTGRGGISSAMKLWGLVV
CHHTSPRCIPFPLRYACEFLMQAFGLQLNMELQLAHQLSEKHILRTQTLLCDMLLRDS
PTGIVTQSPSIMDLVKCDGAALYYHGKYYPLGVTPTESQIKD
IIEWLTVFHGDSTGLSTDSLADAGYLGAAALGEAVCGMAVAYITPSDYLFWFRSHTAK
EIKWGGAKHHPEDKDDGQRMHPRSSFKAFLEVVKSRSLPWEN
AEMDAIHSLQLILRDSFRDAAEGTNNSKAIVNGQVQLRELELRGINELSSVAREMVRL
IETATVPIFAVDTDGCINGWNAKIAELTGLSVEEAMGKSLVN
DLIFKESEATVEKLLSRALRGEEDKNVEIKLKTFGSEQYKGPIFVVVNACSSRDYTQN
IVGVCFVGQDVTGQKVVMDKFVNIQGDYKAIVHNPNPLIPPI
FASDENTSCSEWNTAMEKLTGWSRGEVVGKFLIGEVFGNCCRLKGPDALTKFMVIIHN
AIGGQDYEKFPFSFFDKNGKYVQALLTANTRSKMDGKSIGAF
CFLQIASTEIQQAFEIQRQQEKKCYARMKELAYICQEIKNPLSGIRFTNSLLQMTDLN
DDQRQFLETSSACEKQMSKIVKDASLQSIEDGSLVLEQSEFS
LGDVMNAVVSQAMLLLRERDLQLIRDIPDETKDASAYGDQCRIQQVLADFLLSMVRSA
PSENGWVEIQVRPNVKQNSDGTNTELFIFRFACPGEGLPADV
VQDMFSNSQWSTQEGVGLSTCRKILKLMGGEVQYIRESERSFFLIVLEQPQPRPAAGR
EIV
```

(SEQ ID NO: 3)
```
MGSGSRATPTRSPSSARPAAPRHQHHHSQSSGGSTSRAGGGGGG
GGGGGGGAAAAESVSKAVAQYTLDARLHAVFEQSGASGRSFDYTQSLRASPTPSSEQQ
IAAYLSRIQRGGHIQPFGCTLAVADDSSFRLLAYSENTADLLDLSPHHSVPSLDSSAV
PPPVSLGADARLLFAPSSAVLLERAFAAREISLLNPLWIHSRVSSKPFYAILHRIDVG
VVIDLEPARTEDPALSIAGAVQSQKLAVRAISRLQALPGGDVKLLCDTVVEHVRELTG
YDRVMVYRFHEDEHGEVVAESRRSNLEPYIGLHYPATDIPQASRFLFRQNRVRMIADC
```

-continued

HAAPVRVIQDPALTQPLCLVGSTLRSPHGCHAQYMANMGSIASLVMAVIISSGGDDDH

NIARGSIPSAMKLWGLVVCHHTSPRCIPFPLRYACEFLMQAFGLQLNMELQAHQLSE

KHILRTQTLLCDMLLRDSPTGIVTQSPSIMDLVKCDGAALYYHGKYYPLGVTPTEVQI

KDIIEWLTMCHGDSTGLSTDSLADAGYSGAAALGDAVSGMAVAYITPSDYLFWFRSHT

AKEIKWGGAKHHPEDKDDGQRMHPRSSFKAFLEVVKSRSLPWENAEMDAIHSLQLILR

DSFRDSAEGTSNSKAIVNGQVQLGELELRGIDELSSVAREMVRLIETATVPIFAVDTD

GCINGWNAKVAELTGLSVEEAMGKSLVNDLIFKESEETVNKLLSRALRGDEDKNVEIK

LKTFGPEQSKGPIFVIVNACSSRDYTKNIVGVCFVGQDVTGQKVVMDKFINIQGDYKA

IVHNPNPLIPPIFASDENTCCLEWNTAMEKLTGWSRGEVVGKLLVGEVFGNCCRLKGP

DALTKFMIVLHNAIGGQDCEKFPFSFFDKNGKYVQALLTANTRSRMDGEAIGAFCFLQ

IASPELQQAFEIQRHHEKKCYARMKELAYIYQEIKNPLNGIRFTNSLLEMTDLKDDQR

QFLETSTACEKQMSKIVKDASLQSIEDGSLVLEKGEFSLGSVMNAVVSQVMIQLRERD

LQLIRDIPDEIKEASAYGDQYRIQQVLCDFLLSMVRFAPAENGWVEIQVRPNIKQNSD

GTDTMLFLFRFACPGEGLPPEIVQDMFSNSRWTTQEGIGLSICRKILKLMGGEVQYIR

ESERSFFHIVLELPQPQQAASRGTS (SEQ ID NO: 4)

MASGSRATPTRSPSSARPEAPRHAHHHHHHHSQSSGGSTSRAGG

GGGGGGGGGGTAATATATATESVSKAVAQYTLDARLHAVFEQSGASGRSFDYSQSLRA

PPTPSSEQQIAAYLSRIQRGGHIQPFGCTLAVADDSSFRLLAFSENAADLLDLSPHHS

VPSLDSAAPPPVSLGADARLLFSPSSAVLLERAFAAREISLLNPLWIHSRVSSKPFYA

ILHRIDVGVVIDLEPARTEDPALSIAGAVQSQKLAVRAISRLQALPGGDIKLLCDTVV

EHVRELTGYDRVMVYRFHEDEHGEVVAESRRDNLEPYLGLHYPATDIPQASRFLFRQN

RVRMIADCHATPVRVIQDPGMSQPLCLVGSTLRAPHGCHAQYMANMGSIASLVMAVII

SSGGDDEQTGRGGISSAMKLWGLVVCHHTSPRCIPFPLRYACEFLMQAFGLQLNMELQ

LAHQLSEKHILRTQTLLCDMLLRDSPTGIVTQSPSIMDLVKCDGAALYYHGKYYPLGV

TPTESQIKDIIEWLTVCHGDSTGLSTDSLADAGYLGAAALGDAVCGMAVAYITPSDYL

FWFRSHTAKEIKWGGAKHHPEDKDDGQRMHPRSSFKAFLEVVKSRSLPWENAEMDAIH

SLQLILRDSFRDAAEGTSNSKAIVNGQAQLGELELRGINELSSVPREMVRLIETATVP

IFAVDTDGCINGWNAKIAELTGLSVEEAMGKSLVNDLIFKESEEIVEKLLSRALRGEE

DKNVEIKLKTFGSEQSNGAIFVIVNACSSRDYTQNIVGVCFVGQDVTGQKVVMDKFIN

IQGDYKAIVHNPNPLIPPIFASDENTSCSEWNTAMEKLTGWSRGEVVGKFLIGEVFGS

FCRLKGPDALTKFMVVIHNAIGGQDYEKFPFSFFDKNGKYVQALLTANTRSKMDGKSI

GAFCFLQIASAEIQQAFEIQRQQEKKCYARMKELAYICQEIKNPLSGIRFTNSLLQMT

DLNDDQRQFLETCSACEKQMSKIVKDATLQSIEDGSLVLEKSEFSFGDVMNAVVSQAM

LLLRERDLQLIRDIPDEIKDASAYGDQFRIQQVLADFLLSMVRSAPSENGWVEIQVRP

NVKQNSDGTDTELFIFRFACPGEGLPADIVQDMFSNSQWSTQEGVGLSTCRKILKLMG

GEVQYIRESERSFFLIVLELPQPRPAADREIS (SEQ ID NO: 5)

MASASGAANSSVPPPQIHTSRTKLSHHSSNNNNNIDSMSKAIAQ

YTEDARLHAVFEQSGESGRSFNYSESIRIASESVPEQQITAYLVKIQRGGFIQPFGSM

IAVDEPSFRILGYSDNARDMLGITPQSVPSLDDKNDAAFALGTDVRALFTHSSALLLE

-continued

KAFSAREISLMNPIWIHSRTSGKPFYGILHRIDVGIVIDLEPARTEDPALSIAGAVQS

QKLAVRAISQLQSLPGGDVKLLCDTVVESVRELTGYDRVMVYKFHEDEHGEVVSESKR

PDLEPYIGLHYPATDIPQASRFLFKQNRVRMIVDCHASAVRVVQDEALVQPLCLVGST

LRAPHGCHAQYMANMGSIASLVMAVIINGNDEEGVGGRSSMRLWGLVVCHHTSARCIP

FPLRYACEFLMQAFGLQLNMELQLAAQSLEKRVLRTQTLLCDMLLRDSPTGIVTQSPS

IMDLVKCDGAALYFQGNYYPLGVTPTEAQIRDIIEWLLAFHGDSTGLSTDSLGDAGYP

GAASLGDAVCGMAVAYITEKDFLFWFRSHTAKEIKWGGAKHHPEDKDDGQRMHPRSSF

KAFLEVVKSRSLPWENAEMDAIHSLQLILRDSFKDAEHRNSKAVVDPHVSEQELQGVD

ELSSVAREMVRLIETATAPIFAVDVDGHVNGWNAKVSELTGLPVEEAMGKSLVHDLVF

KESEETMNKLLSRALKGEEDKNVEIKMRTFGPEHQNKAVFLVVNACSSKDFTNNVVGV

CFVGQDVTGQKIVMDKFINIQGDYKAIVHSPNPLIPPIFASDDNTCCLEWNTAMEKLT

GWGRVDVIGKMLVGEVFGSCCQLKGSDSITKFMIVLHNALGGQDTDKFPFSFLDRHGK

YVQTFLTANKRVNMEGQIIGAFCFLQIMSPELQQALKAQRQQEKNSFGRMKELAYICQ

GVKNPLSGIRFTNSLLEATSLTNEQKQFLETSVACEKQMLKIIRDVDLESIEDGSLEL

EKGEFLLGNVINAVVSQVMLLLRERNLQLIRDIPEEIKTLAVYGDQLRIQQVLSDFLL

NIVRYAPSPDGWVEIHVRPRIKQISDGLTLLHAEFRMVCPGEGLPPELIQDMFNNSRW

GTQEGLGLSMSRKILKLMNGEVQYIREAERCYFYVLLELPVTRRSSKKC

MASASGAENSSVPPSPLPPPPPPQIHTSRTKLSHHHHNNNNNNN         (SEQ ID NO: 6)

NNIDSTSKAIAQYTEDARLHAVFEQSGESGRSFDYSQSIRVTSESVPEQQITAYLLKI

QRGGFIQPFGSMIAVDEPSFRILAYSDNARDMLGITPQSVPSLDDKNDAAFALGTDIR

TLFTHSSAVLLEKAFSAREISLMNPIWIHSRTSGKPFYGILHRIDVGIVIDLEPARTE

DPALSIAGAVQSQKLAVRAISQLQSLPGGDVKLLCDTVVESVRELTGYDRVMVYRFHE

DEHGEVVAETKRPDLEPYIGLHYPATDIPQASRFLFKQNRVRMIVDCHASAVRVVQDE

ALVQPLCLVGSTLRAPHGCHAQYMANMGSTASLVMAVIINGNDEEGVGGRTSMRLWGL

VICHHTSARCIPFPLRYACEFLMQAFGLQLNMELQLAAQSLEKRVLRTQTLLCDMLLR

DSPTGIVTQSPSIMDLVKCDGAALYYQGNYYPLGVTPTEAQIRDIIEWLLAFHRDSTG

LSTDSLADAGYPGAASLGDAVCGMAVAYITEKDFLFWFRSHTAKEIKWGGAKHHPEDK

DDGQRMHPRSSFKAFLEVVKSRSLPWENAEMDAIHSLQLILRDSFKDAEHSNSKAVLD

PRMSELELQGVDELSSVAREMVRLIETATAPIFAVDVDGRINGWNAKVSELTGLPVEE

AMGKSLVRDLVFKESEETVDKLLSRALKGEEDKNVEIKMRTFGPEHQNKAVFVVVNAC

SSKDYTNNVVGVCFVGQDVTGQKIVMDKFINIQGDYKAIVHNPNPLIPPIFASDDNTC

CLEWNTAMEKLTGWSRADVIGKMLVGEVFGSCCQLKGSDSITKFMIVLHNALGGHDTD

RFPFSFLDRYGKHVQAFLTANKRVNMDGQIIGAFCFLQIVSPELQQALKAQRQQEKNS

FARMKELAYICQGVKNPLSGIRFTNSLLEATCLSNEQKQFLETSAACEKQMLKIIHDV

DIESIEDGSLELEKGEFLLGNVINAVVSQVMLLLRERNLQLIRDIPEEIKTLAVYGDQ

LRIQQVLSDFLLNIVRYAPSPDGWVEIHVHPRIKQISDGLTLLHAEFRMVCPGEGLPP

ELIQNMFNNSGWGTQEGLGLSMSRKILKLMNGEVQYIREAQRCYFYVLLELPVTRRSS

KKC (SEQ ID NO: 7)
MSKAIAQYTEDARLHAVFEQSGESGRSFNYSESIRIASESVPEQ

QITAYLVKIQRGGFIQPFGSMIAVDEPSFRILGYSDNARDMLGITPQSVPSLDDKNDA

AFALGTDVRALFTHSSALLLEKAFSAREISLMNPIWIHSRTSGKPFYGILHRIDVGIV

IDLEPARTEDPALSIAGAVQSQKLAVRAISQLQSLPGGDVKLLCDTVVESVRELTGYD

RVMVYKFHEDEHGEVVSESKRPDLEPYIGLHYPATDIPQASRFLFKQNRVRMIVDCHA

SAVRVVQDEALVQPLCLVGSTLRAPHGCHAQYMANMGSIASLVMAVIINGNDEEGVGG

RSSMRLWGLVVCHHTSARCIPFPLRYACEFLMQAFGLQLNMELQLAAQSLEKRVLRTQ

TLLCDMLLRDSPTGIVTQSPSIMDLVKCDGAALYFQGNYYPLGVTPTEAQIRDIIEWL

LAFHGDSTGLSTDSLGDAGYPGAASLGDAVCGMAVAYITEKDFLFWFRSHTAKEIKWG

GAKHHPEDKDDGQRMHPRSSFKAFLEVVKSRSLPWENAEMDAIHSLQLILRDSFKDAE

HRNSKAVADPRVSEQELQGVDELSSVAREMVRLIETATAPIFAVDVDGHVNGWNAKVS

ELTGLPVEEAMGKSLVHDLVFKESEETMNKLLSRALKGEEDKNVEIKMRTFGPERQNK

AVFLVVNACSSKDFTNNVVGVCFVGQDVTGQKIVMDKFINIQGDYKAIVHSPNPLIPP

IFASDDNTCCLEWNTAMEKLTGWGRVDVIGKMLVGEVFGSCCQLKGSDSITKFMIVLH

NALGGQDTDKFPFSFLDRHGKYVQTFLTANKRVNMEGQIIGAFCFLQIMSPELQQALK

AQRQQEKNSFGRMKELAYICQGVKNPLSGIRFTNSLLEATSLTNEQKQFLETSVACEK

QMLKIIRDVDLESIEDGSLELEKGEFLLGNVINAVVSQVMLLLRERNLQLIRDIPEEI

KTLAVYGDQLRIQQVLSDFLLNIVRYAPSPDGWVEIHVRPRIKQISDGLTLLHAEFRM

VCPGEGLPPELIQDMFNNSRWGTQEGLGLSMSRKILKLMNGEVQYIREAERCYFVLL

ELPVTRRSSKKC (SEQ ID NO: 8)
MIAVDEPSFRILAYSDNARDMLGITPQSVPSLDDKNDAAFALGT

DIRTLFTHSSAVLLEKAFSAREISLMNPIWIHSRTSGKPFYGILHRIDVGIVIDLEPA

RTEDPALSIAGAVQSQKLAVRAISQLQSLPGGDVKLLCDTVVESVRELTGYDRVMVYR

FHEDEHGEVVAETKRPDLEPYIGLHYPATDIPQASRFLFKQNRVRMIVDCHASAVRVV

QDEALVQPLCLVGSTLRAPHGCHAQYMANMGSTASLVMAVIINGNDEEGVGGRTSMRL

WGLVICHHTSARCIPFPLRYACEFLMQAFGLQLNMELQLAAQSLEKRVLRTQTLLCDM

LLRDSPTGIVTQSPSIMDLVKCDGAALYYQGNYYPLGVTPTEAQIRDIIEWLLAFHRD

STGLSTDSLADAGYPGAASLGDAVCGMAVAYITEKDFLFWFRSHTAKEIKWGGAKHHP

EDKDDGQRMHPRSSFKAFLEVVKSRSLPWESAEMDAIHSLQLILRDSFKDAEHSNSKA

VLDPRMSELELQGVDELSSVAREMVRLIETATAPIFAVDVDGRINGWNAKVSELTGLP

VEEAMGKSLVRDLVFKESEETVDKLLSRALKGEEDKNVEIKMRTFGPEHQNKAVFVVV

NACSSKDYTNNVVGVCFVGQDVTGQKIVMDKFINIQGDYKAIVHNPNPLIPPIFASDD

NTCCLEWNTAMEKLTGWSRADVIGKMLVGEVFGSCCQLKGSDSITKFMIVLHNALGGH

DTDRFPFSFLDRYGKHVQAFLTANKRVNMDGQIIGAFCFLQIVSPELQQALKAQRQQE

KNSFARMKELAYICQGVKNPLSGIRFTNSLLEATCLSNEQKQFLETSAACEKQMLKII

HDVDIESIEDG (SEQ ID NO: 9)
MASGSRTKHSHHNSSQAQSSGTSNVNYKDSISKAIAQYTADARL

HAVFEQSGESGKFFDYSESVKTTTQSVPERQITAYLTKIQRGGHIQPFGCMIAVDEAS

FRVIAYSENAFEMLSLTPQSVPSLEKCEILTIGTDVRTLFTPSSSVLLERAFGAREIT

```
LLNPIWIHSKNSGKPFYAILHRVDVGIAIDLEPARTEDPALSIAGAVQSQKLAVRAIS

HLQSLPGGDIKLLCDTVVESVRELTGYDRVMVYKFHEDEHGEVVAESKRSDLEPYIGL

HYPATDIPQASRFLFKQNRVRMIVDCHATPVRVTQDESLMQPLCLVGSTLRAPHGCHA

QYMANMGSIASLTLAVIINGNDEEAVGGGRNSMRLWGLVVGHHTSVRSIPFPLRYACE

FLMQAFGLQLNMELQLASQLSEKHVLRTQTLLCDMLLRDSPPGIVTQSPSIMDLVKCD

GAALYYQGKYYPLGVTPTEAQIKDIVEWLLAYHGDSTGLSTDSLADAGYPGAASLGDA

VCGMAVAYISSKDFLFWFRSHTAKEIKWGGAKHHPEDKDDGLRMHPRSSFKAFLEVVK

SRSSPWENAEMDAIHSLQLILRDSFKDAEASNSKAIVHAHLGEMELQGIDELSSVARE

MVRLIETATAPIFAVDVEGRINGWNAKVAELTGLSVEEAMGKSLVHELVYKESQETAE

KLLYNALRGEEDKNVEIKLRTFGAEQLEKAVFVVVNACASKDYTNNIVGVCFVGQDVT

GEKVVMDKFINIQGDYKAIVHSPNPLIPPIFASDENTCCSEWNTAMEKLTGWSRGEIV

GKMLVGEIFGSCCRLKGPDAMTKFMIVLHNAIGGQDTDKFPFSFFDRNGKYVQALLTA

NKRVNMEGNTIGAFCFIQIASPELQQALRVQRQQEKKCYSQMKELAYICQEIKSPLNG

IRFTNSLLEATNLTENQKQYLETSAACERQMSKIIRDVDLENIEDGSLTLEKEDFFLG

SVIDAVVSQVMLLLREKGVQLIRDIPEEIKTLTVHGDQVRIQQVLADFLLNMVRYAPS

PDGWVEIQLRPSMMPISDGVTGVHIELRIICPGEGLPPELVQDMFHSSRWVTQEGLGL

STCRKMLKLMNGEIQYIRESERCYFLIVLDLPMTRKGPKSVG
```

(SEQ ID NO: 10)
```
SNNNNNNRNIKRESLSMRKAIAQYTEDAXLHAVFEKSGDSFDYAQ

SIRVTAATESVPEQQITAYLAKIQRGGFIQPFGSMIAVDETSFRVLAYSENARDMLGI

APQSVPSMEDDSSSSSFFSLGVDVRSLFSASSSVLLEKAFSAREISLMNPIWIHSRST

GKPFYGILHRIDIGVVIDLEPARSEDPALSIAGAVQSQKLAVRAISQLQALPGGDVKL

LCDAVVESVRELTGYDRVMVYKFHEDEHGEVVAESKRVDLEPYIGLHYPATDIPQASR

FLFKQNRVRMIVDCNASPVRVFQDEALVQPVCLVGSTLRAPHGCHAQYMANMGSIASL

AMAVIINGNDEDGGGIGGAARGSMRLWGLVVCHHTSARCIPFPLRYACEFLMQAFGLQ

LNMELQLAVQSLEKRVLKTQTLLCDMLLRDSHTGIVTQSPSIMDLVKCDGAALYYQGN

YHPLGVTPTESQIRDIIDWLLAFHSDSTGLSTDSLADAGYPGAASLGDAVCGMAVAYI

TEKDFLFWFRSHTAKEIKWGGAKHHPEDKDDGQKMHPRSSFKAFLEVVKIRSMQWDNA

EMDAIHSLQLILRDSFKEAENNDSKAVVHTHMAELELQGVDELSSVAREMVRLIETAT

APIFAVDVDGRINGWNAKVSELTGLLVEEAMGKSLVHDLVYKESRETVDKLLSHALKG

EEDKNVEIKMKTFGPGNQNKAVFIVVNACSSKDYTNNIVGVCFVGQDITGQKVVMDKF

INIQGDYKAIVHSPNPLIPPIFASDDNTCCLEWNNAMEKLSGWSRADVIGKLLVGEVF

GSFCQLKGSDAMTKFMIVLHNALGGHDTDKFPLSFLDRHGKYVHTFLTANKRVNMDGQ

IIGAFCFLQIVNPELQQALTVQRQQDSSSLARMKELAYICQEVKNPLSGIRFTNSLLE

STCLTDEQKQLLETSVACEKQMLKIVRDIALESIEDGSLELEKQEFLLENVINAVVSQ

VMLLLRDRKLQLIRDIPEEIKALAVYGDQLRIQQVLADFLMNVVRYAPSPDGWVEIHV

FPRIKQISEGLTLLHAEFRMVCPGEGLPPELIQDMFHNSRWVTQEGLGLSMSRKIIKL

MNGEVQYVREAERCYFLVLLELPVTRRSSKAIN
```

(SEQ ID NO: 11)
```
MSSGNRGTQSHHQAQSSGTSNLRVYHTDSMSKAIAQYTMDARLH

AVYEQSGESGKSFDYSQSVRTTTQSVPEQQITAYLSKIQRGGHIQPFGCMLAVDEATF
```

-continued

```
RVIAFSENAREMLGLTPQSVPSLEKPEILLVGTDVRTLFTPSSAVLLEKAFRAREITL
LNPVWIHSKNSGKPFYAILHRIDVGIVIDLEPARTEDPALSIAGAVQSQKLAVRAISH
LQSLPGGDINLLCETVVENVRELTGYDRVMVYKFHEDEHGEVVAESKRSDLEPYIGLH
YPATDIPQASRFLFRQNRVRMIVDCHATPVLVIQDEGLMQPLCLVGSTLRAPHGCHAQ
YMANMGSTASLAMAVIINGSDEEAIGGRNLMRLWGLVVCHHTSARCIPFPLRYACEFL
MQAFGLQLNMELQLASQLSEKHVLRTQTLLCDMLLRDSPTGIVTQSPSIMDLVKCDGA
ALYYQGKYYPTGVTPTEAQIKDIAEWLLANHADSTGLSTDSLADAGYPGAASLGDAVC
GMAVAYITSRDFLFWFRSHTAKEIKWGGAKHHPEDKDDGQRMHPRSSFKAFLEVVKSR
SLPWENAEMDAIHSLQLILRDSFKDATDGSNSKAVMHAQLGELELQGMDELSSVAREM
VRLIETATAPIFAVDVDGCINGWNAKVAELTGLSVEEAMGKSLVHDLVYKESEETVDK
LLHHALRGEEDKNVEIKLRTFDSQQHKKAVFVVVNACSSRDYTNNIVGVCFVGQDVTG
QKVVMDKFIHIQGDYKAIVHSPNPLIPPIFASDENTVCSEWNTAMEKLTGWSRGDIIG
KILVGEIFGSSCRLKGPDALTKFMIVLHNAIGGQDTDKFPFSFFDQNGKYVQALLTAN
KRVNIEGQIIGAFCFLQIASPELQQALKVQRQQEKKCFARMKELAYICQEIKNPLSGI
RFTNSLLEATDLTEDQKQFLETSAACEKQMSKIIRDVDLDSIEDGSLELERAEFLLGS
VINAVVSQVMILLRERDLQLIRDIPEEVKTLAVYGDQVRIQQVLADFLLNMVRYAPSP
DGWIEIQVCPRLKQISEEVKLMHIEFRMVCPGEGLPPNLIQDMFHSSRWMTQEGLGLS
MCRKILKLINGEVQYIRESERCYFLISIELPIPHRGSKSVD"
```

(See FIG. 13)            SEQ ID NO: 12

(See FIG. 13)            SEQ ID NO: 13

(See FIG. 13)            SEQ ID NO: 14

(See FIG. 13)            SEQ ID NO: 15

(See FIG. 13)            SEQ ID NO: 16

(See FIG. 13)            SEQ ID NO: 17

(See FIG. 13)            SEQ ID NO: 18

(See FIG. 13)            SEQ ID NO: 19

(See FIG. 13)            SEQ ID NO: 20

(See FIG. 13)            SEQ ID NO: 21

(See FIG. 13)            SEQ ID NO: 22

*Arabidopsis thaliana* phytochrome B (PHYB) nucleotide (GenBank Accession No NM_127435)

(SEQ ID NO: 23)

```
at ggtttccgga gtcgggggta gtggcggtgg ccgtggcggt
ggccgtggcg gagaagaaga accgtcgtca agtcacactc ctaataaccg aagaggagga
gaacaagctc aatcgtcggg aacgaaatct ctcagaccaa gaagcaacac tgaatcaatg
agcaaagcaa ttcaacagta caccgtcgac gcaagactcc acgccgtttt cgaacaatcc
ggcgaatcag ggaaatcatt cgactactca caatcactca aaacgacgac gtacggttcc
```

-continued

```
tctgtacctg agcaacagat cacagcttat ctctctcgaa tccagcgagg tggttacatt
cagcctttcg gatgtatgat cgccgtcgat gaatccagtt tccggatcat cggttacagt
gaaaacgcca gagaaatgtt agggattatg cctcaatctg ttcctactct tgagaaacct
gagattctag ctatgggaac tgatgtgaga tctttgttca cttcttcgag ctcgattcta
ctcgagcgtg ctttcgttgc tcgagagatt accttgttaa atccggtttg gatccattcc
aagaatactg gtaaaccgtt ttacgccatt cttcatagga ttgatgttgg tgttgttatt
gatttagagc cagctagaac tgaagatcct gcgctttcta ttgctggtgc tgttcaatcg
cagaaactcg cggttcgtgc gatttctcag ttacaggctc ttcctggtgg agatattaag
cttttgtgtg acactgtcgt ggaaagtgtg agggacttga ctggttatga tcgtgttatg
gtttataagt ttcatgaaga tgagcatgga gaagttgtag ctgagagtaa acgagatgat
ttagagcctt atattggact gcattatcct gctactgata ttcctcaagc gtcaaggttc
ttgtttaagc agaaccgtgt ccgaatgata gtagattgca atgccacacc tgttcttgtg
gtccaggacg ataggctaac tcagtctatg tgcttggttg ttctactct tagggctcct
catggttgtc actctcagta tatggctaac atgggatcta ttgcgtcttt agcaatggcg
gttataatca atggaaatga agatgatggg agcaatgtag ctagtggaag aagctcgatg
aggctttggg gtttggttgt ttgccatcac acttcttctc gctgcatacc gtttccgcta
aggtatgctt gtgagttttt gatgcaggct ttcggtttac agttaaacat ggaattgcag
ttagctttgc aaatgtcaga gaaacgcgtt ttgagaacgc agacactgtt atgtgatatg
cttctgcgtg actcgcctgc tggaattgtt acacagagtc ccagtatcat ggacttagtg
aaatgtgacg gtgcagcatt tctttaccac gggaagtatt acccgttggg tgttgctcct
agtgaagttc agataaaaga tgttgtggag tggttgcttg cgaatcatgc ggattcaacc
ggattaagca ctgatagttt aggcgatgcg gggtatcccg gtgcagctgc gttaggggat
gctgtgtgcg gtatggcagt tgcatatatc acaaaaagag actttctttt ttggtttcga
tctcacactg cgaaagaaat caaatgggga ggcgctaagc atcatccgga ggataaagat
gatgggcaac gaatgcatcc tcgttcgtcc tttcaggctt ttcttgaagt tgttaagagc
cggagtcagc catgggaaac tgcggaaatg gatgcgattc actcgctcca gcttattctg
agagactctt ttaaagaatc tgaggcggct atgaactcta aagttgtgga tggtgtggtt
cagccatgta gggatatggc gggggaacag gggattgatg agttaggtgc agttgcaaga
gagatggtta ggctcattga gactgcaact gttcctatat tcgctgtgga tgccggaggc
tgcatcaatg gatggaacgc taagattgca gagttgacag gtctctcagt tgaagaagct
atggggaagt ctctggtttc tgatttaata tacaaagaga tgaagcaac tgtcaataag
cttctttctc gtgctttgag aggggacgag gaaaagaatg tggaggttaa gctgaaaact
ttcagccccg aactacaagg gaaagcagtt tttgtggttg tgaatgcttg ttccagcaag
gactacttga acaacattgt cggcgtttgt tttgttggac aagacgttac tagtcagaaa
atcgtaatgg ataagttcat caacatacaa ggagattaca aggctattgt acatagccca
aaccctctaa tcccgccaat ttttgctgct gacgagaaca cgtgctgcct ggaatggaac
atggcgatgg aaaagcttac gggttggtct cgcagtgaag tgattgggaa atgattgtc
ggggaagtgt ttgggagctg ttgcatgcta aagggtcctg atgctttaac caagttcatg
attgtattgc ataatgcgat tggtggccaa gatacggata agttcccttt cccattcttt
gaccgcaatg ggaagtttgt tcaggctcta ttgactgcaa acaagcgggt tagcctcgag
```

-continued ggaaaggtta ttggggcttt ctgtttcttg caaatcccga gccctgagct gcagcaagct ttagcagtcc aacggaggca ggacacagag tgtttcacga aggcaaaaga gttggcttat atttgtcagg tgataaagaa tcctttgagc ggtatgcgtt tcgcaaactc attgttggag gccacagact tgaacgagga ccagaagcag ttacttgaaa caagtgtttc ttgcgagaaa cagatctcaa ggatcgtcgg ggacatggat cttgaaagca ttgaagacgg ttcatttgtg ctaaagaggg aagagttttt ccttggaagt gtcataaacg cgattgtaag tcaagcgatg ttcttattaa gggacagagg tcttcagctg atccgtgaca ttcccgaaga gatcaaatca atagaggttt ttggagacca gataaggatt caacagctcc tggctgagtt tctgctgagt ataatccggt atgcaccatc tcaagagtgg gtggagatcc atttaagcca actttcaaag caaatggctg atggattcgc cgccatccgc acagaattca gaatggcgtg tccaggtgaa ggtctgcctc cagagctagt ccgagacatg ttccatagca gcaggtggac aagccctgaa ggtttaggtc taagcgtatg tcgaaagatt ttaaagctaa tgaacggtga ggttcaatac atccgagaat cagaacggtc ctatttcctc atcattctgg aactccctgt acctcgaaag cgaccattgt caactgctag tggaagtggt gacatgatgc tgatgatgcc atat Zea mays phytochrome B nucleotide (Phytozome Accession No. GRMZM2G124532)

(SEQ ID NO: 24)

ATGGCGTCGGGCAGCCGCGCCACGCCCACGCGCTCCCCCTCCTCCGCGCGGCCCGAGGCGCCGCGTCACGCGCACCA

CCACCACCACTCCCAGTCGTCGGGCGGGAGCACGTCCCGCGCGGGCGGGGAGCCGCGGCCACGGAGTCGGTCTCCA

AGGCCGTCGCCCAGTACACCCTAGACGCGCGCCTACACGCGGTGTTCGAGCAATCGGGCGCGTCGGGCCGCAGCTTC

GACTACTCCCAATCGCTGCGCGCGCCGCCCACGCCGTCCTCCGAGCAGCAGATCGCCGCCTACCTCTCCCGCATCCA

GCGCGGCGGCCACATCCAGCCCTTCGGCTGCACGCTCGCCGTCGCCGACGACTCCTCCTTCCGCCTCCTCGCCTTCT

CCGAGAACTCCCCCGACCTGCTCGACCTGTCGCCTCACCACTCCGTTCCCTCGCTGGACTCCTCTGCGCCGCCCCAC

GTTTCCCTGGGTGCCGACGCGCGCCTCCTCTTCTCCCCCTCGTCCGCGGTCCTCCTAGAGCGCGCCTTCGCCGCGCG

CGAGATCTCGCTGCTCAACCCGATATGGATCCACTCCAGGGTCTCCTCCAAGCCGTTCTACGCCATCCTCCACCGCA

TCGACGTCGGCGTCGTCATCGACCTCGAGCCCGCCCGCACCGAGGACCCCGCTCTCTCCATCGCCGGTGCAGTCCAG

TCCCAGAAACTGGCGGTCCGCGCCATCTCCCGCCTCCAGGCGCTACCCGGCGGGGACGTCAAGCTTCTCTGCGACAC

AGTCGTGGAGCATGTTCGCGAGCTCACGGGTTATGACCGTGTCATGGTGTACAGGTTCCATGAAGACGAGCACGGGG

AAGTTGTCGCCGAGAGCCGGCGCGACAACCTTGAGCCTTACCTCGGATTGCATTATCCCGCCACAGATATCCCCCAG

GCGTCGCGCTTCCTGTTCCGGCAGAACCGCGTGCGAATGATTGCCGATTGCCATGCCACCCCGGTGAGAGTTATTC

AAGATCCTGGGCTGTCGCAGCCTCTGTGTTTGGTAGGCTCCACGCTACGCGCTCCACACGGGTGTCATGCACAGTAC

ATGGCGAACATGGGGTCAATTGCGTCGCTTGTTATGGCAGTCATCATTAGCAGTGGCGGTGACGATGAGCAAACAGG

TCGGGGTGGCATCTCGTCGGCAATGAAGTTGTGGGGGTTAGTGGTGTGCCACCATACATCACCACGGTGTATCCCTT

TTCCATTGAGGTATGCTTGCGAGTTTCTCATGCAGGCATTTGGGTTGCAGCTCAACATGGAGTTGCAGCTTGCGCAC

CAGCTGTCAGAGAAGCACATTCTGCGAACTCAGACGCTATTGTGTGACATGCTACTACGAGATTCACCAACTGGCAT

CGTCACGCAGAGCCCCAGCATCATGGACCTTGTGAAGTGCGACGGGGCTGCACTGTATTATCATGGGAAATACTATC

CATTGGGTGTCACTCCCACTGAGTCTCAGATTAAGGATATCATCGAGTGGTTGACGGTGTTTCATGGGACTCAACA

GGGCTCAGCACAGATAGCCTGGCTGATGCAGGCTACCTTGGTGCTGCTGCACTAGGGGAGGCTGTGTGTGGAATGGC

GGTGGCTTATATTACACCGAGTGATTACTTGTTTTGGTTTCGGTCACACACAGCTAAAGAGATCAAATGGGGTGGCG

CAAAGCATCACCCTGAGGATAAGGATGATGGTCAGAGGATGCACCCACGGTCGTCATTCAAGGCATTTCTTGAAGTG

GTTAAAAGCAGAAGCCTGCCATGGGAGAATGCAGAAATGGACGCAATACATTCCTTGCAGCTCATATTGCGTGACTC

CTTCAGGGATGCTGCAGAGGGCACCAACAACTCAAAAGCCATTGTCAATGGACAAGTTCAGCTTCGGGAGCTAGAAT

TGCGGGGGATAAATGAGCTTAGTCCGTAGCAAGAGAGATGGTTCGGTTGATAGAGACAGCAACAGTACCCATATT

-continued

```
TGCAGTAGATACTGATGGGTGTATAAATGGTTGGAATGCAAAGATTGCTGAGTTGACAGGGCTTTCAGTTGAGGAGG
CAATGGGCAAATCTCTGGTAAATGATCTTATCTTCAAGGAATCTGAGGCGACAGTTGAAAAACTACTCTCACGAGCT
TTAAGAGGTGAGGAAGACAAAAATGTGGAGATAAAGTTGAAGACATTTGGGTCAGAGCAATATAAGGGACCAATATT
TGTTGTTGTCAATGCTTGTTCTAGTAGAGATTACACACAAAATATTGTAGGTGTCTGTTTTGTTGGACAAGATGTCA
CAGGACAAAAGGTGGTCATGGATAAATTTGTTAACATACAAGGGGACTACAAAGCTATTGTACACAATCCTAATCCT
CTGATACCACCAATTTTTGCATCAGATGAGAACACTTCTTGTTCAGAATGGAATACAGCCATGGAAAAACTTACAGG
ATGGTCGAGAGGTGAAGTTGTTGGTAAGTTTCTTATTGGAGAGGTGTTTGGAAATTGTTGTCGACTCAAGGGCCCAG
ATGCATTGACAAAATTCATGGTTATTATTCACAACGCTATAGGAGGACAGGATTATGAGAAGTTCCCTTTTTCATTT
TTTGACAAGAATGGAAAGTATGTGCAGGCCTTATTGACCGCCAATACAAGGAGCAAAATGGATGGTAAATCCATTGG
AGCCTTTTGTTTCCTGCAGATTGCAAGCACTGAAATACAGCAAGCCTTTGAGATTCAGAGACAACAAGAAAAGAAGT
GTTACGCAAGGATGAAAGAATTGGCCTATATTTGCCAGGAGATAAAGAATCCTCTTAGTGGCATCCGATTTACCAAC
TCTCTGTTGCAGATGACTGATTTAAATGATGACCAGAGGCAGTTCCTTGAAACTAGCTCTGCTTGTGAGAAACAGAT
GTCCAAGATTGTTAAGGACGCCAGTCTCCAAAGTATCGAGGACGGCTCTTTGGTGCTTGAGCAAAGTGAGTTTTCT
CTTGAGACGTTATGAATGCTGTTGTCAGCCAAGCAATGTTATTGTTGAGAGAGAGGGATTTACAACTTATTCGGGA
CATCCCTGATGAAATCAAGGATGCGTCAGCGTATGGTGATCAATGTAGAATTCAACAAGTTTTGGCTGACTTCTTGC
TAAGCATGGTGCGGTCTGCTCCATCCGAGAATGGTTGGGTAGAAATACAAGTCAGACCAAATGTAAAACAGAATTCT
GATGGAACAAATACAGAACTTTTCATATTCAGGTTTGCCTGCCCTGGTGAGGGCCTCCCTGCTGACGTC
GTCCAGGATATGTTCAGCAATTCCCAATGGTCAACACAAGAAGGCGTAGGACTAAGCACATGCAGGAAGATCCTCAA
ATTGATGGGTGGCGAGGTCCAATACATCAGAGAGTCAGAGCGGAGTTTCTTCCTCATCGTCCTCGAGCAGCCCCAAC
CTCGTCCAGCAGCTGGTAGAGAAATCGTC
```

*Oryza sativa Japonica* Group isolate SJ-CDI2 phytochrome b (phyB) nucleotide (GenBank Accession No: JN594210)

(SEQ ID NO: 25)

```
atgggctcgg gtagccgcgc cacgcccacg cgctcccccct cctccgcgcg gcccgcggcg
ccgcggcacc agcaccacca ctcgcagtcc tcgggcggga gcacgtcccg cgcgggaggg
ggtggcgggg gcggggagg gggagggggc ggcgcggccg ccgcggagtc ggtgtccaag
gccgtggcgc agtacaccct ggacgcgcgc ctccacgccg tgttcgagca gtcgggcgcg
tcgggccgca gcttcgacta cacgcagtcg ctgcgtgcgt ccccaccc gtcctccgag
cagcagatcg ccgcctacct ctcccgcatc cagcgcggcg ggcacataca gcccttcggc
tgcacgctcg ccgtcgccga cgactcctcc ttccgcctcc tcgcctactc cgagaacacc
gccgacctgc tcgacctgtc gcccaccac tccgtccct cgctcgactc ctccgcggtg
cctccccccg tctcgctcgg cgcagacgcg cgcctccttt tcgctccctc gtccgccgtc
ctcctcgagc gcgccttcgc cgcgcgcgag atctcgctgc tcaacccgct ctggatccac
tccagggtct cctctaaacc cttctacgcc atcctccacc gcatcgatgt cggcgtcgtc
atcgacctcg agcccgcccg caccgaggat cctgcactct ccatgctgg cgcagtccag
tctcagaagc tcgcggtccg tgccatctcc cgcctccagg cgcttcccgg cggtgacgtc
aagctccttt gcgacaccgt tgttgagcat gttagagagc tcacaggtta tgaccgcgtt
atggtgtaca ggttccatga ggatgagcat ggagaagtcg ttgccgagag ccggcgcagt
aaccttgagc cctacatcgg gttgcattat cctgctacag atatcccaca ggcatcacgc
ttcctgttcc ggcagaaccg tgtgcggatg attgctgatt gccatgctgc gccggtgagg
gtcatccagg atcctgcact aacacagccg ctgtgcttgg ttgggtccac gctgcgttcg
ccgcatggtt gccatgcgca gtatatggcg aacatggggt ccattgcatc tcttgttatg
```

```
gcagtgatca ttagtagtgg tggggatgat gatcataaca ttgcacgggg cagcatcccg tcggcgatga agttgtgggg gttggtagta tgccaccaca catctccacg gtgcatccct ttcccactac ggtatgcatg cgagttcctc atgcaagcct ttgggttgca gctcaacatg gagttgcagc ttgcacacca actgtcagag aaacacattc tgcggacgca gacactgctg tgtgatatgc tactccggga ttcaccaact ggcattgtca cacaaagccc cagcatcatg gaccttgtga agtgtgatgg tgctgctctg tattaccatg ggaagtacta ccctcttggt gtcactccca cagaagttca gattaaggac atcatcgagt ggttgactat gtgccatgga gactccacag ggctcagcac agatagcctt gctgatgcag gctactctgg tgctgctgca ctaggagatg cagtgagcgg aatggcggta gcatatatca cgccaagtga ttatttgttt tggttccggt cacacacagc taaggagata agtgggggtg gtgcaaagca tcatccagag gataaggatg atggacaacg aatgcatcca cgatcatcgt tcaaggcatt tcttgaagtt gtgaagagta ggagcttacc atgggagaat gcagagatgg atgcaataca ttccttgcag ctcatattgc gggactcttt cagagattct gcagagggca caagtaactc aaaagccata gtgaatggcc aggttcagct tggggagcta gaattacggg aatagatga gcttagctcg gtagcgaggg agatggttcg gttgatcgag acagcaacag tacccatctt tgcagtagat actgatggat gtataaatgg ttggaatgca aaggttgctg agctgacagg cctctctgtt gaggaagcaa tgggcaaatc attggtaaat gatctcatct tcaaggaatc tgaggaaaca gtaaacaagc tactctcacg agctttaaga g g tgatgaagac aaaaatgtag agataaagtt gaagacattc gggccagaac aatctaaagg accaatattc gttattgtga atgcttgttc tagcagggat tacactaaaa atattgttgg tgtttgtttt gttggccaag atgtcacagg acaaaggtg gtcatggata aatttatcaa catacaaggg gattacaagg ctatcgtaca caaccctaat cctctcatac ccccaatatt tgcttcagat gagaatactt gttgtttgga gtggaacaca gcaatggaaa aactcacagg atggtcaaga ggggaagttg ttggtaagct tctggtcggt gaggtctttg gtaattgttg tcgactcaag ggcccagatg cattaacgaa attcatgatt gtcctacaca acgctatagg aggacaggat tgtgaaaagt tcccctttc attttttgac aagaatggga aatacgtgca ggccttattg actgcaaaca cgaggagcag aatggatggt gaggccatag gagccttctg tttcttgcag attgcaagtc ctgaattaca gcaagccttt gagattcaga gacaccatga aaagaagtgt tatgcaagga tgaaggaatt ggcttacatt taccaggaaa taaagaatcc tctcaacggt atccgattta caaactcgtt attggagatg actgatctaa aggatgacca gaggcagttt cttgaaacca gcactgcttg tgagaaacag atgtccaaaa ttgttaagga tgctagcctc caaagtattg aggatgg ctcttt ggtgcttgag aaaggtgaat tttcactagg tagtgttatg aatgctgttg tcagccaagt gatgatacag ttgagagaaa gagatttaca acttattcga gatatccctg atgaaattaa agaagcctca gcatatggtg accaatatag aattcaacaa gtttatgtg acttttttgct aagcatggtg aggtttgctc cagctgaaaa tggctgggtg gagatacagg tcagaccaaa tataaaacaa aattctgatg aacagacac aatgcttttc ctcttcag gttt gcctgtcctg gcgaaggcct tccccagag attgttcaag acatgtttag taactcccgc tggacaaccc aagagggtat tggcctaagc atatgcagga agatcctaaa
```

-continued attgatgggt ggcgaggtcc aatatataag ggagtcggag cggagtttct tccatatcgt acttgagctg ccccagcctc agcaagcagc aagtagggg acaagc

*Sorghum bicolor* isolate PHYB-Rtx430 phytochrome B (PHYB) nucleotide (GenBank
Accession No: AY466089)

(SEQ ID NO: 26)

atggcgtcgg gcagccgcgc cacgcccacg cgctcccct cctccgcgcg acccgaggcg ccgcgtcacg cgcaccacca ccaccaccac cactcgcagt cgtcgggcgg gagcacgtcc cgcgcgggcg gggaggtgg aggaggagga ggtggcgggg gcaccgcggc cacggctacg gccacggcca cggagtcggt ctccaaggcc gtggcgcagt acaccctaga cgcgcggctc cacgcggtgt tcgagcaatc gggcgcgtcg ggccgcagct tcgactactc ccagtcgctg cgcgcgccgc ccacgccgtc ctccgagcag cagatcgccg cctacctctc ccgcatccag cgcggcggcc acatccagcc cttcggctgc acgctcgccg tcgccgacga ctcctccttc cgcctcctcg ccttctccga aacgccgcc gacctgctcg acctgtcgcc gcaccactcc gttccctcgc tcgattccgc ggcgccgccc ccgtttccc tgggtgccga cgcgcgcctc ctcttctccc cctcgtccgc ggtcctcctg gagcgcgcct tcgccgcgcg cgagatctcg ctgctcaacc cgctatggat ccactccagg gtctcttcca gccgttcta cgccatcctc caccgcatcg acgtcggcgt cgtcatcgac ctcgagcccg cccgcaccga ggaccccgct ctctccatcg ccggcgcagt ccagtcccag aaactcgcgg tccgtgccat ctcccgcctc caggcgctac ctggcgggga catcaagctc ctctgcgaca cagtcgtgga gcatgttcgc gagctcacgg gttacgaccg tgtcatggtg tacaggttcc atgaagacga gcatggggaa gttgtcgccg agagccggcg cgataacctt gagccttacc tcggattgca ttatcccgcc acagatatcc cccaggcatc gcgcttcctg ttccggcaga accgcgtgcg gatgattgct gattgccatg ccacccggt gagagtcata caagatcctg ggatgtcgca gccactgtgt ttggtaggct ccacgcttcg tgctccacac gggtgccatg cgcagtacat ggcgaacatg gggtcaattg catcacttgt tatggcagtc atcattagca gtggtggtga tgacgagcaa acaggtcggg gaggcatctc ctcggcaatg aagttgtggg ggttagtggt gtgtcaccat acgtcaccac ggtgtatccc ttttccattg aggtatgctt gcgagtttct catgcaggca tttgggctgc agctcaacat ggaattgcag cttgcgcatc agctgtcaga aagcacatt ttgcgaactc agacgctatt gtgtgacatg ctattgcgag attcaccaac tggcatcgtc acgcagagcc ccagcatcat ggaccttgtg aagtgtgatg gggctgcact gtattatcat gggaagtact atccattggg tgtcactccc actgagtctc agattaagga tatcattgag tggttgacgg tgtgtcatgg ggactcaaca gggctcagca cagacagcct tgctgatgca ggctaccttg gtgctgctgc attaggggat gctgtgtgtg aatggcggt ggcttatatt acaccgagtg attacttgtt ttggtttcgg tcacacacag ctaaagagat caaatggggt ggcgcaaagc atcaccctga ggataaggat gatggtcaga ggatgcaccc acggtcatca ttcaaggcat ttcttgaagt ggttaaaagc agaagcctac catgggagaa tgcagaaatg gacgcgatac attccttgca actcatattg cgtgactcct tcagagatgc tgcagagggc actagcaact caaaagccat tgtcaatgga caagctcagc ttggggagct agaattgcgg gggataaatg agcttagctc tgtaccaaga gagatggttc ggttgataga cagcaaca gtacccatat ttgcagtaga tactgatgga tgcataaatg gttggaatgc gaaaattgct gagttgacag gcctttcagt tgaggaggca atgggcaaat ctctggtaaa cgatcttatc ttcaaggaat ctgaggagat agtcgaaaag ctactctcac gagctttaag ag

```
gtgagg aagacaaaaa tgtggagata aagttgaaga catttgggtc agagcaatct aacggagcaa tatttgttat tgtcaatgct tgttccagta gagattacac acaaatatt gttggtgtct gttttgttgg acaagatgtc acaggacaaa aggtggtcat ggataaattt atcaacatac aaggggacta taaagctatt gtacacaatc ctaatcctct gatacccca attttgcat cagatgagaa cacttcttgt tcagaatgga acacagccat ggaaaactt acaggatggt cgagaggtga agttgttggt aaatttctta ttggagaggt gtttggaagt ttttgtcgac tcaagggccc agatgcattg acaaagttca tggttgtcat tcacaatgct ataggagggc aggattatga aagttcccct tttcattt tcgacaagaa tggaaagtat gtgcaggcct tattgaccgc caacacaagg agcaaaatgg atggtaaatc cattggcgcc ttttgtttt tgcagattgc aagcgctgaa atacagcaag cctttgagat tcagagacaa caagaaaaga agtgttatgc aaggatgaaa gaattggcct atatttgcca ggagataaag aatcctctta gtggcatccg atttaccaac tctctgttgc aaaatgactga tttaaatgat gatcagaggc agttccttga aacttgctct gcttgtgaga aacagatgtc caagattgtt aaggacgcca ctctccaaag tattgaggac gg ctctttggta cttgagaaaa gtgagttttc ttttggagac gttatgaatg ctgttgtcag ccaagcaatg ttattgttga gggagaggga tttacaactt attcgggata tccctgatga aatcaaggat gcatcagcat atggtgatca atttagaatt caacaagttt tggctgactt cttgctaagc atggtgcgat ctgctccgtc cgagaatggc tgggtagaaa tacaagtcag accaaatgta aaacagaatt ctgacggaac agatacagag cttttcatct tcag gtttgcct gccctggtga gggccttccc gctgacattg tccaggatat gttcagcaat tcccagtggt caacccaaga aggcgtagga ctaagcacat gcaggaagat cctcaaattg atgggcggtg aggtccaata catcagggag tcagagcgga gtttcttcct catcgtcctc gagctgcccc agcctcgtcc agcagctgat agagaaatca gt
```

Glycine max phytochrome B-1 (phyB) nucletoide (GenBank: EU428749)

(SEQ ID NO: 27)

```
  1 atggcttcag caagcggagc ggcgaattcc tccgttccgc cgccgcaaat ccacacctca
 61 cgaacaaagc tgagccacca cagcagcaac aacaacaaca catcgactc catgagcaag
121 gccatcgcgc agtacacgga ggacgcgcgg ctccacgccg tcttcgagca gtccggcgag
181 tccgggaggt ccttcaacta ctccgaatca atccgcatcg catcggaatc cgtccccgag
241 cagcagataa cggcttacct tgtcaaaatc cagcgcggcg gcttcatcca gcccttcggc
301 tccatgatcg ccgtcgacga gccctccttc cgcatcctcg gttactccga caacgcccgc
361 gacatgctcg gcattactcc gcagtccgtc ccttcgctcg acgacaagaa cgacgccgcc
421 ttcgctctcg gcaccgatgt ccgagccctc ttcactcact ccagcgcctt actcctcgaa
481 aaggccttct ccgcacgcga aattagcctc atgaaccta tctggatcca ctccagaacc
541 tccgggaagc ctttctatgg aatcctccac cgaattgacg tcggaattgt catcgatttg
601 gagcctgcgc gtacggagga tcctgccctc tctatcgctg agctgtcca gtcgcagaag
661 ctcgcggttc gcgcgatttc gcagcttcaa tctctccccg gcggtgatgt taagcttctc
721 tgtgacactg ttgtggaaag tgttagggaa ttgacgggtt atgatagggt tatggtttat
781 aagtttcatg aggatgagca tggagaggtt gtttctgaga gtaagaggcc tgatttggag
841 ccttacattg gattgcatta tcctgctact gatattcctc aggcttctag gtttttgttt
901 aagcaaaata gagttaggat gattgtggat tgtcatgctt ctgctgtgag ggtggtgcag
961 gatgaggctc ttgtgcagcc tttgtgtttg gttgggtcca cccttagggc acctcacggt
```

-continued

```
1021 tgtcatgctc agtatatggc taacatgggc tcgattgcgt ctttggtgat ggcagttatt
1081 atcaatggga atgacgagga aggcgttggt ggtcgcagtt cgatgaggct gtggggctt
1141 gttgtctgcc accatacctc tgccaggtgt attccttttc ccttgaggta tgcttgtgag
1201 tttctgatgc aggcgtttgg gctgcagttg aacatggagc ttcagttggc cgcgcagtcg
1261 ttggagaagc gggttttgag gacacagact ctgttgtgtg atatgcttct tagggactcg
1321 cctactggca ttgttactca gagtcctagt ataatggact tggtgaagtg tgatggggct
1381 gcccctttatt tccaagggaa ctattatccg ttgggtgtga ctccaactga agctcagatt
1441 agggatatta ttgagtggtt gttggccttc catggagatt cgaccggttt gagtactgat
1501 agtctgggtg atgctggata tcccggggct gcctcgcttg gggatgcagt ttgtgggatg
1561 gcggttgctt atattacaga gaaggatttt cttttctggt tcaggtcgca cacggccaaa
1621 gagatcaaat ggggtggtgc aaagcatcat cctgaggaca aggatgatgg gcagagaatg
1681 catccccgtt cttccttcaa ggcgttttta gaagtggtga aaagccgtag cttgccgtgg
1741 gagaatgcgg aaatggatgc aattcactct ttgcagctta ttctgcgtga ctcgtttaaa
1801 gatgctgagc atagaaattc taaggctgtt gtggatcccc atgtgtcaga acaagagttg
1861 caaggggtgg atgaactaag ttctgtggcc agagagatgg ttagattgat agaaacagcc
1921 actgctccaa tatttgctgt tgatgtcgat ggccacgtaa atgggtggaa tgcaaaggtt
1981 tcagaattaa caggactccc agttgaggag gctatgggga agtccttggt tcacgatctt
2041 gtgtttaagg agtctgaaga aactatgaac aagcttcttt ctcgtgcttt aaaaggtgaa
2101 gaagataaga atgttgagat aaaaatgagg acgtttggcc cagaacatca aaataaggca
2161 gtgtttttag tggtgaatgc ttgctccagc aaggatttta caaataatgt agttggagtg
2221 tgctttgttg gtcaggatgt tactggtcaa aaaattgtaa tggacaaatt catcaacata
2281 caaggtgact acaaggctat tgtacatagc ccaaatcctt tgatccctcc cattttgca
2341 tcggacgata acacatgttg cttagagtgg aacactgcaa tggaaaagct tactggttgg
2401 ggccgtgtgg atgtcattgg aaaaatgttg gtgggagagg ttttggtag ttgctgtcag
2461 ttgaagggtt cagattcaat aacaaagttc atgattgtct tacacaatgc acttggtgga
2521 caagatacag ataaattccc tttctcattt cttgatcggc acggaaagta tgtacaaact
2581 ttcctgactg caaataagag ggttaacatg gagggtcaga tcataggagc tttttgcttt
2641 ttgcaaatca tgagtccgga acttcagcag gctcttaagg cacagagaca acaagaaaag
2701 aattcctttg gtaggatgaa agagttagct tatatttgtc aaggagttaa gaatcctttg
2761 agtggcatac gctttacaaa ctctcttttg gaggctacaa gcttgaccaa tgagcaaaag
2821 cagtttcttg agactagtgt tgcttgtgag aagcaaatgt taaagataat acgcgacgtt
2881 gatcttgaaa gcatcgagga tgggtccctg gagcttgaaa aggggggaatt cttgcttgga
2941 aatgtcataa atgcagttgt tagccaagta atgttactgt taagagaaag aaatttacag
3001 ttgattcgtg atattcctga agaaatcaag acattggcag tttatggtga tcaattgagg
3061 attcaacaag tgttgtctga tttcttgttg aatatagtgc gctatgcacc atctccagat
3121 ggctgggtag agattcatgt acgtccaaga ataaaacaaa tctcagatgg gctcactctt
3181 ctccatgctg aatttagaat ggtatgtcct ggtgaaggtc ttcctcctga attgattcaa
3241 gacatgttca ataacagtcg gtgggggact caagaaggtt tagggctgag catgagcagg
3301 aagattctaa agctaatgaa cggcgaagtg cagtatatca gggaggccga acggtgctac
3361 ttctatgttc ttcttgaact acctgtgaca cggagaagct ctaaaaagtg t
```

-continued

Glycine max phytochrome B-2 (phyB) mRNA nucleotide (GenBank Accession NO: EU428750.2)

(SEQ ID NO: 28)

```
   1 atggcttcag caagcggagc ggagaattcc tccgtcccgc cgtcgccgtt gccgcctccg
  61 ccgccgccgc aaatccacac ctcgcggacg aagctgagcc accaccacca caacaacaac
 121 aacaacaaca acaacaacat cgactccacg agcaaggcca tcgcgcagta cacggaggac
 181 gcgcggctcc acgccgtctt tgagcagtcc ggcgagtccg ggaggtcctt tgactactcc
 241 caatcaatcc gcgtcacatc ggaatccgtc ccggagcagc agataacggc ttaccttctc
 301 aaaattcagc gcggcggctt catccagccc ttcggctcca tgatcgccgt cgacgagccc
 361 tccttccgca tccttgccta ctccgacaac gcccgtgaca tgctcggcat tactccacag
 421 tccgtcccct cgctcgacga caagaacgac gccgccttcg cgctcggaac cgatatccga
 481 accctcttca ctcactccag cgccgttctc ctcgaaaagg ccttctccgc gcgcgaaatt
 541 agcctcatga accctatctg gattcactcc agaacctccg ggaagccttt ctatggaatc
 601 ctccaccgaa ttgacgtcgg aattgtcatc gatttggagc ctgcgcggac ggaggatcct
 661 gccctctcca tcgccggagc tgtccagtcg cagaagctcg cggttcgcgc gatttcgcag
 721 cttcaatctc tccccggtgg cgatgttaag cttctttgtg atactgttgt tgagagtgtc
 781 agggaattga cagggtatga taggggttatg gtttataggt tcatgagga tgagcatggg
 841 gaggttgttg ctgagactaa gaggcctgat ttggagcctt acattggatt gcattatccc
 901 gctactgata ttcctcaggc ttctaggttt ttgtttaagc agaatagggt taggatgatt
 961 gtggattgtc atgcttctgc tgtgagggtg gtgcaggatg aggctcttgt gcagcctctg
1021 tgtttggttg gtccacgct cagggcgcct cacggttgcc atgctcagta tatggctaac
1081 atgggctcga ctgcgtcgtt ggtgatggct gttattatca atgggaatga tgaggaaggt
1141 gttggtggcc gcacttcgat gaggttgtgg gggcttgtta tttgccacca tacctctgct
1201 aggtgtattc cttttccctt gaggtatgct tgtgagtttc tgatgcaggc gtttgggctg
1261 cagttgaaca tggagcttca gttggccgca cagtcgttgg agaagcgggt tttgaggaca
1321 cagactctgt tgtgtgatat gcttctcagg gactctccta ctggcattgt aactcagagt
1381 cctagtatta tggacttggt gaagtgtgac ggagctgctc tttattacca agggaactat
1441 tatccgttgg tgtgactcc aactgaggct cagataaggg atattattga gtggttgttg
1501 gcctttcata gagattcgac tggttttgagt actgatagtc tggctgatgc tggctatcct
1561 ggggctgcct cgcttgggga tgcagtttgt gggatggcgg ttgcttatat tacagagaag
1621 gatttttcttt tctggttcag gtcgcacacg gcgaaagaga tcaaatgggg tggtgcaaag
1681 catcatcctg aggacaagga tgatgggcag agaatgcatc cccgttcttc cttcaaggca
1741 ttttagaag tggtgaaaag ccgtagcttg ccgtgggaga tgcggaaat ggatgcaatt
1801 cactctttgc agcttattct gcgtgactcg tttaaagatg ctgagcatag caattctaag
1861 gctgtttgg atccccgtat gtcggaacta gagttgcaag gggtcgatga actaagttct
1921 gtagccagag agatggttag attgatcgaa acagccactg ctccaatatt gctgttgat
1981 gttgatggcc gcataaatgg tgtggaatgca aaggtttcag aattgacagg actcccagtt
2041 gaggaggcta tggggaagtc cttggttcgc gatcttgtgt ttaaggagtc tgaagaaact
2101 gtggacaagc ttctttctcg tgctttaaaa ggtgaagaag ataagaatgt tgagataaaa
2161 atgaggacgt ttggcccaga acatcaaaat aaggcagttt ttgtagtggt gaatgcttgc
2221 tccagcaagg attatacaaa taatgtagtt ggagtgtgct tgttggtca ggatgttact
2281 ggtcaaaaaa ttgtgatgga caaattcatc aacatacaag gcgactacaa ggctattgta
```

-continued

```
2341 cataatccaa atcctttgat ccctcccatt tttgcatcgg atgataacac gtgttgctta 2401 gagtggaaca ctgcaatgga aaagcttact ggttggagcc gcgcggatgt cattggaaaa 2461 atgttggtgg gagaggtttt cggcagttgc tgtcagttga agggttcaga ttcaataaca 2521 aagttcatga ttgtcttaca caatgcgctt ggtggacatg atacagatag attcccgttt 2581 tcatttcttg atcggtatgg caagcatgtg caagctttcc tgactgcaaa taagagggtt 2641 aacatggatg tcagatcat tggggcattt tgcttttgc aaattgtgag tccggaactt 2701 caacaggctc tgaaggcaca gagacaacaa gagaagaatt catttgctag gatgaaagag 2761 ttagcttata tttgtcaagg agttaagaat cctttgagtg gcatacgctt tacaaactct 2821 cttttggagg ctacatgctt gtccaatgag caaaaacagt ttcttgagac tagtgctgct 2881 tgtgagaagc aaatgttaaa gataatacac gatgttgata ttgaaagcat tgaggatggg 2941 tccctggagc ttgaaaaggg ggaattcttg cttggaaatg tcataaatgc agttgttagc 3001 caagtaatgc tactgttaag agaaagaaat ttacagttga ttcgtgatat tcctgaagaa 3061 atcaagacat tggctgttta tggtgatcaa ttgaggattc aacaagtgtt gtctgatttc 3121 ttattgaata tagtgcgcta tgcaccatct ccagatggct gggtagagat tcatgtacat 3181 ccaagaataa aacaaatctc agatgggctc actcttctcc atgctgaatt tagaatggta 3241 tgtcctggtg aaggtcttcc tcctgaattg attcaaaaca tgttcaataa cagtgggtgg 3301 gggactcaag aaggtttagg gctgagcatg agcaggaaga ttctaaagct aatgaacggc 3361 gaagtgcagt atatcaggga ggcccaacgg tgctacttct atgttcttct tgaactacct 3421 gtgacacgga gaagctctaa aaagtgt
```

*Glycine max* phytochrome B-3 (phyB) nucleotide (GenBank Accession No: EU428751.1)

(SEQ ID NO: 29)

```
atgagcaagg ccatcgcgca gtacacggag gacgcgcggc tccacgccgt cttcgagcag tccggcgagt ccgggaggtc cttcaactac tccgaatcaa tccgcatcgc atcggaatcc gtccccgagc agcagataac ggcttacctt gtcaaaatcc agcgcggcgg cttcatccag cccttcggct ccatgatcgc cgtcgacgag ccctccttcc gcatcctcgg ttactccgac aacgcccgcg acatgctcgg cattactccg cagtccgtcc cttcgctcga cgacaagaac gacgccgcct tcgctctcgg caccgatgtc cgagccctct tcactcactc cagcgcccta ctcctcgaaa aggccttctc cgcacgcgaa attagcctca tgaaccctat ctggatccac tccagaacct ccgggaagcc tttctatgga atcctccacc gaattgacgt cggaattgtc atcgatttgg agcctgcgcg tacggaggat cctgccctct ctatcgctgg agctgtccag tcgcagaagc tcgcggttcg cgcgatttcg cagcttcaat ctctccccgg cggtgatgtt aagcttctct gtgacactgt tgtggaaagt gttagggaat tgacgggtta tgatagggtt atggtttata agtttcatga ggatgagcat ggagaggttg tttctgagag taagaggcct gatttggagc cttacattgg attgcattat cctgctactg atattcctca ggcttctagg ttttttgttta agcaaaatag agttaggatg attgtggatt gtcatgcttc tgctgtgagg gtggtgcagg atgaggctct tgtgcagcct ttgtgtttgg ttgggtccac ccttagggca cctcacggtt gtcatgctca gtatatggct aacatgggct cgattgcgtc tttggtgatg gcagttatta tcaatgggaa tgacgaggaa ggcgttggtg gtcgcagttc gatgaggctg tggggggcttg ttgtctgcca ccatacctct gccaggtgta ttccttttcc cttgaggtat gcttgtgagt ttctgatgca ggcgtttggg ctgcagttga acatggagct tcagttggcc gcgcagtcgt
```

```
tggagaagcg gttttgagg acacagactc tgttgtgtga tatgcttctt agggactcgc ctactggcat tgttactcag agtcctagta taatggactt ggtgaagtgt gatggggctg ccctttattt ccaagggaac tattatccgt tgggtgtgac tccaactgaa gctcagatta gggatattat tgagtggttg ttggccttcc atggagattc gaccggtttg agtactgata gtctgggtga tgctggatat cccggggctg cctcgcttgg ggatgcagtt tgtgggatgg cggttgctta tattacagag aaggattttc ttttctggtt caggtcgcac acggccaaag agatcaaatg gggtggtgca agcatcatc ctgaggacaa ggatgatggg cagagaatgc atccccgttc ttccttcaag gcgtttttag aagtggtgaa aagccgtagc ttgccgtggg agaatgcgga atggatgca attcactctt tgcagcttat tctgcgtgac tcgtttaaag atgctgagca tagaaattct aaggctgtcg cggatccccg tgtgtcagaa caagagttgc aagggtgga tgaactaagt tctgtggcca gagagatggt tagattgata gaaacagcca ctgctccaat atttgctgtt gatgtcgatg ccacgtaaa tgggtggaat gcaaaggttt cagaattaac aggactccca gttgaggagg ctatggggaa gtccttggtt cacgatcttg tgtttaagga gtctgaagaa actatgaaca agcttctttc tcgtgcttta aaaggtgaag aagataagaa tgttgagata aaaatgagga cgtttggccc agaacgtcaa aataaggcag tgttttagt ggtgaatgct tgctccagca aggatttac aaataatgta gttggagtgt gctttgttgg tcaggatgtt actggtcaaa aaattgtaat ggacaaattc atcaacatac aaggtgacta caaggctatt gtacatagcc caaatccttt gatccctccc atttttgcat cggacgataa cacatgttgc ttagagtgga acactgcaat ggaaaagctt actggttggg gccgtgtgga tgtcattgga aaaatgttgg tgggagaggt ttttggtagt tgctgtcagt tgaagggttc agattcaata acaaagttca tgattgtctt acacaatgca cttggtggac aagatacaga taaattccct ttctcatttc ttgatcggca cggaaagtat gtacaaactt tcctgactgc aaataagagg gttaacatgg agggtcagat cataggagct ttttgctttt tgcaaatcat gagtccggaa cttcagcagg ctcttaaggc acagagacaa caagaaaaga attcctttgg taggatgaaa gagttagctt atatttgtca aggagttaag aatcctttga gtggcatacg ctttacaaac tctcttttgg aggctacaag cttgaccaat gagcaaaagc agtttcttga gactagtgtt gcttgtgaga agcaaatgtt aaagataata cgcgacgttg atcttgaaag catcgaggat gggtccctgg agcttgaaaa ggggaattc ttgcttggaa atgtcataaa tgcagttgtt agccaagtaa tgttactgtt aagagaaaga aatttacagt tgattcgtga tattcctgaa gaaatcaaga cattggcagt ttatggtgat caattgagga ttcaacaagt gttgtctgat ttcttgttga atatagtgcg ctatgcacca tctccagatg gctgggtaga gattcatgta cgtccaagaa taaaacaaat ctcagatggg ctcactcttc tccatgctga atttagaatg gtatgtcctg gtgaaggtct tcctcctgaa ttgattcaag acatgttcaa taacagtcgg tgggggactc aagaaggttt agggctgagc atgagcagga agattctaaa gctaatgaac ggcgaagtgc agtatatcag ggaggccgaa cggtgctact tctatgttct tcttgaacta cctgtgacac ggagaagctc taaaaagtgt
```

*Glycine max* phytochrome B-4 (phyB) nucletoide
GenBank: EU428752.1

(SEQ ID NO: 30)

```
at gatcgccgtc gacgagccct ccttccgcat ccttgcctac tccgacaacg cccgtgacat gctcggcatt actccacagt ccgtcccttc gctcgacgac aagaacgacg ccgccttcgc gctcggaacc gatatccgaa
```

-continued

```
     ccctcttcac tcactccagc gccgttctcc tcgaaaaggc cttctccgcg cgcgaaatta gcctcatgaa ccctatctgg attcactcca gaacctccgg gaagcctttc tatggaatcc tccaccgaat tgacgtcgga attgtcatcg atttggagcc tgcgcggacg gaggatcctg 661 ccctctccat cgccggagct gtccagtcgc agaagctcgc ggttcgcgcg atttcgcagc 721 ttcaatctct ccccggtggc gatgttaagc ttctttgtga tactgttgtt gagagtgtca 781 gggaattgac agggtatgat agggttatgg tttataggtt tcatgaggat gagcatgggg 841 aggttgttgc tgagactaag aggcctgatt tggagcctta cattggattg cattatcccg 901 ctactgatat tcctcaggct tctaggtttt tgtttaagca gaatagggtt aggatgattg 961 tggattgtca tgcttctgct gtgagggtgg tgcaggatga ggctcttgtg cagcctctgt 1021 gtttggttgg gtccacgctc agggcgcctc acggttgcca tgctcagtat atggctaaca 1081 tgggctcgac tgcgtcgttg gtgatggctg ttattatcaa tgggaatgat gaggaaggtg 1141 ttggtggccg cacttcgatg aggttgtggg ggcttgttat ttgccaccat acctctgcta 1201 ggtgtattcc ttttcccttg aggtatgctt gtgagtttct gatgcaggcg tttgggctgc 1261 agttgaacat ggagcttcag ttggccgcac agtcgttgga gaagcgggtt tgaggacac 1321 agactctgtt gtgtgatatg cttctcaggg actctcctac tggcattgta actcagagtc 1381 ctagtattat ggacttggtg aagtgtgacg gagctgctct ttattaccaa gggaactatt 1441 atccgttggg tgtgactcca actgaggctc agataaggga tattattgag tggttgttgg 1501 cctttcatag agattcgact ggtttgagta ctgatagtct ggctgatgct ggctatcctg 1561 gggctgcctc gcttggggat gcagtttgtg ggatggcggt tgcttatatt acagagaagg 1621 attttctttt ctggttcagg tcgcacacgg cgaaagagat caaatggggt ggtgcaaagc 1681 atcatcctga ggacaaggat gatgggcaga gaatgcatcc ccgttcttcc ttcaaggcat 1741 ttttagaagt ggtgaaaagc cgtagcttgc cgtgggagag tgcggaaatg gatgcaattc 1801 actctttgca gcttattctg cgtgactcgt ttaaagatgc tgagcatagc aattctaagg 1861 ctgttttgga tccccgtatg tcggaactag agttgcaagg ggtcgatgaa ctaagttctg 1921 tagccagaga gatggttaga ttgatcgaaa cagccactgc tccaatatt gctgttgatg 1981 ttgatggccg cataaatggg tggaatgcaa aggtttcaga attgacagga ctcccagttg 2041 aggaggctat ggggaagtcc ttggttcgcg atcttgtgtt taaggagtct gaagaaactg 2101 tggacaagct tctttctcgt gctttaaaag gtgaagaaga taagaatgtt gagataaaaa 2161 tgaggacgtt tggcccagaa catcaaaata aggcagtttt tgtagtggtg aatgcttgct 2221 ccagcaagga ttatacaaat aatgtagttg gagtgtgctt tgttggtcag gatgttactg 2281 gtcaaaaaat tgtgatggac aaattcatca acatacaagg cgactacaag gctattgtac 2341 ataatccaaa tcctttgatc cctcccattt ttgcatcgga tgataacacg tgttgcttag 2401 agtggaacac tgcaatggaa aagcttactg gttggagccg cgcggatgtc attggaaaaa 2461 tgttggtggg agaggttttc ggcagttgct gtcagttgaa gggttcagat tcaataacaa 2521 agttcatgat tgtcttacac aatgcgcttg gtggacatga tacagataga ttcccttttt 2581 catttcttga tcggtatggc aagcatgtgc aagcttccct gactgcaaat aagagggtta 2641 acatggatgg tcagatcatt ggggcatttt gcttttttgca aattgtgagt ccggaacttc 2701 aacaggctct gaaggcacag agacaacaag agaagaattc atttgctagg atgaaagagt 2761 tagcttatat ttgtcaagga gttaagaatc ctttgagtgg catacgcttt acaaactctc 2821 ttttggaggc tacatgcttg tccaatgagc aaaaacagtt tcttgagact agtgctgctt 2881 gtgagaagca aatgttaaag ataatacacg atgttgatat tgaaagcatt gaggatgga
```

-continued

Solanum tuberosum phytochrome B nucleotide
GenBank: DQ342235.1
(SEQ ID NO: 31)

```
   1 atggcttctg gaagtagaac aaagcattcc catcataatt catctcaagc tcaatcttca 61 ggtacaagta atgtaaatta caaagattca ataagcaaag ctatagcaca gtacacagct 121 gatgctaggc ttcatgctgt gtttgaacaa tctggtgagt ctggaaagtt ttttgattat 181 tcagagtctg ttaaaactac tacacaatct gtgcctgaaa ggcaaatcac tgcttatttg 241 actaaaattc aaagaggagg tcatattcag ccttttggtt gtatgatagc tgtagatgag 301 gctagttttc gtgtaatagc ttatagtgaa atgcctttg aaatgcttag tttaactcca 361 caatctgttc caagccttga gaagtgtgag atcctcacta ttggaactga tgttaggacc 421 cttttttaccc cttctagctc tgttttgcta gaaagagcat ttggggcacg tgagatcact 481 ttactcaacc caatttggat tcattccaag aattctggaa agcccttttta tgcaattttg 541 cacagggttg atgttggtat tgccattgat ttggagcctg ctagaactga ggaccctgct 601 ttatctattg ctggagcagt gcagtcacag aaacttgcag tgagggctat ttctcatttg 661 caatcacttc ctggtgggga cattaagctt ttgtgtgata ctgttgttga gagtgtcagg 721 gagttaaccg ggtatgaccg ggttatggta tataaatttc atgaggatga gcatggagag 781 gtagtggctg agagtaaaag atcagattta gagccctata tcggtttgca ttatcctgct 841 actgatattc ctcaagcttc acggttttg tttaagcaga acagggtgag aatgattgtg 901 gactgtcatg ctacccctgt gcgggttact caggatgaat cactgatgca gcctttatgt 961 ctagttggtt ccacacttag agcacctcat ggttgccacg cacagtacat ggcaaatatg 1021 gggtctattg cctcattaac actggcagtt attatcaacg gaaatgatga ggaagctgtg 1081 ggtggcggtc gaaattcaat gaggctatgg ggcttggttg ttggacacca cacttctgtt 1141 cggtccattc ctttccctct taggtatgca tgtgaattcc ttatgcaggc ctttggactc 1201 caattgaaca tggagttgca attggcgtca cagttgtctg agaaacatgt tttaaggaca 1261 caaacactgt tatgtgacat gctccttcga gactctccac cggggattgt tacccaaagc 1321 cccagtatta tggaccttgt gaagtgcgat ggtgctgctc tatactacca ggggaagtac 1381 tatccattag gtgtcacacc aactgaagct cagataaagg acattgtgga gtggttattg 1441 gcttaccatg gagactcaac aggtttaagt actgacagtt tggctgatgc tgggtatcct 1501 ggagcagctt cacttggtga tgcagttttgt ggtatggctg tcgcttatat atcttctaaa 1561 gatttcttgt tttggttttcg ctcccacaca gcgaaagaaa taagtgggg tggtgcaaag 1621 catcatcctg aagacaagga tgatggactg agaatgcatc cacgttcttc cttcaaggca 1681 tttctggaag ttgttaaaag tcggagctca ccatggaaaa atgccgaaat ggatgcaatc 1741 cactctttgc agctaattct gcgagattca tttaaggatg ctgaggcaag taattctaag 1801 gctattgtgc atgctcatct tggggaaatg gagttgcaag ggatagatga actgagttct 1861 gttgccagag aaatggttag attgatcgaa actgcaacag ctcccatatt tgctgttgat 1921 gtcgaaggtc gcataaatgg gtggaatgca aggtcgctg aattgacagg tttatcagtt 1981 gaagaagcaa tggggaagtc cttggttcat gagcttgtgt acaaagaatc acaggagact 2041 gctgagaagc ttctgtataa tgctctaaga ggcgaggaag ataaaaatgt agaaataaag 2101 ttgaggacat ttgagctga caactggag aaagctgttt ttgtggtggt taatgcttgc 2161 gctagcaaag attacacaaa caacattgtt ggtgtttgct tgttgggca ggatgttact 2221 ggggaaaaag ttgttatgga caagtttatt aacatccaag gtgattacaa ggccattgtg 2281 cacagcccca atcctctgat ccctccaata tttgcatcag atgagaacac ttgttgctcc
```

-continued

```
2341 gagtggaaca ctgccatgga aaaactcact ggttggtcta gaggggagat tgttggaaaa
2401 atgttagttg gtgagatttt tggaagttgt tgtcggctca agggcccaga tgccatgaca
2461 aagttcatga tcgtgttgca taatgcaatt ggaggacagg atacagacaa gtttccattt
2521 tcctttttg accgaaatgg gaaatatgtg caagctcttt tgactgctaa caagagagtc
2581 aatatggagg gcaatactat tggggctttc tgtttcatac agatagccag tcccgaactg
2641 cagcaagctc taagagttca aaggcaacag gaaaagaagt gttattctca gatgaaagag
2701 ctggcataca tttgtcagga aataaaaagt cctcttaatg gtatacgctt tacaaattca
2761 ttgttggagg ccacaaattt gacagaaaat cagaagcagt atctagagac aagtgctgct
2821 tgtgagaggc agatgtctaa gatcattagg gatgttgatc tggaaaacat tgaggacggt
2881 tcactgaccc ttgagaaaga agattttttt cttgggagtg taatagatgc tgttgttagc
2941 caagtgatgt tattgctgag ggaaaaaggc gtgcagttaa tccgtgatat accagaggaa
3001 attaagacat taacagtaca tggtgatcaa gtgagaattc aacaggtctt ggcagatttc
3061 ttgttgaaca tggtacggta tgcaccatca cctgatgggt gggtagaaat ccaacttcga
3121 ccaagtatga tgccaatatc tgatggagta actggtgtgc atattgaact caggattata
3181 tgccctggcg aagggcttcc tcctgaattg gttcaagata tgttccacag cagtcggtgg
3241 gtaactcagg aaggcctagg actgagcacg tgcagaaaaa tgttaaagct tatgaatgga
3301 gaaatccagt atatcagaga atcagaaaga tgctatttcc tgattgtcct tgacctgcca
3361 atgacccgca aaggtccaaa gagtgttggc
```

Pisum sativum phytochrome B (PHYB) nucleotide
GenBank: AF069305.1

(SEQ ID NO: 32)

```
  1 agcaacaaca ataacaacag aaatattaaa agagaatcgt tatcaatgag aaaagccata
 61 gctcagtaca cagaagacgc aagnctccat gctgttttg aaaaatccgg tgactctttc
121 gattatgccc aatccattcg cgtcacggcg gctactgaat cagttcctga acagcaaatc
181 actgcttact tagccaaaat ccaacgcggt ggtttcattc aacctttcgg ttcaatgatc
241 gccgtcgacg aaacttcttt tcgcgttctt gcttactctg aaaacgcacg tgacatgctt
301 ggtatcgcgc tcaatcggt tccttctatg gaagatgatt cttcttcttc ttcgtttttc
361 tcttaggcg ttgatgttcg ttctcttttt agtgcttcca gttctgtact tcttgagaaa
421 gcttttttcag ctcgggagat tagtttaatg aatcctattt ggatccactc tcgttctact
481 ggtaagcctt tttatggaat tcttcaccga attgatattg gtgttgttat tgatttggag
541 cctgcgagat ctgaggatcc agcgctttcg attgccggtg ctgttcagtc tcagaagctt
601 gcggttcgtg cgatttcgca gctccaggcg cttcctggtg gtgatgtcaa gcttctttgt
661 gatgctgttg ttgagagtgt tagggaattg actggttatg ataggttat ggtttataag
721 tttcatgagg atgagcatgg tgaggttgtt gctgagagta agaggggtga tttagagcct
781 tatattggtt tgcattatcc tgctactgat attcctcagg cttctaggtt tttgtttaag
841 cagaataggg ttaggatgat tgtggattgt aatgcttctc ctgttagggt ttttcaggat
901 gaggcgcttg ttcagcctgt ttgtttggtt gggagtactc ttcgggctcc tcatggttgt
961 catgctcagt acatggcaaa tatgggttcc attgcttctt tggctatggc tgttattatt
1021 aatgggaatg atgaagacgg tggtgggatt ggtggtgctc acgtggctc gatgaggctt
1081 tggggtcttg ttgtttgtca tcatacttct gctaggtgta ttcctttccc tcttaggtat
1141 gcttgtgagt ttctaatgca ggcttttggg cttcagttga atatggagct tcagttagcc
1201 gtgcagtcgt tggagaaaag ggttttgaag acacagactc tgttgtgtga tatgttactt
```

-continued

```
1261 agggattctc atacagggat tgttactcag agtcctagta ttatggattt ggttaagtgt
1321 gatggggctg ctttgtatta tcaaggaaac taccacccct tgggtgttac tccgaccgag
1381 tctcagataa gggatatcat agattggttg ttggcctttc atagtgattc gacgggtttg
1441 agtactgata gtttggctga tgctggttat cctggggctg cttctcttgg ggatgcagtt
1501 tgtggaatgg ctgttgcgta tattactgaa aaagactttc ttttctggtt cagatctcat
1561 acggctaaag aaattaaatg gggtggtgca agcatcacc cggaggataa ggatgacggg
1621 cagaaaatgc atcctcgttc ttcttcaag gccttttag aagtggtgaa gatccgtagt
1681 atgcagtggg ataatgcaga aatggatgca attcactcct tgcagcttat cctgcgagac
1741 tcgtttaagg aagctgagaa taacgattca aaggctgtcg tgcataccca tatggcagaa
1801 ctagagttgc aaggggtgga tgaactgagt tctgtggcta gagaaatggt taggttgata
1861 gaaacagcca ctgctcccat atttgctgtt gatgtcgatg gtcgcatcaa tgggtggaat
1921 gcaaaggttt ctgaattgac aggacttctg gtagaggagg ctatgggcaa gtctttggtt
1981 catgatctcg tgtataagga gtctcgagaa actgtggaca agcttctttc tcatgcttta
2041 aaaggtgaag aagataaaaa tgttgagata aaaatgaaga cttttggccc ggggaatcaa
2101 aataaggcag ttttatagt ggtgaatgct tgctccagca aggattatac aaataatata
2161 gttggagtgt gctttgttgg ccaggatatt actggtcaaa aagttgtaat ggacaaattc
2221 attaacatac aaggtgacta caaggctatt gtacatagtc caaatccatt gatccctccc
2281 attttttgcat cggatgacaa cacatgttgc ttagagtgga acaatgctat ggaaaagctc
2341 agcggctgga gccgtgcaga tgtcattggc aaattgttag tgggagaggt ttttggtagt
2401 ttctgtcagt tgaagggttc ggatgctatg acaaaattca tgattgtttt gcacaatgca
2461 cttggtggac acgacacaga caaattccca ttgtcatttc ttgacagaca tggaaagtat
2521 gtgcatactt tcttgaccgc aaataagagg gttaacatgg atggtcagat cattggcgca
2581 ttttgctttt tacaaattgt gaaccctgaa cttcaacagg ctttgacagt ccagagacaa
2641 caggatagta gttccttagc tagaatgaag gagttagctt atatttgtca agaagtaaag
2701 aatcccttga gtggcatacg ctttacaaac tctcttttgg agtctacatg cctgactgat
2761 gagcaaaagc agcttcttga gactagtgtt gcttgtgaga agcaaatgct gaagatagta
2821 cgggacattg ctctagaaag catcgaggat gggtccctgg agcttgaaaa gcaggaattc
2881 ttgctcgaga atgtcataaa tgcagttgtt agccaagtaa tgctattgct aagagataga
2941 aagttacagt taattcgtga tattcctgaa gaaatcaagg cattggctgt ttatggtgat
3001 cagttgagga ttcaacaagt cttggctgat ttcttaatga atgtggtgcg ctatgcacca
3061 tctccagatg gttgggtaga gattcatgta tttccaagaa taaaacaaat tcagaggggg
3121 ctcactcttc tgcatgctga atttaggatg gtgtgtcctg gtgaaggtct tccacctgaa
3181 ttgattcaag acatgttcca taacagtcgg tgggtgactc aagaaggctt agggctgagc
3241 atgagcagga agattataaa gttaatgaac ggcgaagtcc agtatgtaag ggaggcagaa
3301 cggtgctact tcttagttct tcttgaacta cccgtgacac ggagaagctc taaagctatt
3361 aat
```

*Vitis vinifera* genotype PN40024 phytochrome B (PHYB) nucleotide
GenBank: EU436650.1
(SEQ ID NO: 33)

```
    atgagttcagga aacagaggaa cgcagtcgca ccaccaagct cagtcgtcgg ggacaagcaa
361 tttgagagtt taccacactg attcaatgag caaagccatt gcgcaatata caatggatgc
```

-continued

```
 421 tcgcctccac gccgtatacg aacagtccgg cgagtccggt aagtcattcg actactcgca
 481 gtcggttaga accacaacgc aatcggtccc tgagcaacaa atcactgcgt atttatcgaa
 541 aattcaacgg ggtggccata tacagccctt tgggtgtatg cttgcggtcg atgaggccac
 601 ttttcgggtc attgctttca gcgaaaatgc ccgagaaatg ctcggtctca ctccgcaatc
 661 ggttccgagc cttgagaagc ccgagatcct cctagtaggt actgatgttc gcacgctttt
 721 cactccctcg agcgcagttc tcctcgaaaa ggcgtttcgg gctcgggaaa ttacgttgtt
 781 aaatcccgtg tggattcatt ccaagaattc tggaaaaccc ttttacgcaa ttttgcatag
 841 aattgatgtg ggaattgtaa ttgatttgga gcctgcaagg actgaggacc ctgctctgtc
 901 cattgctggg gcggtgcagt cgcagaagtt ggccgttcga gcaatttccc atcttcaatc
 961 tcttcccggt ggtgatatta acctttgtgt tgaaactgtg gttgagaatg tgagggagct
1021 tactgggtat gatcgggtca tggtttacaa atttcacgag gatgaacatg gtgaggtcgt
1081 ggctgagagc aagaggtctg atttggagcc ttatattggg ttacactatc ctgccacgga
1141 cattccacag gcttcaaggt ttttgtttag gcagaatcgg gttaggatga tcgttgattg
1201 ccatgccacg cctgttctgg tgattcaaga tgaagggctt atgcagcctc tatgcttagt
1261 tggttcaacc cttcgggctc ctcatggctg ccatgcacag tatatggcca acatgggttc
1321 aactgcctca ttagcgatgg ctgtcatcat caatggaagt gatgaggaag ctattggtgg
1381 gcgaaacttg atgaggctat ggggcctggt tgtttgtcat cacacatctg ctaggtgcat
1441 tccatttcct cttcgatatg cctgtgagtt cctaatgcag gcatttggac tccaattgaa
1501 catggaactg cagttagcat cgcaattgtc tgagaaacat gttttaagga cacagactct
1561 cttgtgtgac atgctccttc gtgattcccc tactggaatt gttacccaaa gtcctagtat
1621 tatggatctt gtgaagtgtg atggagcagc actttattac caggggaagt attatccaac
1681 tggggtgacc ccgactgaag cccagataaa ggatattgca gagtggttgt ggcaaaacca
1741 tgcggattca acaggtttaa gcactgacag tttggctgat gctggctacc ctggggcagc
1801 ctcacttggt gatgcagttt gtggaatggc tgttgcttat atcacttcaa gagattttct
1861 attctggttt cggtcccaca cagcaaaaga gatcaaatgg ggtggtgcaa agcatcatcc
1921 agaggacaag gacgatgggc agaggatgca tcctcgttct tcattcaagg cattttttaga
1981 agtggtcaag agtcggagtt tgccatggga gaatgcggaa atggatgcaa ttcattctct
2041 gcagcttatt ctgcgtgact cttttaagga tgctactgat ggaagcaatt ctaaggctgt
2101 aatgcatgct cagctcgggg agctagagtt gcaagggatg gatgagttga gctctgttgc
2161 aagagaaatg gttaggttga ttgaaactgc aacagctccc atatttgcgg tcgatgttga
2221 tggctgcata aatggttgga atgcaaaggt tgcggagttg acggggcttt ctgttgagga
2281 agctatgggg aagtccttgg ttcatgatct tgtttacaag gaatctgaag aaactgttga
2341 caagcttctt catcatgctc tacgag gt gaagaagata
3361 agaatgtaga gataaaattg aggacatttg actcacaaca gcataagaag gctgttttg
3421 tggtcgttaa tgcttgctcc agtagggatt acacaaataa tatagttgga gtttgctttg
3481 ttggtcagga tgttactggt cagaaagtgg taatggacaa atttatccat atacaaggtg
3541 attacaaagc tattgtacat agtcccaacc ctttgattcc tcctatattt gcttcagatg
3601 agaacacagt ttgctctgag tggaacactg ccatggaaaa gctcactggg tggagcaggg
3661 gggacatcat tggaagatc ttggttgggg agattttttgg cagtagctgt cggctgaagg
3721 gtccggatgc tctgacaaaa ttcatgattg tgttgcacaa tgcaattgga gggcaagaca
3781 cagacaagtt tccatttcc ttctttgacc agaatggaaa atatgtgcaa gctcttttga
```

```
3841 cagcaaataa gagagttaat attgagggcc agattattgg tgccttctgc tttttgcaga 3901 ttgcaagtcc tgaattgcag caagctctca aagtccaaag gcaacaggag aaaaaatgtt 3961 ttgcaaggat gaaagagttg gcttacattt gtcaggaaat aaagaaccct ttaagtggca 4021 tacgtttcac taactctctt ttggaggcca ctgacttaac tgaagatcaa aagcagtttc 4081 ttgagactag tgctgcttgt gagaagcaga tgtcaaagat cataagggat gttgatctgg 4141 acagcattga ggatgg ttcactg gagcttgaga 5041 gggctgaatt tttacttgga agtgtcataa atgctgttgt tagccaagta atgatattgt 5101 tgagggaaag agatttacaa ttgatccggg acattcctga ggaagtcaaa acactggctg 5161 tttatggcga tcaagtaaga attcaacagg ttttggctga tttcttactg aatatggtgc 5221 gttatgcacc atccccagac ggttggatag agattcaagt ttgtccaaga ttgaagcaaa 5281 tttctgaaga agtaaaactt atgcatattg aattcag gat ggtatgccct ggtgaaggtc ttcctcctaa 7621 tctgattcaa gacatgttcc atagcagtcg ttggatgact caggaaggtc tagggctgag 7681 catgtgcagg aagatcttaa agctcattaa tggcgaagtc caatatatca gagaatcaga 7741 aagatgttat tttctaatca gcatagaact tcctatacct cacagaggct caaagagcgt 7801 tgac
```

---

What is claimed is:

1. An isolated polynucleotide comprising a contiguous coding sequence encoding a polypeptide having at least 95% identity to at least one amino acid sequence selected from SEQ ID NOs: 1-22, and having an amino acid other than tyrosine at the position corresponding to Y361 of SEQ ID NO:1, wherein the polypeptide confers increased light sensitivity in a plant expressing the polypeptide relative to a control plant lacking the polypeptide.

2. A vector comprising the polynucleotide of claim 1.

3. A polynucleotide construct comprising a promoter not natively associated with the polynucleotide of claim 1 operably linked to the polynucleotide of claim 1.

4. A plant cell comprising the polynucleotide of claim 1 operably linked to a promoter not natively associated with the polynucleotide of claim 1.

5. A plant comprising the plant cell of claim 4.

6. The plant of claim 5, wherein the plant exhibits increased light sensitivity relative to a control plant lacking the polynucleotide.

7. The plant of claim 5, wherein the plant exhibits a decreased height, decreased diameter or a combination thereof relative to a control plant lacking the polynucleotide.

8. The plant of claim 5, wherein the plant exhibits at least one characteristic selected from, increased hyponasty, decreased petiole length, decreased internode length, and decreased hypocotyl length under an R fluence rate of less than 1 µmole m$^{-2}$ sec$^{-1}$, relative to a control plant lacking the polynucleotide.

9. The plant of claim 5, wherein the plant exhibits enhanced germination relative to the control plant.

10. The plant of claim 9, wherein the plant is corn, soybean or rice.

11. The plant of claim 9, wherein the plant is an ornamental plant.

12. A method of producing a transgenic plant comprising:
(a) introducing into a plant cell a polynucleotide encoding a polypeptide comprising an amino acid sequence having at least 95% identity to at least one amino acid sequence selected from SEQ ID NOs: 1-22 and having an amino acid other than tyrosine at the position corresponding to Y361 of SEQ ID NO:1, wherein the polypeptide confers increased light sensitivity in a plant expressing the polypeptide relative to a control plant lacking the polypeptide; and
(b) regenerating the transformed cell to produce a transgenic plant.

13. The method of claim 12, wherein the transgenic plant exhibits increased light sensitivity relative to a control plant lacking the polynucleotide.

14. The method of claim 13, wherein the transgenic plant exhibits decreased height, decreased diameter, or a combination thereof relative to a control plant lacking the polynucleotide.

15. The method of claim 13, wherein the transgenic plant exhibits at least one characteristic selected from decreased petiole length, decreased internode number, increased hyponasty, and decreased hypocotyl length under an R fluence rate of less than 1 µmole m$^{-2}$ sec$^{-1}$, relative to a control plant lacking the polynucleotide.

16. The method of claim 12, wherein the transgenic plant exhibits enhanced germination relative to the control plant.

17. The method of claim 16, wherein the transgenic plant is a corn, soybean or rice plant.

18. The method of claim 16, wherein the transgenic plant is an ornamental plant.

19. A transgenic plant produced by the method of claim 12.

20. An isolated polypeptide comprising an amino acid sequence having at least 95% identity to at least one amino acid sequence selected from SEQ ID NOs: 1-22, and having an amino acid other than tyrosine at the position corresponding to Y361 of SEQ ID NO:1, wherein the polypeptide confers increased light sensitivity in a plant expressing the polypeptide relative to a control plant lacking the polypeptide.

21. The isolated polynucleotide of claim 1, further comprising at least one of (i) an amino acid other than aspartate (D) at the position corresponding to 307 of SEQ ID NO:1, (ii) an amino acid other than arginine (R) at the position corresponding to 322 of SEQ ID NO: 1, (iii) an amino acid other than arginine (R) at the position corresponding to 352 of SEQ ID NO: 1, and (iv) an amino acid other than arginine (R) at the position corresponding to 582 of SEQ ID NO: 1.

* * * * *